(12) United States Patent
Takahashi et al.

(10) Patent No.: US 11,873,337 B2
(45) Date of Patent: Jan. 16, 2024

(54) ANTIBODY BINDING TO CELL ADHESION MOLECULE 3

(71) Applicants: Kyowa Kirin Co., Ltd., Tokyo (JP); KAGOSHIMA UNIVERSITY, Kagoshima (JP)

(72) Inventors: Nobuaki Takahashi, Tokyo (JP); Ryosuke Nakano, Tokyo (JP); Sayaka Maeda, Tokyo (JP); Takenao Yamada, Tokyo (JP); Yuji Ito, Kagoshima (JP)

(73) Assignees: KYOWA KIRIN CO., LTD., Tokyo (JP); KAGOSHIMA UNIVERSITY, Kagoshima (JP)

( * ) Notice: Subject to any disclaimer, the term of this patent is extended or adjusted under 35 U.S.C. 154(b) by 442 days.

(21) Appl. No.: 17/255,784

(22) PCT Filed: Jun. 26, 2019

(86) PCT No.: PCT/JP2019/025454
§ 371 (c)(1),
(2) Date: Dec. 23, 2020

(87) PCT Pub. No.: WO2020/004492
PCT Pub. Date: Jan. 2, 2020

(65) Prior Publication Data
US 2021/0147541 A1    May 20, 2021

(30) Foreign Application Priority Data
Jun. 26, 2018    (JP) .................. 2018-120477

(51) Int. Cl.
*C07K 16/28*    (2006.01)
*A61K 39/00*    (2006.01)

(52) U.S. Cl.
CPC .... *C07K 16/2803* (2013.01); *A61K 2039/505* (2013.01); *C07K 2317/14* (2013.01);
(Continued)

(58) Field of Classification Search
CPC ............ C07K 16/2803; C07K 2317/14; C07K 2317/31; C07K 2317/33; C07K 2317/565; A61K 2039/505
See application file for complete search history.

(56) References Cited

U.S. PATENT DOCUMENTS

2012/0207760 A1*  8/2012  Grandea, III .... G01N 33/56983
                                                    424/139.1
2015/0322149 A1  11/2015  Bohrmann et al.
(Continued)

FOREIGN PATENT DOCUMENTS

CA    2 623 841       4/2007
JP    2012-62312      3/2012
(Continued)

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*
(Continued)

*Primary Examiner* — Adam Weidner
*Assistant Examiner* — Laura Ann Essex
(74) *Attorney, Agent, or Firm* — Wenderoth, Lind & Ponack, L.L.P.

(57) ABSTRACT

The invention relates to an antibody which binds to cell adhesion molecule 3 (CADM3) or an antibody fragment thereof, a hybridoma which produces the antibody or the antibody fragment thereof, a nucleic acid comprising a nucleotide sequence encoding the antibody or the antibody fragment thereof, a transformant cell comprising a vector comprising the nucleic acid, a method for producing the antibody or the antibody fragment thereof, a composition comprising the antibody or the antibody fragment thereof, and a method for detecting or measuring an antigen present in the brain, a method for diagnosing or treating a brain disease, a method for enhancing the property of accumulat-
(Continued)

ing in a brain of an antibody, and a method for increasing the amount of an antibody in the brain, each of which using the antibody or the antibody fragment thereof, and the like.

29 Claims, 8 Drawing Sheets

Specification includes a Sequence Listing.

(52) U.S. Cl.
CPC ...... *C07K 2317/31* (2013.01); *C07K 2317/33* (2013.01); *C07K 2317/565* (2013.01)

(56) References Cited

U.S. PATENT DOCUMENTS

| 2016/0347831 | A1 | 12/2016 | Lafaye et al. |
| 2018/0057604 | A1 | 3/2018 | Liu et al. |
| 2018/0085453 | A1 | 3/2018 | Kurihara et al. |
| 2018/0134797 | A1 | 5/2018 | Zhang et al. |
| 2019/0276530 | A1 | 9/2019 | Bohrmann et al. |

FOREIGN PATENT DOCUMENTS

| JP | 2015-119637 | 7/2015 |
| JP | 2017-503475 | 2/2017 |
| WO | 2012/023623 | 2/2012 |
| WO | 2013/184912 | 12/2013 |
| WO | 2014/033074 | 3/2014 |
| WO | 2016/081640 | 5/2016 |
| WO | 2016/081643 | 5/2016 |
| WO | 2016/175307 | 11/2016 |

OTHER PUBLICATIONS

Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*

Extended European Search Report dated Feb. 28, 2022 in corresponding European Patent Application No. 19824999.7.

International Search Report dated Sep. 17, 2019 in corresponding International (PCT) Application No. PCT/JP2019/025454, with English translation.

Written Opinion of the International Searching Authority dated Sep. 17, 2019 in corresponding International (PCT) Application No. PCT/JP2019/025454, with English translation.

Rodgers, K. R. and Chou, R. C., "Therapeutic monoclonal antibodies and derivatives: Historical perspectives and future directions", Biotechnology Advances, 2016, vol. 34, pp. 1149-1158.

Pardridge, W. M., "Re-Engineering Biopharmaceuticals for Delivery to Brain with Molecular Trojan Horses", Bioconjugate Chemistry, 2008, vol. 19, No. 7, pp. 1327-1338.

Wang et al., "Monoclonal Antibody Pharmacokinetics and Pharmacodynamics", Clinical Pharmacology & Therapeutics, 2008. vol. 84, No. 5, pp. 548-558.

Garg, A. and Balthasar, J. P., "Investigation of the Influence of FcRn on the Distribution of IgG to the Brain", AAPS Journal. 2009, vol. 11, No. 3, pp. 553-557.

Blennow et al., "Effect of Immunotherapy With Bapineuzumab on Cerebrospinal Fluid Biomarker Levels in Patients With Mild to Moderate Alzheimer Disease", Arch. Neurol., 2012, vol. 69, No. 8, pp. 1002-1010.

Wraith et al., "Enzyme Replacement Therapy for Mucopoly saccharidosis I: A Randomized, Double-Blinded, Placebo-Controlled, Multinational Study of Recombinant Human α-L-Iduronidase (Laronidase)", Journal Pediatrics, 2004, vol. 144, No. 5, pp. 581-588.

Muenzer et al., "A phase II/III clinical study of enzyme replacement therapy with idursulfase in mucopoly saccharidosis II (Hunter syndrome)", Genetics in Medicine, 2006, vol. 8, No. 8, pp. 465-473.

Brooks et al., "Significance of immune response to enzyme-replacement therapy for patients with a lysosomal storage disorder", TRENDS in Molecular Medicine, Oct. 2003, vol. 9, No. 10, pp. 450-453.

Sorrentino, N. C., and Fraldi, A. "Brain Targeting in MPS-IIIA", Pediatric Endocrinolgy Reviews, Jun. 2016, vol. 13, suppl. 1, pp. 630-638.

Couch et al., "Addressing Safety Liabilities of TfR Bispecific Antibodies That Cross the Blood-Brain Barrier", Science Translational Medicine, 2013, vol. 5, issue 183: 183ra57, pp. 1-12.

Yu et al., "Therapeutic bispecific antibodies cross the blood-brain barrier in nonhuman primates", Science Translational Medicine, 2014, vol. 6, issue 261: 261ra154, pp. 1-10.

Niewoehner et al., "Increased Brain Penetration and Potency of a Therapeutic Antibody Using a Monovalent Molecular Shuttle", Neuron, 2014, vol. 81, pp. 49-60.

Yue et al., "Fluorescence-Labeled Immunomicelles: Preparation, in vivo Biodistribution, and Ability to Cross the Blood-Brain Barrier", Macromolecular Bioscience, 2012, vol. 12, pp. 1209-1219.

Pardridge, W. M., and Boado, R., "Reengineering Biopharmaceuticals for Targeted Delivery Across the Blood-Brain Barrier", Methods in Enzymology, 2012, vol. 503, pp. 269-292.

Boado, R. J., and Pardridge, W. M., "Comparison of Blood-Brain Barrier Transport of Glial-Derived Neurotrophic Factor (GDNF) and an IgG-GDNF Fusion Protein in the Rhesus Monkey", Drug Metabolism and Disposition, 2009, vol. 37, No. 12, pp. 2299-2304.

Boado et al., "Drug Targeting of Erythropoietin Across the Primate Blood-Brain Barrier with an IgG Molecular Trojan Horse", Journal Pharmacology Experimental Therapeutics, 2010, vol. 333, No. 3, pp. 961-969.

Boado et al., "IgG-Enzyme Fusion Protein: Pharmacokinetics and Anti-Drug Antibody Response in Rhesus Monkeys", Bioconjugate Chemistry, 2013, vol. 24, pp. 97-104.

Zhang, Y., and Pardridge, W. M., "Delivery of—Galactosidase to Mouse Brain via the Blood-Brain Barrier Transferrin Receptor", Journal Pharmacology Experimental Therapeutics, 2005, vol. 313, No. 3, pp. 1075-1081.

Abulrob et al., "The blood-brain barrier transmigrating single domain antibody: mechanisms of transport and antigenic epitopes in human brain endothelial cells", Journal of Neurochemistry, 2005, vol. 95, pp. 1201-1214.

Farrington et al., "A novel platform for engineering blood-brain barrier-crossing bispecific biologics", FASEB Journal, 2014, vol. 28, pp. 4764-4778.

Webster et al., "Brain penetration, target engagement, and disposition of the blood-brain barrier-crossing bispecific antibody antagonist of metabotropic glutamate receptor type 1", FASEB Journal, 2016, vol. 30, pp. 1927-1940.

Zhang et al., "Mediated efflux of IgG molecules from brain to blood across the blood-brain barrier", Journal of Neuroimmunology, 2001, vol. 114, pp. 168-172.

Cooper et al., "Efflux monoclonal antibodies from rat brain by neonatal Fc receptor, FcRn", Brain Research, 2013, vol. 1534, pp. 13-21.

Kakunaga et al., "Nectin-like molecule-1/TSLL 1/SynCAM3: a neural tissue-specific immunoglobulin-like cell-cell adhesion molecule localizing at non-junctional contact sites of presynaptic nerve terminals, axons and glia cell processes", Journal of Cell Science, 2005, vol. 118, No. 6, pp. 1267-1277.

Zhou et al., "Nectin-like molecule 1 is a protein 4. IN associated protein and recruits protein 4.IN from cytoplasm to the plasma membrane", Biochimica et Biophysica Acta, 2005, vol. 1669, pp. 142-154.

Gao et al., "Nectin-like molecule 1 is a glycoprotein with a single N-glycosylation site at N290KS which influences its adhesion activity", Biochimica et Biophysica Acta, 2008, vol. 1778, pp. 1429-1435.

(56) References Cited

OTHER PUBLICATIONS

Dong et al., "Crystal Structure of the V Domain of Human Nectin-like Molecule-1/Syncam3/Tsl11/Igsf4b, a Neural Tissue-specific Immunoglobulin-like Cell-Cell Adhesion Molecule" Journal of Biological Chemistry, 2006, vol. 281, No. 15, pp. 10610-10617.

Park et al., "Disruption of Nectin-Like 1 Cell Adhesion Molecule Leads to Delayed Axonal Myelination in the CNS", Journal of Neuroscience, 2008, vol. 28, No. 48, pp. 12815-12819.

Gruber-Olipitz et al. "Nectin-like molecule 1 is a high abundance protein in cerebellar neurons", Amino Acids, 2006, vol. 30, pp. 409-415.

Takai et al., "Nectins and nectin-like molecules: Roles in cell adhesion, migration, and polarization", Cancer Sci, 2003, vol. 94, No. 8, pp. 655-667.

Sakisaka, T. and Takai, Y., "Biology and pathology of nectins and nectin-like molecules", Current Opinion in Cell Biology, 2004, vol. 16, pp. 513-521.

Hunter et al., "Localization of Cadm2a and Cadm3 proteins during development of the zebrafish nervous system", Journal of Comparative Neurology, 2011, vol. 519, pp. 2252-2270.

Atlas Antibodies, Product No. HPA002981, Anti-CADM3, 2012, Product Specification.

R&D systems, Catalog No. MAB3678, Human IGSF4B/SynCAM3 Antibody, Feb. 7, 2018.

Miyamoto et al., "Isolation of transferrin receptor-specific VHH antibodies aimed at passing through the blood-brain barrier", The 89th Conference of the Japanese Biochemical Society, 2016, pp. 542-543.

Package insert of intravenous infusion 2.9 mg of Aldurazyme™ (revised Jun. 2018, 8th edition), prepared and published by Sanofi Genzyrne, with an Annex containing a concise explanation of relevance, and cited as "NPL 8" in the Specification.

Package insert of intravenous infusion 6 mg of Elaprase™ (revised Jul. 2016, 6th edition), prepared and published by Sanofi Genzyrne, with an Annex containing a concise explanation of relevance, and cited as "NPL 9" in the Specification.

\* cited by examiner (A)

(B)

(A) SERUM (B) BRAIN (A)

(B)

ANTIBODY BINDING TO CELL ADHESION MOLECULE 3

TECHNICAL FIELD

The present invention relates to, for example, an antibody which binds to cell adhesion molecule 3 (CADM3) or an antibody fragment thereof, a hybridoma which produces the antibody or the antibody fragment thereof, a nucleic acid comprising a nucleotide sequence encoding the antibody or the antibody fragment thereof, a transformant cell comprising a vector comprising the nucleic acid, a method for producing the antibody or the antibody fragment thereof, a composition comprising the antibody or the antibody fragment thereof, and a method for detecting or measuring an antigen present in the brain, a method for diagnosing or treating a brain disease, a method for enhancing the property of accumulating in a brain of an antibody, and a method for increasing the amount of an antibody in the brain, each using the antibody or the antibody fragment thereof, and the like.

BACKGROUND ART

Since the approval of a mouse anti-CD3 antibody, muromonab-CD3 (OKT3) as the first antibody drug by FDA in 1986, many antibody drugs have been developed. In 1994, a chimeric antibody, abciximab, in which a variable region of a mouse antibody and a constant region of a human antibody are linked to reduce the antigenicity of the mouse antibody, was approved.

To further reduce the antigenicity, a humanized antibody technique in which a complementarity determining region (CDR), which plays an important role in binding to an antigen, of a variable region of a mouse antibody is grafted into a frame work region (FR) of a human antibody was developed, and a humanized anti-CD20 antibody, dacizumab was approved in 1997.

In addition, a phage display technique using a human antibody sequence library has been used, and a fully human anti-TNF-α antibody, adalimumab was approved in 2002 as the first antibody obtained using the phage display technique. Sixty or more antibody drugs targeting antigens such as CD20, CD52, TNF-α, HER2, and EGFR have already been approved (NPL 1).

In this manner, antibodies have become a widely recognized drug format. Most of the antibody drugs that have been approved so far are those for cancers and immune diseases, which account for about 75% or more of all the antibody drugs.

The importance of a biologic such as an antibody is increasing also in the treatment of central nervous system diseases, and it is reported that a monoclonal antibody to amyloid β is studied in Alzheimer's disease and that various types of neurotrophic factors (brain-derived neurotorophic factor BDNF and glial-derived neurotorophic factor GDNF) having a neuroprotective effect exhibit a neuroprotective effect in central nervous system diseases in an animal model (NPL 2).

However, when an antibody is peripherally administered, the amount delivered to the central nervous system is lower than that to the other organs, and the antibody migration ratio (the ratio of the concentration in the cerebrospinal fluid (CSF) to the serum concentration) is reported to be 0.1 to 0.3% (NPLs 3 to 5).

A reason why the drug delivery amount decreases in the central nervous system comprising the brain and the bone marrow is the mechanism called blood-brain barrier (BBB) which limits the transportation of a substance between the blood and the interstitial fluid of the brain. The blood-brain barrier has a physical/nonspecific control mechanism due to the intercellular adhesion of the vascular endothelial cells and a substrate-specific efflux mechanism due to efflux transporters, and protects the central nervous system from foreign matters or drugs and plays an important role in maintaining the homeostasis.

However, due to the existence of the blood-brain barrier, the effective concentration at the time of drug administration is not easily obtained in the central nervous system, and the drug development is difficult. For example, although enzyme replacement therapy is conducted by intravenously administering α-L-iduronidase to Hurler syndrome (mucopolysaccharidosis I) or iduronate-2-sulfatase to Hunter syndrome (mucopolysaccharidosis II), the enzymes do not pass through the blood-brain barrier due to their high molecular weights, and therefore, no efficacy against central nervous system symptoms has been observed (NPLs 6 to 9). Further, it is reported that a side effect such as production of a neutralizing antibody is caused because a certain amount of a recombinant enzyme is continuously administered regularly (NPL 10).

In addition, an attempt to directly administer biologics into the medullary cavity or the brain has also been made to increase the concentration in the brain. For example, a method for administering iduronate-2-sulfatase into the brain of patients with Hunter syndrome (mucopolysaccharidosis II) to prevent the progress of brain disorders of the patients is reported (PTL 1). However, direct administration into the medullary cavity or the brain is highly invasive (NPL 11).

Therefore, various delivery techniques have been studied to increase the concentration of a substance with a high molecular weight such as biologics in the brain. For example, methods in which a complex of a substance with a high molecular weight and a membrane protein which is expressed in brain vascular endothelial cells is formed by binding the substance to the membrane protein, and allowed to pass through the blood-brain barrier through endocytosis are reported.

Most of the reported techniques use receptor-mediated transcytosis (RMT), and the receptor expressed in the brain vascular endothelium to serve as a target comprises, for example, a transferrin receptor, an insulin receptor, an insulin-like growth factor receptor, a low-density lipoprotein receptor family (LDLRf), and the like.

Techniques for passing through the blood-brain barrier via a transferrin receptor by producing a fusion protein of an anti-transferrin receptor antibody and a nerve growth factor are reported. As techniques using an anti-transferrin receptor antibody, bispecific antibodies of an anti-transferrin receptor antibody and an anti-beta secretase (BACE1) antibody (PTLs 2 and 3 and NPLs 12 and 13), and fusion antibodies obtained by fusing a monovalent anti-transferrin receptor antibody to the carboxyl-terminal side of an anti-amyloid β antibody (PTL 4 and NPL 14) are reported.

It is reported that, regarding the brain delivery using a bispecific antibody of an anti-transferrin receptor antibody and an anti-BACE1 antibody, the amount of the antibody incorporated in the brain increases by about 4 times the amount of the control when the antibody is administered to a mouse at 20 mg/kg body weight (NPL 13).

Further, a technique for allowing a drug to pass through the blood-brain barrier by encapsulating the drug with a liposome having an anti-transferrin receptor antibody on its surface is reported. It is reported that the amount incorporated in the brain of a rat increases by about 2 to 5 times by a fusion body of an anti-rat transferrin receptor antibody and an immunomicelle (NPL 15).

Further, techniques for passing through the blood-brain barrier via an insulin receptor by producing a fusion protein of a neurotrophic factor, an enzyme, or an anti-amyloid antibody fused to the carboxyl-terminal side of an anti-insulin receptor antibody are reported (NPLs 16 to 19).

It is reported that in a rhesus monkey, the amount incorporated in the brain 2 hours after administering a fusion antibody of a labeled anti-human insulin receptor antibody and GDNF is about 15 times as compared with that of GDNF (NPL 17).

However, a transferrin receptor and an insulin receptor are expressed not only in the brain vascular endothelial cells but also in the whole body comprising the liver and the like, and therefore, a drug is delivered also to the liver and the like as the amount of the drug delivered to the central nervous system increases in these techniques (NPL 20). Further, because the antigen is expressed in the whole body, the half-life of the antibody in the blood is short (NPL 12).

In addition, it is reported that an antibody (Fc5) to TMEM30A, which is an antigen expressed in the brain vascular endothelial membrane, shows an RMT-like activity (PTL 5 and NPLs 21 and 22). Fc5 is an antibody of a variable domain of a heavy chain of a heavy chain antibody (VHH) of a single domain derived from llama, and it is demonstrated in an in vitro BBB model and in a rat in vivo model that the amount of a fusion body of Fc5 and human Fc delivered to the brain increases as compared with that of the control IgG.

It is reported that the CSF exposure of a fusion body of a Fc5-derived single chain antibody (scFv) and a metabotropic glutamate receptor type I (mGluRI) antibody increases as compared with that of a fusion body of a control single chain antibody and a mGluRI antibody in a rat model, but the increase in the amount is around 5 times (NPL 23).

It is also reported that an IgG antibody is rapidly discharged from the brain to the circulating blood by a neonatal Fc receptor (FcRn) (NPLs 24 and 25), and for example, the half-life of IgG in the brain after the administration into the brain is as short as 48 minutes in a rat (NPL 24).

CADM3 is a calcium ion-independent immunoglobulin-like cell adhesion molecule (NPLs 26 to 31). CADM3 is divided into structures comprising three immunoglobulin-like domains as extracellular domains, one transmembrane domain, and one cytoplasmic domain (NPL 29).

From the RNA blot and in situ hybridization analyses, CADM3 is specifically expressed in both nerve tissues of various central nerves comprising cerebellum, cerebral cortex, hippocampus, amygdaloid body, olfactory bulb, and medulla oblongata and peripheral nerves (NPLs 26, 27, and 32). CADM3 is localized between two axon terminals, between an axon terminal and an axon shaft, and at a contact site between an axon terminal and a glial cell process at an axon terminal (NPL 26).

CADM3 exhibits a cell-cell adhesion activity by calcium ion-independent homophilic binding. In addition, CADM3 exhibits a cell-cell adhesion activity by calcium ion-independent heterophilic binding with Necl-2, nectin-1, and nectin-3, but does not exhibit an adhesion activity with Necl-5 and nectin-2. CADM3 that interacts with nectin-1 and nectin-3 is involved in neuronal activity-dependent synaptic remodeling process in the same manner as in the formation of cerebellar morphology (NPLs 32 and 33). From the in vitro binding analysis, it is demonstrated that protein 4.1N involved in actin cytoskeleton rearrangement and CADM3 bind to each other (NPL 27).

In a CADM3 knockout mouse, the number of myelinated axons in the optic nerve and the spinal cord is decreased at the early stage after birth. However, there is no difference in the number of myelinated axons or the thickness of the myelin sheath between a normal individual and a mutant after maturation (NPL 30). In addition, a polyclonal antibody which binds to CADM3 is reported (NPL 27).

CITATION LIST

Patent Literature

PTL 1: WO 2012/023623
PTL 2: WO 2016/081640
PTL 3: WO 2016/081643
PTL 4: WO 2014/033074
PTL 5: Canadian Patent No. 2623841

Non Patent Literature

NPL 1: Kyla R R, and Richard C C., Biotechnol Adv, pii: S0734-9750 (16), 30091-X, 2016
NPL 2: Pardridge W M., Bioconjugate Chem., 19, 1327-1338, 2008
NPL 3: Wang W., et al., Clin. pharmacol. Ther., 84, 548-558, 2008
NPL 4: Garg A., el al., AAPSJ., 11, 553-557, 2009
NPL 5: Kaj B., et al., Arch. Neurol., 69 (8), 1002-1010, 2012
NPL 6: Wraith J E. et al., J. Pediatr. 144 (5), 581-588, 2004
NPL 7: Muenzer J. et al., Genet Med. 8 (8), 465-473, 2006
NPL 8: Package insert of intravenous infusion 2.9 mg of Aldurazyme (registered trademark) (July, 2016, 8th edition)
NPL 9: Package insert of intravenous infusion 6 mg of Elaprase (registered trademark) (July, 2016, 6th edition)
NPL 10: Brooks, D. A. et al., Trends Mol. Med. 9, 450453, 2003
NPL 11: Sorrentino N C. et al., Pediatr Endocrinol Rev. 1, 630-638, 2016
NPL 12: Couch J A., et al., Science Translational Medicine, 5, 183ra57, 2013
NPL 13: Yu Y J., et al., Science Translational Medicine. 6, 261ra154, 2014
NPL 14: Niewoehner J., et al., Neuron. 81, 49-60, 2014
NPL 15: Jun Y., et al., Macromol. Biosci. 12, 1209-1219, 2012
NPL 16: Pardridge W M, and Boado R J., Methods in Enzymology, 503, 269-292, 2012
NPL 17: Boado R J., et al., Drug Metab. Dispos., 37 (12), 2299-2304, 2009
NPL 18: Boado R J., et al., J. Pharmacol. Exp. Ther., 333 (3), 961-969, 2010
NPL 19: Boado R J., et al., Bioconjugate Chem., 1, 97-104, 2012
NPL 20: Yun Zhang. et al., J. Pharmacol. Exp. Ther., 313 (3), 1075-1081, 2005
NPL 21: Abulrob A., et al., J. Neuyrochem., 95 (4), 1201-1214, 2005
NPL 22: Farrington G K., et al., FASEB J., 28, 4764-4778, 2014
NPL 23: Webster C I., et al., FASEB J., 30, 1927-1940, 2016
NPL 24: Zhang Y. et al., J. Neuroimmunol., 114 (1-2), 168-172, 2001
NPL 25: Philip R C., et al., Brain Research, 1534, 13-21, 2013

NPL 26: Kakunaga S., et al., J. Cell Science, 118, 1267-1277, 2005
NPL 27: Zhou Y., et al., Biochim. Biophys. Acta. 1669, 142-154, 2005
NPL 28: Gao J., et al., Biochim. Biophys. Acta, 1778, 1429-1435, 2008
NPL 29: Dong X., et al., J. Biol. Chem., 281, 10610-10617, 2006
NPL 30: Park J., et al., J. Neurosci., 28, 12815-12819, 2008
NPL 31: Gruber-Olipitz M., et al., Amino Acids, 30, 409-415, 2006
NPL 32: Takai Y., et al., Cancer Sci., 94, 655-667, 2003
NPL 33: Sakisaka T. et al., Curr. Opin. Cell. Biol., 16, 513-521, 2004

SUMMARY OF INVENTION

Technical Problem

The invention relates to, for example, a CADM3-binding molecule which binds to CADM3 and methods using the molecule, and the like. Specifically, an object is to provide an antibody which binds to CADM3 or an antibody fragment thereof, a hybridoma which produces the antibody or the antibody fragment thereof, a nucleic acid comprising a nucleotide sequence encoding the antibody or the antibody fragment thereof, a transformant cell comprising a vector comprising the nucleic acid, a method for producing the antibody or the antibody fragment thereof, a composition comprising the antibody or the antibody fragment thereof, and a method for detecting or measuring an antigen present in the brain, a method for diagnosing or treating a brain disease, a method for enhancing the property of accumulating in a brain of an antibody, and a method for increasing the amount of an antibody in the brain, each using the antibody or the antibody fragment thereof, and the like.

Solution to Problem

As a means for solving the problems, the invention provides a CADM3-binding molecule which binds to CADM3 and methods using the molecule, specifically, an antibody which binds to CADM3 or an antibody fragment thereof.

That is, the invention relates to the following <1> to <22>.

<1> An antibody which binds to cell adhesion molecule 3 (CADM3) or an antibody fragment thereof.

<2> The antibody or the antibody fragment thereof according to <1>, wherein the antibody has a property of accumulating in a brain.

<3> The antibody or the antibody fragment thereof according to <1> or <2>, wherein the antibody has affinity for neurons and/or nerve tissues.

<4> The antibody or the antibody fragment thereof according to any one of <1> to <3>, wherein the antibody or the antibody fragment thereof is selected from the group consisting of the following (a) to (x):

(a) an antibody in which the amino acid sequences of complementarity determining regions (CDRs) 1 to 3 of a variable domain of a heavy chain (VH) comprise the amino acid sequences represented by SEQ ID NOS: 23, 24, and 25, respectively, and in which the amino acid sequences of CDR1 to CDR3 of a variable domain of a light chain (VL) comprise the amino acid sequences represented by SEQ ID NOS: 28, 29, and 30, respectively;

(b) an antibody in which the amino acid sequences of CDR1 to CDR3 of VH comprise the amino acid sequences represented by SEQ ID NOS: 33, 34 and 35, respectively, and in which the amino acid sequences of CDR1 to CDR3 of VL comprise the amino acid sequences represented by SEQ ID NOS: 38, 39, and 40, respectively;

(c) an antibody fragment in which the amino acid sequences of CDR1 to CDR3 of a variable domain of a heavy chain of a heavy chain antibody (VHH) comprise the amino acid sequences represented by SEQ ID NOS: 3, 4, and 5, respectively;

(d) an antibody fragment in which the amino acid sequences of CDR1 to CDR3 of VHH comprise the amino acid sequences represented by SEQ ID NOS: 8, 9, and 10, respectively;

(e) an antibody fragment in which the amino acid sequences of CDR1 to CDR3 of VHH comprise the amino acid sequences represented by SEQ ID NOS: 13, 14, and 15, respectively;

(f) an antibody fragment in which the amino acid sequences of CDR1 to CDR3 of VHH comprise the amino acid sequences represented by SEQ ID NOS: 18, 19, and 20, respectively;

(g) an antibody in which the amino acid sequences of CDR1 to CDR3 of VH comprise the amino acid sequences represented by SEQ ID NOS: 89, 90, and 91, respectively, and in which the amino acid sequences of CDR1 to CDR3 of VL comprise the amino acid sequences represented by SEQ ID NOS: 94, 95, and 96, respectively;

(h) an antibody in which the amino acid sequences of CDR1 to CDR3 of VH comprise the amino acid sequences represented by SEQ ID NOS: 99, 100, and 101, respectively, and in which the amino acid sequences of CDR1 to CDR3 of VL comprise the amino acid sequences represented by SEQ ID NOS: 134, 135, and 136, respectively;

(i) an antibody in which the amino acid sequences of CDR1 to CDR3 of VH comprise the amino acid sequences represented by SEQ ID NOS: 104, 105, and 106, respectively, and in which the amino acid sequences of CDR1 to CDR3 of VL comprise the amino acid sequences represented by SEQ ID NOS: 134, 135, and 136, respectively;

(j) an antibody in which the amino acid sequences of CDR1 to CDR3 of VH comprise the amino acid sequences represented by SEQ ID NOS: 109, 110, and 111, respectively, and in which the amino acid sequences of CDR1 to CDR3 of VL comprise the amino acid sequences represented by SEQ ID NOS: 134, 135, and 136, respectively;

(k) an antibody in which the amino acid sequences of CDR1 to CDR3 of VH comprise the amino acid sequences represented by SEQ ID NOS: 114, 115, and, 116, respectively, and in which the amino acid sequences of CDR1 to CDR3 of VL comprise the amino acid sequences represented by SEQ ID NOS: 134, 135, and 136, respectively;

(l) an antibody in which the amino acid sequences of CDR1 to CDR3 of VH comprise the amino acid sequences represented by SEQ ID NOS: 119, 120, and 121, respectively, and in which the amino acid sequences of CDR1 to CDR3 of VL comprise the amino acid sequences represented by SEQ ID NOS: 134, 135, and 136, respectively;

(m) an antibody in which the amino acid sequences of CDR1 to CDR3 of VH comprise the amino acid sequences represented by SEQ ID NOS: 124, 125, and 126, respectively, and in which the amino acid sequences of CDR1 to CDR3 of VL comprise the amino acid sequences represented by SEQ ID NOS: 134, 135, and 136, respectively;

(n) an antibody in which the amino acid sequences of CDR1 to CDR3 of VH comprise the amino acid sequences represented by SEQ ID NOS: 129, 130, and 131, respectively, and in which the amino acid sequences of CDR1 to CDR3 of VL comprise the amino acid sequences represented by SEQ ID NOS: 134, 135, and 136, respectively;

(o) an antibody in which the amino acid sequences of CDR1 to CDR3 of VH comprise the amino acid sequences represented by SEQ ID NOS: 139, 140, and 141, respectively, and in which the amino acid sequences of CDR1 to CDR3 of VL comprise the amino acid sequences represented by SEQ ID NOS: 164, 165, and 166, respectively;

(p) an antibody in which the amino acid sequences of CDR1 to CDR3 of VH comprise the amino acid sequences represented by SEQ ID NOS: 144, 145, and 146, respectively, and in which the amino acid sequences of CDR1 to CDR3 of VL comprise the amino acid sequences represented by SEQ ID NOS: 164, 165, and 166, respectively;

(q) an antibody in which the amino acid sequences of CDR1 to CDR3 of VH comprise the amino acid sequences represented by SEQ ID NOS: 149, 150, and 151, respectively, and in which the amino acid sequences of CDR1 to CDR3 of VL comprise the amino acid sequences represented by SEQ ID NOS: 164, 165, and 166, respectively;

(r) an antibody in which the amino acid sequences of CDR1 to CDR3 of VH comprise the amino acid sequences represented by SEQ ID NOS: 154, 155, and 156, respectively, and in which the amino acid sequences of CDR1 to CDR3 of VL comprise the amino acid sequences represented by SEQ ID NOS: 164, 165, and 166, respectively;

(s) an antibody in which the amino acid sequences of CDR1 to CDR3 of VH comprise the amino acid sequences represented by SEQ ID NOS: 159, 160, and 161, respectively, and in which the amino acid sequences of CDR1 to CDR3 of VL comprise the amino acid sequences represented by SEQ ID NOS: 164, 165, and 166, respectively;

(t) an antibody in which the amino acid sequences of CDR1 to CDR3 of VH comprise the amino acid sequences represented by SEQ ID NOS: 169, 170, and 171, respectively, and in which the amino acid sequences of CDR1 to CDR3 of VL comprise the amino acid sequences represented by SEQ ID NOS: 174, 175, and 176, respectively;

(u) an antibody which competes for binding to CADM3 with at least one of the antibodies or the antibody fragments described in (a) to (t);

(v) an antibody which binds to an epitope comprising an epitope to which any one of the antibodies or the antibody fragments described in (a) to (t) binds;

(w) an antibody which binds to the same epitope as an epitope to which any one of the antibodies or the antibody fragments described in (a) to (t) binds; and (x) an antibody which comprises an amino acid sequence having 85% or more homology with the amino acid sequence of any one of the antibodies or the antibody fragments described in (a) to (t).

<5> The antibody or the antibody fragment thereof according to any one of <1> to <4>, wherein the antibody or the antibody fragment thereof is selected from the group consisting of the following (1) to (31):

(1) an antibody in which the amino acid sequence of VH comprises the amino acid sequence represented by SEQ ID NO: 22 and in which the amino acid sequence of VL comprises the amino acid sequence represented by SEQ ID NO: 27;

(2) an antibody in which the amino acid sequence of VH comprises the amino acid sequence represented by SEQ ID NO: 32 and in which the amino acid sequence of VL comprises the amino acid sequence represented by SEQ ID NO: 37;

(3) an antibody fragment in which the amino acid sequence of VHH comprises the amino acid sequence represented by SEQ ID NO: 2;

(4) an antibody fragment in which the amino acid sequence of VHH comprises the amino acid sequence represented by SEQ ID NO: 7;

(5) an antibody fragment in which the amino acid sequence of VHH comprises the amino acid sequence represented by SEQ ID NO: 12;

(6) an antibody fragment in which the amino acid sequence of VHH comprises the amino acid sequence represented by SEQ ID NO: 17;

(7) an antibody fragment in which the amino acid sequence of VHH comprises the amino acid sequence represented by SEQ ID NO: 68;

(8) an antibody fragment in which the amino acid sequence of VHH comprises the amino acid sequence represented by SEQ ID NO: 70;

(9) an antibody fragment in which the amino acid sequence of VHH comprises the amino acid sequence represented by SEQ ID NO: 72;

(10) an antibody fragment in which the amino acid sequence of VHH comprises the amino acid sequence represented by SEQ ID NO: 74;

(11) an antibody fragment in which the amino acid sequence of VHH comprises the amino acid sequence represented by SEQ ID NO: 76;

(12) an antibody fragment in which the amino acid sequence of VHH comprises the amino acid sequence represented by SEQ ID NO: 78;

(13) an antibody fragment in which the amino acid sequence of VHH comprises the amino acid sequence represented by SEQ ID NO: 80;

(14) an antibody fragment in which the amino acid sequence of VHH comprises the amino acid sequence represented by SEQ ID NO: 82;

(15) an antibody fragment in which the amino acid sequence of VHH comprises the amino acid sequence represented by SEQ ID NO: 84;

(16) an antibody fragment in which the amino acid sequence of VHH comprises the amino acid sequence represented by SEQ ID NO: 86;

(17) an antibody in which the amino acid sequence of VH comprises the amino acid sequence represented by SEQ ID NO: 88 and in which the amino acid sequence of VL comprises the amino acid sequence represented by SEQ ID NO: 93;

(18) an antibody in which the amino acid sequence of VH comprises the amino acid sequence represented by SEQ ID NO: 98 and in which the amino acid sequence of VL comprises the amino acid sequence represented by SEQ ID NO: 133;
(19) an antibody in which the amino acid sequence of VH comprises the amino acid sequence represented by SEQ ID NO: 103 and in which the amino acid sequence of VL comprises the amino acid sequence represented by SEQ ID NO: 133;
(20) an antibody in which the amino acid sequence of VH comprises the amino acid sequence represented by SEQ ID NO: 108 and in which the amino acid sequence of VL comprises the amino acid sequence represented by SEQ ID NO: 133;
(21) an antibody in which the amino acid sequence of VH comprises the amino acid sequence represented by SEQ ID NO: 113 and in which the amino acid sequence of VL comprises the amino acid sequence represented by SEQ ID NO: 133;
(22) an antibody in which the amino acid sequence of VH comprises the amino acid sequence represented by SEQ ID NO: 118 and in which the amino acid sequence of VL comprises the amino acid sequence represented by SEQ ID NO: 133;
(23) an antibody in which the amino acid sequence of VH comprises the amino acid sequence represented by SEQ ID NO: 123 and in which the amino acid sequence of VL comprises the amino acid sequence represented by SEQ ID NO: 133;
(24) an antibody in which the amino acid sequence of VH comprises the amino acid sequence represented by SEQ ID NO: 128 and in which the amino acid sequence of VL comprises the amino acid sequence represented by SEQ ID NO: 133;
(25) an antibody in which the amino acid sequence of VH comprises the amino acid sequence represented by SEQ ID NO: 138 and in which the amino acid sequence of VL comprises the amino acid sequence represented by SEQ ID NO: 163;
(26) an antibody in which the amino acid sequence of VH comprises the amino acid sequence represented by SEQ ID NO: 143 and in which the amino acid sequence of VL comprises the amino acid sequence represented by SEQ ID NO: 163;
(27) an antibody in which the amino acid sequence of VH comprises the amino acid sequence represented by SEQ ID NO: 148 and in which the amino acid sequence of VL comprises the amino acid sequence represented by SEQ ID NO: 163;
(28) an antibody in which the amino acid sequence of VH comprises the amino acid sequence represented by SEQ ID NO: 153 and in which the amino acid sequence of VL comprises the amino acid sequence represented by SEQ ID NO: 163;
(29) an antibody in which the amino acid sequence of VH comprises the amino acid sequence represented by SEQ ID NO: 158 and in which the amino acid sequence of VL comprises the amino acid sequence represented by SEQ ID NO: 163;
(30) an antibody in which the amino acid sequence of VH comprises the amino acid sequence represented by SEQ ID NO: 168 and in which the amino acid sequence of VL comprises the amino acid sequence represented by SEQ ID NO: 173; and
(31) an antibody which comprises an amino acid sequence having 85% or more homology with the amino acid sequence of any one of the antibodies or the antibody fragments described in (1) to (30).

<6> The antibody or the antibody fragment thereof according to any one of <1> to <5>, wherein the antibody or the antibody fragment thereof is a bispecific antibody.

<7> The bispecific antibody according to <6>, wherein the bispecific antibody binds to CADM3 and an antigen present in a brain.

<8> The bispecific antibody according to <6> or <7>, wherein the bispecific antibody comprises an antigen-binding site which binds to CADM3 and an antigen-binding site which binds to an antigen present in a brain.

<9> The antibody fragment according to any one of <1> to <8>, wherein the antibody fragment is selected from the group consisting of Fab, Fab', F(ab')$_2$, a single chain antibody (scFv), a dimerized V region (diabody), a disulfide-stabilized V region (dsFv), VHH, and a peptide comprising CDR <10> The antibody and the antibody fragment thereof according to any one of <1> to <9>, wherein the antibody is a genetically recombinant antibody.

<11> The antibody and the antibody fragment thereof according to any one of <1> to <10>, wherein the antibody is selected from the group consisting of a mouse antibody, a rat antibody, a rabbit antibody, an alpaca antibody, a camel antibody, a llama antibody, a chimeric antibody, a humanized antibody, and a human antibody.

<12> A fusion antibody or a fusion antibody fragment thereof, which is obtained by binding at least one selected from the group consisting of the following (i) to (iii) to the antibody or the antibody fragment thereof which binds to CADM3 according to any one of <1> to <11>:
  (i) a hydrophilic polymer;
  (ii) an amphipathic polymer; and
  (iii) a functional molecule.

<13> A hybridoma which produces the antibody, the antibody fragment thereof, the fusion antibody, or the fusion antibody fragment thereof according to any one of <1> to <12>.

<14> A nucleic acid, comprising a nucleotide sequence encoding the antibody, the antibody fragment thereof, the fusion antibody, or the fusion antibody fragment thereof according to any one of <1> to <12>.

<15> A transformant cell, comprising a vector comprising the nucleic acid according to <14>.

<16> A method for producing the antibody, the antibody fragment thereof, the fusion antibody, or the fusion antibody fragment thereof according to any one of <1> to <12>, comprising:
  culturing the hybridoma according to <13> or the transformant cell according to <15>, and
  collecting the antibody, the antibody fragment thereof, the fusion antibody, or the fusion antibody fragment thereof according to any one of <1> to <12> from a culture solution.

<17> A composition, comprising the antibody, the antibody fragment thereof, the fusion antibody, or the fusion antibody fragment thereof according to any one of <1> to <12>.

<18> The composition according to <17>, which is a composition for detecting or measuring an antigen present in a brain.

<19> The composition according to <17>, which is a composition for diagnosing or treating a brain disease.

<20> A method for detecting or measuring an antigen present in a brain using the antibody, the antibody fragment thereof, the fusion antibody, or the fusion antibody fragment thereof according to any one of <1> to <12> or the composition according to <17>.

<21> A method for diagnosing or treating a brain disease using the antibody, the antibody fragment thereof, the fusion antibody, or the fusion antibody fragment thereof according to any one of <1> to <12> or the composition according to <17>.

<22> A method for enhancing the property of accumulating in a brain of an antibody, an antibody fragment thereof, a fusion antibody, or a fusion antibody fragment thereof using the antibody, the antibody fragment thereof, the fusion antibody, or the fusion antibody fragment thereof according to any one of <1> to <12> or the composition according to <17>.

<23> A method for increasing the amount of an antibody, the amount of an antibody fragment thereof, the amount of a fusion antibody, or the amount of a fusion antibody fragment thereof in a brain using the antibody, the antibody fragment thereof, the fusion antibody, or the fusion antibody fragment thereof according to any one of <1> to <12> or the composition according to <17>.

Advantageous Effects of Invention

The CADM3-binding molecule of the invention not only enhances the property of accumulating in a brain of the binding molecule itself by specifically binding to CADM3, but also can be applied to the treatment of a brain disease by modifying the CADM3-binding molecule with another target molecule and transporting and retaining the target molecule in the brain. As a specific CADM3-binding molecule of the invention, an antibody or an antibody fragment thereof is exemplified. The antibody or the antibody fragment thereof of the invention is an antibody or an antibody fragment thereof having the property of accumulating in a brain by binding to CADM3 in the brain. Therefore, the antibody or the antibody fragment thereof of the invention can be used as a composition for detecting or measuring an antigen present in the brain (CADM3, or CADM3 and another antigen present in the brain), a composition for diagnosing a brain disease, and a pharmaceutical composition for treating a brain disease.

BRIEF DESCRIPTION OF DRAWINGS

FIG. 1(A) shows the antibody concentration in serum 3 days after administering the antibody. The vertical axis represents the antibody concentration (ng/mL), and the horizontal axis represents the administered antibodies. FIG. 1(B) shows the antibody concentration in a brain tissue 3 days after administering the antibody. The vertical axis represents the antibody concentration (ng/g brain), and the horizontal axis represents the administered antibodies.

FIG. 2(A) shows the antibody concentration in serum 7 days after administering the antibody. The vertical axis represents the antibody concentration (ng/mL), and the horizontal axis represents the administered antibodies. FIG. 2(B) shows the antibody concentration in a brain tissue 7 days after administering the antibody. The vertical axis represents the antibody elution amount (ng/g brain), and the horizontal axis represents the administered antibodies.

FIG. 3(A) shows the antibody concentration in serum 7 days after administering the antibody. The vertical axis represents the antibody concentration (ng/mL), and the horizontal axis represents the administered antibodies. FIG. 3(B) shows the antibody concentration in a brain tissue 7 days after administering the antibody. The vertical axis represents the antibody elution amount (ng/g brain), and the horizontal axis represents the administered antibodies. The antibody concentration is expressed as a value obtained by conversion from the molar concentration using the molecular weight (150 kDa) of a monoclonal antibody.

FIG. 4(A) shows the imaging images of the brain 9 days after administering the antibody. FIG. 4(B) shows the ratio of a value of the fluorescence amount in the brain corrected by the fluorescence intensity of the administered antibody to the anti-AVM antibody. The vertical axis represents the ratio to the anti-AVM antibody, and the horizontal axis represents the administered antibodies.

FIG. 7(A) shows the antibody concentration in serum 7 days after administering the antibody. The vertical axis represents the antibody concentration (ng/mL), and the horizontal axis represents the administered antibodies. FIG. 7(B) shows the antibody concentration in a brain tissue 7 days after administering the antibody. The vertical axis represents the antibody elution amount (ng/g brain), and the horizontal axis represents the administered antibodies.

FIG. 8(A) shows the imaging images of the brain 7 days after administering the antibody. FIG. 8(B) shows the ratio of a value of the fluorescence amount in the brain corrected by the fluorescence intensity of the administered antibody to the anti-AVM antibody. The vertical axis represents the ratio to the anti-AVM antibody, and the horizontal axis represents the administered antibodies.

DESCRIPTION OF EMBODIMENTS

Figure 1:
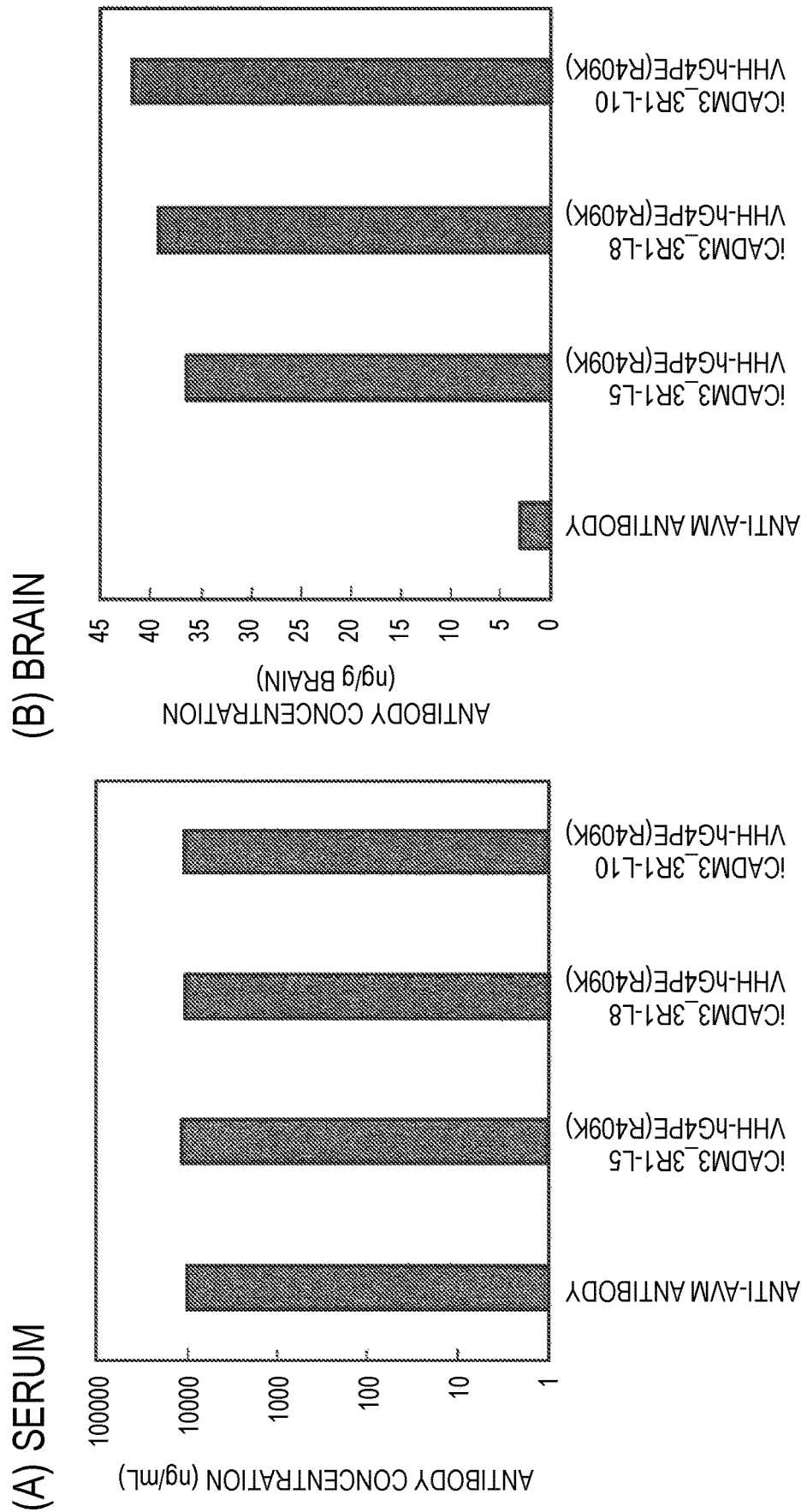
FIG. 1 shows the results of measuring the concentration of each antibody in a tissue.

The invention relates to an antigen-binding molecule which binds to CADM3. More specifically, the invention relates to an antibody which binds to CADM3 or an antibody fragment thereof.

The CADM3-binding molecule of the invention may be in any molecular form as long as the molecule specifically binds to CADM3 and the resulting molecule is retained in the brain, and may be any molecule such as a protein, a nucleic acid, or a low molecular weight compound/high molecular weight compound obtained by organic synthesis. Specifically, the CADM3-binding molecule may be any of a recombinant protein, an antibody, an aptamer, a low molecular weight compound obtained by low molecular weight screening, and the like, but preferably, an antibody and an antibody fragment thereof are exemplified. The CADM3- binding molecule is preferably a molecule which binds to the extracellular domain of CADM3.

CADM3 is a calcium ion-independent immunoglobulin-like cell adhesion molecule, and exhibits a cell-cell adhesion activity by calcium ion-independent homophilic binding. For example, the full length of human CADM3 comprising a signal sequence is composed of 398 amino acids, and is expressed between two axon terminals, between an axon terminal and an axon shaft, and at a contact site between an axon terminal and a glial cell process at an axon terminal in the central nervous system and the peripheral nervous system, and plays a role in the cell adhesion effect.

The animal species of CADM3 to which the CADM3-binding molecule of the invention binds are a mouse, a rat, a cynomolgus monkey, and/or a human, and the like, but are not particularly limited to these species, and an appropriate animal species can be selected according to the use of the antibody. For example, when the antibody of the invention is used for medical purposes for humans, the antibody is preferably an antibody which binds to at least human CADM3.

In the invention, as human CADM3, a polypeptide which comprises the amino acid sequence represented by SEQ ID NO: 52 or the amino acid sequence of NCBI accession No. AAH33819, a polypeptide which is composed of an amino acid sequence in which one or more amino acids are deleted, substituted, or added in the amino acid sequence represented by SEQ ID NO: 52 or the amino acid sequence of NCBI accession No. AAH33819, and which has the function of human CADM3, a polypeptide which is composed of an amino acid sequence having 60% or more, preferably 80% or more, more preferably 90% or more, and most preferably 95% or more homology with the amino acid sequence represented by SEQ ID NO: 52 or the amino acid sequence of NCBI accession No. AAH33819, and which has the function of human CADM3, or the like is exemplified.

The polypeptide which has an amino acid sequence in which one or more amino acids are deleted, substituted, or added in the amino acid sequence represented by SEQ ID NO: 52 or the amino acid sequence represented by NCBI accession No. AAH33819 can be obtained by, for example, introducing a site-specific mutation into a DNA encoding a polypeptide comprising the amino acid sequence of SEQ ID NO: 52 using a site-directed mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985)] or the like.

The number of amino acids that are deleted, substituted, or added is not particularly limited, but is preferably one to several tens, for example, 1 to 20, more preferably one to several, for example, 1 to 5 amino acids.

The same applies to the amino acid sequence of mouse CADM3 [SEQ ID NO: 54 or NCBI accession No. NP_444429.1], the amino acid sequence of rat CADM3 [NCBI accession No. AAI61811.1], and the amino acid sequence of cynomolgus monkey CADM3 [SEQ ID NO: 56 or NCBI accession No. NP_001270618.1].

In the invention, as a gene encoding human CADM3, the nucleotide sequence represented by SEQ ID NO: 51 or the nucleotide sequence of NCBI accession No. BC033819.1 is exemplified. A gene which is composed of a nucleotide sequence in which one or more nucleotides are deleted, substituted, or added in the nucleotide sequence represented by SEQ ID NO: 51 or the nucleotide sequence of NCBI accession No. BC033819.1, and which comprises a DNA encoding a polypeptide having the function of CADM3, a gene which is composed of a nucleotide sequence having at least 60% or more homology, preferably a nucleotide sequence having 80% or more homology, and more preferably a nucleotide sequence having 95% or more homology with the nucleotide sequence represented by SEQ ID NO: 51 or the nucleotide sequence of NCBI accession No. BC033819.1, and which comprises a DNA encoding a polypeptide having the function of CADM3, or a gene which is composed of a DNA that hybridizes with a DNA comprising the nucleotide sequence represented by SEQ ID NO: 51 or the nucleotide sequence of NCBI accession No. BC033819.1 under stringent conditions, and which encodes a polypeptide having the function of CADM3, or the like is also comprised in the gene encoding CADM3 in the invention.

The DNA that hybridizes under stringent conditions refers to a hybridizable DNA obtained by a colony hybridization method, a plaque hybridization method, a southern blot hybridization method, a DNA microarray method, or the like using a DNA comprising the nucleotide sequence represented by SEQ ID NO: 51 or the nucleotide sequence of NCBI accession No. BC033819.1 as a probe.

Specifically, a DNA that can be identified by performing a hybridization method [Molecular Cloning, A Laboratory Manual, Second Edition, Cold Spring Harbor Laboratory Press (1989), Current Protocols in Molecular Biology, John Wiley & Sons (1987-1997), DNA Cloning I: Core Techniques, A Practical Approach, Second Edition, Oxford University (1995)] at 65° C. in the presence of 0.7 to 1.0 mol/L sodium chloride using a filter or a microscope slide on which a DNA derived from a hybridized colony or plaque, or a PCR product or an oligo DNA having the sequence is immobilized, and thereafter washing the filter or the microscope slide under the condition of 65° C. using a saline sodium citrate (SSC) solution having a concentration of 0.1 to 2 times (a composition of the SSC solution having a concentration of 1 time is composed of 150 mmol/L sodium chloride and 15 mmol/L sodium citrate) can be exemplified.

As the hybridizable DNA, a DNA having at least 60% or more homology, preferably a DNA having 80% or more homology, and more preferably a DNA having 95% or more homology with the nucleotide sequence represented by SEQ ID NO: 51 or the nucleotide sequence of NCBI accession No. BC033819.1 can be exemplified.

The same applies to the nucleotide sequence of mouse CADM3 [SEQ ID NO: 53 or NCBI accession No. NM_053199.3], the nucleotide sequence of rat CADM3 [NCBI accession No. NM_001047103.1], and the nucleotide sequence of cynomolgus monkey CADM3 [SEQ ID NO: 55 or NCBI accession No. NM_001283689.1].

Examples of the function of CADM3 comprise involvement in cell adhesion between axon terminals and other sites in the central nervous system and the peripheral nervous system as described above, and the like.

A gene polymorphism is often observed in a nucleotide sequence of a gene encoding a protein of a eukaryote. A gene in which a small-scale mutation has occurred in a nucleotide sequence due to such a polymorphism in a gene used in the invention is also comprised in the gene encoding CADM3 in the invention.

The numerical value of homology in the invention may be a numerical value calculated using a homology search program known to those skilled in the art unless otherwise specified, however, with respect to a nucleotide sequence, a numerical value calculated using a default parameter in BLAST [J. Mol. Biol., 215, 403 (1990)], and the like are exemplified, and with respect to an amino acid sequence, a numerical value calculated using a default parameter in BLAST2 [Nucleic Acids Res., 25, 3389 (1997), Genome Res., 7, 649 (1997), www.ncbi.nlm.nih.gov], and the like are exemplified.

As for the default parameters, G (Cost to open gap) is 5 in the case of a nucleotide sequence and 11 in the case of an amino acid sequence, -E (Cost to extend gap) is 2 in the case of a nucleotide sequence and 1 in the case of an amino acid sequence, -q (Penalty for nucleotide mismatch) is -3, -r (reward for nucleotide match) is 1, -e (expect value) is 10, -W (wordsize) is 11 in the case of a nucleotide sequence and 3 in the case of an amino acid sequence, -y [Dropoff (X) for blast extensions in bits] is 20 in the case of blastn and 7 in the case of programs other than blastn, -X (X dropoff value for gapped alignment in bits) is 15, and -Z (final X dropoff value for gapped alignment in bits) is 50 in the case of blastn and 25 in the case of programs other than blastn (www.ncbi.nlm.nih.gov).

A polypeptide comprising a partial sequence of the amino acid sequence of any of the above-mentioned various types of CADM3 can be produced by a method known to those skilled in the art. Specifically, the polypeptide can be produced by deleting a part of a DNA encoding the amino acid sequence of any of the above-mentioned various types of CADM3 and culturing a transformant transfected with an expression vector comprising the resulting DNA. In addition, a polypeptide having an amino acid sequence in which one or more amino acids are deleted, substituted, or added in the amino acid sequence of any of various types of CADM3 can be obtained in the same manner as described above.

Further, a polypeptide composed of the amino acid sequence of any of various types of CADM3, or a polypeptide having an amino acid sequence in which one or more amino acids are deleted, substituted, or added in the amino acid sequence of any of various types of CADM3 can also be produced by a chemical synthesis method such as a fluorenylmethyloxycarbonyl (Fmoc) method or a t-butyloxycarbonyl (tBoc) method.

In the invention, the extracellular domain of human CADM3 refers to the amino acid sequence from position 25 to position 330 in the amino acid sequence represented by SEQ ID NO: 52 or NCBI accession No. AAH33819.

The extracellular domain of mouse CADM3 refers to the amino acid sequence from position 23 to position 328 in the amino acid sequence represented by SEQ ID NO: 54 or NCBI accession No. NP_444429.1. The extracellular domain of rat CADM3 refers to the amino acid sequence from position 23 to position 328 in the amino acid sequence represented by NCBI accession No. AAI61811.1.

The extracellular domain of cynomolgus monkey CADM3 refers to the amino acid sequence from position 23 to position 328 in the amino acid sequence represented by SEQ ID NO: 56 or NCBI accession No. NP_001270618.1.

It can be confirmed that the CADM3-binding molecule of the invention binds to the extracellular domain of CADM3 by measuring the affinity of the CADM3-binding molecule of the invention for CADM3-expressing cells or a recombinant CADM3 protein using an enzyme-linked immunosorbent assay (ELISA), flow cytometry, a surface plasmon resonance method, or the like. Further, it can also be confirmed using known immunological detection methods [Monoclonal Antibodies-Principles and practice, Third edition, Academic Press (1996), Antibodies-A Laboratory Manual, Cold Spring Harbor Laboratory (1988), Manual for monoclonal antibody experiments, Kodansha scientific books (1987)], and the like in combination.

The CADM3-binding molecule of the invention is a molecule having a property of accumulating in a brain by specifically binding to CADM3 in the brain, and for example, the antibody of the invention is an antibody having a property of accumulating in a brain by binding to CADM3 in the brain. Further, the antibody of the invention is an antibody having a property of accumulating in a brain by penetrating through the blood-brain barrier in the brain from the periphery, migrating into the brain, and binding to CADM3 in the brain, when administrating the antibody at the periphery of an animal. The antibody of the invention is preferably an antibody having an excellent property of accumulating in a brain or an antibody having an enhanced property of accumulating in a brain.

In the invention, the "property of accumulating in a brain" refers to a property in which when a target subject is administered to a test animal, the target subject is retained in the brain. That is, it means that the concentration in the brain (or the amount in the brain) of the target subject increases or that the target subject exists at a fixed concentration to such an extent that it can be detected due to at least any one cause selected from an increase in migration into the brain, an increase in accumulation in the brain, a decrease in migration from the inside to the outside of the brain, a decrease in efflux from the inside to the outside of the brain, and a decrease in decomposition in the brain.

In the invention, the "having an excellent property of accumulating in a brain", "having a high property of accumulating in a brain", or "having an enhanced property of accumulating in a brain" means that when a target subject is administered to a test animal, the concentration in the brain (or the amount in the brain) of the target subject after the elapse of the same number of days from the administration increases as compared with that of the control, or the target subject exists at a fixed concentration (amount) to such an extent that it can be detected for a long time in the brain.

Such a phenomenon occurs due to at least any one cause of an increase in migration of the target subject into the brain, an increase in accumulation in the brain, a decrease in migration from the inside to the outside of the brain, a decrease in efflux from the inside to the outside of the brain, and a decrease in decomposition in the brain as compared with the control.

In the invention, the "having an excellent property of accumulating in a brain", "having a high property of accumulating in a brain", or "having an enhanced property of accumulating in a brain" comprises, for example, that when the target subject is administered to a test animal, the concentration (amount) in the brain of the target subject 1 to 10 days after the administration, preferably 2 to 10 days, 3 to 10 days, and more preferably 4 to 10 days after the administration is higher as compared with that of the control, or the concentration in the brain (or the amount in the brain) of the target subject reaches its peak on day 4 or later after the administration, preferably on day 5 or later, day 6 or later, day 7 or later, day 8 or later, day 9 or later, and more preferably on day 10 or later after the administration, and the like.

The antibody having an excellent property of accumulating in a brain, the antibody having a high property of accumulating in a brain, or the antibody having an enhanced property of accumulating in a brain may be any antibody as long as the antibody is an antibody whose antibody concentration (antibody amount) in the brain is higher than that of a control antibody or an antibody having a characteristic capable of existing in the brain for a long time.

For example, an antibody having a characteristic that the migration ability into the brain and/or the accumulation ability in the brain is higher than that of a control antibody, a characteristic that the migration ability from the inside to the outside of the brain, the efflux ability and/or the decomposition ability in the brain is lower than that of a control antibody, and a characteristic that the migration ability into the brain and/or the accumulation ability in the brain is higher than the migration ability from the inside to the outside of the brain, the efflux ability, and/or the decomposition ability in the brain, or the like is exemplified.

Therefore, as the antibody or the antibody fragment thereof of the invention, when the antibody or the antibody fragment thereof is administered to an animal, an antibody or an antibody fragment thereof whose antibody concentration (or antibody amount) in the brain after the elapse of the same number of days from the administration is higher than that of a control antibody or an antibody or an antibody fragment thereof capable of existing in the brain for a long time, or the like is exemplified.

The change in the antibody concentration (or the antibody amount) in the brain may be any change, and for example, a case where after the antibody concentration in the brain has once reached its peak during the measurement period, the antibody concentration gradually decreases, a case where after the antibody concentration in the brain has reached its peak, the antibody concentration is continuously maintained, or a case where the antibody concentration in the brain continues to increase after administering the antibody, or the like is exemplified.

As the antibody or the antibody fragment thereof of the invention, for example, an antibody whose antibody concentration or antibody amount in the brain is higher than that of a control antibody on day 4 or day 10 after the administration to a rat, an antibody whose antibody concentration or antibody amount in the brain is maintained or increases during a period from day 4 to day 10 after the administration to a rat, or an antibody whose existence in the brain can be clearly confirmed even on day 10 or later after the administration to a rat, or the like is exemplified, but it is not limited thereto.

The control antibody may be any antibody as long as the control antibody is an antibody of the same type or subclass as that of the test antibody, but for example, an anti-avermectin (AVM) antibody or the like can be used.

In the invention, as the "in the brain", for example, in the brain parenchyma, in the cerebral ventricle, in the cerebrospinal fluid, or the like is exemplified, but it is not limited thereto.

By immunoelectron microscopy, staining of CADM3 is confirmed, for example, at a parallel fiber terminal of a granule cell, a contact site between a parallel fiber terminal and a parallel fiber axon, and a contact site between a parallel fiber terminal and a glial cell process (NPL 26). Therefore, as one aspect of the CADM3-binding molecule of the invention, a molecule which has affinity for neurons by specifically binding to CADM3 in neurons and/or nerve tissues, thereby having a property of accumulating in a brain is exemplified. As one aspect of the antibody of the invention, for example, an antibody which has affinity for neurons by binding to CADM3 in neurons and/or nerve tissues, thereby having a property of accumulating in a brain is exemplified.

In the invention, as a method for administering an antibody to an animal, for example, intravenous administration, intraventricular administration, intraperitoneal administration, subcutaneous administration, intradermal administration, intranasal administration, intrathecal administration, or the like is exemplified, but it is not limited thereto.

In the invention, as a method for measuring the property of accumulating in a brain of an antibody, for example, a method in which a brain tissue is collected several days after administering an antibody to an animal, followed by homogenization and centrifugation, and then, the antibody concentration in the resulting supernatant is measured, and the antibody amount per unit brain weight is calculated, a method in which the existence of an antibody is detected by a known immunological method using a collected brain tissue, a method in which a labeled antibody is administered to an animal and the existence of the antibody is detected over time using an in vivo imaging system, or the like is exemplified.

As the antibody or the antibody fragment thereof of the invention, an antibody or an antibody fragment selected from the group consisting of the following (a) to (x) is exemplified. Among these, (d), (j), (o), or (t) is preferred from the viewpoint of the property of accumulating in a brain of the antibody and the antibody amount in the brain.

(a) an antibody in which the amino acid sequences of CDR1 to CDR3 of VH comprise the amino acid sequences represented by SEQ ID NOS: 23, 24, and 25, respectively, and in which the amino acid sequences of CDR1 to CDR3 of VL comprise the amino acid sequences represented by SEQ ID NOS: 28, 29, and 30, respectively (b) an antibody in which the amino acid sequences of CDR1 to CDR3 of VH comprise the amino acid sequences represented by SEQ ID NOS: 33, 34 and 35, respectively, and in which the amino acid sequences of CDR1 to CDR3 of VL comprise the amino acid sequences represented by SEQ ID NOS: 38, 39, and 40, respectively (c) an antibody fragment in which the amino acid sequences of CDR1 to CDR3 of VHH comprise the amino acid sequences represented by SEQ ID NOS: 3, 4, and 5, respectively (d) an antibody fragment in which the amino acid sequences of CDR1 to CDR3 of VHH comprise the amino acid sequences represented by SEQ ID NOS: 8, 9, and 10, respectively (e) an antibody fragment in which the amino acid sequences of CDR1 to CDR3 of VHH comprise the amino acid sequences represented by SEQ ID NOS: 13, 14, and 15, respectively (f) an antibody fragment in which the amino acid sequences of CDR1 to CDR3 of VHH comprise the amino acid sequences represented by SEQ ID NOS: 18, 19, and 20, respectively (g) an antibody in which the amino acid sequences of CDR1 to CDR3 of VH comprise the amino acid sequences represented by SEQ ID NOS: 89, 90, and 91, respectively, and in which the amino acid sequences of CDR1 to CDR3 of VL comprise the amino acid sequences represented by SEQ ID NOS: 94, 95, and 96, respectively (h) an antibody in which the amino acid sequences of CDR1 to CDR3 of VH comprise the amino acid sequences represented by SEQ ID NOS: 99, 100, and 101, respectively, and in which the amino acid sequences of CDR1 to CDR3 of VL comprise the amino acid sequences represented by SEQ ID NOS: 134, 135, and 136, respectively (i) an antibody in which the amino acid sequences of CDR1 to CDR3 of VH comprise the amino acid sequences represented by SEQ ID NOS: 104, 105, and 106, respectively, and in which the amino acid sequences of CDR1 to CDR3 of VL comprise the amino acid sequences represented by SEQ ID NOS: 134, 135, and 136, respectively (j) an antibody in which the amino acid sequences of CDR1 to CDR3 of VH comprise the amino acid sequences represented by SEQ ID NOS: 109, 110, and 111, respectively, and in which the amino acid sequences of CDR1 to CDR3 of VL comprise the amino acid sequences represented by SEQ ID NOS: 134, 135, and 136, respectively (k) an antibody in which the amino acid sequences of CDR1 to CDR3 of VH comprise the amino acid sequences represented by SEQ ID NOS: 114, 115, and, 116, respectively, and in which the amino acid sequences of CDR1 to CDR3 of VL comprise the amino acid sequences represented by SEQ ID NOS: 134, 135, and 136, respectively (l) an antibody in which the amino acid sequences of CDR1 to CDR3 of VH comprise the amino acid sequences represented by SEQ ID NOS: 119, 120, and 121, respectively, and in which the amino acid sequences of CDR1 to CDR3 of VL comprise the amino acid sequences represented by SEQ ID NOS: 134, 135, and 136, respectively (m) an antibody in which the amino acid sequences of CDR1 to CDR3 of VH comprise the amino acid sequences represented by SEQ ID NOS: 124, 125, and 126, respectively, and in which the amino acid sequences of CDR1 to CDR3 of VL comprise the amino acid sequences represented by SEQ ID NOS: 134, 135, and 136, respectively (n) an antibody in which the amino acid sequences of CDR1 to CDR3 of VH comprise the amino acid sequences represented by SEQ ID NOS: 129, 130, and 131, respectively, and in which the amino acid sequences of CDR1 to CDR3 of VL comprise the amino acid sequences represented by SEQ ID NOS: 134, 135, and 136, respectively (o) an antibody in which the amino acid sequences of CDR1 to CDR3 of VH comprise the amino acid sequences represented by SEQ ID NOS: 139, 140, and 141, respectively, and in which the amino acid sequences of CDR1 to CDR3 of VL comprise the amino acid sequences represented by SEQ ID NOS: 164, 165, and 166, respectively (p) an antibody in which the amino acid sequences of CDR1 to CDR3 of VH comprise the amino acid sequences represented by SEQ ID NOS: 144, 145, and 146, respectively, and in which the amino acid sequences of CDR1 to CDR3 of VL comprise the amino acid sequences represented by SEQ ID NOS: 164, 165, and 166, respectively (q) an antibody in which the amino acid sequences of CDR1 to CDR3 of VH comprise the amino acid sequences represented by SEQ ID NOS: 149, 150, and 151, respectively, and in which the amino acid sequences of CDR1 to CDR3 of VL comprise the amino acid sequences represented by SEQ ID NOS: 164, 165, and 166, respectively (r) an antibody in which the amino acid sequences of CDR1 to CDR3 of VH comprise the amino acid sequences represented by SEQ ID NOS: 154, 155, and 156, respectively, and in which the amino acid sequences of CDR1 to CDR3 of VL comprise the amino acid sequences represented by SEQ ID NOS: 164, 165, and 166, respectively (s) an antibody in which the amino acid sequences of CDR1 to CDR3 of VH comprise the amino acid sequences represented by SEQ ID NOS: 159, 160, and 161, respectively, and in which the amino acid sequences of CDR1 to CDR3 of VL comprise the amino acid sequences represented by SEQ ID NOS: 164, 165, and 166, respectively (t) an antibody in which the amino acid sequences of CDR1 to CDR3 of VH comprise the amino acid sequences represented by SEQ ID NOS: 169, 170, and 171, respectively, and in which the amino acid sequences of CDR1 to CDR3 of VL comprise the amino acid sequences represented by SEQ ID NOS: 174, 175, and 176, respectively (u) an antibody which competes for binding to CADM3 with at least one of the antibodies or the antibody fragments described in (a) to (t)

(v) an antibody which binds to an epitope comprising an epitope to which any one of the antibodies or the antibody fragments described in (a) to (t) binds (w) an antibody which binds to the same epitope as an epitope to which any one of the antibodies or the antibody fragments described in (a) to (t) binds (x) an antibody which comprises an amino acid sequence having 85% or more homology with the amino acid sequence of any one of the antibodies or the antibody fragments described in (a) to (t)

As the antibody of the invention, an antibody which comprises the amino acid sequences of CDR1 to CDR3 of VH and CDR1 to CDR3 of VL of an antibody having 85% or more, preferably 90% or more homology with the amino acid sequences of CDR1 to CDR3 of VH and CDR1 to CDR3 of VL of any one of the antibodies or the antibody fragments described in (a) to (t) is comprised. The 90% or more homology is more preferably 91%, 92%, 93%, 94%, 95%, 96%, 97%, 98%, or 99% homology, or the like.

In the invention, as one aspect of the antibodies or the antibody fragments described in (a) to (t), a CADM301 antibody, a CADM3102 antibody, a CADM3219 antibody, a CADM3301 antibody, a CADM3309 antibody, a CADM3312 antibody, a CADM3314 antibody, a CADM3316 antibody, a CADM3349 antibody, a CADM3351 antibody, a CADM3402 antibody, a CADM3404 antibody, a CADM3432 antibody, a CADM3448 antibody, a CADM3458 antibody, and a CADM3501 antibody, each as a human anti-CADM3 monoclonal antibody, and an iCADM3-3R1-L5 antibody, an iCADM3-3R1-L8 antibody, an iCADM3-3R1-L10 antibody, and an iCADM3-3R1-L11 antibody, each as an alpaca anti-CADM3 monoclonal VHH antibody, are exemplified. Among these, a CADM3312 antibody, a CADM3402 antibody, a CADM3502 antibody, or an iCADM3-3R1-L8 antibody is preferred from the viewpoint of the property of accumulating in a brain of the antibody and the antibody amount in the brain.

Additional examples thereof comprise a human chimeric antibody and a humanized antibody produced from any of the above-mentioned monoclonal antibodies by a genetic recombination technique, and the like. Specific examples thereof also comprise an iCADM3-3R1-L8_01 humanized antibody, an iCADM3-3R1-L8_02 humanized antibody, an iCADM3-3R1-L8_03 humanized antibody, an iCADM3-3R1-L8_04 humanized antibody, an iCADM3-3R1-L11_01 humanized antibody, an iCADM3-3R1-L11_02 humanized antibody, an iCADM3-3R1-L11_03 humanized antibody, an iCADM3-3R1-L11_04 humanized antibody, an iCADM3-3R1-L11_05 humanized antibody, an iCADM3-3R1-L11_06 humanized antibody, and the like.

In the invention, the antibody (u) refers to a second antibody which inhibits binding of a first antibody to CADM3 when any one of the antibodies or the antibody fragments described in (a) to (t) is defined as the first antibody.

In the invention, the antibody (w) refers to a second antibody which binds to a second epitope comprising a first epitope when any one of the antibodies or the antibody fragments described in (a) to (t) is defined as a first antibody, and an epitope to which the first antibody binds is defined as the first epitope.

Further, the antibody (x) of the invention refers to a second antibody which binds to a first epitope when any one of the antibodies or the antibody fragments described in (a) to (t) is defined as a first antibody, and an epitope to which the first antibody binds is defined as the first epitope.

In addition, as the antibody or the antibody fragment thereof of the invention, specifically, an antibody or an antibody fragment selected from the group consisting of the following (1) to (31) is also exemplified. Among these, (4), (20), (25), or (30) is preferred from the viewpoint of the property of accumulating in a brain of the antibody and the antibody amount in the brain.

(1) an antibody in which the amino acid sequence of VH comprises the amino acid sequence represented by SEQ ID NO: 22 and in which the amino acid sequence of VL comprises the amino acid sequence represented by SEQ ID NO: 27
(2) an antibody in which the amino acid sequence of VH comprises the amino acid sequence represented by SEQ ID NO: 32 and in which the amino acid sequence of VL comprises the amino acid sequence represented by SEQ ID NO: 37
(3) an antibody fragment in which the amino acid sequence of VHH comprises the amino acid sequence represented by SEQ ID NO: 2
(4) an antibody fragment in which the amino acid sequence of VHH comprises the amino acid sequence represented by SEQ ID NO: 7
(5) an antibody fragment in which the amino acid sequence of VHH comprises the amino acid sequence represented by SEQ ID NO: 12
(6) an antibody fragment in which the amino acid sequence of VHH comprises the amino acid sequence represented by SEQ ID NO: 17
(7) an antibody fragment in which the amino acid sequence of VHH comprises the amino acid sequence represented by SEQ ID NO: 68
(8) an antibody fragment in which the amino acid sequence of VHH comprises the amino acid sequence represented by SEQ ID NO: 70
(9) an antibody fragment in which the amino acid sequence of VHH comprises the amino acid sequence represented by SEQ ID NO: 72
(10) an antibody fragment in which the amino acid sequence of VHH comprises the amino acid sequence represented by SEQ ID NO: 74
(11) an antibody fragment in which the amino acid sequence of VHH comprises the amino acid sequence represented by SEQ ID NO: 76
(12) an antibody fragment in which the amino acid sequence of VHH comprises the amino acid sequence represented by SEQ ID NO: 78
(13) an antibody fragment in which the amino acid sequence of VHH comprises the amino acid sequence represented by SEQ ID NO: 80
(14) an antibody fragment in which the amino acid sequence of VHH comprises the amino acid sequence represented by SEQ ID NO: 82
(15) an antibody fragment in which the amino acid sequence of VHH comprises the amino acid sequence represented by SEQ ID NO: 84
(16) an antibody fragment in which the amino acid sequence of VHH comprises the amino acid sequence represented by SEQ ID NO: 86
(17) an antibody in which the amino acid sequence of VH comprises the amino acid sequence represented by SEQ ID NO: 88 and in which the amino acid sequence of VL comprises the amino acid sequence represented by SEQ ID NO: 93
(18) an antibody in which the amino acid sequence of VH comprises the amino acid sequence represented by SEQ ID NO: 98 and in which the amino acid sequence of VL comprises the amino acid sequence represented by SEQ ID NO: 133
(19) an antibody in which the amino acid sequence of VH comprises the amino acid sequence represented by SEQ ID NO: 103 and in which the amino acid sequence of VL comprises the amino acid sequence represented by SEQ ID NO: 133
(20) an antibody in which the amino acid sequence of VH comprises the amino acid sequence represented by SEQ ID NO: 108 and in which the amino acid sequence of VL comprises the amino acid sequence represented by SEQ ID NO: 133
(21) an antibody in which the amino acid sequence of VH comprises the amino acid sequence represented by SEQ ID NO: 113 and in which the amino acid sequence of VL comprises the amino acid sequence represented by SEQ ID NO: 133
(22) an antibody in which the amino acid sequence of VH comprises the amino acid sequence represented by SEQ ID NO: 118 and in which the amino acid sequence of VL comprises the amino acid sequence represented by SEQ ID NO: 133
(23) an antibody in which the amino acid sequence of VH comprises the amino acid sequence represented by SEQ ID NO: 123 and in which the amino acid sequence of VL comprises the amino acid sequence represented by SEQ ID NO: 133
(24) an antibody in which the amino acid sequence of VH comprises the amino acid sequence represented by SEQ ID NO: 128 and in which the amino acid sequence of VL comprises the amino acid sequence represented by SEQ ID NO: 133
(25) an antibody in which the amino acid sequence of VH comprises the amino acid sequence represented by SEQ ID NO: 138 and in which the amino acid sequence of VL comprises the amino acid sequence represented by SEQ ID NO: 163
(26) an antibody in which the amino acid sequence of VH comprises the amino acid sequence represented by SEQ ID NO: 143 and in which the amino acid sequence of VL comprises the amino acid sequence represented by SEQ ID NO: 163
(27) an antibody in which the amino acid sequence of VH comprises the amino acid sequence represented by SEQ ID NO: 148 and in which the amino acid sequence of VL comprises the amino acid sequence represented by SEQ ID NO: 163

(28) an antibody in which the amino acid sequence of VH comprises the amino acid sequence represented by SEQ ID NO: 153 and in which the amino acid sequence of VL comprises the amino acid sequence represented by SEQ ID NO: 163

(29) an antibody in which the amino acid sequence of VH comprises the amino acid sequence represented by SEQ ID NO: 158 and in which the amino acid sequence of VL comprises the amino acid sequence represented by SEQ ID NO: 163

(30) an antibody in which the amino acid sequence of VH comprises the amino acid sequence represented by SEQ ID NO: 168 and in which the amino acid sequence of VL comprises the amino acid sequence represented by SEQ ID NO: 173

(31) an antibody which comprises an amino acid sequence having 85% or more homology with the amino acid sequence of any one of the antibodies or the antibody fragments described in (1) to (30)

As the antibody of the invention, an antibody which comprises the amino acid sequences of VH and VL of an antibody having 85% or more, preferably 90% or more homology with the amino acid sequences of VH and VL of any one of the antibodies or the antibody fragments described in (1) to (30) is comprised. The 90% or more homology is more preferably 91%, 92%, 93%, 94%, 95%, 96%, 97%, 98%, or 99% homology, or the like.

In the invention, as one aspect of the antibodies or the antibody fragments described in (1) to (31), a CADM301 antibody, a CADM3102 antibody, a CADM3219 antibody, a CADM3301 antibody, a CADM3309 antibody, a CADM3312 antibody, a CADM3314 antibody, a CADM3316 antibody, a CADM3349 antibody, a CADM3351 antibody, a CADM3402 antibody, a CADM3404 antibody, a CADM3432 antibody, a CADM3448 antibody, a CADM3458 antibody, and a CADM3501 antibody, each as a human anti-CADM3 monoclonal antibody, and an iCADM3-3R1-L5 antibody, an iCADM3-3R1-L8 antibody, an iCADM3-3R1-L10 antibody, and an iCADM3-3R1-L11 antibody, each as an alpaca anti-CADM3 monoclonal VHH antibody, are exemplified. Among these, a CADM3312 antibody, a CADM3402 antibody, a CADM3502 antibody, or an iCADM3-3R1-L8 antibody is preferred from the viewpoint of the property of accumulating in a brain of the antibody and the antibody amount in the brain.

Additional examples thereof comprise a human chimeric antibody and a humanized antibody produced from any of the above-mentioned monoclonal antibodies by a genetic recombination technique, and the like. Specific examples thereof also comprise a humanized antibody in which at least one amino acid residue at a position selected from position 6, position 27, position 37, position 44, position 45, position 47, position 49, position 79, and position 98 in the amino acid sequence of SEQ ID NO: 177 are substituted, a humanized antibody in which at least one amino acid residue at a position selected from position 1, position 12, position 14, position 27, position 28, position 29, position 37, position 44, position 45, position 46, position 47, position 49, position 78, position 96, and position 97 in the amino acid sequence of SEQ ID NO: 178 are substituted, a humanized antibody comprising at least one amino acid residue substitution among amino acid residue substitutions of substituting an amino acid residue at position 6 with Glu, an amino acid residue at position 27 with Arg, an amino acid residue at position 37 with Phe, an amino acid residue at position 44 with Glu, an amino acid residue at position 45 with Arg, an amino acid residue at position 47 with Phe, an amino acid residue at position 49 with Ala, an amino acid residue at position 79 with Val, and an amino acid residue at position 98 with Ala in the amino acid sequence of SEQ ID NO: 177, a humanized antibody comprising at least one amino acid residue substitution among amino acid residue substitutions of substituting an amino acid residue at position 1 with Gln, an amino acid residue at position 12 with Val, an amino acid residue at position 14 with Ala, an amino acid residue at position 27 with Ser, an amino acid residue at position 28 with Ile, an amino acid residue at position 29 with Phe, an amino acid residue at position 37 with Tyr, an amino acid residue at position 44 with Gln, an amino acid residue at position 45 with Arg, an amino acid residue at position 46 with Gly, an amino acid residue at position 47 with Leu, an amino acid residue at position 49 with Ala, an amino acid residue at position 78 with Val, an amino acid residue at position 96 with Asn, and an amino acid residue at position 97 with Ala in the amino acid sequence of SEQ ID NO: 178, an iCADM3-3R1-L8_01 humanized antibody, an iCADM3-3R1-L8_02 humanized antibody, an iCADM3-3R1-L8_03 humanized antibody, an iCADM3-3R1-L8_04 humanized antibody, an iCADM3-3R1-L11_01 humanized antibody, an iCADM3-3R1-L11_02 humanized antibody, an iCADM3-3R1-L11_03 humanized antibody, an iCADM3-3R1-L11_04 humanized antibody, an iCADM3-3R1-L11_05 humanized antibody, an iCADM3-3R1-L11_06 humanized antibody, and the like.

In the invention, the EU index refers to the position of an amino acid residue according to Sequences of Proteins of Immunological Interest, Fifth edition (1991). The positions of the amino acid residues shown below all indicate the positions of the amino acid residues according to the EU index unless otherwise specified.

An antibody molecule is also called an immunoglobulin (Ig), and its basic structure is a tetramer having two polypeptides called heavy chains (H chains) and two polypeptides called light chains (L chains).

Further, each H chain is composed of respective domains of a variable domain of an H chain (also referred to as VH) and a constant domain of an H chain (also referred to as CH) from the N-terminal side, and each L chain is composed of respective domains of a variable domain of an L chain (also referred to as VL) and a constant domain of an L chain (also referred to as CL) from the N-terminal side.

As the CH, α, δ, ε, γ, and μ chains are known for each subclass. The CH is further composed of respective domains of a CH1 domain, a hinge domain, a CH2 domain, and a CH3 domain from the N-terminal side.

The domain refers to a functional structural unit which constitutes each polypeptide of an antibody molecule. Further, the CH2 domain and the CH3 domain are collectively referred to as an Fc (Fragment, crystallizable) region or simply Fc. As the CL, a $C_\lambda$ chain and a $C_\kappa$ chain are known.

The subclasses of an antibody in which the CH is α, δ, ε, γ, and μ chains are referred to as IgA, IgD, IgE, IgG, and IgM, respectively. There sometimes exist isotypes for a subclass of each antibody depending on the animal. In a human, there are IgA1 and IgA2 isotypes for IgA, and there are IgG1, IgG2, IgG3, and IgG4 isotypes for IgG.

In the invention, the CH1 domain, the hinge domain, the CH2 domain, the CH3 domain, and the Fc region can be specified by numbers of amino acid residues from the N-terminus according to the EU index.

Specifically, CH1 is specified as the amino acid sequence at positions 118 to 215 according to the EU index, the hinge is specified as the amino acid sequence at positions 216 to 230 according to the EU index, CH2 is specified as the amino acid sequence at positions 231 to 340 according to the EU index, CH3 is specified as the amino acid sequence at positions 341 to 447 according to the EU index, and the Fc region is specified as the amino acid sequence at positions 231 to 447 according to the EU index.

As the antibody of the invention, a polyclonal antibody, a monoclonal antibody, and an oligoclonal antibody are all comprised. The polyclonal antibody refers to a group of antibody molecules secreted by antibody-producing cells of different clones. The monoclonal antibody is an antibody secreted by antibody-producing cells of a single clone, and refers to an antibody, which recognizes only one epitope (also referred to as an antigenic determinant), and in which the amino acid sequence (primary sequence) constituting the monoclonal antibody is uniform. The oligoclonal antibody refers to a group of antibody molecules in which a plurality of different monoclonal antibodies are mixed.

As the monoclonal antibody in the invention, an antibody produced by a hybridoma or a genetically recombinant antibody produced by a transformant transformed with an expression vector comprising an antibody gene is exemplified.

As the epitope, a single amino acid sequence, a conformation composed of an amino acid sequence, a conformation composed of an amino acid sequence, an amino acid sequence modified after translation, and a conformation composed of an amino acid sequence modified after translation, each of which the monoclonal antibody recognizes and binds to, and the like are exemplified.

As the amino acid sequence modified after translation, an O-linked glycan in which a glycan is attached to Tyr and Ser having an OH substituent, an N-linked glycan in which a glycan is attached to Gln and Asn having an $NH_2$ substituent, and a tyrosine-sulfated amino acid sequence in which a sulfuric acid molecule is attached to Tyr having an OH substituent are exemplified.

The epitope of CADM3 to which the antibody of the invention binds can be identified by performing an antibody binding test using a deletion variant in which some domains of CADM3 are deleted, a mutant in which some domains of CADM3 are substituted with domains derived from another protein, a partial peptide fragment of CADM3, or the like. Further, the antibody binding test can also be performed using cells expressing the deletion variant or the mutant.

Alternatively, the epitope of CADM3 to which the antibody of the invention binds can also be identified by adding the antibody of the invention to peptide fragments of CADM3 obtained by digestion using a protease and performing epitope mapping using known mass spectrometry.

As the antibody of the invention, genetically recombinant antibodies such as a mouse antibody, a rat antibody, a hamster antibody, a rabbit antibody, a llama antibody, a camel antibody, an alpaca antibody, a chimeric antibody, a humanized antibody (also referred to as a "CDR-grafted antibody"), and a human antibody produced by a genetic recombination technique are also comprised.

In the invention, the chimeric antibody refers to an antibody in which VH and VL are derived from an animal species different from that of CH and CL. An antibody composed of VH and VL of an antibody of an animal other than a human (a non-human animal) and CH and CL of a human antibody is called a human chimeric antibody, and an antibody composed of VH and VL of an antibody of an animal other than a mouse and CH and CL of a mouse antibody is called a mouse chimeric antibody. Other chimeric antibodies are also named in the same manner.

As the non-human animal, any animal such as a mouse, a rat, a hamster, a rabbit, a llama, a camel, or an alpaca can be used as long as it is an animal capable of producing a hybridoma or an antibody phage library.

The hybridoma refers to a cell which is obtained by cell fusion of a B cell obtained by immunizing a non-human animal with an antigen and a myeloma cell derived from a mouse or the like and which produces a monoclonal antibody having a desired antigen specificity.

An antibody phage library refers to a library produced by cloning a gene of an immunoglobulin variable region into a phage and expressing an antigen-binding molecule on its surface. As the phage used, M13 phage or the like is exemplified, but it is not particularly limited.

The antigen-binding molecule which is displayed on a phage may be in any form, but is preferably an antibody fragment such as scFv, Fab, or VHH.

In the invention, the antibody phage library may be any library of an immune library, a naive library, and a synthetic library.

The immune library refers to an antibody phage library constructed based on an antibody gene derived from lymphocytes of an animal immunized with an antigen or a patient. The naive library refers to an antibody phage library constructed based on an antibody gene derived from lymphocytes of a normal animal or a healthy human. The synthetic library refers to a library in which CDR of a V gene in a genomic DNA or a reconstructed functional V gene is substituted with an oligonucleotide encoding a random amino acid sequence of an appropriate length.

As a method for producing a chimeric antibody, a method for producing a human chimeric antibody will be described below. Other chimeric antibodies can also be produced in the same manner.

The human chimeric antibody can be produced by obtaining cDNAs encoding VH and VL from a hybridoma derived from a non-human animal cell which produces a monoclonal antibody, inserting each of the cDNAs into an expression vector for animal cells having DNAs encoding CH and CL of a human antibody, thereby constructing a human chimeric antibody expression vector, and then introducing the vector into an animal cell and expressing the antibody.

Further, the human chimeric antibody can also be produced by cloning genes encoding VH and VL from an antibody phage library derived from a non-human animal, inserting each of the genes into an expression vector for animal cells having DNAs encoding CH and CL of a human antibody, thereby constructing a human chimeric antibody expression vector, and then introducing the vector into an animal cell and expressing the antibody.

The humanized antibody refers to an antibody in which the amino acid sequences of CDRs of VH and VL of a non-human animal antibody are grafted into the corresponding CDRs of VH and VL of a human antibody. A region other than the CDRs of VH and VL is called FR The humanized antibody can be produced by constructing a cDNA encoding the amino acid sequence of VH composed of the amino acid sequence of CDR of VH of a non-human animal antibody and the amino acid sequence of FR of VH of an arbitrary human antibody, and a cDNA encoding the amino acid sequence of VL composed of the amino acid sequence of CDR of VL of a non-human animal antibody and the amino acid sequence of FR of VL of an arbitrary human antibody, inserting each of the cDNAs into an expression vector for animal cells having DNAs encoding CH and CL of a human antibody, thereby constructing a humanized antibody expression vector, and then introducing the vector into an animal cell and expressing the antibody.

The human antibody originally refers to an antibody that naturally exists in the human body, but also comprises antibodies obtained from a human antibody phage library or a human antibody-producing transgenic animal, and the like.

The human antibody can be obtained by immunizing a mouse having a human immunoglobulin gene (Tomizuka K. et al., Proc Natl Acad Sci USA. 97, 722-7, 2000.) with a desired antigen. In addition, the human antibody can be obtained without immunization by selecting a human antibody having a desired binding activity using a phage display library obtained by amplifying an antibody gene from human-derived B cells (Winter G. et al., Annu Rev Immunol. 12: 433-55, 1994).

Further, the human antibody can be obtained by producing cells which produce a human antibody having a desired binding activity by immortalizing human B cells using an EB virus (Rosen A. et al., Nature 267, 52-54, 1977).

The human antibody phage library is a library of phages in which an antibody fragment such as Fab, scFv, or VHH is expressed on the surface thereof by inserting an antibody gene prepared from lymphocytes of a human (a healthy human or a patient) into a phage gene. It is possible to collect a phage that expresses an antibody fragment having a desired antigen-binding activity from the library using a binding activity to a substrate onto which an antigen is immobilized as an index. The antibody fragment can also be further converted into a human antibody molecule composed of two complete H chains and two complete L chains using a genetic engineering technique.

The human antibody-producing transgenic animal refers to an animal in which a human antibody gene is incorporated into the chromosome of a host animal. Specifically, a human antibody-producing transgenic animal can be produced by introducing a human antibody gene into a mouse ES cell, implanting the ES cell into an early embryo of another mouse and then allowing the embryo to develop into an animal.

The production of the human antibody from the human antibody-producing transgenic animal can be performed by culturing a human antibody-producing hybridoma obtained by a general hybridoma production method to be performed using a mammal other than a human so as to produce and accumulate the human antibody in the culture, and purifying the antibody from the culture.

The antibody of the invention comprises a heavy chain antibody composed only of a heavy chain. The heavy chain antibody refers to an antibody obtained from an animal of the family Camelidae such as a llama, a camel, and an alpaca or a genetically recombinant antibody produced based on the antibody.

In the invention, the antibody fragment is a fragment of an antibody and refers to a fragment having an antigen-binding activity. Examples thereof comprise Fab, Fab', F(ab')$_2$, scFv, a diabody, dsFv, a peptide comprising a plurality of CDRs, VHH, and the like. Further, the antibody fragment of the invention also comprises any antibody fragment as long as the antibody fragment comprises a partial fragment of an antibody and has a CADM3 binding activity, such as an antibody fragment obtained by fusing the full length or a part of a constant region or Fc of an antibody to the antibody fragment or an antibody fragment comprising a constant region or Fc.

The Fab is an antibody fragment, which has a molecular weight of about 50,000 and has an antigen-binding activity, and in which about a half of an H chain at the N-terminal side and the entire L chain are bound through a disulfide bond (S—S bond) among the fragments obtained by treating an IgG antibody with a protease papain (cleaved at an amino acid residue at position 224 in the H chain).

The F(ab')$_2$ is an antibody fragment, which has a molecular weight of about 100,000 and has an antigen-binding activity, and is slightly larger than a molecule obtained by binding Fabs through an S—S bond in the hinge region among the fragments obtained by treating IgG with a protease pepsin (cleaved at an amino acid residue at position 234 in the H chain).

The Fab' is an antibody fragment, which has a molecular weight of about 50,000 and has an antigen-binding activity, and in which an S—S bond in the hinge region of the above F(ab')$_2$ is cleaved.

The scFv is a VH-P-VL or VL-P-VH polypeptide in which one VH and one VL are linked using an appropriate peptide linker (P) such as a linker peptide obtained by connecting an arbitrary number of linkers (G4S) composed of four Gly residues and one Ser residue, and is an antibody fragment having an antigen-binding activity.

The diabody is an antibody fragment in which scFvs having the same or different antigen-binding specificities form a dimer, and is an antibody fragment having a divalent antigen-binding activity to the same antigen or antigen-binding activities specific for different antigens.

The dsFv is an antibody fragment, which is obtained by binding polypeptides in which one amino acid residue in each of VH and VL is substituted with a cysteine residue through an S—S bond between the cysteine residues, and which has an antigen-binding activity.

The peptide comprising CDR is configured to comprise at least one or more regions of CDRs of VH or VL, and is an antibody fragment having an antigen-binding activity. In a peptide comprising a plurality of CDRs, the CDRs can be bound directly or through an appropriate peptide linker. As the peptide comprising CDR of the invention, a peptide comprising six CDRs derived from the antibody of the invention is exemplified.

The peptide comprising CDR can be produced by constructing DNAs encoding CDRs of VH and VL of the antibody of the invention, inserting the DNAs into an expression vector for a prokaryote or an expression vector for a eukaryote, and then introducing the expression vector into a prokaryote or a eukaryote and expressing the peptide. In addition, the peptide comprising CDR can also be produced by a chemical synthesis method such as an Fmoc method or a tBoc method.

The VHH is a variable domain of a heavy chain antibody and is also called a nanobody. The antibody fragment of the invention comprises any antibody fragment as long as the antibody fragment comprises any of the antibody fragments described above or a partial fragment thereof and has a CADM3 binding activity.

In the invention, an antibody having one antigen-binding site or an antibody fragment thereof is called a monovalent antibody. Examples of the format of a monovalent antibody comprise the formats of an antibody having one antigen-binding site or an antibody fragment thereof described in WO 2014/054804, WO 2011/090754, WO 2007/048037, WO 2012/116927, and the like, and other formats.

In the invention, an antibody of one molecule which binds to three or more different antigens or epitopes or an antibody fragment thereof is called a multispecific antibody. In addition, in the invention, an antibody of one molecule which binds to two different antigens or epitopes or an antibody fragment thereof is called a bispecific antibody.

Examples of the formats of a multispecific antibody or a bispecific antibody comprise the formats described in WO 2009/131239, WO 2014/054804, WO 01/077342, US Patent Application Publication No. 2007/0071675, WO 2007/024715, Wu el al., [Nature Biotechnology, 2007, 25(11), pp. 1290-1297], Labrijn et al., [PNAS 2013, vol. 110, no. 13, pp. 5145-5150], Jong et al., [see 10.1371/journal.pbio.1002344, on the website: dx.doi.org], Kontermann et al., [mAbs 2012, vol. 4, issue 2, pp. 182-197], Spiess et al., [Molecular Immunology 67 (2015) 95-106], Ridgway el al., [Protein engineering, 1996 vol. 9, no. 7, pp. 617-621, WO 2009/080251, WO 2010/151792, WO 2014/033074, and the like, and other formats.

Specific examples of the bispecific antibody comprise the bispecific antibodies described below, and the like.
  (1) A bispecific antibody in which amino acid modifications S354C/T366W are introduced into CH3 of one heavy chain (heavy chain A) of the two heavy chains of an antibody and amino acid modifications Y349C/T366S/L368A/Y407V are introduced into CH3 of the other heavy chain (heavy chain B).
  (2) A bispecific antibody in which an antibody fragment is fused to the C-terminus of an antibody.
  (3) A bispecific antibody in which an antibody fragment is fused to the N-terminus of an antibody.

The bispecific antibody described in (1) may be a bispecific antibody in which the antigen-binding site comprising VH of the heavy chain A binds to CADM3 and in which the antigen-binding site comprising VH of the heavy chain B binds to an antigen present in the brain or a bispecific antibody in which the antigen-binding sites bind the other way around.

Examples of the bispecific antibody described in (2) comprise a bispecific antibody in which an antibody fragment is bound to the C-terminus of one of the two heavy chains constituting an antibody, a bispecific antibody in which an antibody fragment is bound to the C-termini of both two heavy chains constituting an antibody, a bispecific antibody in which an antibody fragment is bound to the C-terminus of one of the two light chains constituting an antibody, a bispecific antibody in which an antibody fragment is bound to the C-termini of both two light chains constituting an antibody, a bispecific antibody in which an antibody fragment is bound to each of the C-termini of the two light chains and the C-termini of the two heavy chains constituting an antibody, and the like. Note that an appropriate linker may be present between the C-terminus of the antibody and the antibody fragment.

The antibody fragment comprised in the bispecific antibody described in (2) is preferably scFv, Fab, VHH, or the like, but is not particularly limited thereto.

The bispecific antibody described in (2) may be a bispecific antibody in which the antigen-binding site at the N-terminus binds to CADM3 and in which the antigen-binding site at the C-terminus binds to an antigen present in the brain or a bispecific antibody in which the antigen-binding sites bind the other way around.

The bispecific antibody described in (3) refers to a bispecific antibody in which an antibody fragment is bound to the N-terminus of at least any one of the two heavy chains or the two light chains constituting an antibody. Further, an appropriate linker may be present between the N-terminus of the heavy chain and/or the light chain of the antibody and the antibody fragment. The antibody fragment comprised in the bispecific antibody described in (3) is preferably scFv, Fab, VHH, or the like, but is not particularly limited thereto.

Further, examples of the bispecific antibody described in (3) comprise a bispecific antibody having a structure of $VH_1$-CH1-$VH_2$-CH1-Hinge-CH2-CH3 from the N-terminus of a heavy chain, a bispecific antibody, which has the heavy chain structure described above, and in which $VH_1$ and $VH_2$ each form an antigen-binding site together with VL, and the like. The VLs with which $VH_1$ and $VH_2$ form antigen-binding sites may have the same amino acid sequence or different amino acid sequences.

In the invention, the multispecific antibody or the bispecific antibody may be any antibody as long as the antibody is a multispecific antibody or a bispecific antibody which binds to CADM3. Among such antibodies, a multispecific antibody or a bispecific antibody which binds to CADM3 and an antigen present in the brain is preferred, and a multispecific antibody or a bispecific antibody comprising an antigen-binding site which binds to CADM3 and an antigen-binding site which binds to an antigen present in the brain is more preferred.

In the invention, examples of the antigen present in the brain comprise a protein, a glycan, a lipid, and the like, and the antigen is preferably a protein among these.

Examples of the protein present in the brain comprise Prion, 5T4, AFP, ADAM10, ADAM12, ADAM17, AFP, AXL, BCAM, BSG, C5, C5R, CA9, CA72-4, CADM3, CCL11, CCL2, CCR1, CCR4, CCR5, CCR6, CD2, CD3E, CD4, CD5, CD6, CD8, CD11, CD18, CD19, CD20, CD22, CD24, CD25, CD29, CD30, CD32B, CD33, CD37, CD38, CD40, CD40LG, CD44, CD47, CD52, CD55SC1, CD56, CD66E, CD71, CD72, CD74, CD79a, CD79b, CD80, CD86, CD95, CD98, CD137, CD147, CD138, CD168, CD200, CD248, CD254, CD257, CDH2, CDH3, CEA, CEACAM1, CEACAM5, CEACAM6, CEACAM8, Claudin3, Claudin4, CSF-1, CSF2RA, CSPG-4, CSPG5, CTLA4, CRF-1, Cripto, CXCR4, CXCR5, DJ-1, DLL4, DR4, DR5, ED-B, EFNA2, EGFR, EGFRvlII, ETBR, ENPP3, EPCAM, EphA2, EphA4, EPOR, ERBB2, ERBB3, ERBB4, FAPα, FAS, FcγRI, FCER2, FGFR1, FGFR2, FGFR3, FGFR4, FLT1, FOLH1, FOLR1, GDF2, GFR, GLP1R, glypican-3, GPNMB, GRP78, HAPLN4, HB-EGF, HGF, HLA-DRβ, HMGB1, ICAM1, ICAM5, IFNA1, IFNB, IgE, IgE-Fc, IGF1R, IL10, IL12B, IL13, IL15, IL17A, ILIA, IL1B, IL2RA, IL4, IL5, IL5RA, IL6, IL6R, IL9, IL2Rα, IL2Rβ, IL2Rγ, INSR, ITGA2, ITGA2B2, ITGB3, ITGA4, ITGB7, ITGA5, ITGAL, ITGAV, ITGB3, ITGB2, KDR, L1CAM, LAG3, LRP3, mesothelin, MAG, MMP14, MMP15, MOG, MSTIR, MSTN, MUC1, MUC4, MUC16, MUC5AC, myostatin, NECTIN4, NCAN, NGF, NMDAR, NOTCH, NRG1, NRP, OX40, OX40L, P2Y6, PAR1, PDGFA, PDGFB, PDGFRA, PDGFRB, PD1, PDL1, PLP1, PSCA, PTPRZ, RET, RGMA, SLAM7, SLC44A4, TAG-72, TCR, TGFB1, TGFB2, TGFBR, TIMP2, TLR9, TNF, TNFR, TNFRSF10A, TNFRSF10B, TNFRSF12A, TNFSF13, TNFSF14, TNFSF2, TNFSF7, TREM2, TRAILR2, TRKA, TRKB, TRKC, Transferrin, VEGF, VEGFR, VLA-4, CGRP, alpha-synuclein, TDP-43, Tau, FUS, Amyloid-beta (AP), APP, BACE1, Presenilin, LINGO-1, Nogo, Troy, polyQ, an androgen receptor, huntingtin, ataxin 1, ataxin 2, Phospho-Tau, Phospho-alpha-synuclein, and the like, but the protein is not limited to these proteins.

Examples of the glycan present in the brain comprise Lewis-x, Lewis-y, CD15, and the like, but the glycan is not limited to these glycans.

Examples of the lipid present in the brain comprise GD1a, GD2, GD3, GM1, GM2, GM3, phosphatidylserine, and the like, but the lipid is not limited to these lipids.

The antibody or the antibody fragment thereof of the invention also comprises an antibody comprising any amino acid modified after translation. Examples of the modification after translation comprise deletion of a lysine residue at the C-terminus of an H chain (lysine clipping), conversion of a glutamine residue at the N-terminus of a polypeptide into pyroglutamine (pyroGlu), and the like [Beck el al., Analytical Chemistry, 85, 715-736 (2013)].

In the antibody or the antibody fragment thereof of the invention, an amino acid modification of the Fc region may be performed. As the amino acid modification of the Fc region, for example, an amino acid modification for stabilizing the antibody or regulating the half-life in the blood, or the like is exemplified. Specific examples of the amino acid modification of the Fc region comprise those in WO 2006/033386, WO 2006/075668, WO 2011/122011, WO 2009/125825, and the like.

The antibody or the antibody fragment thereof of the invention also comprises a fusion antibody or a fusion antibody fragment thereof modified by binding a desired molecule to the antibody or the antibody fragment thereof. A method for modifying an antibody is not particularly limited, and any method can be used as long as the method can modify a desired amino acid residue and glycan.

For example, chemical modification using a chemical reaction [Introduction to Antibody Engineering, Chijinshokan Co., Ltd. (1994), Kolb et al., Angew Chem Int Ed Engl. 40, 2004-21, 2001], modification by a genetic engineering technique in which a recombinant protein expression vector is introduced into an appropriate host cell for expression using a genetic recombination technique, and the like are exemplified.

In the invention, examples of the molecule for modifying the antibody or the antibody fragment thereof comprise a hydrophilic polymer, an amphipathic polymer, a functional molecule, and the like. Examples of the hydrophilic polymer and the amphipathic polymer comprise a polyoxyalkylene, a molecule comprising a polyol or a polysaccharide, and the like.

In the invention, when the antibody or the antibody fragment thereof is modified with another molecule by chemical modification, as the modification site, a constant region of the antibody or the antibody fragment is exemplified, and in particular, a Cys residue at the C-terminus or the S—S bond site is preferred. It is also possible to introduce a residue that can be chemically modified later at an arbitrary position of the antibody or the antibody fragment in advance by a genetic engineering technique.

Further, when the antibody or the antibody fragment thereof is directly modified with another molecule by a genetic engineering technique, as the modification site, the N-terminus or the C-terminus of a light chain or a heavy chain of the antibody or the antibody fragment is exemplified.

Examples of the polyoxyalkylene comprise polyethylene glycol (PEG) composed of a linear or branched chain, polypropylene glycol, polypropylene ethylene glycol, and the like.

Examples of the molecule comprising a polyol or a polysaccharide comprise linear or branched polysaccharides, in which glucose is polymerized, such as amylose, dextran, pullulan, and glycogen, and the like. Further, the molecule is not limited to a homopolysaccharide, but may be a heteropolysaccharide.

The molecular weight of the molecule comprising a hydrophilic polymer or an amphipathic polymer is not particularly limited but is preferably 100 Da or more, and is preferably, for example, 100 Da to 100 kDa.

Examples of the functional molecule comprise an antigen-binding molecule, a fragment of an antigen-binding molecule, a drug, a bioactive peptide, a bioactive protein, a nucleic acid, a radiolabeling compound, a glycan, a lipid, a fluorescent compound, and the like. A molecule with bispecificity as a result of modification with a functional molecule such as an antigen-binding molecule is a bispecific antibody.

Examples of the antigen-binding molecule comprise an antibody, a receptor, a ligand, and the like.

The fragment of an antigen-binding molecule may be any as long as the fragment is a fragment of the antigen-binding molecule and has an antigen-binding activity.

Examples of the drug comprise anticancer agents such as an alkylating agent, a nitrosourea agent, an antimetabolite, an antiviral agent, an antibiotic, a plant alkaloid, a topoisomerase inhibitor, a tubulin polymerization inhibitor, a hormonal therapy agent, a hormone antagonist, an aromatase inhibitor, a P-glycoprotein inhibitor, a platinum complex derivative, an M-phase inhibitor, and a kinase inhibitor [Clinical oncology, Japanese Journal of Cancer and Chemotherapy (1996)], anti-inflammatory agents such as a steroidal agent, a nonsteroidal agent, an immunomodulatory agent, an immunosuppressive agent, and an antihistamine agent [Inflammation and anti-inflammatory therapy, Ishiyaku Publishers, Inc. (1982)], and the like.

More specific examples thereof comprise mertansine, emtansine, amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (Adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, peplomycin, estramustine, paclitaxel (Taxol), docetaxel (Taxotere), Aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (Iressa), imatinib (STI571), erlotinib, an FMS-like tyrosine kinase 3 (Flt3) inhibitor, a vascular endothelial growth factor receptor (VEGFR) inhibitor, a fibroblast growth factor receptor (FGFR) inhibitor, an epidermal growth factor receptor (EGFR) inhibitor such as Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, bucillamine, azathioprine, mizoribine, cyclosporine, rapamycin, hydrocortisone, bexarotene (Targretin), tamoxifen, dexamethasone, a progestin, an estrogen, anastrozole (Arimidex), Leuplin, aspirin, indomethacin, celecoxib, azathioprine, penicillamine, gold thiomalate, chlorpheniramine maleate, chlorpheniramine, clemastine, tretinoin, arsenic, bortezomib, allopurinol, calicheamicin, ibritumomab tiuxetan, targretin, ozogamine, clarithromycin, leucovorin, ketoconazole, aminoglutethimide, suramin, methotrexate, maytansinoid, and the like, and may also comprise derivatives thereof.

Examples of a method for binding the drug and the antibody or the antibody fragment thereof comprise a method for binding the drug and an amino group of the antibody through glutaraldehyde, a method for binding an amino group of the drug and a carboxyl group of the antibody through water-soluble carbodiimide, and the like in addition to the above-mentioned method.

Examples of the bioactive peptide or the bioactive protein comprise interferon (IFN)-α, IFN-β, IFN-γ, interleukin (IL)-2, IL-12, IL-15, IL-18, IL-21, IL-23, a granulocyte colony stimulating factor (G-CSF), a granulocyte/macrophage colony stimulating factor (GM-CSF), a macrophage colony stimulating factor (M-CSF), a cytokine or a growth factor which activates immunocompetent cells such as NK cells, macrophages, or neutrophils, proteases such as hydrase, lyase, and isomerase, enzymes such as acid sphingomyelinase and glucocerebrosidase, toxins comprising bacterial toxins and phytotoxins such as ricin, diphtheria toxin, or ONTAK, and the like, an antimicrobial peptide having a cell membrane damaging activity, a peptide having cell membrane affinity or cell membrane permeability, derivatives thereof, and the like.

The nucleic acid may be any molecule as long as it is a molecule in which a nucleotide or a molecule having a function equivalent to that of the nucleotide is polymerized, and examples thereof comprise a siRNA, a microRNA, an antisense RNA/DNA, a DNA aptamer, and the like.

The radiolabeling compound may be any as long as it is a nuclide to be used for diagnostic or therapeutic purposes, and examples thereof comprise $^{3}$H, $^{14}$C, $^{32}$P, $^{33}$P, $^{35}$S, $^{51}$Cr, $^{57}$CO, $^{18}$F, $^{153}$Gd, $^{159}$Gd, $^{64}$Cu, $^{68}$Ge, $^{166}$Ho, $^{115}$In, $^{113}$In, $^{112}$In, $^{111}$In, $^{131}$I, $^{125}$I, $^{123}$I, $^{121}$I, $^{140}$La, $^{177}$Lu, $^{54}$Mn, $^{99}$Mo, $^{103}$Pd, $^{142}$Pr, $^{149}$Pm, $^{186}$Re, $^{188}$Re, $^{211}$At, $^{105}$Rh, $^{97}$Ru, $^{153}$Sm, $^{47}$Sc, $^{75}$Se, $^{85}$Sr, $^{99}$Tc, $^{201}$Ti, $^{113}$Sn, $^{117}$Sn, $^{133}$Xe, $^{169}$Yb, $^{175}$Yb, $^{90}$Y, $^{66}$Zn, and the like, or compounds comprising any of the nuclides.

The radiolabeling compound can be directly bound to the antibody by a chloramine T method or the like. In addition, a substance that chelates the radiolabeling compound may be bound to the antibody. Examples of the chelating agent comprise 1,4,7,10-tetraazacyclododecane tetraacetic acid (DOTA), 1-[2-(4-aminophenyl)ethyl]-1,4,7,10-tetraazacyclododecane tetraacetic acid (PA-DOTA), 1,4,7,10-tetraazacyclotridecane tetraacetic acid (TRITA), diethylenetriaminepentaacetic acid (DTPA), and the like, and an antibody modified with the chelating agent and a modified antibody labeled with the radiolabeling compound through the chelating agent are also comprised in the antibody of the invention.

Examples of the glycan comprise a monosaccharide, a disaccharide, an oligosaccharide, and the like, and more specific examples thereof comprise fucose, mannose, glucose, allose, altose, gulose, idose, galactose, talose, ribose, arabinose, xylose, lyxose, erythose, erythrose, threose, cellobiose, maltose, isomaltose, lactose, lipoarabinomannan, Lewis X trisaccharide, sialyl-Lewis X tetrasaccharide, and the like. Further, the glycan may be a natural product comprising a glycan known as an immunoadjuvant, and examples thereof comprise β(1→3) glucan (lentinan or schizophyllan), α-galactosylceramide (KRN7000), and the like.

Examples of the lipid comprise a simple lipid (neutral lipid), which is an ester of a fatty acid and any of various types of alcohols or an analogue thereof. Examples thereof comprise a fat (for example, triacylglycerol), a wax (for example, a fatty acid ester of a higher alcohol), a sterol ester, a cholesterol ester, a fatty acid ester or the like of a vitamin, a complex lipid having a polar group such as phosphoric acid, a saccharide, sulfuric acid, or an amine in addition to a fatty acid and an alcohol, for example, a phospholipid (for example, a glycerophospholipid, a sphingophospholipid, or the like) and a glycolipid (for example, a glyceroglycolipid, a sphingoglycolipid, or the like), a derived lipid which refers to a lipid-soluble compound among compounds produced by hydrolysis of a simple lipid or a complex lipid such as a fatty acid, a higher alcohol, a lipid-soluble vitamin, a steroid, a carbohydrate, and the like.

Examples of the fluorescent compound comprise fluorescent dyes comprising fluorescein series such as fluorescein isothiocyanate (FITC), rhodamine series such as rhodamine isothiocyanate (RITC), Cy3, Cy5, eosine series, Alexa Fluor series, NBD series, and the like, a light-emitting substance such as an acridinium ester or lophine, fluorescent proteins such as green fluorescent protein (GFP), and the like.

To the antibody or the antibody fragment thereof of the invention, the hydrophilic polymer, the amphipathic polymer, or the functional molecule can be bound directly or through an appropriate linker. Examples of the linker comprise an ester, a disulfide, a hydrazone, a dipeptide, and the like.

When a fusion antibody or a fusion antibody fragment is produced by modifying the antibody or the antibody fragment thereof of the invention by a genetic engineering technique, a fusion antibody or a fusion antibody fragment can be produced by linking a cDNA encoding a protein to a cDNA encoding an antibody, thereby constructing a DNA encoding the fusion antibody or the fusion antibody fragment, inserting the DNA into an expression vector for a prokaryote or a eukaryote, introducing the expression vector into a prokaryote or a eukaryote, and expressing the fusion antibody or the fusion antibody fragment.

The composition of the invention may be any as long as the composition comprises the antibody or the antibody fragment thereof of the invention. The composition may comprise an appropriate carrier or an additive such as a stabilizing agent in addition to the antibody or the antibody fragment thereof.

Examples of the composition of the invention comprise a composition for detection or measurement comprising the antibody or the antibody fragment thereof of the invention, and the like. Examples of the composition of the invention comprise a pharmaceutical composition (therapeutic agent) comprising the antibody or the antibody fragment thereof of the invention as an active ingredient, and the like, and the composition is formulated into a desired dosage form together with a pharmacologically acceptable carrier.

In the invention, the composition for detection or measurement may be any composition as long as the composition comprises the antibody or the antibody fragment thereof of the invention and can detect or measure an antigen to which the antibody or the antibody fragment thereof of the invention specifically binds. As the antigen to which the antibody or the antibody fragment thereof of the invention specifically binds, CADM3, or CADM3 and an antigen present in the brain, or the like is exemplified.

The antibody or the antibody fragment thereof of the invention has a property of binding to CADM3 in the brain and being accumulated in the brain when it is administered to an animal. Therefore, by using the composition for detection or measurement comprising the antibody or the antibody fragment thereof, the antibody can be maintained in the brain, or the antibody concentration in the brain can be improved, so that CADM3 or CADM3 and an antigen present in the brain can be detected or measured for a long time, and/or CADM3 or CADM3 and an antigen present in the brain can also be detected or measured with high sensitivity.

For example, when the composition for detection or measurement is a composition comprising a bispecific antibody which binds to CADM3 and an antigen present in the brain, CADM3 and the antigen present in the brain, to which the bispecific antibody binds, can be detected or measured for a long time, and/or CADM3 and the antigen present in the brain can be detected or measured with high sensitivity.

Further, for example, when the composition for detection or measurement is a composition comprising a fusion antibody or a fusion antibody fragment thereof which is labeled with a radiolabeling compound or a fluorescent dye and which binds to CADM3, CADM3 can be detected or measured for a long time, and/or CADM3 can be detected or measured with high sensitivity.

The pharmaceutical composition (therapeutic agent) comprising the antibody or the antibody fragment thereof of the invention may be a therapeutic agent for any disease as long as the antigen to which the antibody or the antibody fragment thereof of the invention specifically binds is expressed in the disease but is preferably a therapeutic agent for a brain disease.

Examples of the brain disease comprise Alzheimer's disease, a prodromal stage of Alzheimer's disease, Huntington disease, Parkinson's disease, a brain tumor, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, a cerebrovascular disorder, epilepsy, migraine, a hyperactivity disorder, Creutzfeldt-Jakob disease, corticobasal degeneration, a lysosomal storage disease, depression, dystonia, and the like.

The antibody or the antibody fragment thereof of the invention has a property of binding to CADM3 in the brain and being accumulated in the brain when it is administered to an animal. Therefore, by using the therapeutic agent comprising the antibody or the antibody fragment thereof, the antibody or the antibody fragment thereof can be maintained in the brain for a long time, and the antibody concentration in the brain can be improved, so that a therapeutic effect on the above-mentioned diseases can be exhibited.

For example, when the therapeutic agent is a therapeutic agent comprising a fusion antibody of an anti-CADM3 antibody of the invention, by delivering a fused molecule into the brain, a therapeutic effect of the molecule can be exhibited. Specifically, when the therapeutic agent is a therapeutic agent comprising a fusion antibody in which a drug, an enzyme, or the like is fused to an anti-CADM3 antibody, a therapeutic effect of the drug or the enzyme can be exhibited, and when the therapeutic agent is a therapeutic agent comprising a bispecific antibody which binds to CADM3 and an antigen present in the brain, a therapeutic effect on a brain disease associated with the antigen, which is present in the brain, and to which the bispecific antibody binds, can be exhibited.

Further, for example, when the therapeutic agent is a fusion antibody or a fusion antibody fragment which is modified with a low molecular weight drug and which binds to CADM3, a therapeutic effect on a brain disease targeted by the low molecular weight drug can be exhibited. At that time, the therapeutic effect is preferably higher when the therapeutic agent of the invention is used as compared with a case when the low molecular weight drug is used alone.

The therapeutic agent comprising the antibody or the antibody fragment thereof of the invention may be a therapeutic agent comprising only the antibody or the antibody fragment thereof as an active ingredient, however, in general, the therapeutic agent is desirably provided as a pharmaceutical preparation produced by mixing with one or more pharmacologically acceptable carriers using an arbitrary method known in the technical field of pharmaceutics.

As the route of administration, it is preferred to use the most effective route for the treatment, and examples thereof comprise oral administration or parenteral administration such as intraoral, intra-airway, intrarectal, subcutaneous, intradermal, intramuscular, intraventricular, intrathecal, intranasal, intraperitoneal, or intravenous administration, and intravenous or intraventricular administration or the like is particularly preferably exemplified. Examples of the dosage form comprise a spray, a capsule, a tablet, a powder, a granule, a syrup, an emulsion, a suppository, an injection, an ointment, a tape, and the like.

The dose or the frequency of administration varies depending on an intended therapeutic effect, an administration method, a treatment duration, an age, a body weight, or the like, but is generally 10 μg/kg to 20 mg/kg per day for an adult.

Further, the invention also comprises a method for retaining an antibody in the brain, a method for enhancing the property of accumulating in a brain of an antibody, and a method for increasing the antibody concentration (or the antibody amount) in the brain, each using the antibody or the antibody fragment thereof of the invention.

Further, the invention also relates to a peptide which binds to CADM3, a nucleic acid comprising a nucleotide sequence encoding the peptide, a transformant cell comprising a vector comprising the nucleic acid, a method for producing the peptide comprising culturing the transformant cell and collecting the peptide from the culture solution, a composition comprising the peptide, or a method for detecting or measuring an antigen present in the brain, a method for diagnosing or treating a brain disease, a method for enhancing the property of accumulating in a brain of a peptide, or a method for increasing the amount of the peptide in the brain, each using the peptide or the composition.

The peptide of the invention comprises a fusion peptide in which a peptide is modified.

As for the definitions of various terms related to the peptide which binds to CADM3 and the like, the same ones as the definitions of the terms described for the antibody which binds to CADM3 and the like described above are used unless otherwise specified.

Hereinafter, the method for producing the antibody or the antibody fragment thereof of the invention, the method for treating a disease, the method for diagnosing a disease, and the like will be specifically described.

1. Method for Producing Antibody
(1) Preparation of Antigen

CADM3 to serve as an antigen or CADM3-expressing cells can be obtained by introducing an expression vector comprising a cDNA encoding the full length of CADM3 or a partial length thereof into *E. coli*, yeast, an insect cell, an animal cell, or the like. In addition, CADM3 can also be obtained by purifying CADM3 from various types of animal cell lines, animal cells, animal tissues, and the like in which CADM3 is expressed in a large amount.

Further, the animal cell lines, the animal cells, the animal tissues, and the like can also be used as they are as an antigen. In addition, a synthetic peptide having a partial sequence of CADM3 is prepared using a chemical synthesis method such as an Fmoc method or a tBoc method and can also be used as an antigen.

A known tag such as FLAG or His may be added to the C-terminus or the N-terminus of CADM3 or a synthetic peptide having a partial sequence of CADM3.

CADM3 used in the invention can be produced using the method or the like described in Molecular Cloning, A Laboratory Manual, Second Edition, Cold Spring Harbor Laboratory Press (1989), Current Protocols In Molecular Biology, John Wiley & Sons (1987-1997) or the like, by, for example, expressing a DNA encoding CADM3 in a host cell by the following method.

First, a recombinant vector is produced by inserting a full-length cDNA comprising a region encoding CADM3 downstream of a promoter in an appropriate expression vector. A DNA fragment that has been prepared based on the full-length cDNA and has an appropriate length and comprises a region encoding a polypeptide may be used in place of the full-length cDNA. Subsequently, by introducing the obtained recombinant vector into a host cell suitable for the expression vector, a transformant which produces the polypeptide can be obtained.

As the expression vector, any vector can be used as long as it can replicate autonomously or can be integrated into a chromosome in a host cell to be used and comprises a suitable promoter at a position capable of transcribing a DNA encoding the polypeptide. As the host cell, any cell such as a microorganism belonging to the genus Escherichia such as E. coli, yeast, an insect cell, an animal cell, or the like, can be used as long as a target gene can be expressed.

In the case where a prokaryote such as E. coli is used as the host cell, the expression vector is preferably a vector that can replicate autonomously in the prokaryote and also comprises a promoter, a ribosomal binding sequence, a DNA comprising a region encoding human CADM3, and a transcription termination sequence. In addition, although the transcription termination sequence is not essentially needed for the expression vector, the transcription termination sequence is preferably located immediately downstream of a structural gene. Further, the recombinant vector may comprise a gene that controls the promoter.

As the expression vector, it is preferred to use a plasmid in which a distance between a Shine-Dalgarno sequence (also referred to as an SD sequence) that is a ribosomal binding sequence and a start codon is adjusted to an appropriate length (for example, 6 to 18 nucleotides).

In addition, in the nucleotide sequence of the DNA encoding CADM3, a nucleotide can be substituted so that a codon becomes optimum for expression in a host, and as a result, the production rate of target CADM3 can be improved.

As the expression vector, any vector can be used as long as it can exhibit its function in a host cell to be used, and examples thereof comprise pBTrp2, pBTac1, pBTac2 (hereinabove manufactured by Roche Diagnostics K.K.), pKK233-2 (manufactured by Pharmacia Corporation), pSE280 (manufactured by Invitrogen, Inc.), pGEMEX-1 (manufactured by Promega Corporation), pQE-8 (manufactured by QIAGEN, Inc.), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK (−) (manufactured by Stratagene Corporation), pTrs30 [prepared from E coli JM109/pTrS30 (FERM BP-5407)], pTrs32 [prepared from E. coli JM109/pTrS32 (FERM BP-5408)], pGHA2 [prepared from E. coli IGHA2 (FERM BP-400), JP-A-S60-221091], pGKA2 [prepared from E. coli IGKA2 (FERM BP-6798), JP-A-S60-221091], pTerm2 (U.S. Pat. Nos. 4,686,191, 4,939,094, and 160,735), pSupex, pUB110, pTP5, pC194, pEG400 [J. Bacteriol., 172, 2392 (1990)], pGEX (manufactured by Pharmacia Corporation), pET System (manufactured by Novagen, Inc.), pME18SFL3, and the like.

As the promoter, any promoter may be used as long as it can exhibit its function in a host cell to be used. For example, a promoter derived from E. coli, a phage, or the like such as a trp promoter (Ptrp), a lac promoter, a PL promoter, a PR promoter, or a T7 promoter is exemplified. Further, for example, an artificially designed and modified promoter such as a tandem promoter in which two Ptrp's are linked in series, a tac promoter, a lacT7 promoter, or a let I promoter, or the like is exemplified.

Examples of the host cell comprise E. coli XL1-Blue, E. coli XL2-Blue, E. coli DH1, E. coli MC1000, E. coli KY3276, E. coli W1485, E. coli JM109, E. coli HB101, E. coli No. 49, E. coli W3110, E. coli NY49, E. coli DH5α, and the like.

As a method for introducing a recombinant vector into a host cell, any method can be used as long as it is a method for introducing a DNA into a host cell to be used, and for example, a method using calcium ions [Proc. Natl. Acad. Sci. USA, 69, 2110 (1972), Gene, 17, 107 (1982), and Molecular & General Genetics, 168, 111 (1979)] is exemplified.

When an animal cell is used as a host, as the expression vector, any vector can be used as long as it can exhibit its function in the animal cell, and examples thereof comprise pcDNAI, pCDM8 (manufactured by Funakoshi Co., Ltd.), pAGE107 [JP-A-H3-22979; Cytotechnology, 3, 133 (1990)], pAS3-3 (JP-A-H2-227075), pCDM8 [Nature, 329, 840 (1987)], pcDNAI/Amp (manufactured by Invitrogen, Inc.), pcDNA3.1 (manufactured by Invitrogen, Inc.), pREP4 (manufactured by Invitrogen. Inc.), pAGE103 [J. Biochemistry, 101, 1307 (1987)], pAGE210, pME18SFL3, pKANTEX93 (WO 97/10354), N5KG1val (U.S. Pat. No. 6,001,358), INPEP4 (manufactured by Biogen-IDEC, Inc.), pCI (manufactured by Promega Corporation), a transposon vector (WO 2010/143698), and the like.

As the promoter, any promoter can be used as long as it can exhibit its function in an animal cell, and examples thereof comprise a cytomegalovirus (CMV) immediate early (IE) gene promoter, an SV40 early promoter, a retrovirus promoter, a metallothionein promoter, a heat-shock promoter, an SRα promoter, and a Moloney murine leukemia virus promoter or enhancer. In addition, a human CMV IE gene enhancer may be used together with the promoter.

Examples of the host cell comprise a human leukemia cell Namalwa cell, a monkey cell COS cell, a Chinese hamster ovary cell CHO cell [Journal of Experimental Medicine, 108, 945 (1958); Proc. Natl. Acad. Sci. USA, 60, 1275 (1968): Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci. USA, 60, 1275 (1968); Cell, 6, 121 (1975); Molecular Cell Genetics, Appendix I, II (pp. 883-900)]; a dihydrofolate reductase gene (dhfr)-deficient CHO cell (CHO/DG44 cell) [Proc. Natl. Acad. Sci. USA, 77, 4216 (1980)], CHO-K1 (ATCC CCL-61), DUkXB11 (ATCC CCL-9096), Pro-5 (ATCC CCL-1781), CHO-S (Life Technologies, Cat #11619), Pro-3, a rat myeloma cell YB2/3HL.P2.G11.16Ag.20 (or also called YB2/0), a mouse myeloma cell NS0, a mouse myeloma cell SP2/0-Ag14, a Syrian hamster cell BHK or HBT5637 (JP-A-S63-000299), and the like.

As a method for introducing an expression vector into a host cell, any method can be used as long as it is a method for introducing a DNA into an animal cell. Examples thereof comprise an electroporation method [Cytotechnology, 3, 133 (1990)], a calcium phosphate method (JP-A-H2-227075), a lipofection method [Proc. Natl. Acad. Sci. USA, 84, 7413 (1987)], and the like.

CADM3 can be produced by culturing a transformant derived from a microorganism, an animal cell, or the like having an expression vector incorporating a DNA encoding CADM3 obtained as described above in a culture medium so as to produce and accumulate the CADM3 in a culture solution, and then collecting the CADM3 from the culture solution. A method for culturing the transformant in a culture medium can be carried out according to a conventional method used for culturing a host.

In the case of being expressed in a cell derived from a eukaryote, CADM3 to which a sugar or a glycan is added can be obtained.

When culturing a microorganism transformed with an expression vector using an inducible promoter, an inducer may be added to a culture medium as needed. For example, when a microorganism transformed with an expression vector using a lac promoter is cultured, isopropyl-β-D-thiogalactopyranoside or the like may be added to a culture medium, and when a microorganism transformed with an expression vector using a trp promoter is cultured, indoleacrylic acid or the like may be added to a culture medium.

Examples of the culture medium in which the transformant obtained using an animal cell as a host is cultured comprise RPMI 1640 medium [The Journal of the American Medical Association, 199,519 (1967)], Eagle's MEM medium [Science, 122, 501 (1952)], Dulbecco's modified MEM medium [Virology, 8, 396 (1959)], Medium 199 [Proc. Soc. Exp. Biol. Med., 73, 1 (1950)], Iscove's modified Dulbecco's medium (IMDM), which are generally used, or a culture medium in which fetal bovine serum (FBS) or the like is added to any of these culture media, and the like. The culture is usually carried out for 1 to 7 days under the conditions of pH 6 to 8 and 30 to 40° C. in the presence of 5% $CO_2$, or the like. In addition, during the culture, an antibiotic such as kanamycin or penicillin may be added to the culture medium as needed.

As a method for expressing a gene encoding CADM3, for example, a method such as secretory production or fusion protein expression [Molecular Cloning, A Laboratory Manual, Second Edition, Cold Spring Harbor Laboratory Press (1989)] is exemplified in addition to direct expression.

Examples of a method for producing CADM3 comprise a method for producing CADM3 in a host cell, a method for secreting CADM3 out of a host cell, and a method for producing CADM3 on an outer membrane of a host cell, and an appropriate method can be selected by changing a host cell to be used or the structure of CADM3 to be produced.

When CADM3 is produced in a host cell or on an outer membrane of a host cell, CADM3 can be actively secreted out of the host cell using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)], or the method described in JP-A-H05-336963, WO 94/23021, or the like. In addition, the amount of production of CADM3 can also be increased by utilizing a gene amplification system using a dihydrofolate reductase gene or the like (JP-A-H2-227075).

The obtained CADM3 can be isolated and purified, for example, as follows. When CADM3 is expressed in cells in a dissolved state, the cells are collected by centrifugation after completion of the culture, suspended in an aqueous buffer solution, followed by homogenization of the cells using an ultrasonic homogenizer, a French press, a Manton Gaulin homogenizer, a Dyno mill, or the like, whereby a cell-free extract solution is obtained. It is possible to obtain a purified preparation from a supernatant obtained by centrifugation of the cell-free extract solution using methods such as conventional protein isolation and purification methods, that is, a solvent extraction method, a salting-out method using ammonium sulfate or the like, a desalting method, a precipitation method using an organic solvent, anion exchange chromatography using a resin such as diethylaminoethyl (DEAE)-Sepharose or DIAION HPA-75 (manufactured by Mitsubishi Chemical Corporation), cation exchange chromatography using a resin such as S-Sepharose FF (manufactured by Pharmacia Corporation), hydrophobic chromatography using a resin such as Butyl Sepharose or Phenyl Sepharose, a gel filtration method using a molecular sieve, affinity chromatography, chromatofocusing, electrophoresis such isoelectric focusing electrophoresis, and the like alone or in combination.

When CADM3 is expressed in cells by forming an insoluble body, the cells are collected and then homogenized in the same manner as described above, followed by centrifugation, whereby the insoluble body of the CADM3 is collected as a precipitated fraction. The collected insoluble body of the CADM3 is solubilized with a protein denaturing agent. The CADM3 is returned to a normal conformation by diluting or dialyzing the solubilized solution, and thereafter, a purified preparation of a polypeptide can be obtained by the same isolation and purification methods as described above.

When CADM3 or a derivative such as a sugar-modified body thereof is extracellularly secreted, the CADM3 or the derivative such as a sugar-modified body thereof can be collected in a culture supernatant. The culture is subjected to a treatment using a method such as centrifugation in the same manner as described above, thereby obtaining a soluble fraction, and then, by using the same isolation and purification methods as described above, a purified preparation can be obtained from the soluble fraction.

In addition, CADM3 used in the invention can also be produced using a chemical synthesis method such an Fmoc method or a tBoc method. Further, chemical synthesis can also be carried out using a peptide synthesizer manufactured by Advanced Chemtech, Inc., PerkinElmer, Inc., Pharmacia Corporation, Protein Technology Instrument, Inc., Synthecell-Vega Biomolecules Corporation, Perceptive, Inc., Shimadzu Corporation, or the like.

(2) Immunization of Animal and Preparation of Antibody-Producing Cells for Fusion An animal such as a mouse, a rat, a rabbit, or a hamster at 3 to 20 weeks of age is immunized with the antigen obtained in (1), and antibody-producing cells in the spleen, the lymph node, or the peripheral blood of the animal are collected. In addition, an animal such as a llama, an alpaca, or a camel can also be used as the animal to be immunized.

The immunization is carried out by subcutaneously, intravenously, or intraperitoneally administering an antigen to an animal, for example, together with an appropriate adjuvant such as a Freund's complete adjuvant, an aluminum hydroxide gel, or *Bordetella pertussis* vaccine. When the antigen is a partial peptide, a conjugate of the antigen with a carrier protein such as bovine serum albumin (BSA) or Keyhole Limpet hemocyanin (KLH) is produced and used as an immunogen.

When a mouse or a rat is immunized, the administration of the antigen is carried out 5 to 10 times every 1 to 2 weeks after the first administration. On day 3 to 7 after each administration, the blood is collected from a venous plexus of the fundus, and the antibody titer of the serum thereof is measured using an enzyme immunoassay method [Antibodies—A Laboratory Manual, Cold Spring Harbor Laboratory (1988)] or the like. An animal whose serum shows a sufficient antibody titer against the antigen used for the immunization is used as a supply source for the antibody-producing cells for fusion.

On day 3 to 7 after the final administration of the antigen, a tissue comprising the antibody-producing cells such as the spleen is extracted from the immunized animal, and the antibody-producing cells are collected. When spleen cells are used, the spleen is shredded and loosened, followed by centrifugation, and then, erythrocytes are removed, whereby the antibody-producing cells for fusion are obtained.

Other animals to be immunized can also be immunized in the same manner, and antibody-producing cells can be obtained. Appropriate conditions for the interval of immunizations and the period between the final immunization and the extraction of the tissue can be selected in accordance with an animal species to be immunized.

(3) Preparation of Myeloma Cells

As myeloma cells, an established cell line obtained from a mouse is used, and for example, an 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)], or the like is used.

The myeloma cells are subcultured in a normal culture medium [RPMI 1640 medium supplemented with glutamine, 2-mercaptoethanol, gentamicin, FBS, and 8-azaguanine], and then subcultured in a normal culture medium 3 to 4 days before cell fusion, and $2\times10^7$ or more cells are ensured on the day of the fusion.

(4) Cell Fusion and Preparation of Monoclonal Antibody-Producing Hybridoma

The antibody-producing cells for fusion obtained in (2) and the myeloma cells obtained in (3) are thoroughly washed with Minimum Essential Medium (MEM) or phosphate buffered saline (PBS: 1.83 g of disodium phosphate, 0.21 g of monopotassium phosphate, 7.65 g of sodium chloride, 1 L of distilled water, pH 7.2), and mixed so that the cell count becomes as follows: the antibody-producing cells for fusion: the myeloma cells=5:1 to 10:1, followed by centrifugation, and then, the supernatant is removed.

After the precipitated cell aggregate is well loosened, a mixed solution of polyethylene glycol 1000 (PEG-1000), MEM medium, and dimethylsulfoxide is added thereto while stirring at 37° C. Further, 1 to 2 mL of MEM medium is added thereto several times every 1 to 2 minutes, and then, MEM medium is added thereto so that the total amount becomes 50 mL.

After centrifugation, the supernatant is removed. The precipitated cell aggregate is gently loosened, and then, the cells are gently suspended in HAT medium [a normal culture medium supplemented with hypoxanthine, thymidine, and aminopterin]. The resulting suspension is cultured in a 5% $CO_2$ incubator at 37° C., for 7 to 14 days.

After the culture, a portion of the culture supernatant is withdrawn, and a cell aggregate that reacts with CADM3 but does not react with an antigen other than CADM3 is selected by a hybridoma selection method such as the below-mentioned binding assay. Subsequently, cloning is performed by a limiting dilution method, and a cell in which a high antibody titer is stably observed is selected as a monoclonal antibody-producing hybridoma.

(5) Preparation of Purified Monoclonal Antibody

The monoclonal antibody-producing hybridoma obtained in (4) is intraperitoneally injected into a mouse or a nude mouse at 8 to 10 weeks of age having been subjected to a pristane treatment [0.5 mL of 2,6,10,14-tetramethylpentadecane (pristane) is intraperitoneally administered, followed by breeding for 2 weeks]. In 10 to 21 days, the hybridoma is converted into an ascites tumor.

The ascites is collected from this mouse, followed by centrifugation to remove solids, and then, salting out is carried out with 40 to 50% ammonium sulfate. Thereafter, purification is carried out by a caprylic acid precipitation method, a DEAE-Sepharose column, a protein A column, or a gel filtration column, and then, an IgG or IgM fraction is collected, whereby a purified monoclonal antibody is prepared.

Further, after culturing the monoclonal antibody-producing hybridoma obtained in (4) in RPMI 1640 medium supplemented with 10% FBS, or the like, the supernatant is removed by centrifugation, and the residue is suspended in Hybridoma-SFM medium, and then cultured for 3 to 7 days.

The obtained cell suspension is centrifuged, and purification by a protein A column or a protein G column is carried out from the obtained supernatant, and then an IgG fraction is collected, and thus, a purified monoclonal antibody can also be obtained. Note that 5% Daigo's GF21 can also be added to the Hybridoma-SFM medium.

The determination of the subclass of the antibody is carried out by an enzyme immunoassay method using a subclass typing kit. The quantitative determination of the amount of a protein can be carried out by a Lowry method or by calculation from an absorbance at 280 nm.

(6) Selection of Antibody

The selection of an antibody is carried out by measuring the affinity of the antibody for the CADM3-expressing cells using flow cytometry or the like as shown below. The CADM3-expressing cells may be any cells as long as CADM3 is expressed on the cell surface, and examples thereof comprise animal cells, an animal cell line, the CADM3 forced expression cell line obtained in (1), and the like.

After dispensing the CADM3-expressing cells in a plate such as a %-well plate, a test substance such as serum, a culture supernatant of a hybridoma, or a purified antibody is dispensed therein as the first antibody and allowed to react. The cells after the reaction are thoroughly washed with PBS comprising 1 to 10% BSA (hereinafter referred to as BSA-PBS) or the like, and an anti-immunoglobulin antibody labeled with a fluorescent reagent or the like is then dispensed therein as the second antibody and allowed to react. After thoroughly washing with BSA-PBS or the like, the fluorescence amount of the labeled antibody is measured using a flow cytometer, whereby an antibody which specifically reacts with the CADM3-expressing cells is selected.

Further, the selection of an antibody can also be carried out by measuring the affinity of a monoclonal antibody for the CADM3-expressing cells, a CADM3 protein, or the like using ELISA or surface plasmon resonance described below. The CADM3 protein may be a protein composed of some domains of CADM3 or a protein to which a tag such as GST is added.

In ELISA, after dispensing the CADM3-expressing cells or the CADM3 protein in a plate such as a 96-well plate, the wells are blocked with BSA-PBS, and a test substance such as serum, a culture supernatant of a hybridoma, or a purified antibody is dispensed therein as the first antibody and allowed to react. Subsequently, after thoroughly washing with PBS or the like, an anti-immunoglobulin antibody labeled with a fluorescent reagent or the like is dispensed therein as the second antibody and allowed to react.

Then, after thoroughly washing with PBS or the like, a coloring reagent is added. At the end, a coloring reaction is stopped with a reaction stopping solution, and the absorbance in each well is measured with a microplate reader, whereby an antibody which specifically reacts with the CADM3-expressing cells or the CADM3 protein is selected.

In the surface plasmon resonance, by using a known protocol, the affinity of an antibody which binds to CADM3 can be measured by immobilizing the antibody on an appropriate sensor chip and using the CADM3 protein as an analyte.

By using the affinity of the antibody obtained, an antibody having desired affinity for the CADM3 protein can be selected. Further, the affinity of an antibody which binds to CADM3 can also be measured by immobilizing the CADM3 protein on a sensor chip and using the antibody as an analyte.

In addition, an antibody which binds to CADM3 competitively with the antibody of the invention can be obtained by adding a test antibody to an assay system using flow cytometry or ELISA described above to cause a reaction. That is, by screening an antibody which inhibits binding of the antibody of the invention to CADM3 when the test antibody is added, an antibody that competes with the antibody of the invention for binding to the amino acid sequence of CADM3 or the conformation thereof can be obtained.

Further, an antibody which binds to an epitope comprising an epitope to which the antibody of the invention binds can be obtained by identifying the epitope for an antibody obtained by the screening method described above by a known method, producing a synthetic peptide comprising the identified epitope, a synthetic peptide which is made to mimic the conformation of the epitope, or the like, and then performing immunization therewith.

Further, an antibody which binds to the same epitope as the epitope to which the antibody of the invention binds can be obtained by identifying the epitope for an antibody obtained by the screening method described above, producing a partial synthetic peptide of the identified epitope, a synthetic peptide which is made to mimic the conformation of the epitope, or the like, and then performing immunization therewith.

(7) Acquisition of Antibody by Phage Display Method (7-1) Method for Producing Antibody Phage Library In the invention, as an antibody phage library, an immune library, a naive library, and a synthetic library can be used. The production methods for the respective libraries will be described below Lymphocytes derived from an animal immunized in the same manner as described in the above (1) or a patient are collected for an immune library, and lymphocytes derived from a normal animal or a healthy human are collected for a naive library, and RNA is extracted from the lymphocytes, and cDNAs are synthesized by a reverse transcription reaction.

An antibody gene fragment amplified by PCR using each cDNA as a template is inserted into a phagemid vector, and E. coli is transformed by the phagemid vector. When the obtained transformant is infected with a helper phage, an antibody phage library of the antibody gene can be obtained.

Further, with respect to the synthetic library, CDR of a V gene in a genomic DNA or a reconstructed functional V gene is substituted with an oligonucleotide encoding a random amino acid sequence of an appropriate length, and E. coli is transformed with a phagemid vector into which the V gene has been inserted. When the obtained transformant is infected with a helper phage, an antibody phage library can be obtained.

As the cDNAs derived from lymphocytes and the antibody phage library, commercially available ones can also be used.

As the phagemid vector, pCANTAB 5E (Amersham Pharmacia Biotech, Inc.), pUC118/pUC119 vector (TAKARA. Inc.), pBlueScript II Phagemid Vector (Agilent Technologies, Inc.), pKSTV-02 (Miyazaki et al, J. Biochem. 158(3), 205-215, 2015), and the like can be used.

As the helper phage, M13KO7 helper phage (Invitrogen, Inc.), VCSM13 Interference Resistant Helper Phage (Agilent Technologies, Inc.), R408 Interference Resistant Helper Phage (Agilent Technologies, Inc.), and the like can be used.

In the phage display, a phage vector can also be used. There are a peptide phage library in which a filamentous phage g3p is used as a displayed molecule (manufactured by New England Biolabs, Inc, or the like), a method in which g7p, g8p, or g9p is used as a displayed molecule, and the like.

Further, phage display using T7 phage can also be used. As a display system on T7 phage, there are T7 Select vector (Novagen, Inc.) and the like.

(7-2) Selection of Antibody Phage Clone

The selection of an antibody phage clone from the antibody phage library produced in (7-1) can be carried out using the ELISA method shown below.

CADM3 is immobilized on an immuno tube, and the tube is blocked with a blocking buffer. The antibody phage library produced in (7-1) is added to each well of the tube and allowed to react. Subsequently, the wells are washed, and a fluorescently labeled anti-phage antibody is added and allowed to react. Thereafter, the wells are washed again, and a coloring solution is added. Thereafter, a coloring reaction is stopped with a reaction stopping solution, and the absorbance in each well is measured with a microplate reader. In this manner, an antibody phage clone which binds to CADM3 is selected.

2. Production of Genetically Recombinant Antibody

As production examples of a genetically recombinant antibody, production methods for a human chimeric antibody and a humanized antibody will be described below. A genetically recombinant mouse antibody, rat antibody, rabbit antibody, hamster antibody, camel antibody, llama antibody, alpaca antibody, and human antibody, various types of chimeric antibodies, a heavy chain antibody, and the like can also be produced in the same manner.

(1) Construction of Expression Vector for Genetically Recombinant Antibody

An expression vector for a genetically recombinant antibody is an expression vector for animal cells into which DNAs encoding CH and CL of a human antibody are incorporated, and can be constructed by cloning each of the DNAs encoding CH and CL of a human antibody into an expression vector for animal cells.

As a constant region (C region) of a human antibody, CH and CL of an arbitrary human antibody can be used. For example, CH of γ1 subclass and CL of K class of a human antibody, or the like are used. As the DNA encoding CH or CL of a human antibody, a cDNA is used, but a chromosomal DNA composed of an exon and an intron can also be used.

As the expression vector for animal cells, any vector can be used as long as it can incorporate a gene encoding a C region of a human antibody and express the gene. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)], or the like is used.

As the promoter and the enhancer in the expression vector for animal cells, an SV40 early promoter [J. Biochem., 101, 1307 (1987)], Moloney murine leukemia virus LTR [Biochem. Biophys. Res. Commun., 149, 960 (1987)], or an immunoglobulin H chain promoter [Cell, 41, 479 (1985)] and enhancer [Cell, 33, 717 (1983)], and the like are exemplified.

As the expression vector for a genetically recombinant antibody, an expression vector for a genetically recombinant antibody of a type (tandem-type) in which the antibody H chain and L chain are present on the same vector [J. Immunol. Methods, 167, 271 (1994)] is used from the viewpoints of ease of construction of the expression vector for a genetically recombinant antibody, ease of introduction into an animal cell, balancing of the expression levels of the antibody H chain and L chain in the animal cell, and the like, however, a type in which the antibody H chain and L chain are present on separate vectors can also be used. As the tandem-type expression vector for a genetically recombinant antibody, pKANTEX93 (WO 97/10354), pEE18 [Hybridoma, 17, 559 (1998)], or the like is used.

(2) Acquisition of cDNA Encoding Variable Region (V Region) of Antibody Derived from Animal Other than Human and Analysis of Amino Acid Sequence Acquisition of cDNAs encoding VH and VL of a non-human antibody and an analysis of an amino acid sequence can be carried out as follows.

(2-1) When Antibody is Obtained by Hybridoma Method mRNA is extracted from hybridoma cells which produce a non-human antibody, and cDNAs are synthesized. The synthesized cDNAs are each cloned into a vector such as a phage or a plasmid, thereby producing a cDNA library.

A recombinant phage or a recombinant plasmid comprising each cDNA encoding VH or VL is isolated from the library using a DNA encoding a C region domain or a V region domain of a non-human antibody as a probe. Each entire nucleotide sequence of the target VH or VL of the non-human antibody on the recombinant phage or the recombinant plasmid is determined, and each entire amino acid sequence of VH or VL is deduced from the nucleotide sequence.

As an animal other than a human for producing hybridoma cells which produce a non-human antibody, a mouse, a rat, a hamster, a rabbit, a llama, a camel, an alpaca, or the like is used, but any animal can be used as long as it can produce hybridoma cells.

For the preparation of the total RNA from hybridoma cells, a guanidine thiocyanate-cesium trifluoroacetate method [Methods in Enzymol., 154, 3 (1987)], or a kit such as RNeasy Kit (manufactured by QIAGEN, Inc.), or the like is used.

In the preparation of mRNA from the total RNA, an oligo(dT)-immobilized cellulose column method [Molecular Cloning, A Laboratory Manual, Second Edition, Cold Spring Harbor Laboratory Press (1989)], or a kit such as Oligo-dT30<Super> mRNA Purification (registered trademark) Kit (manufactured by Takara Bio, Inc.), or the like is used. Further, mRNA can also be prepared from hybridoma cells using a kit such as Fast Track mRNA Isolation (registered trademark) Kit (manufactured by Invitrogen. Inc.), or QuickPrep mRNA Purification (registered trademark) Kit (manufactured by Pharmacia Corporation).

In the synthesis of the cDNAs and the production of the cDNA library, a known method [Molecular Cloning, A Laboratory Manual, Second Edition, Cold Spring Harbor Laboratory Press (1989), Current Protocols in Molecular Biology, Supplement 1, John Wiley & Sons (1987-1997)], or a kit such as SuperScript Plasmid System for cDNA Synthesis and Plasmid Cloning (manufactured by Invitrogen, Inc.) or ZAP-cDNA Synthesis (registered trademark) Kit (manufactured by Stratagene Corporation), or the like is used.

When the cDNA library is produced, as the vector into which a cDNA synthesized using mRNA extracted from hybridoma cells as a template is incorporated, any vector can be used as long as it is a vector capable of incorporating the cDNA. For example, ZAP ExPress [Strategies, 5, 58 (1992)], pBluescript II SK (+) [Nucleic Acids Research, 17, 9494 (1989)], λZAPII (manufactured by Stratagene Corporation), λgt 10, λgt 11 [DNA Cloning: A Practical Approach, I, 49 (1985)], Lambda BlueMid (manufactured by Clontech Laboratories, Inc.), λEx Cell, pT7T3-18U (manufactured by Pharmacia Corporation), pCD2 [Mol. Cell. Biol., 3, 280 (1983)], pUC18 [Gene, 33, 103 (1985)], or the like is used.

As the E. coli into which the cDNA library constructed by a phage or a plasmid vector is introduced, any E. coli can be used as long as it can introduce, express, and maintain the cDNA library. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)], or the like is used.

In the selection of the cDNA clone encoding VH or VL of a non-human antibody from the cDNA library, a colony hybridization method using an isotope- or fluorescence-labeled probe, or a plaque hybridization method [Molecular Cloning, A Laboratory Manual, Second Edition, Cold Spring Harbor Laboratory Press (1989)], or the like is used.

In addition, the cDNA encoding VH or VL can also be prepared by preparing a primer and performing a polymerase chain reaction (PCR) method [Molecular Cloning, A Laboratory Manual, Second Edition, Cold Spring Harbor Laboratory Press (1989), Current Protocols in Molecular Biology, Supplement 1, John Wiley & Sons (1987-1997)] using the cDNA synthesized from mRNA or the cDNA library as a template.

The selected cDNA is cleaved with an appropriate restriction enzyme or the like, and then cloned into a plasmid such as pBluescript SK (−) (manufactured by Stratagene Corporation), and the nucleotide sequence of the cDNA is determined by a commonly used nucleotide sequence analysis method or the like. In the nucleotide sequence analysis method, for example, after performing a reaction such as a dideoxy method [Proc. Natl. Acad. Sci. USA, 74, 5463 (1977)], an automatic nucleotide sequence analyzer such as ABI Prism 3700 (manufactured by PE Biosystems, Inc.) or an A.L.F. DNA sequencer (manufactured by Pharmacia Corporation), or the like is used.

(2-2) When Antibody is Obtained by Phage Display Method

Each entire nucleotide sequence of VH or VL is determined from the plasmid vector of the selected phage clone using a DNA encoding the vector region or the V region domain as a probe, and then, each entire amino acid sequence of VH or VL can be deduced from the nucleotide sequence.

In either the hybridoma method or the phage display method, by deducing the entire amino acid sequences of VH and VL from the determined nucleotide sequences and comparing with the entire amino acid sequences of VH and VL of a known antibody [Sequences of Proteins of Immunological Interest, US Dept. Health and Human Services (1991)], respectively, it is confirmed whether the obtained cDNAs encode the complete amino acid sequences of VH and VL of an antibody comprising a secretion signal sequence.

With respect to the complete amino acid sequences of VH and VL of the antibody comprising a secretion signal sequence, by comparison with the entire amino acid sequences of VH and VL of a known antibody [Sequences of Proteins of Immunological Interest, US Dept. Health and Human Services (1991)], the length of the secretion signal sequence and the N-terminal amino acid sequence can be deduced, and further, the subgroup to which these belong can be found.

In addition, the amino acid sequences of CDRs of VH and VL can also be found out by comparison with the amino acid sequences of VH and VL of a known antibody [Sequences of Proteins of Immunological Interest, US Dept. Health and Human Services (1991)].

Further, by using the obtained complete amino acid sequences of VH and VL, it is possible to confirm whether the complete amino acid sequences of VH and VL are new by, for example, carrying out a homology search by a BLAST method [J. Mol. Biol., 215, 403 (1990)] or the like with respect to an arbitrary database such as SWISS-PROT or PIR-Protein.

(3) Construction of Human Chimeric Antibody Expression Vector

By cloning each cDNA encoding VH or VL of a non-human antibody upstream of each gene encoding CH or CL of a human antibody in the expression vector for a genetically recombinant antibody obtained in (1), a human chimeric antibody expression vector can be constructed.

In order to ligate the cDNA encoding VH or VL of a non-human antibody at the 3' end side to CH or CL of a human antibody at the 5' end side, cDNAs of VH and VL designed so that the nucleotide sequence of a ligation region encodes an appropriate amino acid and becomes an appropriate restriction enzyme recognition sequence are produced.

The produced cDNAs of VH and VL are each cloned upstream of each gene encoding CH or CL of a human antibody in the expression vector for a genetically recombinant antibody obtained in (1) so that the cDNAs are expressed in an appropriate form, whereby a human chimeric antibody expression vector is constructed.

In addition, each cDNA encoding VH or VL of a non-human antibody is amplified by a PCR method using a synthetic DNA comprising an appropriate restriction enzyme recognition sequence at both ends, and can also be cloned into the expression vector for a genetically recombinant antibody obtained in (1).

(4) Construction of cDNA Encoding V Region of Humanized Antibody

A cDNA encoding VH or VL of a humanized antibody can be constructed as follows.

Each amino acid sequence of FR of VH or VL of a human antibody for grafting the amino acid sequence of CDR of VH or VL of anon-human antibody is selected. As the amino acid sequence of FR to be selected, any amino acid sequence can be used as long as it is derived from a human antibody.

For example, an amino acid sequence of FR of a human antibody registered in a database such as Protein Data Bank, or a common amino acid sequence in each subgroup of FR of a human antibody [Sequences of Proteins of Immunological Interest, US Dept. Health and Human Services (1991)], or the like is used. In order to suppress a decrease in the binding activity of an antibody, an amino acid sequence of FR with the highest possible homology (at least 60% or more) with the amino acid sequence of FR of VH or VL of the original antibody is selected.

Subsequently, each of the amino acid sequences of the CDRs of the original antibody is grafted into the selected amino acid sequence of FR of VH or VL of a human antibody, and each amino acid sequence of VH or VL of a humanized antibody is designed. By converting the designed amino acid sequence into a DNA sequence in consideration of the usage frequency of codons found in the nucleotide sequence of the antibody gene [Sequences of Proteins of Immunological Interest, US Dept. Health and Human Services (1991)], each DNA sequence encoding the anno acid sequence of VH or VL of a humanized antibody is designed.

Based on the designed DNA sequences, several synthetic DNAs having a length of around 100 nucleotides are synthesized, and a PCR reaction is carried out using the DNAs. In this case, in consideration of the reaction efficiency of the PCR reaction and the synthesizable length of DNA, 6 synthetic DNAs are preferably designed for each of the VH and V L.

Further, by introducing an appropriate restriction enzyme recognition sequence at the 5' or 3' end of the synthetic DNA located at both ends, a cDNA encoding VH or VL of a humanized antibody can be easily cloned into the expression vector for a genetically recombinant antibody obtained in (1).

After the PCR reaction, the amplified products are each cloned into a plasmid such as pBluescript SK (−) (manufactured by Stratagene Corporation), and the nucleotide sequences are determined in the same manner as described in (2), and a plasmid having the DNA sequence encoding the amino acid sequence of VH or VL of a desired humanized antibody is obtained.

Alternatively, the full length of VH and the full length of VL each synthesized as a single long chain DNA based on the designed DNA sequences can also be used in place of the PCR amplified products. Further, by introducing an appropriate restriction enzyme recognition sequence at both ends of the synthesized long chain DNA, the cDNA encoding VH or VL of the humanized antibody can be easily cloned into the expression vector for a genetically recombinant antibody obtained in (1).

(5) Modification of Amino Acid Sequence of V Region of Humanized Antibody

The antigen-binding activity of a humanized antibody prepared merely by grafting only the CDRs of VH and VL of a non-human antibody into FRs of VH and VL of a human antibody is decreased as compared with that of the original non-human antibody [BIO/TECHNOLOGY, 9, 266 (1991)].

In the humanized antibody, the lowered antigen-binding activity can be increased by identifying an amino acid residue directly involved in the binding to an antigen, an amino acid residue interacting with an amino acid residue of CDR, and an amino acid residue maintaining the conformation of the antibody and indirectly involved in the binding to an antigen in the amino acid sequences of FRs of VH and VL of a human antibody, and substituting such an amino acid residue with an amino acid residue of the original non-human antibody.

In order to identify such an amino acid residue of FR involved in the antigen-binding activity, the conformation of the antibody can be constructed and analyzed using X-ray crystallography [J. Mol. Biol., 112, 535 (1977)], or computer modeling [Protein Engineering, 7, 1501 (1994)], or the like. Further, a humanized antibody having a necessary antigen-binding activity can be obtained by producing several types of variants for each antibody, and repeatedly examining the correlation with the antigen-binding activity thereof through trial and error.

The amino acid residues of FRs of VH and VL of a human antibody can be modified by carrying out the PCR reaction described in (4) using a synthetic DNA for modification. With respect to the amplification product after the PCR reaction, the nucleotide sequence is determined to confirm whether the intended modification has been carried out by the method described in (2).

(6) Construction of Humanized Antibody Expression Vector

A humanized antibody expression vector can be constructed by cloning each cDNA encoding VH or VL of a constructed genetically recombinant antibody upstream of each gene encoding CH or CL of a human antibody in the expression vector for a genetically recombinant antibody obtained in (1).

For example, the cloning is carried out upstream of each gene encoding CH or CL of a human antibody in the expression vector for a genetically recombinant antibody obtained in (1) by introducing an appropriate restriction enzyme recognition sequence at the 5' or 3' end of the synthetic DNA located at both ends among the synthetic DNAs used when constructing VH or VL of any of the humanized antibodies obtained in (4) and (5) so that the cDNA is expressed in an appropriate form.

(7) Transient Expression of Genetically Recombinant Antibody

By transiently expressing genetically recombinant antibodies using any of the genetically recombinant antibody expression vectors obtained in (3) and (6), or a modified expression vector thereof, the antigen-binding activities of many types of human chimeric antibodies and humanized antibodies produced can be efficiently evaluated.

As a host cell into which the expression vector is introduced, any cell can be used as long as it is a host cell capable of expressing a genetically recombinant antibody, but for example, a COS-7 cell [American Type Culture Collection (ATCC) number: CRL 1651] is used [Methods in Nucleic Acids Res., CRC Press, 283 (1991)].

In the introduction of the expression vector into a COS-7 cell, a DEAE-dextran method [Methods in Nucleic Acids Res., CRC Press (1991)], a lipofection method [Proc. Natl. Acad. Sci. USA, 84, 7413 (1987)], or the like is used.

After the introduction of the expression vector, the expression level and the antigen-binding activity of the genetically recombinant antibody in a culture supernatant are measured using an enzyme immunoassay method [Monoclonal Antibodies-Principles and practice, Third Edition, Academic Press (1996), Antibodies-A Laboratory Manual, Cold Spring Harbor Laboratory (1988), Monoclonal Antibody Experimental Manual, Kodansha scientific books (1987)], or the like.

(8) Acquisition of Transformant Stably Expressing Genetically Recombinant Antibody and Preparation of Genetically Recombinant Antibody A transformant that stably expresses a genetically recombinant antibody can be obtained by introducing any of the genetically recombinant antibody expression vectors obtained in (3) and (6) into an appropriate host cell.

In the introduction of the expression vector into a host cell, an electroporation method [JP-A-H2-257891, Cytotechnology, 3, 133 (1990)], or the like is used.

As the host cell into which the genetically recombinant antibody expression vector is introduced, any cell can be used as long as it is a host cell capable of expressing a genetically recombinant antibody. For example, CHO-KI (ATCC CCL-61), DUKXB11 (ATCC CCL-9096), Pro-5 (ATCC CCL-1781), CHO-S (Life Technologies, Cat #11619), a rat myeloma cell YB2/3HL.P2.G11.16Ag.20 (ATCC No. CRL1662, also called YB2/0), a mouse myeloma cell NS0, a mouse myeloma cell SP2/0-Ag14 (ATCC No. CRL1581), a mouse P3X63-Ag8.653 cell (ATCC No. CRL1580), a dhfr-deficient CHO cell (CHO/DG44 cell) [Proc. Natl. Acad. Sci. USA, 77, 4216 (1980)], or the like is used.

In addition, a host cell in which the activity of a protein such as an enzyme involved in the intracellular synthesis of sugar nucleotide GDP-fucose, a protein such as an enzyme involved in glycan modification such that the 1-position of fucose is α-linked to the 6-position of N-acetylglucosamine at the reducing terminus of an N-glycoside-linked complex glycan, a protein involved in the intracellular transport of sugar nucleotide GDP-fucose to the Golgi body, or the like is decreased or lost, for example, an α1,6-fucosyltransferase gene-deficient CHO cell (WO 2005/035586 and WO 02/31140), Lec13 having acquired lectin resistance [Somatic Cell and Molecular genetics, 12, 55 (1986)], or the like can also be used.

After introduction of the expression vector, a transformant that stably expresses a genetically recombinant antibody is selected by culturing the transformant in a medium for animal cell culture comprising a drug such as G418 sulfate (hereinafter referred to as G418) (JP-A-H2-257891).

As the medium for animal cell culture, RPMI 1640 medium (manufactured by Invitrogen, Inc.), GIT medium (manufactured by Nippon Pharmaceutical Co., Ltd.), EX-CELL 301 medium (manufactured by JRH Biosciences, Inc.), IMDM medium (manufactured by Invitrogen, Inc.) or Hybridoma-SFM (manufactured by Invitrogen, Inc.), or a medium in which any of various additives such as FBS is added to any of these media, or the like is used.

By culturing the obtained transformant in the medium, a genetically recombinant antibody is expressed and accumulated in the culture supernatant. The expression level and the antigen-binding activity of the genetically recombinant antibody in the culture supernatant can be measured by an ELISA method or the like. In addition, the expression level of the genetically recombinant antibody produced by the transformant can be increased using a dhfr gene amplification system (JP-A-H2-257891) or the like.

The genetically recombinant antibody is purified using a protein A column from the culture supernatant of the transformant [Monoclonal Antibodies—Principles and practice, Third edition, Academic Press (1996), Antibodies—A Laboratory Manual, Cold Spring Harbor Laboratory (1988)]. In addition, methods used for purifying a protein such as gel filtration, ion exchange chromatography, and ultrafiltration can also be combined.

The molecular weight of an H chain, an L chain, or the entire antibody molecule of a purified genetically recombinant antibody can be measured using polyacrylamide gel electrophoresis [Nature, 227, 680 (1970)], or Western blotting [Monoclonal Antibodies—Principles and Practice, Third Edition, Academic Press (19%), Antibodies—A Laboratory Manual, Cold Spring Harbor Laboratory (1988)], or the like.

(9) Method for Producing Antibody Fragment

The antibody fragment of the invention can be produced according to a known method. The antibody fragment of the invention may be produced by cleaving an antibody produced according to the method described in the above (1) to (8) using an enzyme or the like or may be produced by a genetic engineering technique after preparing a nucleotide sequence encoding a desired antibody fragment.

(10) Method for Producing Monovalent Antibody

In the invention, a monovalent antibody can be produced by the method described in WO 2014/054804, WO 2011/090754, WO 2007/048037, WO 2012/116927, or the like, or another method.

(11) Method for Producing Bispecific Antibody or Multispecific Antibody

The bispecific antibody or the multispecific antibody of the invention can be produced according to the method for producing the antibody described above. For example, the bispecific antibody or the multispecific antibody can be produced using the method described in WO 2009/131239, WO 2014/054804, WO 01/077342, US Patent Application Publication No. 2007/0071675, WO 2007/024715, Wu et al., [Nature Biotechnology, 2007, 25(11), pp. 1290-1297], Labrijn et al., [PNAS 2013, vol. 110, no. 13, pp. 5145-5150], Jong et al., [see 10.1371/journal.pbio.1002344, on the website: dx.doi.org], Kontermann et al., [mAbs 2012, vol. 4, issue 2, pp. 182-197], Spiess et al., [Molecular Immunology 67 (2015) 95-106], Ridgway et al., [Protein engineering, 1996 vol. 9 no. 7 pp. 617-621, WO 2009/080251, WO 2010/151792, WO 2014/033074, or the like.

For example, an expression vector for a bispecific antibody in which scFv that binds to CADM3 is fused to the C-terminus of an IgG antibody which binds to an antigen present in the brain can be produced by the method described below, and the bispecific antibody can be produced according to the method for expressing an antibody and the method for purifying an antibody described above. In addition, a bispecific antibody in which an antibody fragment is fused to the C-terminus of an antibody can also be produced in the same manner.

The gene fragment of a CH1-Hinge-CH2-CH3-linker region is amplified by a PCR method using a synthetic gene of a heavy chain constant region of an IgG antibody which binds to an antigen present in the brain as a template. Subsequently, by using the nucleotide sequence of an antibody which binds to CADM3 as a template, the nucleotide sequence of a scFv region in which VH and VL of the antibody are linked with an appropriate linker is prepared using a PCR method or the like. The two regions are linked by a PCR method or the like, and the obtained gene fragment is inserted into an appropriate vector such as a pCI vector.

Further, each of the gene fragments of the light chain domains (VL and CL) of an IgG antibody which binds to an antigen present in the brain and the gene fragment of VH of the antibody is amplified by a PCR method using an appropriate template and is inserted at an appropriate position of the vector.

In addition, the bispecific antibody of the invention can also be produced by binding an antigen-binding site comprising an antibody fragment to an IgG antibody by a chemical method.

3. Evaluation of Activity of Antibody or Antibody Fragment Thereof

In the invention, the activity of an antibody or an antibody fragment thereof can be evaluated as follows.

(1) Binding Activity to CADM3

The binding activity of the antibody or the antibody fragment thereof of the invention to CADM3 is measured using flow cytometry, ELISA, or surface plasmon resonance detection described in the above 1-(6), or the like. Further, the binding activity can also be measured using a fluorescent antibody method [Cancer Immunol. Immunother., 36, 373 (1993)].

Also when the antibody or the antibody fragment thereof of the invention is a monovalent antibody which binds to CADM3, the binding activity of the monovalent antibody to CADM3 can be measured in the same manner. Also when the antibody or the antibody fragment thereof of the invention is a bispecific antibody or a multispecific antibody which binds to CADM3 and an antigen present in the brain, the binding activity of the bispecific antibody or the multispecific antibody to CADM3 or the antigen present in the brain can be measured in the same manner.

(2) Measurement Method for Property of Accumulating in a Brain

The property of accumulating in a brain of the antibody or the antibody fragment thereof of the invention can be measured by the method described below.

A method in which a brain tissue is collected several days after administering the antibody or the antibody fragment thereof to an animal, the brain tissue is homogenized and centrifuged, and then, the concentration of the antibody or the antibody fragment thereof in the resulting supernatant is measured, and the amount of the antibody or the antibody fragment thereof per unit brain weight is calculated, a method in which the presence of the antibody or the antibody fragment thereof is detected by a known immunological method using the collected brain tissue, or the like is exemplified. Further, a method in which the antibody or the antibody fragment thereof labeled with a pharmacologically acceptable label is administered to an animal and the presence of the antibody or the antibody fragment thereof is detected over time by an in vivo imaging system, or the like is exemplified.

As the animal used for evaluation of the property of accumulating in a brain, a suitable animal depending on the use of the antibody or the antibody fragment thereof of the invention can be selected.

(3) Measurement Method for Antibody-Dependent Cellular Cytotoxicity Activity (ADCC) and Complement-Dependent Cytotoxicity Activity (CDC)

The CDC or ADCC of the antibody or the antibody fragment thereof of the invention to human CADM3-expressing cells or cells expressing CADM3 and an antigen present in the brain can be measured by a known measurement method [Cancer Immunol. Immunother., 36, 373 (1993): Current protocols in Immunology, Chapter 7. Immunologic studies in humans. Editor, John E, Coligan el al., John Wiley & Sons, Inc., (1993)].

4. Method for Controlling Effector Activity of Antibody or Antibody Fragment As a method for controlling the effector activity of the antibody or the antibody fragment thereof of the invention, a method for controlling the amount of α1,6-fucose (also called a core fucose) which binds to N-acetylglucosamine (GlcNAc) present at the reducing terminus of the N-linked complex glycan which binds to asparagine (Asn) at position 297 in the Fc region of the antibody or the antibody fragment thereof comprising Fc (WO 2005/035586, WO 2002/31140, WO 00/61739), a method for controlling by modifying an amino acid residue in the Fc region of the antibody or the antibody fragment thereof, and the like are known. The effector activity of the antibody or the antibody fragment thereof of the invention can be controlled using any of the methods.

The effector activity refers to an antibody-dependent activity that is caused through the Fc region of the antibody or the antibody fragment thereof, and ADCC, CDC, antibody-dependent phagocytosis (ADP) that is caused by phagocytes such as macrophages or dendritic cells, and the like are known.

As the measurement method for the effector activity, for example, the target cells, human peripheral blood mononuclear cells (PBMCs) as the effector, and a target cell-specific antibody or an antibody fragment thereof are mixed, followed by incubation for about 4 hours, and thereafter, released lactate dehydrogenase (LDH) can be measured as an index of cytotoxicity. In addition, the effector activity can also be measured by a $^{51}$Cr-release method, a flow cytometry method, or the like.

The effector activity of the antibody or the antibody fragment comprising Fc can be increased or decreased by controlling the content of the core fucose in the N-linked complex glycan of Fc of the antibody. As a method for decreasing the content of fucose which binds to the N-linked complex glycan bound to Fc of the antibody or the antibody fragment thereof, an antibody or an antibody fragment thereof to which fucose is not bound can be obtained by expressing the antibody or the antibody fragment thereof using CHO cells deficient in the α1,6-fucosyltransferase gene. The antibody or the antibody fragment thereof to which fucose is not bound has high ADCC.

On the other hand, as a method for increasing the content of fucose which binds to the N-linked complex glycan bound to Fc of the antibody or the antibody fragment thereof, an antibody or an antibody fragment thereof to which fucose is bound can be obtained by expressing the antibody or the antibody fragment thereof using a host cell into which the α1,6-fucosyltransferase gene has been introduced. The antibody or the antibody fragment thereof to which fucose is bound has lower ADCC than the antibody or the antibody fragment thereof to which fucose is not bound.

Further, by modifying an amino acid residue in the Fc region of the antibody or the antibody fragment thereof, the ADCC or CDC can be increased or decreased. For example, the CDC of the antibody or the antibody fragment thereof can be increased using the amino acid sequence of the Fc region described in US Patent Application Publication No. 2007/0148165.

Further, the ADCC or CDC can be increased or decreased by performing the amino acid modification described in U.S. Pat. Nos. 6,737,056, 7,297,775, or U.S. Pat. No. 7,317,091.

Further, the antibody or the antibody fragment thereof of the invention also comprises an antibody or an antibody fragment thereof whose half-life in the blood is controlled by controlling the reactivity with an Fc receptor, for example through the amino acid modification described in JP-A-2013-165716, JP-A-2012-021004, or the like in accordance with the amino acid modification or the glycan modification in the constant region comprised in the antibody or the antibody fragment thereof described above.

Further, by combing and using the above-mentioned methods for one antibody or an antibody fragment thereof, an antibody or an antibody fragment thereof whose effector activity or half-life in the blood is controlled can be obtained.

5. Method for Treating Disease Using Antibody or Antibody Fragment Thereof of Invention The antibody or the antibody fragment thereof of the invention can be used for treating a brain disease of an animal in which CADM3 is expressed in the brain.

Examples of the brain disease comprise Alzheimer's disease, a prodromal stage of Alzheimer's disease, Huntington disease, Parkinson's disease, a brain tumor, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, a cerebrovascular disorder, epilepsy, migraine, a hyperactivity disorder, Creutzfeldt-Jakob disease, corticobasal degeneration, a lysosomal storage disease, depression, dystonia, and the like.

The brain disease that can be treated with the antibody or the antibody fragment thereof of the invention differs depending on the antigen to which the antibody or the antibody fragment thereof of the invention binds, the type of the molecule which modifies the antibody or the antibody fragment thereof in the fusion antibody or the fusion antibody fragment thereof of the invention, or the like.

The therapeutic agent comprising the antibody or the antibody fragment thereof of the invention may be a therapeutic agent comprising only the antibody or the antibody fragment thereof as an active ingredient, however, in general, the therapeutic agent is provided as a pharmaceutical preparation produced by mixing with one or more pharmacologically acceptable carriers using a method known in the technical field of pharmaceutics.

Examples of the route of administration comprise oral administration or parenteral administration such as intraoral, intra-airway, intrarectal, subcutaneous, intramuscular, intraventricular, intraperitoneal administration, intradermal administration, intranasal administration, intrathecal administration, or intravenous administration. Examples of the dosage form comprise a spray, a capsule, a tablet, a powder, a granule, a syrup, an emulsion, a suppository, an injection, an ointment, a tape, and the like.

Examples of a formulation suitable for oral administration comprise an emulsion, a syrup, a capsule, a tablet, a powder, a granule, and the like.

A liquid preparation such as an emulsion or a syrup is produced using water, a saccharide such as sucrose, sorbitol, or fructose, a glycol such as polyethylene glycol or propylene glycol, an oil such as sesame oil, olive oil, or soybean oil, a preservative such as a p-hydroxybenzoic acid ester, a flavor such as strawberry flavor or peppermint, or the like as an additive.

A capsule, a tablet, a powder, a granule, or the like is produced using an excipient such as lactose, glucose, sucrose, or mannitol, a disintegrating agent such as starch or sodium alginate, a lubricant such as magnesium stearate or talc, a binder such as polyvinyl alcohol, hydroxypropyl cellulose, or gelatin, a surfactant such as a fatty acid ester, a plasticizer such as glycerin, or the like as an additive.

Examples of a formulation suitable for parenteral administration comprise an injection, a suppository, a spray, and the like. An injection is produced using a carrier composed of a salt solution, a glucose solution, or a mixture of both solutions, or the like. A suppository is produced using a carrier such as cacao butter, a hydrogenated fat, or carboxylic acid.

A spray is produced using a carrier which does not stimulate the buccal or airway mucous membrane of a recipient and disperses the antibody or the antibody fragment thereof of the invention as fine particles so as to facilitate absorption thereof, or the like. As the carrier, for example, lactose, glycerin, or the like is used. In addition, the spray can also be produced as an aerosol or a dry powder. Further, a component exemplified as the additive for the formulation suitable for oral administration can also be added to the above-mentioned parenteral preparation.

6. Method for Detecting or Measuring Antigen Present in Brain or Method for Diagnosing Disease Using Antibody or Antibody Fragment Thereof of Invention By using the antibody or the antibody fragment thereof of the invention, CADM3 or CADM3 and an antigen present in the brain can be detected or measured. Further, by detecting or measuring CADM3 or CADM3 and an antigen present in the brain, a brain disease of an animal in which CADM3 is expressed in the brain can be diagnosed.

Examples of the brain disease comprise Alzheimer's disease, a prodromal stage of Alzheimer's disease, Huntington disease, Parkinson's disease, a brain tumor, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, a cerebrovascular disorder, epilepsy, migraine, a hyperactivity disorder, Creutzfeldt-Jakob disease, corticobasal degeneration, a lysosomal storage disease, depression, dystonia, and the like, however, the brain disease that can be diagnosed with the antibody or the antibody fragment thereof of the invention differs depending on the antigen to which the antibody or the antibody fragment thereof of the invention binds, the type of the molecule which modifies the antibody or the antibody fragment thereof in the fusion antibody or the fusion antibody fragment thereof of the invention, and the like.

The brain disease of an animal in which CADM3 is expressed in the brain can be diagnosed, for example, by detecting or measuring CADM3 present in the brain of a patient or a diseased animal by an immunological method. Further, the brain disease can be diagnosed by detecting CADM3 that is expressed or present in cells in the brain of a patient or a diseased animal using an immunological method such as flow cytometry.

When a monovalent antibody which binds to CADM3 is used as the antibody or the antibody fragment thereof of the invention, CADM3 in the brain can be measured in the same manner as described above. When a bispecific antibody or a multispecific antibody which binds to CADM3 and an antigen present in the brain is used as the antibody or the antibody fragment thereof of the invention, CADM3 in the brain or the antigen present in the brain can be detected or measured in the same manner as described above.

The immunological method is a method for detecting or measuring the amount of an antibody or the amount of an antigen using a labeled antigen or antibody, or the like. For example, a radioactive material labeled immune antibody method, an enzyme immunoassay method, a fluorescence immunoassay method, a luminescence immunoassay method, a Western blotting method, a physicochemical method, or the like is used.

In the radioactive material labeled immune antibody method, for example, the antibody or the antibody fragment thereof of the invention is allowed to react with an antigen or cells expressing an antigen, or the like, and then, an anti-immunoglobulin antibody or an antibody fragment thereof subjected to radiolabeling is further allowed to react therewith, followed by measurement with a scintillation counter or the like.

In the enzyme immunoassay method, for example, the antibody or the antibody fragment thereof of the invention is allowed to react with an antigen or cells expressing an antigen, or the like, and then, an anti-immunoglobulin antibody or an antibody fragment thereof subjected to labeling with an enzyme or the like is further allowed to react therewith, followed by adding a substrate and measuring the absorbance of the reaction solution with an absorptiometer. For example, a sandwich ELISA method or the like is used. As a labeling substance used in the enzyme immunoassay method, a known [Enzyme Immunoassay Method, Igaku-Shoin Ltd. (1987)] enzyme label can be used.

For example, an alkaline phosphatase label, a peroxidase label, a luciferase label, a biotin label, or the like is used. The sandwich ELISA method is a method in which after an antibody is bound to a solid phase, an antigen to be detected or measured is trapped, and then, a second antibody is allowed to react with the trapped antigen.

In the ELISA method, two types of antibodies which recognize the antigen desired to be detected or measured and which have different antigen recognition sites are prepared, and among these, a first antibody is adsorbed on a plate (for example, a 96-well plate) in advance, and subsequently, a second antibody is labeled with a fluorescent substance such as FITC, an enzyme such as peroxidase, or biotin, or the like beforehand.

With the plate on which the first antibody is adsorbed, cells or a homogenate thereof, tissues or a homogenate thereof, a cell culture supernatant, serum, pleural effusion, ascites, intraocular fluid, or the like separated from the living body is allowed to react, and thereafter the second antibody is allowed to react, followed by a detection reaction according to the labeling substance. From a calibration curve created by serially diluting the antigen at a known concentration, the antigen concentration in the test sample is calculated.

As the antibody used in the sandwich ELISA method, either a polyclonal antibody or a monoclonal antibody may be used. Further, an antibody fragment such as Fab, Fab' or $F(ab)_2$ may be used in place of the antibody. The combination of the two types of antibodies used in the sandwich ELISA method may be a combination of monoclonal antibodies or antibody fragments thereof which recognize different epitopes or may be a combination of a polyclonal antibody and a monoclonal antibody or antibody fragments thereof.

In the fluorescence immunoassay method, measurement is carried out by the method described in the documents [Monoclonal Antibodies-Principles and practice, Third edition, Academic Press (1996), Manual for monoclonal antibody experiments, Kodansha scientific books (1987)] or the like. As the labeling substance used in the fluorescence immunoassay method, a known [Fluorescent Antibody Method, Soft Science, Inc. (1983)]fluorescent label can be used. For example, FITC, RITC, or the like is used.

In the luminescence immunoassay method, measurement is carried out by the method described in the document [Bioluminescence and Chemiluminescence, Clinical Test 42, Hirokawa-Shoten Ltd. (1998)] or the like. As the labeling substance used in the luminescence immunoassay method, a known luminescent label is exemplified, and an acridinium ester, lophine, or the like is used.

In the Western blotting method, after fractionating an antigen, cells expressing an antigen, or the like by SDS (sodium dodecyl sulfate)-PAGE (polyacrylamide gel) [Antibodies—A Laboratory Manual Cold Spring Harbor Laboratory (1988)], the gel is blotted on a polyvinylidene fluoride (PVDF) membrane or a nitrocellulose membrane, an antibody or an antibody fragment thereof that recognizes the antigen is allowed to react with the membrane, and further, an anti-mouse IgG antibody or a binding fragment subjected to labeling with a fluorescent substance such as FITC, labeling with an enzyme such as peroxidase, biotin labeling or the like is allowed to react therewith, followed by visualizing the label, whereby measurement is carried out. An example is shown below.

Cells or tissues expressing a polypeptide having the amino acid sequence of CADM3 are lysed, and 0.1 to 30 µg as a protein amount per lane is subjected to electrophoresis by the SDS-PAGE method under reducing conditions. The electrophoresed proteins are transferred to a PVDF membrane and allowed to react with BSA-PBS at room temperature for 30 minutes to perform a blocking operation.

Here, the antibody or the antibody fragment thereof of the invention is allowed to react, and the membrane is washed with PBS comprising 0.05 to 0.1% polyoxyethylene sorbitan monolaurate (Tween 20) (hereinafter referred to as Tween-PBS) and allowed to react with a goat anti-mouse IgG labeled with peroxidase at room temperature for 2 hours.

By washing with Tween-PBS and detecting a band to which the antibody or the antibody fragment thereof of the invention is bound using ECL Western Blotting Detection Reagents (manufactured by Amersham, Inc.) or the like, the polypeptide having the amino acid sequence of CADM3 is detected.

As the antibody or the antibody fragment thereof used for detection by Western blotting, an antibody or an antibody fragment thereof capable of binding to a polypeptide which does not retain the natural conformation is used.

The physicochemical method is carried out, for example, by binding CADM3, which is the antigen, to the antibody or the antibody fragment thereof of the invention to form an aggregate and detecting the aggregate. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)], or the like can also be used.

In the latex immunoturbidimetric method, when a carrier such as a polystyrene latex having a particle size of about 0.1 to 1 µm sensitized with an antibody or an antigen is used to cause the antigen-antibody reaction with a corresponding antigen or antibody, the scattered light is increased in a reaction solution, and the transmitted light is decreased. The antigen concentration or the like in a test sample is measured by detecting this change as an absorbance or an integrating sphere turbidity.

For the detection or measurement of cells expressing CADM3, a known immunological detection method can be used, but particularly, an immunoprecipitation method, an immunocytochemical staining method, an immunohistochemical staining method, a fluorescent antibody staining method, or the like is preferably used.

In the immunoprecipitation method, after allowing cells or the like expressing CADM3 to react with the antibody or the antibody fragment thereof of the invention, a carrier having a specific binding ability to an immunoglobulin such as Protein G-Sepharose is added thereto to precipitate an antigen-antibody complex. Alternatively, the method can also be carried out by the following method.

The antibody or the antibody fragment thereof of the invention described above is immobilized on a 96-well plate for ELISA, followed by blocking with BSA-PBS. When the antibody is, for example, in an unpurified state such as a hybridoma culture supernatant, anti-mouse immunoglobulin, anti-rat immunoglobulin, protein A, protein G, or the like is immobilized on a 96-well plate for ELISA in advance, followed by blocking with BSA-PBS, and thereafter, the hybridoma culture supernatant is dispensed and bound thereto.

Subsequently, BSA-PBS is discarded, and the plate is thoroughly washed with PBS, and then, a lysate solution of cells or tissues expressing human CADM3 is allowed to react therewith. From the plate after being thoroughly washed, an immunoprecipitate is extracted with a sample buffer for SDS-PAGE, and then detected by the above-mentioned Western blotting.

The immunocytostaining method or the immunohistochemical staining method is a method in which cells or tissues expressing an antigen, or the like are treated with a surfactant or methanol, or the like for enhancing the permeability of the antibody in some cases, and then are allowed to react with the antibody of the invention, and further allowed to react with an anti-immunoglobulin antibody or a binding fragment thereof fluorescently labeled with FITC or the like, labeled with an enzyme such as peroxidase, or labeled with biotin, or the like, and thereafter the label is visualized, and then observed with a microscope.

In addition, detection can be carried out by a fluorescent antibody staining method in which a fluorescently labeled antibody is allowed to react with a cell and analyzed with a flow cytometer [Monoclonal Antibodies—Principles and Practice, Third edition, Academic Press (1996), Monoclonal Antibody Experimental Manual, Kodansha scientific books (1987)]. In particular, the antibody or the antibody fragment thereof of the invention enables detection of a cell which expresses the detection target while retaining the natural conformation by a fluorescent antibody staining method.

In addition, when the FMAT 8100 HTS system (manufactured by Applied Biosystems, Inc.) or the like is used in the fluorescent antibody staining method, the amount of an antigen or the amount of an antibody can be measured without separating the formed antibody-antigen complex from a free antibody or antigen that is not involved in the formation of the antibody-antigen complex.

Hereinafter, the invention will be more specifically described by way of Examples, however, the invention is not limited to the following Examples.

EXAMPLES

[Example 1] Acquisition of Anti-CADM3 Antibody (1) Acquisition of Antibody Using Alpaca Antibody Library Emulsions were produced using hCADM3-FLAG_Fc and mCADM3-FLAG_Fc produced in Example 4 described below as immunogens with TiterMax (manufactured by TiterMax USA, Inc.) for the first immunization and with an incomplete adjuvant (manufactured by BD company) for the second to fifth immunization, and an alpaca was immunized therewith.

Lymphocytes ($2\times10^7$ cells) were collected from the blood (50 mL) of the immunized alpaca, and RNA was extracted from the obtained cells using RNA IsoPlus (manufactured by TAKARA, Inc.). Further, cDNAs were synthesized by a reverse transcription reaction using SuperScript (registered trademark) III First-Strand Synthesis System for RT-PC (manufactured by Invitrogen, Inc.), and thereafter, a VHH gene was amplified using primers specific to alpaca IgG2 (Short hinge-heavy chain antibody) and IgG3 (Long hinge-heavy chain antibody). The VHH gene fragment was inserted into a phagemid vector pKSTV402 (Miyazaki el al., J. Biochem., 158(3), 205-215, 2015), and E. coli TG1 was transformed by electroporation using a MicroPulser electroporator (manufactured by Bio-Rad Laboratories. Inc.).

The obtained transformant was infected with M13KO7 Helper Phage (manufactured by Invitrogen, Inc.), whereby an alpaca antibody M13 phage library of the VHH gene was obtained.

By using the alpaca antibody M13 phage library, anti-CADM3 antibodies were obtained using the biopanning method described below. hCADM3-GST of Example 4 described below was immobilized on an immuno tube, and the tube was blocked using 0.5% BSA. The alpaca antibody M13 phage library was allowed to react with the tube at room temperature for 1 hour, and washing was carried out with PBS-T, and then, the phage was eluted with a 0.1 mol/L glycine-hydrochloride buffer solution (Gly-HCl) (pH 2.7). The eluate was neutralized by adding a trishydroxymethyl-aminomethane hydrochloride buffer solution (Tris-HCl) (pH 9.1) thereto. E. coli TG1 was infected with the eluted phage, and the phage was amplified.

Thereafter, the phage was allowed to react with mCADM3-GST immobilized on an immuno tube, followed by washing and elution. Further, the phage was allowed to react with hCADM3-GST immobilized on an immuno tube, followed by washing and elution, whereby phages displaying VHH which specifically binds to hCADM3-GST and mCADM3-GST were concentrated. The concentrated phages were monocloned, and clones having affinity for hCADM3-GST and mCADM3-GST were selected by ELISA.

In the ELISA, hCADM3-GST and mCADM3-GST were immobilized (50 ng/50 µL) on MAXISORP (manufactured by NUNC, Inc.), followed by blocking using 0.5% BSA. To each well, each phage clone was added and allowed to react at room temperature for 1 hour, and thereafter, each well was washed 5 times with PBS-T. Subsequently, a biotinylated anti-M13 phage antibody (manufactured by Abcam plc) and horseradish peroxidase-labeled streptavidin (manufactured by Vector Co., Ltd.) were added to each well in an amount of 50 µL, followed by incubation at room temperature for 1 hour.

After the microplate was washed with PBS-T, a 3,3',5,5'-tetramethylbenzidine (TMB) chromogenic substrate solution (manufactured by Calbiochem, Inc.) was added to each well, followed by incubation at room temperature. The coloring reaction was stopped by adding a 1 mol/L hydrochloric acid to each well, and an absorbance at a wavelength of 450 nm (reference wavelength: 570 nm) was measured using a microplate reader.

A sequence analysis was carried out for clones bound to hCADM3-GST and mCADM3-GST, and the following anti-CADM3 VHH antibodies: iCADM3_3R1-L5, iCADM3_3R1-L8, iCADM3_3R1-L10, and iCADM3_3R1-L11 were obtained. The nucleotide sequences encoding VHH of various types of anti-CADM3 antibodies, and the amino acid sequences deduced from the nucleotide sequences are shown in Table 1.

TABLE 1

| | Clone Name | | | |
|---|---|---|---|---|
| | iCADM3_3R1-L5 | iCADM3_3R1-L8 | iCADM3_3R1-L10 | iCADM3_3R1-L11 |
| Nucleotide sequence encoding VHH (excluding signal sequence) | SEQ ID NO: 1 | SEQ ID NO: 6 | SEQ ID NO: 11 | SEQ ID NO: 16 |
| Amino acid sequence of VHH (excluding signal sequence) | SEQ ID NO: 2 | SEQ ID NO: 7 | SEQ ID NO: 12 | SEQ ID NO: 17 |
| Amino acid sequence of CDR1 | SEQ ID NO: 3 | SEQ ID NO: 8 | SEQ ID NO: 13 | SEQ ID NO: 18 |
| Amino acid sequence of CDR2 | SEQ ID NO: 4 | SEQ ID NO: 9 | SEQ ID NO: 14 | SEQ ID NO: 19 |
| Amino acid sequence of CDR3 | SEQ ID NO: 5 | SEQ ID NO: 10 | SEQ ID NO: 15 | SEQ ID NO: 20 |

(2) Acquisition of Antibody Using Human Antibody Phage Libraries

A VH gene fragment and a VL gene fragment were amplified from human PBMC-derived cDNAs by PCR. Each of the VH gene fragment and the VL gene fragment was inserted into a phagemid vector pCANTAB 5E (manufactured by Amersham Pharmacia Biotech, Inc.), and plasmids were obtained by transforming E. coli TG1 (manufactured by Lucigen Corporation). The obtained plasmids were infected with M13KO7 Helper Phage (manufactured by Invitrogen, Inc.), whereby human antibody M13 phage libraries of the VH gene and the VL gene were obtained.

By using the human antibody M13 phage libraries, anti-CADM3 monoclonal antibodies were obtained using the phage display method described below. hCADM3-FLAG_Fc, rCADM3-FLAG_Fc, or mCADM3-FLAG_Fc of Example 4 described below was immobilized on a MAXISORP STARTUBE (manufactured by NUNC, Inc.), followed by blocking using SuperBlock Blocking Buffer (manufactured by Thermo Fisher Scientific, Inc.).

The human antibody M13 phage library was allowed to react with the tube at room temperature for 1 hour, and washing was carried out with PBS or PBS-T, and thereafter, the phage was eluted with 0.1 mol/L Gly-HCl (pH 2.2). The eluate was neutralized by adding Tris-HCl (pH 8.5) thereto. TG1 competent cells were infected with the eluted phage, and the phage was amplified.

Thereafter, the phage was allowed to react with hCADM3-FLAG_Fc, rCADM3-FLAG_Fc, or mCADM3-FLAG_Fc immobilized on the MAXISORP STARTUBE again, followed by washing and elution. This procedure was repeated to concentrate phages displaying scFv which specifically binds to hCADM3-FLAG_Fc, rCADM3-FLAG_Fc, and mCADM3-FLAG_Fc. The concentrated phages were monocloned, and clones having affinity for CADM3 were selected by ELISA.

In the ELISA, hCADM3-FLAG_Fc, rCADM3-FLAG_Fc, and mCADM3-FLAG_Fc were immobilized on MAXISORP (manufactured by NUNC, Inc.), followed by blocking using SuperBlock Blocking Buffer (manufactured by Thermo Fisher Scientific, Inc.). As a negative control, a plate on which Fc was immobilized was also prepared.

To each well, each phage clone was added and allowed to react at room temperature for 30 minutes, and thereafter, each well was washed with PBS-T. Subsequently, a solution obtained by diluting an anti-M13 antibody (manufactured by GE Healthcare, Inc.) labeled with horseradish peroxidase with PBS-T comprising 10% Block Ace (manufactured by Dainippon Pharmaceutical Co., Ltd.) was added to each well and incubated at room temperature for 30 minutes.

After the microplate was washed 3 times with PBS-T, a TMB chromogenic substrate solution (manufactured by DAKO. Inc.) was added thereto, followed by incubation at room temperature. The coloring reaction was stopped by adding a 0.5 mol/L sulfuric acid to each well, and an absorbance at a wavelength of 450 nm (reference wavelength: 570 nm) was measured using a microplate reader.

A sequence analysis was carried out for clones obtained by panning using CADM3-FLAG_Fc, and phagemid vectors encoding CADM301, CADM3102, CADM3219, CADM3301, CADM3309, CADM3312, CADM3314, CADM3316, CADM3349, CADM3351, CADM3402, CADM3404, CADM3432, CADM3448, CADM3458, or CADM3501 were obtained, respectively.

The nucleotide sequences encoding VH or VL of various types of anti-CADM3 antibodies, and the amino acid sequences deduced from the nucleotide sequences are shown in Table 2A and Table 2B.

TABLE 2A

|  | Clone Name | |
|---|---|---|
|  | CADM301 | CADM3102 |
| Nucleotide sequence encoding VH (excluding signal sequence) | SEQ ID NO: 21 | SEQ ID NO: 31 |
| Amino acid sequence of VH (excluding signal sequence) | SEQ ID NO: 22 | SEQ ID NO: 32 |
| Amino acid sequence of HCDR1 | SEQ ID NO: 23 | SEQ ID NO: 33 |
| Amino acid sequence of HCDR2 | SEQ ID NO: 24 | SEQ ID NO: 34 |
| Amino acid sequence of HCDR3 | SEQ ID NO: 25 | SEQ ID NO: 35 |
| Nucleotide sequence encoding VL (excluding signal sequence) | SEQ ID NO: 26 | SEQ ID NO: 36 |
| Amino acid sequence of VL (excluding signal sequence) | SEQ ID NO: 27 | SEQ ID NO: 37 |
| Amino acid sequence of LCDR1 | SEQ ID NO: 28 | SEQ ID NO: 38 |
| Amino acid sequence of LCDR2 | SEQ ID NO: 29 | SEQ ID NO: 39 |
| Amino acid sequence of LCDR3 | SEQ ID NO: 30 | SEQ ID NO: 40 |

TABLE 2B

|  | Clone Name | | | | | | | |
|---|---|---|---|---|---|---|---|---|
|  | CADM3219 | CADM3301 | CADM3309 | CADM3312 | CADM3314 | CADM3316 | CADM3349 | CADM3351 |
| Nucleotide sequence encoding VH (excluding signal sequence) | SEQ ID NO: 87 | SEQ ID NO: 97 | SEQ ID NO: 102 | SEQ ID NO: 107 | SEQ ID NO: 112 | SEQ ID NO: 117 | SEQ ID NO: 122 | SEQ ID NO: 127 |
| Amino acid sequence of VH (excluding signal sequence) | SEQ ID NO: 88 | SEQ ID NO: 98 | SEQ ID NO: 103 | SEQ ID NO: 108 | SEQ ID NO: 113 | SEQ ID NO: 118 | SEQ ID NO: 123 | SEQ ID NO: 128 |
| Amino acid sequence of HCDR1 | SEQ ID NO: 89 | SEQ ID NO: 99 | SEQ ID NO: 104 | SEQ ID NO: 109 | SEQ ID NO: 114 | SEQ ID NO: 119 | SEQ ID NO: 124 | SEQ ID NO: 129 |
| Amino acid sequence of HCDR2 | SEQ ID NO: 90 | SEQ ID NO: 100 | SEQ ID NO: 105 | SEQ ID NO: 110 | SEQ ID NO: 115 | SEQ ID NO: 120 | SEQ ID NO: 125 | SEQ ID NO: 130 |
| Amino acid sequence of HCDR3 | SEQ ID NO: 91 | SEQ ID NO: 101 | SEQ ID NO: 106 | SEQ ID NO: 111 | SEQ ID NO: 116 | SEQ ID NO: 121 | SEQ ID NO: 126 | SEQ ID NO: 131 |
| Nucleotide sequence encoding VL (excluding signal sequence) | SEQ ID NO: 92 | | | | SEQ ID NO: 132 | | | |
| Amino acid sequence of VL (excluding signal sequence) | SEQ ID NO: 93 | | | | SEQ ID NO: 133 | | | |
| Amino acid sequence of LCDR1 | SEQ ID NO: 94 | | | | SEQ ID NO: 134 | | | |
| Amino acid sequence of LCDR2 | SEQ ID NO: 95 | | | | SEQ ID NO: 135 | | | |
| Amino acid sequence of LCDR3 | SEQ ID NO: 96 | | | | SEQ ID NO: 136 | | | |

|  | Clone Name | | | | | |
|---|---|---|---|---|---|---|
|  | CADM3402 | CADM3404 | CADM3432 | CADM3448 | CADM3458 | CADM3501 |
| Nucleotide sequence encoding VH (excluding signal sequence) | SEQ ID NO: 137 | SEQ ID NO: 142 | SEQ ID NO: 147 | SEQ ID NO: 152 | SEQ ID NO: 157 | SEQ ID NO: 167 |
| Amino acid sequence of VH (excluding signal sequence) | SEQ ID NO: 138 | SEQ ID NO: 143 | SEQ ID NO: 148 | SEQ ID NO: 153 | SEQ ID NO: 158 | SEQ ID NO: 168 |
| Amino acid sequence of HCDR1 | SEQ ID NO: 139 | SEQ ID NO: 144 | SEQ ID NO: 149 | SEQ ID NO: 154 | SEQ ID NO: 159 | SEQ ID NO: 169 |
| Amino acid sequence of HCDR2 | SEQ ID NO: 140 | SEQ ID NO: 145 | SEQ ID NO: 150 | SEQ ID NO: 155 | SEQ ID NO: 160 | SEQ ID NO: 170 |
| Amino acid sequence of HCDR3 | SEQ ID NO: 141 | SEQ ID NO: 146 | SEQ ID NO: 151 | SEQ ID NO: 156 | SEQ ID NO: 161 | SEQ ID NO: 171 |
| Nucleotide sequence encoding VL (excluding signal sequence) | | | SEQ ID NO: 162 | | | SEQ ID NO: 172 |

TABLE 2B-continued

| | | |
|---|---|---|
| Amino acid sequence of VL (excluding signal sequence) | SEQ ID NO: 163 | SEQ ID NO: 173 |
| Amino acid sequence of LCDR1 | SEQ ID NO: 164 | SEQ ID NO: 174 |
| Amino acid sequence of LCDR2 | SEQ ID NO: 165 | SEQ ID NO: 175 |
| Amino acid sequence of LCDR3 | SEQ ID NO: 166 | SEQ ID NO: 176 |

[Example 2] Production of Antibody (1) Construction of CADM3 VHH-hG4PE(R409K) Expression Vector An expression vector was constructed for producing a VHH-Fc antibody in which each anti-CADM3 VHH antibody was bound to the Fc region of a human IgG4 antibody comprising amino acid residue substitutions of S228P, L235E, and R409K according to the EU numbering (hereinafter sometimes abbreviated as "IgG4 variant").

The gene fragment of the VHH region was amplified by PCR using a synthetic gene of VHH of each of iCADM3_3R1-L5, iCADM3_3R1-L8, iCADM3_3R1-L10, and iCADM3_3R1-L11 as a template. The gene fragment of the Hinge-CH2-CH3 region was amplified by PCR using a synthetic gene of the heavy chain constant region as a template. The obtained gene fragments were inserted into a pCI vector (manufactured by Promega, Inc.), whereby a pCI_iCADM3_3R1-L5 VHH-hG4PE(R409K) vector was produced.

Antibody expression vectors in which the gene fragment of the VHH region of each of the various types of anti-CADM3 antibodies shown in Table 1 was inserted were produced in the same manner and named pCI_iCADM3_3R1-L8 VHH-hG4PE(R409K) vector, pCI_iCADM3_3R1-L10 VHH-hG4PE(R409K) vector, and pCI_iCADM3_3R1-L11 VHH-hG4PE(R409K) vector, respectively.

(2) Construction of CADM3 scFv-hG4PE(R409K) Expression Vector

An expression vector was constructed for producing a scFv-Fc antibody in which the antibody variable region of an anti-CADM3 antibody was bound to the Fc region of the human IgG4 variant. The gene fragment of the scFv region was amplified by PCR using the phagemid vector encoding CADM301 obtained in Example 1(2) as a template. The gene fragment of the Hinge-CH2-CH3 region was amplified by PCR using a synthetic gene of the heavy chain constant region as a template.

The obtained gene fragments were inserted into an N5 vector (manufactured by IDEC, Inc.), whereby an N5_CADM301 scFv-hG4PE vector was produced. An N5_CADM3102 scFv-hG4PE vector was produced using the phagemid vector encoding CADM3102 obtained in Example 1(2) as a template.

(3) Construction of CADM3 hG4PE(R409K) Expression Vector

Each gene fragment of the variable region was amplified by PCR using each of the phagemid vectors encoding CADM3219, CADM3301, CADM3309, CADM3312, CADM3314, CADM3316, CADM3349, CADM3351, CADM3402, CADM3404, CADM3432, CADM3448, CADM3458, or CADM3501 obtained in Example 1(2) as a template. Each of the obtained gene fragments was inserted into a pCI vector (manufactured by Promega, Inc.), whereby pCI-hKG4PE(R409K)_CADM3219, pCI-hKG4PE(R409K)_ CADM3301, pCI-hKG4PE(R409K)_CADM3309, pCI-hKG4PE(R409K)_CADM3312, pCI-hKG4PE(R409K)_CADM3314, pCI-hKG4PE(R409K)_CADM3316, pCI-hKG4PE(R409K)_CADM3349, pCI-hKG4PE(R409K)_CADM3351, pCI-hKG4PE(R409K)_CADM3402, pCI-hKG4PE(R409K)_CADM3404, pCI-hKG4PE(R409K)_CADM3432, pCI-hKG4PE(R409K)_CADM3448, pCI-hKG4PE(R409K)_CADM3458, and pCI-hKG4PE(R409K)_CADM3501 were produced, respectively.

(4) Construction of pCI_AVM-hLG4PE(R409K)-CADM3 VHH Vector

An expression vector was constructed for producing an anti-AVM-IgG4-CADM3 VHH bispecific antibody in which two anti-CADM3 VHH antibodies were bound to the C-terminal side of an anti-AVM-IgG4 antibody. The gene fragments of the VL and VH regions were amplified by PCR using a variable region of an anti-AVM antibody as a template, and the gene fragments of CL and the CH1-Hinge-CH2-CH3-linker region were amplified by PCR using a synthetic gene as a template. Further, the gene fragment the VHH region was amplified by PCR using a synthetic gene of VHH of each of iCADM3_3R1-L5, iCADM3_3R1-L8, iCADM3_3R1-L10, and iCADM3_3R1-L11 as a template.

The obtained gene fragments were inserted into a pCI vector (manufactured by Promega. Inc.), whereby a pCI_AVM-hLG4PE(R409K)-iCADM3_3R1-L5 VHH vector, a pCI_AVM-hLG4PE(R409K)-iCADM3_3R1-L8 VHH vector, a pCI_AVM-hLG4PE(R409K)-iCADM3_3R1-L10 VHH vector, and a pCI_AVM-hLG4PE(R409K)-iCADM3_3R1-L11 VHH vector were produced.

The names of the antibody expression vectors, the nucleotide sequences encoding the heavy chain or the light chain of the antibodies, and the amino acid sequences deduced from the nucleotide sequences are shown in Table 3.

TABLE 3

| Name of antibody expression vector | Nucleotide sequence encoding light chain (excluding signal sequence) | Amino acid sequence of light chain (excluding signal sequence) | Nucleotide sequence encoding heavy chain (excluding signal sequence) | Amino acid sequence of heavy chain (excluding signal sequence) |
|---|---|---|---|---|
| pCI_AVM-hLG4PE(R409K)-iCADM3_3R1-L5 VHH | SEQ ID NO: 41 | SEQ ID NO: 42 | SEQ ID NO: 43 | SEQ ID NO: 44 |
| pCI_AVM-hLG4PE(R409K)-iCADM3_3R1-L8 VHH | | | SEQ ID NO: 45 | SEQ ID NO: 46 |

TABLE 3-continued

| Name of antibody expression vector | Nucleotide sequence encoding light chain (excluding signal sequence) | Amino acid sequence of light chain (excluding signal sequence) | Nucleotide sequence encoding heavy chain (excluding signal sequence) | Amino acid sequence of heavy chain (excluding signal sequence) |
|---|---|---|---|---|
| pCI_AVM-hLG4PE(R409K)-iCADM3_3R1-L10 VHH | | | SEQ ID NO: 47 | SEQ ID NO: 48 |
| pCI_AVM-hLG4PE(R409K)-iCADM3_3R1-L11 VHH | | | SEQ ID NO: 49 | SEQ ID NO: 50 |

(5) Construction of Anti-Avermectin Antibody Expression Vector and pCI_AVM-hLG4PE(R409K)_AVMscFv5 Vector As a negative control antibody, a chimeric anti-Avermectin (AVM) antibody was produced. An SD rat was immunized with AVM, and an anti-AVM antibody-producing hybridoma was established by a conventional method. The gene fragments of VL and VH were amplified by PCR using a variable region derived from the hybridoma as a template. A synthesized nucleotide sequence encoding the lambda chain constant region of human IgG and the amplified variable region were inserted into an N5KG4PE vector (described in WO 2002/088186), whereby an expression vector N5LG4PE_AVM was produced.

The gene fragments of CL and the CH1-Hinge-CH2-CH3-linker region were amplified by PCR using a synthetic gene as a template. Further, the gene fragments of VH and VL of AVM were amplified by PCR using N5LG4PE_AVM as a template. The obtained gene fragments were inserted into a pCI vector (manufactured by Promega, Inc.), whereby a pCI_AVM-hLG4PE(R409K)-AVMscFv5 vector was produced.

(6) Preparation of Antibody

The antibody expression plasmid vector was introduced into Expi293F cells (manufactured by Thermo Fisher Scientific, Inc.) using Expi293 (trademark) Expression System (manufactured by Thermo Fisher Scientific, Inc.), and the cells were cultured to express the antibody in a transient expression system. The culture supernatant was collected 3 to 4 days after the introduction of the vector and filtered through a membrane filter having a pore size of 0.22 m (manufactured by Merck Millipore Corporation). The antibody protein in this culture supernatant was subjected to affinity purification using a Protein A resin (MabSelect SuRe, manufactured by GE Healthcare Biosciences, Inc.).

As the washing solution, a phosphate buffer solution was used. The protein adsorbed on the Protein A was eluted with a 20 mmol/L sodium citrate and 50 mmol/L NaCl buffer solution (pH 3.4) and collected in a tube comprising 1 mol/L Tris-HCl (pH 8.0). Subsequently, the solvent in the eluate was replaced with PBS by ultrafiltration using Amicon Ultra (manufactured by Merck Millipore Corporation) and a NAP column (manufactured by GE Healthcare Biosciences, Inc.), and thereafter, the obtained solution was sterilized by filtration through a membrane filter having a pore size of 0.22 μm (manufactured by Merck Millipore Corporation). An absorbance at 280 nm of the antibody solution was measured, and the concentration of the purified antibody was calculated.

Anti-CADM3 VHH-Fc antibodies obtained by expressing the vectors produced in Example 2(1) were named iCADM3_3R1-L5 VHH-hG4PE(R409K), iCADM3_3R1-L8 VHH-hG4PE(R409K), iCADM3_3R1-L10 VHH-hG4PE(R409K), and iCADM3_3R1-L11 VHH-hG4PE(R409K), respectively.

Anti-CADM3 scFv-Fc antibodies obtained by expressing the vectors produced in Example 2(2) were named CADM301 scFv-hG4PE and CADM3102 scFv-hG4PE, respectively.

Anti-CADM3 antibodies obtained by expressing the vectors produced in Example 2(3) were named CADM3219-hG4PE, CADM3301-hG4PE, CADM3309-hG4PE, CADM3312-hG4PE, CADM3314-hG4PE, CADM3316-hG4PE, CADM3349-hG4PE, CADM3351-hG4PE, CADM3402-hG4PE, CADM3404-hG4PE, CADM3432-hG4PE, CADM3448-hG4PE, CADM3458-hG4PE, and CADM3501-hG4PE, respectively.

Anti-AVM-IgG4-CADM3 VHH bispecific antibodies obtained by expressing the pCI_AVM-hLG4PE(R409K)-iCADM3_3R1-L5 VHH vector, the pCI_AVM-hLG4PE(R409K)-iCADM3_3R1-L8 VHH vector, the pCI_AVM-hLG4PE(R409K)-iCADM3_3R1-L10 VHH vector, and the pCI_AVM-hLG4PE(R409K)-iCADM3_3R1-L11 VHH vector produced in Example 2(4) were named AVM IgG4PE(R409K)_iCADM3_3R1-L5 dVHH, AVM IgG4PE(R409K)_ iCADM3_3R1-L8 dVHH, AVM IgG4PE(R409K)_iCADM3_3R1-L10 dVHH, and AVM IgG4PE(R49K)_iCADM3_3R1-L11 dVHH, respectively.

Further, an anti-AVM-IgG4 antibody obtained by expressing the N5LG4PE_AVM produced in Example 2(5), and an anti-AVM-IgG4-AVM dscFv bispecific antibody obtained by expressing the pCI_AVM-hLG4PE(R409K)-AVMscFv5 vector produced in Example 2(4) were named anti-AVM antibody and AVM IgG4PE(R409K)_AVM dscFv5, respectively.

[Example 3] Analysis of Reactivity with CADM3-Expressing Cells

The nucleotide sequence encoding human CADM3 is represented by SEQ ID NO: 51, an amino acid sequence deduced from the nucleotide sequence is represented by SEQ ID NO: 52, the nucleotide sequence encoding mouse CADM3 is represented by SEQ ID NO: 53, an amino acid sequence deduced from the nucleotide sequence is represented by SEQ ID NO: 54, the nucleotide sequence encoding monkey CADM3 is represented by SEQ ID NO: 55, and an amino acid sequence deduced from the nucleotide sequence is represented by SEQ ID NO: 56.

The full-length gene sequences of human CADM3, mouse CADM3, and monkey CADM3 were synthesized, and the gene sequences were each inserted into the BamHI-NotI site of a pEF6/V5-His (manufactured by Thermo Fisher Scientific, Inc.) vector, whereby the following plasmid vectors for membrane expression of various types of CADM3:

pEF6_human CADM3, pEF6_mouse CADM3, and pEF6_cynomolgus CADM3 were produced.

The various types of membrane CADM3 antigen expression vectors were separately introduced into Expi293F cells using FreeStyle (trademark) 293 Expression System (manufactured by Thermo Fisher Scientific, Inc.), and the cells were cultured to express the membrane antigens in a transient expression system. By using the cells, the reactivity of the antibodies produced in Example 2 with the CADM3-expressing cells was analyzed by a fluorescence activated cell sorting (FACS) method according to the following procedure.

Expi293F cells, human CADM3/Expi293F cells, mouse CADM3/Expi293F cells, and monkey CADM3/Expi293F cells were separately suspended in Staining Buffer (SB) of PBS comprising 0.1% $NaN_3$ and 1% FBS and dispensed in a round-bottom 96-well plate (manufactured by Becton, Dickinson and Company).

After centrifugation (2000 rpm, 4° C. 2 minutes), the supernatant was removed, and to the resulting pellet, 10 μg/mL of each antibody obtained in Example 2 was added to suspend the pellet, and the resulting suspension was left to stand for 30 minutes at ice temperature. After further centrifugation (2000 rpm, 4° C. 2 minutes), the supernatant was removed, and the resulting pellet was washed with SB, and thereafter, 1 sg/mL of an RPE fluorescently labeled goat anti-human antibody (manufactured by Southern Biotech, Inc.) was added thereto, and the resultant was incubated for 30 minutes at ice temperature.

After washing with SB, the cells were suspended in SB, and the fluorescence intensity of each cell was measured using a flow cytometer FACS CANTO II (manufactured by Becton, Dickinson and Company). Note that as a negative control, 10 μg/mL of the anti-AVM antibody was used.

The detection results were analyzed, and a mean fluorescence intensity (MFI) was calculated using a geometric mean. Further, with respect to the MFI when the concentration of each antibody was 10 μg/mL, the ratio of the MFI (mean fluorescence intensity ratio) between the human CADM3/Expi293F cells and the Expi293F cells (parent cell line) was calculated.

Also for the monkey CADM3/Expi293F cells and the mouse CADM3/Expi293F cells, the mean fluorescence intensity ratio relative to the Expi293F cells (parent cell line) was calculated by the same procedure, and the results are shown in Table 4.

TABLE 4

| | Mean fluorescence intensity ratio | | |
|---|---|---|---|
| | Human CADM3-expressing cells/parent cell line | Monkey CADM3-expressing cells/parent cell line | Mouse CADM3-expressing cells/parent cell line |
| Anti-AVM antibody | 1.02 | 1.02 | 1.07 |
| CADM301 scFv-hG4PE | 4.22 | 5.72 | 8.08 |
| CADM3102 scFv-hG4PE | 52.33 | 51.52 | 42.60 |
| iCADM3_3R1-L5 VHH-hG4PE(R409K) | 25.05 | 26.65 | 4.21 |
| iCADM3_3R1-L8 VHH-hG4PE(R409K) | 5.84 | 6.91 | 8.20 |
| iCADM3_3R1-L10 VHH-hG4PE(R409K) | 37.53 | 36.49 | 8.87 |
| iCADM3_3R1-L11 VHH-hG4PE(R409K) | 32.24 | 35.32 | 35.52 |
| CADM3219 hG4PE(R409K) | 7.3 | Not Evaluated | 9.2 |
| CADM3301 hG4PE(R409K) | 6 | Not Evaluated | 6.2 |
| CADM3309 hG4PE(R409K) | 10.2 | Not Evaluated | 12.5 |
| CADM3312 hG4PE(R409K) | 34.4 | Not Evaluated | 31.6 |
| CADM3314 hG4PE(R409K) | 10 | Not Evaluated | 9.2 |
| CADM3316 hG4PE(R409K) | 6.5 | Not Evaluated | 7.1 |
| CADM3349 hG4PE(R409K) | 4.8 | Not Evaluated | 48.7 |
| CADM3351 hG4PE(R409K) | 8.2 | Not Evaluated | 8.8 |
| CADM3402 hG4PE(R409K) | 10.8 | Not Evaluated | 9.4 |
| CADM3404 hG4PE(R409K) | 8.7 | Not Evaluated | 8.2 |
| CADM3432 hG4PE(R409K) | 14.7 | Not Evaluated | 14.6 |
| CADM3448 hG4PE(R409K) | 9.4 | Not Evaluated | 10.4 |
| CADM3458 hG4PE(R409K) | 5.7 | Not Evaluated | 5.4 |
| CADM3501 hG4PE(R409K) | 44.9 | Not Evaluated | 36.1 |

As shown in Table 4, in the case of all the anti-CADM3 antibodies, the mean fluorescence intensity ratio was increased as compared with that of the anti-AVM antibody that is the negative control, and the anti-CADM3 antibodies showed reactivity with the human CADM3/Expi293F cells, the mouse CADM3/Expi293F cells, and the monkey CADM3/Expi293F cells (however, with respect to some anti-CADM3 antibodies, the reactivity with the monkey CADM3/Expi293F cells was not evaluated). Therefore, it was revealed that the anti-CADM3 antibodies recognize and bind to human CADM3, mouse CADM3, or monkey CADM3.

Further, also with respect to AVM IgG4PE(R409K)_iCADM3_3R1-L5 dVHH, AVM IgG4PE(R409K)_iCADM3_3R1-L8 dVHH, AVM IgG4PE(R409K)_iCADM3_3R1-L10 dVHH, and AVM IgG4PE(R409K)_iCADM3_3R1-L11 dVHH, reactivity with the Expi293F cells, the human CADM3/Expi293F cells, and the mouse CADM3/Expi293F cells was analyzed by the same procedure, and the results are shown in Table 5.

TABLE 5

| | Mean fluorescence intensity ratio | |
|---|---|---|
| | Human CADM3-expressing cells/parent cell line | Mouse CADM3-expressing cells/parent cell line |
| Anti-AVM antibody | 1.08 | 1.15 |
| AVM IgG4PE(R409K)_AVM dscFv5 | 1.10 | 1.15 |
| AVM IgG4PE(R409K)_iCADM3_3R1-L5 dVHH | 5.14 | 1.96 |
| AVM IgG4PE(R409K)_iCADM3_3R1-L8 dVHH | 2.92 | 3.65 |
| AVM IgG4PE(R409K)_iCADM3_3R1-L10 dVHH | 4.22 | 1.78 |
| AVM IgG4PE(R409K)_iCADM3_3R1-L11 dVHH | 5.76 | 4.66 |

As shown in Table 5, in the case of all the antibodies, the mean fluorescence intensity ratio was increased as compared with that of the anti-AVM antibody that is the negative control, and it was revealed that the antibodies react with the human CADM3/Expi293F cells and the mouse CADM3/Expi293F cells.

[Example 4] Production of Soluble CADM3 Antigen (1) Production of Extracellular Domain Protein of CADM3 to which FLAG_Fc is Bound As a soluble antigen of human CADM3, mouse CADM3, or rat CADM3, an extracellular domain protein of CADM3 to which FLAG_Fc was added at the C-terminus was produced by the method described below.

A synthetic gene of the extracellular domain of human CADM3 and a synthetic gene of FLAG_Fc were inserted into an INPEP4 (manufactured by IDEC, Inc.) vector, whereby a plasmid vector for expressing the extracellular domain of human CADM3 to which FLAG_Fc was added at the C-terminal side: INPEP4-hCADM3-FLAG_Fc was produced. The nucleotide sequence encoding hCADM3-FLAG_Fc is represented by SEQ ID NO: 57, and an amino acid sequence deduced from the nucleotide sequence is represented by SEQ ID NO: 58.

Also for mouse CADM3 and rat CADM3, plasmid vectors INPEP4-mCADM3-FLAG_Fc and INPEP4-rCADM3-FLAG_Fc were produced in the same manner. The nucleotide sequence encoding mCADM3-FLAG_Fc is represented by SEQ ID NO: 59, an amino acid sequence deduced from the nucleotide sequence is represented by SEQ ID NO: 60, the nucleotide sequence encoding rCADM3-FLAG_Fc is represented by SEQ ID NO: 61, and an amino acid sequence deduced from the nucleotide sequence is represented by SEQ ID NO: 62.

INPEP4-hCADM3-FLAG_Fc, INPEP4-mCADM3-FLAG_Fc, and INPEP4-rCADM3-FLAG_Fc were separately introduced into Expi293F cells using Expi293 (trademark) Expression System (manufactured by Thermo Fisher Scientific, Inc.), and the cells were cultured to express the proteins in a transient expression system, and the proteins were purified in the same manner as in Example 2. The concentrations of the purified human, mouse, and rat CADM3-FLAG_Fc proteins in the solutions were determined based on the absorbance at 280 nm.

(2) Production of Extracellular Domain Protein of CADM3 to which GST is Bound

As a soluble antigen of human CADM3 or mouse CADM3, an extracellular domain protein of CADM3 to which GST was added at the C-terminus was produced by the method described below.

A synthetic gene of the extracellular domain of human or mouse CADM3 and a synthetic gene of GST were inserted into an N5 vector (manufactured by IDEC, Inc.), whereby the following plasmid vectors for expressing the extracellular domains of human and mouse CADM3 to which GST was added at the C-terminal side: N5-hCADM3-GST and N5-mCADM3-GST were produced.

The nucleotide sequence encoding hCADM3-GST is represented by SEQ ID NO: 63, an amino acid sequence deduced from the nucleotide sequence is represented by SEQ ID NO: 64, the nucleotide sequence encoding mCADM3-GST is represented by SEQ ID NO: 65, and an amino acid sequence deduced from the nucleotide sequence is represented by SEQ ID NO: 66.

N5-hCADM3-GST and N5-mCADM3-GST were separately introduced into Expi293F cells using Expi293 (trademark) Expression System (manufactured by Thermo Fisher Scientific, Inc.), and the cells were cultured to express the proteins in a transient expression system. The culture supernatant was collected 3 to 4 days after the introduction of the vector and filtered through a membrane filter having a pore size of 0.22 μm (manufactured by Merck Millipore Corporation).

The protein in this culture supernatant was subjected to affinity purification using a Glutathione Sepharose 4B (manufactured by GE Healthcare Biosciences, Inc.). As the washing solution, a phosphate buffer solution was used. The protein adsorbed on the Glutathione Sepharose 4B was eluted with 50 mmol/L Tris-HCl and 10 mmol/L reduced glutathione (pH 8.0).

Subsequently, the solvent in the solution was replaced with PBS by ultrafiltration using Amicon Ultra (manufactured by Merck Millipore Corporation) and a NAP column (manufactured by GE Healthcare Biosciences, Inc.). The obtained solution was sterilized by filtration through a membrane filter having a pore size of 0.22 μm (manufactured by Merck Millipore Corporation). The concentrations of the purified human and mouse CADM3-GST proteins in the solutions were determined based on the absorbance at 280 nm.

[Example 5] Evaluation of Affinity for CADM3 by Surface Plasmon Resonance Detection The affinity of the anti-CADM3 antibodies produced in Example 2 for human CADM3 and mouse CADM3 was measured using Biacore T-100 (GE Healthcare). Each of the antibodies was immobilized on a CM5 sensor chip using a Human antibody Capture kit, and the binding ability was evaluated using hCADM3-GST and mCADM3-GST produced in Example 4 as analytes.

The obtained sensorgram was analyzed with BIA evaluation software, and the dissociation constant ($K_D$ value) was calculated. As a result, all the anti-CADM3 antibodies produced in Example 2 exhibited affinity for human CADM3 and mouse CADM3.

[Example 6] Evaluation of Migration Ability into Mouse Brain (1) Measurement of Antibody Amount Each of the antibodies was administered to a mouse through the tail vein (i.v.) at 9 mg/kg body weight, and after 3 days, the blood was collected. On the same day as the blood collection, whole body perfusion was performed under anesthesia, and thereafter, a brain tissue was collected and the weight thereof was measured. Further, a buffer solution was added to the collected brain tissue, and the brain tissue was homogenized, followed by centrifugation, and an antibody solution eluted in the supernatant was collected. The volume thereof was measured, and also the antibody concentration was measured using AlphaLISA (manufactured by PerkinElmer, Inc.), and the antibody amount per unit brain weight was calculated. Note that the standard curve was created using the antibody attached to the kit.

The antibody concentration in the serum 3 days after administering the antibody is shown in FIG. 1(A), and the antibody amount in the brain tissue per unit brain weight is shown in FIG. 1(B). As shown in FIG. 1(A), there was no difference in serum concentration of the anti-CADM3 VHH-Fc antibody 3 days after administering the antibody as compared with that of the negative control (anti-AVM antibody). On the other hand, as shown in FIG. 1(B), it was demonstrated that the antibody amount in the brain of each of the anti-CADM3 VHH-Fc antibodies: iCADM3_3R1-L5 VHH-hG4PE(R409K), iCADM3_3R1-L8 VHH-hG4PE(R409K), and iCADM3_3R1-L10 VHH-hG4PE(R409K) is increased by about 10 times as compared with that of the negative control.

Further, a test method carried out under conditions different from those described above and the results will be shown.

The negative control antibody (anti-AVM antibody), the anti-CADM3 VHH-Fc antibody: iCADM3_3R1-L8, and the anti-CADM3 antibodies: CADM3312 hG4PE(R409K), CADM3402 hG4PE(R409K), and CADM3501 hG4PE(R409K) were separately administered through the tail vein (i.v.) at 5 mg/kg, and after 7 days, the blood was collected. After the blood was collected, whole body perfusion was performed under anesthesia, and thereafter, a brain tissue was collected and the weight thereof was measured. A buffer solution was added to the collected brain tissue, and the brain tissue was homogenized, followed by centrifugation, and an antibody solution eluted in the supernatant was collected. The volume thereof was measured, and also the antibody concentration was measured using AlphaLISA (manufactured by PerkinElmer, Inc.), and the antibody amount per unit brain weight was calculated. Note that the standard curve was created using each antibody.

Figure 2:
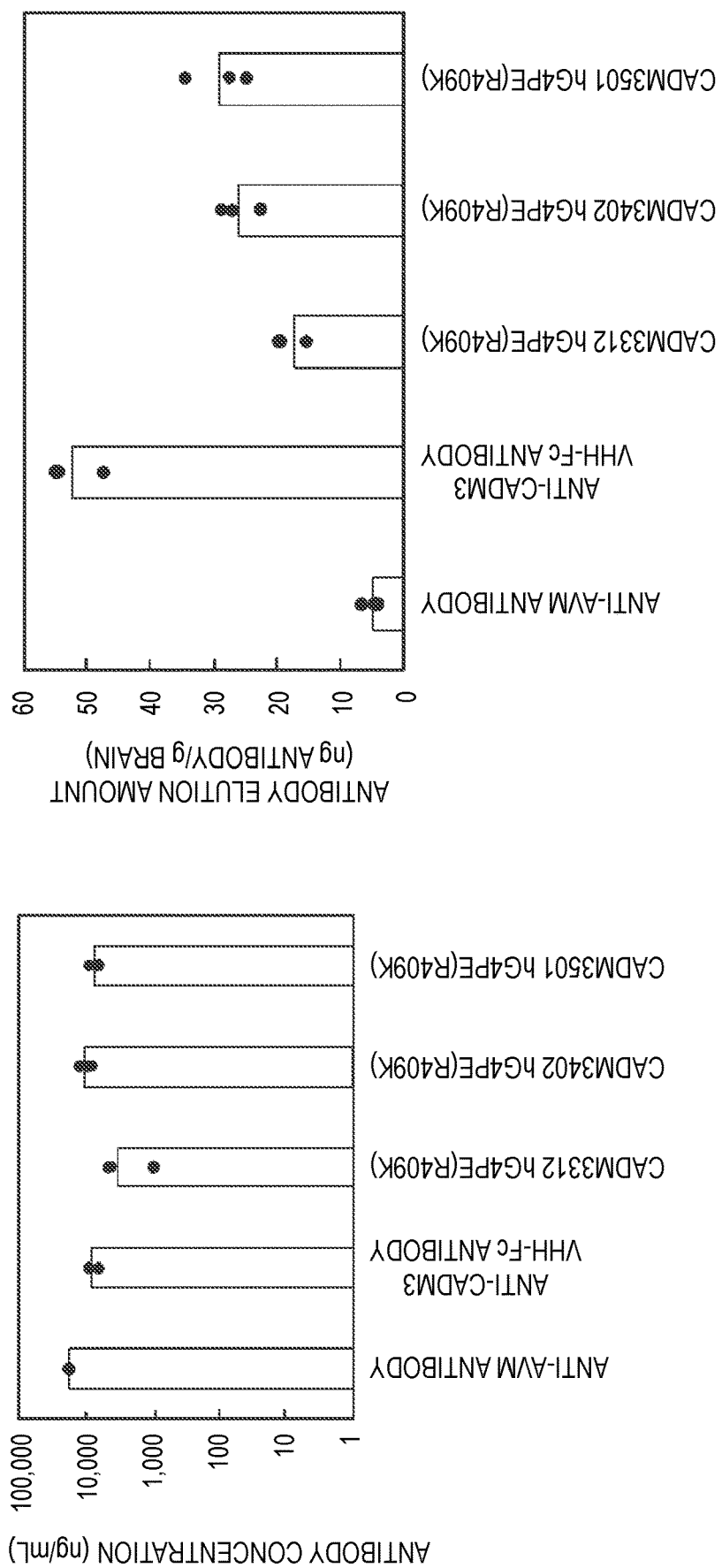
FIG. 2 shows the results of measuring the concentration of each antibody in a tissue.

The antibody concentration in the serum 7 days after administering the antibody is shown in FIG. 2(A), and the antibody amount in the brain tissue per unit brain weight is shown in FIG. 2(B). As shown in FIG. 2(A), there was no significant difference in serum concentration of each of the anti-CADM3 VHH-Fc antibody: iCADM3_3R1-L8, and the anti-CADM3 antibodies: CADM3312 hG4PE(R409K), CADM3402 hG4PE(R409K), and CADM3501 hG4PE(R409K) antibodies 7 days after administering the antibody as compared with that of the negative control (anti-AVM antibody). On the other hand, as shown in FIG. 2(B), the antibody amount in the brain of each of the anti-CADM3 VHH-Fc antibody: iCADM3_3R1-L8, and the anti-CADM3 antibodies: CADM3312 hG4PE(R409K), CADM3402 hG4PE(R409K), and CADM3501 hG4PE(R409K) was increased as compared with that of the anti-AVM antibody. Accordingly, the effect of increasing the antibody amount in the brain was confirmed.

Subsequently, a test method carried out under conditions different from those described above and the results will be shown.

Each of the antibodies was administered to a mouse through the tail vein (i.v.) at 35 nmol/kg body weight, and after 7 days, the blood was collected. On the same day as the blood collection, whole body perfusion was performed under anesthesia, and thereafter, a brain tissue was collected and the weight thereof was measured. Further, a buffer solution was added to the collected brain tissue, and the brain tissue was homogenized, followed by centrifugation, and an antibody solution eluted in the supernatant was collected. The volume thereof was measured, and also the antibody concentration was measured using AlphaLISA (manufactured by PerkinElmer, Inc.), and the antibody amount per unit brain weight was calculated. The antibody concentration was expressed as a value obtained by conversion from the molar concentration using the molecular weight (150 kDa) of a monoclonal antibody. Note that the standard curve was created using each antibody.

Figure 3:
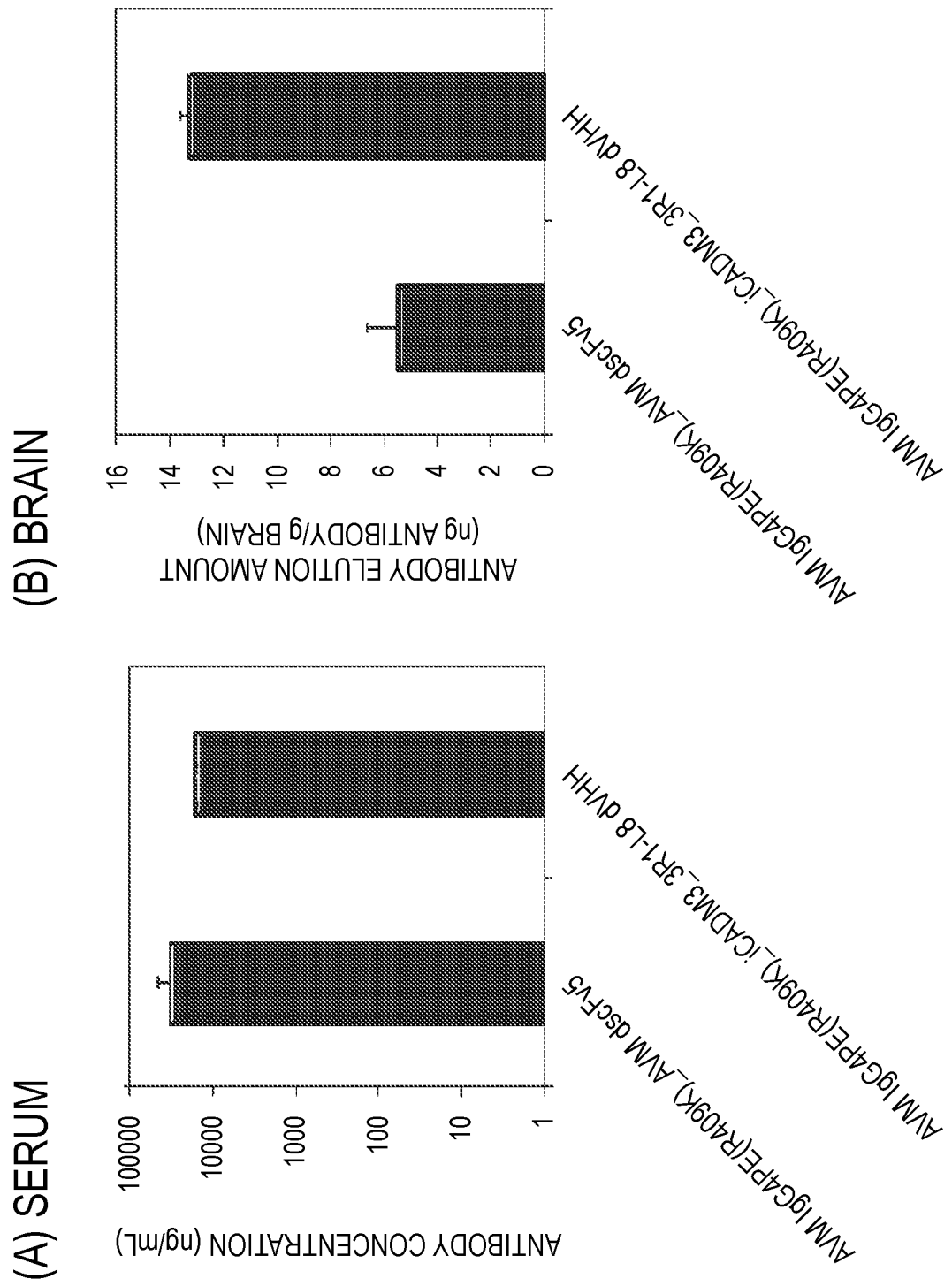
FIG. 3 shows the results of measuring the concentration of each antibody in a tissue.

The antibody concentration in the serum of each of AVM IgG4PE(R409K)_AVM dscFv5 and AVM IgG4PE(R409K)_ iCADM3_3R1-L8 dVHH is shown in FIG. 3(A), and the antibody amount per unit brain weight in the brain tissue thereof is shown in FIG. 3(B).

As shown in FIG. 3(B), it was demonstrated that the antibody amount in the brain of the anti-AVM-IgG4-CADM3 VHH bispecific antibody: AVM IgG4PE(R409K)_iCADM3_3R1-L8 dVHH is increased as compared with that of the anti-AVM-IgG4-AVM dscFv bispecific antibody: AVM IgG4PE(R409K) AVM dscFv5 that is the negative control of the bispecific antibody. Accordingly, it was demonstrated that the bispecific antibody which binds to CADM3 can increase the antibody amount in the brain as compared with the bispecific antibody which does not bind to CADM3.

(2) Imaging Analysis

The anti-CADM3 VHH-Fc antibodies and the negative control (anti-AVM antibody) were labeled using Alexa FluorR 488 Protein Labeling Kit (manufactured by Molecular Probes, Inc.). Each of the labeled antibodies was administered to a mouse through the tail vein (i.v.) at 9 mg/kg body weight, and after 9 days, the blood was collected. After the blood was collected, whole body perfusion was performed under anesthesia, and thereafter, a brain tissue was collected, and the fluorescence intensity was measured using IVIS Spectrum (manufactured by PerkinElmer, Inc.).

Figure 4:
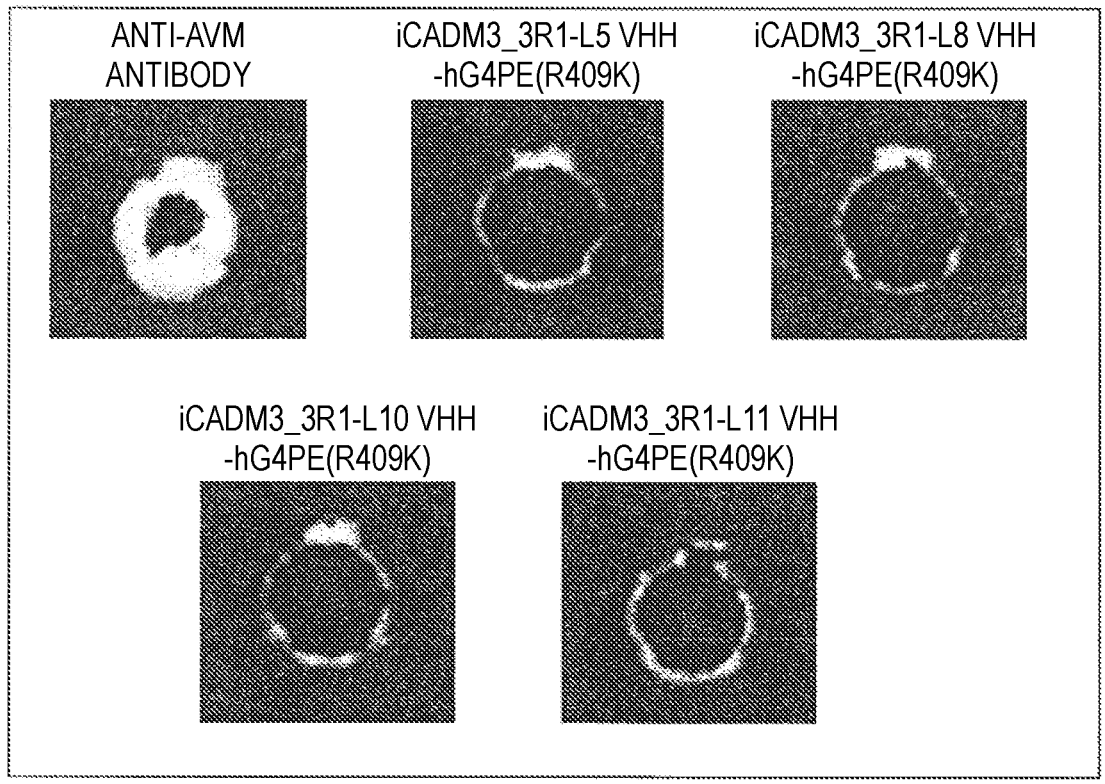
FIG. 4 shows the results of imaging evaluation of the migration ability into a mouse brain of each antibody.
Figure 4:
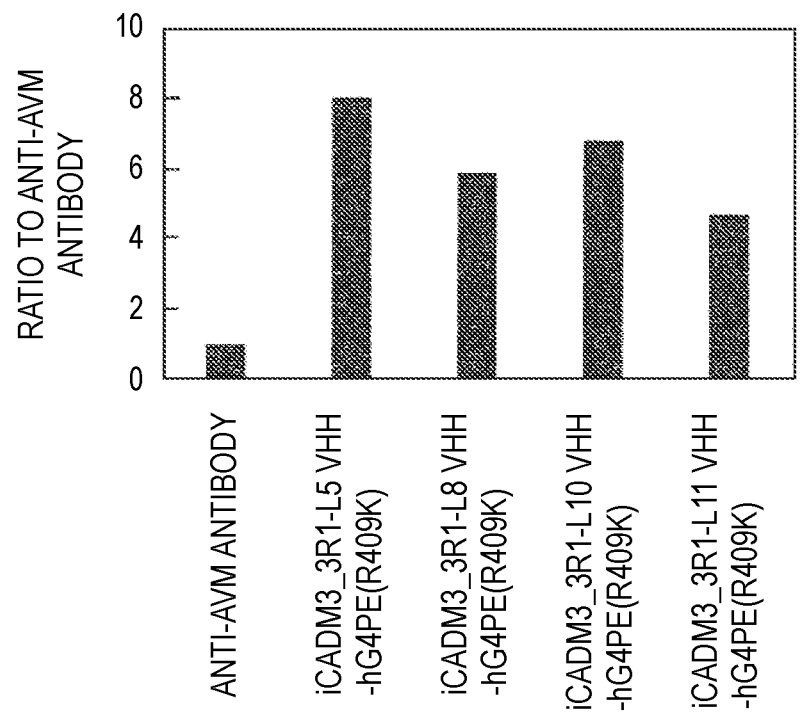

Imaging images of the brain 9 days after administering the antibody are shown in FIG. 4(A). The ratio of a value of the fluorescence amount in the brain corrected by the fluorescence intensity of the administered antibody to the negative control is shown in FIG. 4(B). As shown in FIGS. 4(A) and (B), the antibody amount in the brain of any of the anti-CADM3 VHH-Fc antibodies: iCADM3_3R1-L5 VHH-hG4PE(R409K), iCADM3_3R1-L8 VHH-hG4PE(R409K), iCADM3_3R1-L10 VHH-hG4PE(R409K), and iCADM3_3R1-L11 VHH-hG4PE(R409K) is increased by several times as compared with that of the negative control, and it was demonstrated that the distribution of the antibody spreads over the entire area of the brain.

Further, a test method carried out under conditions different from those described above and the results will be shown.

The negative control antibody (anti-AVM antibody), the anti-CADM3 VHH-Fc antibody: iCADM3_3R1-L8, and the anti-CADM3 antibodies: CADM3312 hG4PE(R409K), CADM3402 hG4PE(R409K), and CADM3501 hG4PE (R409K) were fluorescently labeled using SAIVI Alexa Fluor 647 Antibody/Protein 1 mg-Labeling Kit, and were separately administered through the tail vein (i.v.) at 5 mg/kg, and after 7 days, the blood was collected. After the blood was collected, whole body perfusion was performed under anesthesia, and thereafter, a brain tissue was collected, and the fluorescence intensity was measured using IVIS Spectrum (manufactured by PerkinElmer, Inc.).

Figure 5:
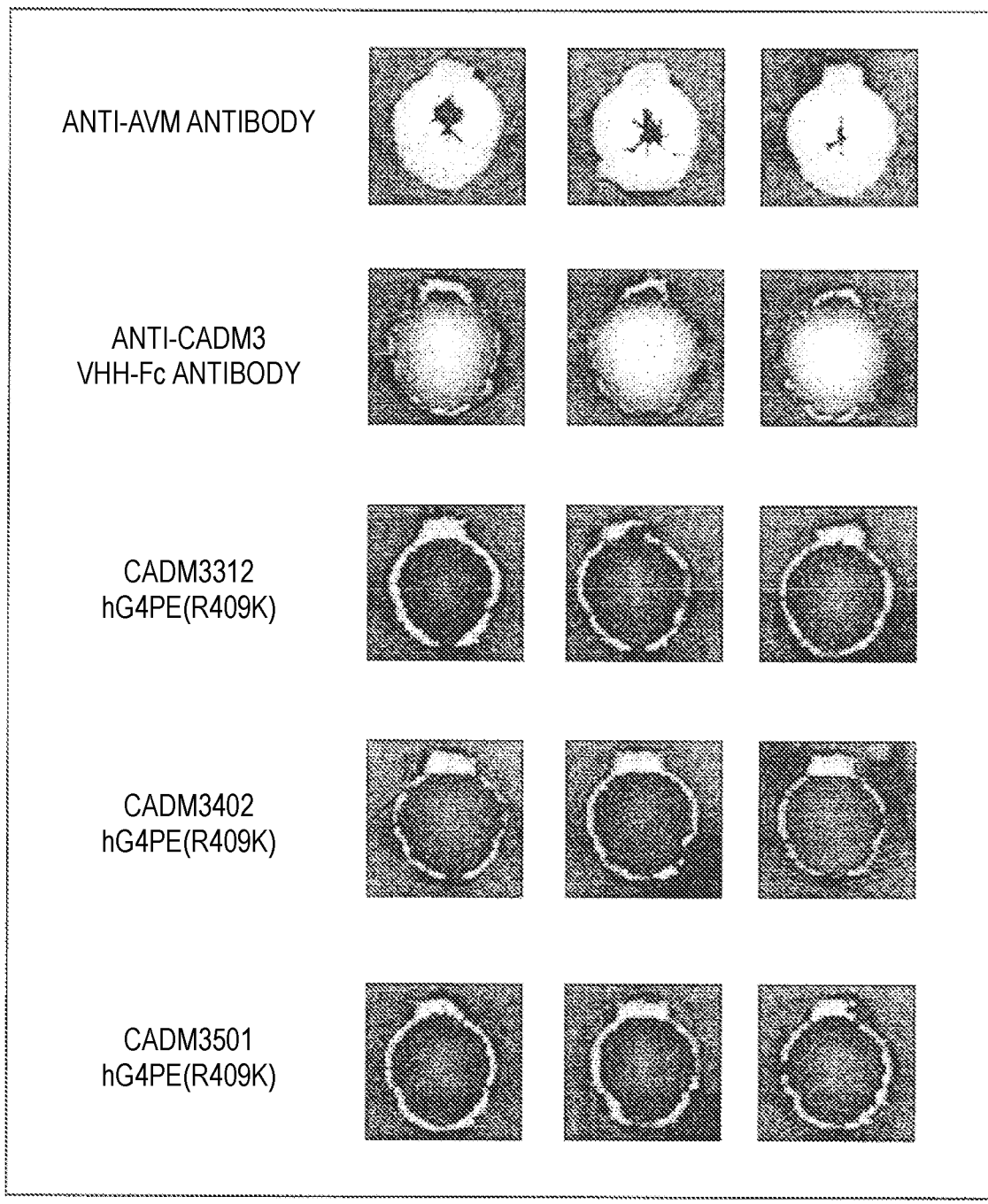
FIG. 5 shows the results of imaging evaluation of the migration ability into a mouse brain of each antibody and indicates the imaging images of the brain 7 days after administering the antibody.

Imaging images of the brain 7 days after administering the antibody are shown in FIG. 5. While the administered antibody of the negative control is slightly observed in a central portion of the brain (a color is developed only in the central portion of the brain), it was demonstrated that the distribution of any of the CADM3 antibodies spreads over the entire area of the brain (a color is developed in the entire brain). Note that in the monochrome images, in the case of the anti-CADM3 VHH-Fc antibody: iCADM3_3R1-L8, the developed color is too intense, and therefore, the image appears white as a whole, however, this is different from the image of the negative control which appears white without developing a color.

Figure 6:
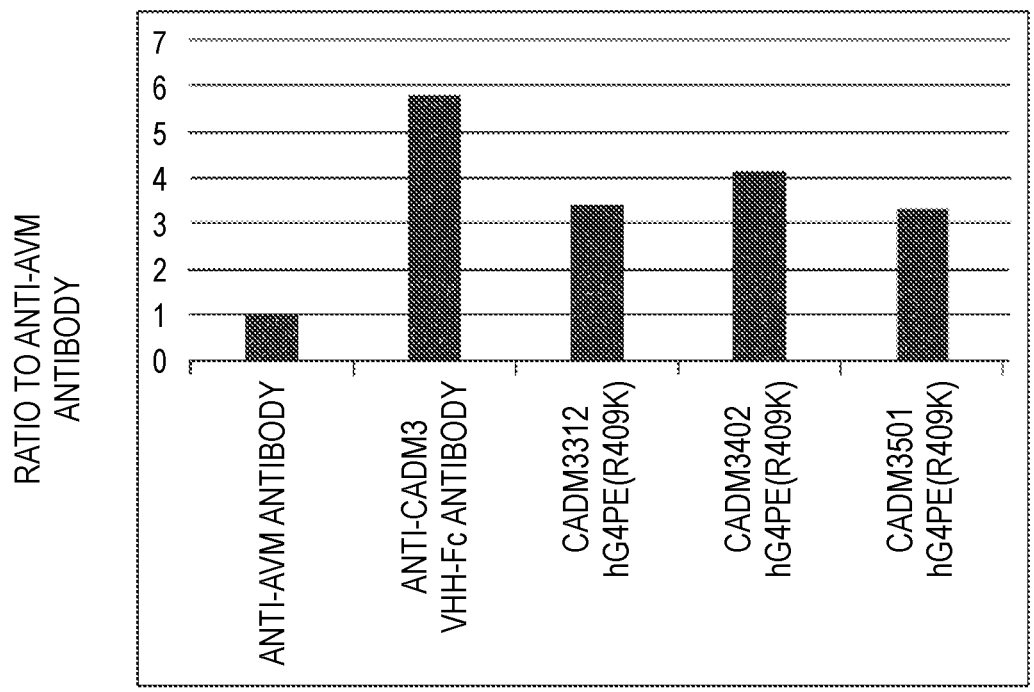
FIG. 6 shows the results of imaging evaluation of the migration ability into a mouse brain of each antibody and indicates the ratio of a value of the fluorescence amount in the brain corrected by the fluorescence intensity of the administered antibody to the anti-AVM antibody. The vertical axis represents the ratio to the anti-AVM antibody, and the horizontal axis represents the administered antibodies.

Subsequently, the ratio of a value of the fluorescence amount in the brain 7 days after administering the antibody corrected by the fluorescence intensity of the administered antibody to the negative control is shown in FIG. 6. The antibody amount in the brain of any of the anti-CADM3 VHH-Fc antibody: iCADM3_3R1-L8, and the anti-CADM3 antibodies: CADM3312 hG4PE(R409K), CADM3402 hG4PE(R409K), and CADM3501 hG4PE(R409K) is increased by several times as compared with that of the negative control.

[Example 7] Production of Humanized Anti-CADM3Antibody (1) Designing of Amino Acid Sequence of Various Types of VHHs of iCADM3_3R1-L8 Humanized Antibody By the method described below, the amino acid sequences of various types of VHHs of the iCADM3_3R1-L8 humanized antibody were designed. With respect to VHH, homology between the amino acid sequence of FR of the iCADM3_3R1-L8 antibody and the human FR consensus sequence reported by Kabat et al. [Sequences of Proteins of Immunological Interest, US Dept. Health and Human Services (1991)] was compared. As a result, GenBank accession No. ACR16109.1 had the highest homology with the amino acid sequence of FR of VHH of the iCADM3_3R1-L8 antibody. Therefore, an iCADM3_3R1-L8_00 antibody comprising an amino acid sequence in which the amino acid sequences of CDR1 to CDR3 of the iCADM3_3R1-L8 antibody represented by SEQ ID NOS: 8, 9, and 10, respectively, were grafted at appropriate positions of the amino acid sequence of FR of ACR16109.1 was designed (SEQ ID NO: 177). The iCADM3_3R1-L8_00 antibody is a humanized antibody comprising an amino acid sequence in which only the amino acid sequences of CDR1 to CDR3 derived from an alpaca antibody iCADM3_3R1-L8 antibody were grafted into the amino acid sequence of FR of the selected human antibody.

However, in general, when a humanized antibody is produced, the binding activity of the humanized antibody is often deteriorated merely by grafting only the amino acid sequence of CDR of an antibody derived from an animal such as a rodent, a rabbit, or an alpaca into the amino acid sequence of FR of a human antibody. In order to avoid such deterioration of the binding activity, modification of an amino acid residue which is considered to affect the binding activity of the antibody among the amino acid residues of FR different between the human antibody and the alpaca antibody is carried out along with the grafting of the amino acid sequence of CDR.

Therefore, also in this Example, an amino acid residue of FR which is considered to affect the binding activity of the antibody was identified and modified as follows. The three-dimensional structure of the variable region of the iCADM3_3R1-L8_(x) antibody was constructed using a computer modeling technique.

For the production of a three-dimensional structure coordinate and display of the three-dimensional structure, Discovery Studio (BIOVIA, Inc.) was used. Further, a computer model of the three-dimensional structure of the variable region of the iCADM3_3R1-L8 antibody was also constructed in the same manner. Further, an amino acid sequence in which, in the amino acid sequence of FR of VHH of the iCADM3_3R1-L8_00 antibody, an amino acid residue different from that of the iCADM3_3R1-L8 antibody was substituted with an amino acid residue present at the same position as that of the iCADM3_3R1-L8 antibody was produced and a three-dimensional structure model was constructed in the same manner.

The three-dimensional structures of the variable regions of these produced iCADM3_3R1-L8 antibody, iCADM3_3R1-L8_00 antibody, and variants were compared, and an amino acid residue presumed to affect the binding activity of the antibody was identified.

The VHHs of a humanized antibody having various modifications were designed by substituting at least one or more amino acid residues among the identified amino acid residues of the iCADM3_3R1-L8_00 antibody with an amino acid residue present at the same position of the iCADM3_3R1-L8 antibody.

Specifically, an amino acid sequence of a humanized antibody comprising at least one amino acid residue substitution selected from amino acid residue substitutions of Gin at position 6 with Glu, Phe at position 27 with Arg, Val at position 37 with Phe, Gly at position 44 with Glu, Leu at position 45 with Arg, Trp at position 47 with Phe, Ser at position 49 with Ala, Leu at position 79 with Val, and Lys at position 98 with Ala in the amino acid sequence represented by SEQ ID NO: 177 among the identified amino acid residues was produced, and the VHH of the humanized antibody having various modifications were designed.

Specifically, as the VHH of the iCADM3_3R1-L8 humanized antibody, iCADM3_3R1-L8_01 (SEQ ID NO: 68), iCADM3_3R1-L8_02 (SEQ ID NO: 70), iCADM3_3R1-L8_03 (SEQ ID NO: 72), and iCADM3_3R1-L8_04 (SEQ ID NO: 74) were designed. The amino acid sequences encoding the various types of VHHs of the iCADM3_3R1-L8 humanized antibody are shown in Table 6.

(2) Designing of Amino Acid Sequence of Various Types of VHHs of iCADM3_3R1-L11 Humanized Antibody The amino acid sequence of VHH of the iCADM3_3R1-L11 humanized antibody was also designed in the same manner as in Example 7(1). The human FR having an amino acid sequence with the highest homology was GenBank accession No. AAQ05734.1, but its antigenicity was presumed to be high, and therefore, the germline sequence VH3-53 was used.

An iCADM3_3R1-L11_00 antibody comprising an amino acid sequence in which the amino acid sequences of CDR1 to CDR3 of VHH of the iCADM3_3R1-L11 antibody (SEQ ID NOS: 18, 19, and 20, respectively) were grafted at appropriate positions of the amino acid sequence of FR of VH3-53 was designed (SEQ ID NO: 178). Also an amino acid residue of FR considered to affect the binding activity of the iCADM3_3R1-L11_00 antibody was selected in the same manner as in Example 7(1).

An amino acid sequence of a humanized antibody comprising at least one amino acid residue substitution selected from amino acid residue substitutions of Glu at position 1 with Gln, Ile at position 12 with Val, Pro at position 14 with Ala, Phe at position 27 with Ser, The at position 28 with Ile, Val at position 29 with Phe, Val at position 37 with Tyr, Gly at position 44 with Gln, Lys at position 45 with Arg, Glu at position 46 with Gly, Trp at position 47 with Leu, Ser at position 49 with Ala, Leu at position 78 with Val, Ala at position 96 with Asn, and Arg at position 97 with Ala in the amino acid sequence represented by SEQ ID NO: 178 among the selected amino acid residues was produced, and the VHH of the humanized antibody having various modifications were designed.

Specifically, as the VHH of the iCADM3_3R1-L1 humanized antibody, iCADM3_3R1-L11_01 (SEQ ID NO: 76), iCADM3_3R1-L11_02 (SEQ ID NO: 78), iCADM3_3R1-L11_03 (SEQ ID NO: 80), iCADM3_3R1-L11_04 (SEQ ID NO: 82), iCADM3_3R1-L11_05 (SEQ ID NO: 84), and iCADM3_3R1-L11_106 (SEQ ID NO: 86) were designed. The amino acid sequences encoding various types of VHHs of the iCADM3_3R1-L11 humanized antibody are shown in Table 6.

The nucleotide sequences encoding the amino acid sequences of the variable regions of the humanized antibodies shown in Table 6 were designed using a codon to be used with high frequency in animal cells, and shown in Table 6.

TABLE 6

| Clone Name | Nucleotide sequence encoding VHH (excluding signal sequence) | Amino acid sequence of VHH (excluding signal sequence) |
| --- | --- | --- |
| iCADM3-3R1-L8_01 | SEQ ID NO: 67 | SEQ ID NO: 68 |
| iCADM3-3R1-L8_02 | SEQ ID NO: 69 | SEQ ID NO: 70 |
| iCADM3-3R1-L8_03 | SEQ ID NO: 71 | SEQ ID NO: 72 |
| iCADM3-3R1-L8_04 | SEQ ID NO: 73 | SEQ ID NO: 74 |
| iCADM3-3R1-L11_01 | SEQ ID NO: 75 | SEQ ID NO: 76 |
| iCADM3-3R1-L11_02 | SEQ ID NO: 77 | SEQ ID NO: 78 |
| iCADM3-3R1-L11_03 | SEQ ID NO: 79 | SEQ ID NO: 80 |
| iCADM3-3R1-L11_04 | SEQ ID NO: 81 | SEQ ID NO: 82 |
| iCADM3-3R1-L11_05 | SEQ ID NO: 83 | SEQ ID NO: 84 |
| iCADM3-3R1-L11_06 | SEQ ID NO: 85 | SEQ ID NO: 86 |

(3) Preparation of CADM3 Humanized Antibody

In the same manner as in Example 2(1), antibody expression vectors in which the gene fragment of each of the various types of VHH regions of the humanized anti-CADM3 antibodies shown in Table 6 was inserted were produced. Antibodies were obtained by expressing each of the produced vectors in the same manner as in Example 2(5).

The produced humanized anti-CADM3 VHH-Fc antibodies were named iCADM3_3R1-L8_01 VHH-hG4PE (R409K), iCADM3_3R1-L8_02 VHH-hG4PE(R409K), iCADM3_3R1-L8_03 VHH-hG4PE(R409K), iCADM3_3R1-L8_04 VHH-hG4PE(R409K), iCADM3_3R1-L11_01 VHH-hG4PE(R409K), iCADM3_3R1-L11_02 VHH-hG4PE(R409K), iCADM3_3R1-L11_03 VHH-hG4PE(R409K), iCADM3_3R1-L11_04 VHH-hG4PE(R409K), iCADM3_3R1-L11_05 VHH-hG4PE(R409K), and iCADM3_3R1-L11_06 VHH-hG4PE(R409K), respectively.

(4) Analysis of Reactivity of CADM3 Humanized Antibody with CADM3-Expressing Cells With respect to the produced humanized anti-CADM3 VHH-Fc antibodies, reactivity with Expi293F cells, human CADM3/Expi293F cells, and mouse CADM3/Expi293F cells was analyzed by the same procedure as in Example 3. The results are shown in Tables 7 and 8.

TABLE 7

| | Mean fluorescence intensity ratio | |
| --- | --- | --- |
| | Human CADM3-expressing cells/ parent cell line | Mouse CADM3-expressing cells/ parent cell line |
| Anti-AVM antibody | 1.08 | 1.02 |
| iCADM3-3R1-L8_01 VHH-hG4PE(R409K) | 2.21 | 3.71 |
| iCADM3-3R1-L8_02 VHH-hG4PE(R409K) | 2.80 | 4.83 |
| iCADM3-3R1-L8_03 VHH-hG4PE(R409K) | 5.65 | 8.54 |
| iCADM3-3R1-L8_04 VHH-hG4PE(R409K) | 6.20 | 9.62 |

TABLE 8

| | Mean fluorescence intensity ratio | |
| --- | --- | --- |
| | Human CADM3-expressing cells/ parent cell line | Mouse CADM3-expressing cells/ parent cell line |
| Anti-AVM antibody | 1.08 | 1.02 |
| iCADM3-3R1-L11_01 VHH-hG4PE(R409K) | 12.21 | 12.52 |
| iCADM3-3R1-L11_02 VHH-hG4PE(R409K) | 12.38 | 27.85 |
| iCADM3-3R1-L11_03 VHH-hG4PE(R409K) | 24.38 | 33.84 |
| iCADM3-3R1-L11_04 VHH-hG4PE(R409K) | 22.47 | 26.74 |
| iCADM3-3R1-L11_05 VHH-hG4PE(R409K) | 11.10 | 24.62 |
| iCADM3-3R1-L11_06 VHH-hG4PE(R409K) | 32.99 | 42.25 |

As shown in Tables 7 and 8, in the case of all the antibodies, the mean fluorescence intensity ratio was increased as compared with the anti-AVM antibody that is the control, and it was revealed that the humanized anti-CADM3 antibodies react with the human CADM3/Expi293F cells and the mouse CADM3/Expi293F cells.

With respect to the produced humanized anti-CADM3 antibodies, affinity for CADM3 by surface plasmon resonance detection was evaluated by the same procedure as in Example 6. As a result, as shown in Tables 9 and 10, all the antibodies exhibited affinity for human CADM3 and mouse CADM3.

TABLE 9

Affinity for human CADM3

| Antibody | ka (1/Ms) | kd (1/s) | KD (M) |
|---|---|---|---|
| iCADM3_3R1-L8 | 4.1E+04 | 5.1E−04 | 1.25E−08 |
| iCADM3_3R1-L8_03 | 1.9E+05 | 1.9E−03 | 1.03E−08 |
| iCADM3_3R1-L8_04 | 1.5E+05 | 7.8E−04 | 5.34E−09 |

TABLE 10

Affinity for mouse CADM3

| Antibody | ka (1/Ms) | kd (1/s) | KD (M) |
|---|---|---|---|
| iCADM3_3R1-L8 | 1.4E+05 | 6.3E−04 | 4.39E−09 |
| iCADM3_3R1-L8_03 | 1.5E+05 | 1.1E−03 | 7.38E−09 |
| iCADM3_3R1-L8_04 | 1.2E+05 | 6.4E−04 | 5.22E−09 |

[Example 8] Evaluation of Migration Ability into Mouse Brain of Humanized Anti-CADM3 Antibody The negative control antibody (anti-AVM antibody), the anti-CADM3 VHH-Fc antibody (iCADM3_3R1-L8 VHH-hG4PE(R409K)), and the humanized anti-CADM3 VHH-Fc antibody (iCADM3_3R1-L8_04 VHH-hG4PE(R409K)) were labeled using SAI Alexa Fluor 647 Antibody/Protein 1 mg-Labeling Kit. Each of the labeled antibodies was administered through the tail vein (i.v.) at 5 mg/kg body weight, and after 7 days, the blood was collected.

After the blood was collected, whole body perfusion was performed under anesthesia, and thereafter, a brain tissue was collected and the weight thereof was measured. A buffer solution was added to the collected brain tissue, and the brain tissue was homogenized, followed by centrifugation, and an antibody solution eluted in the supernatant was collected. The volume thereof was measured, and also the antibody concentration was measured using AlphaLISA (manufactured by PerkinElmer, Inc.), and the antibody amount per unit brain weight was calculated. Note that the standard curve was created using each antibody. Further, with respect to a brain tissue collected under the same conditions, the fluorescence intensity was measured using IVIS Spectrum (manufactured by PerkinElmer, Inc.).

Figure 7:
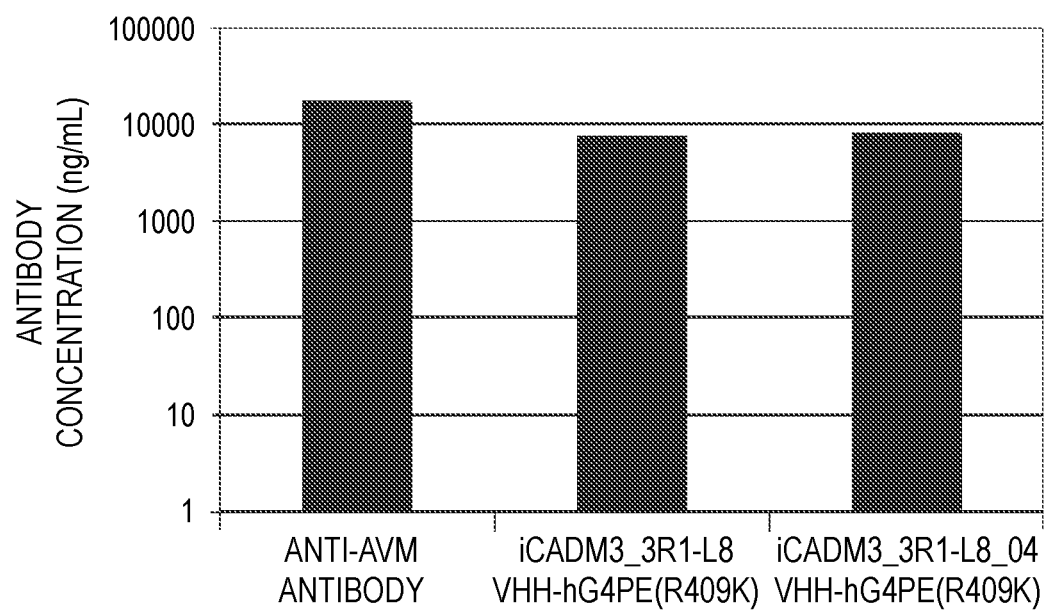
FIG. 7 shows the results of measuring the concentration of each antibody in a tissue.
Figure 7:
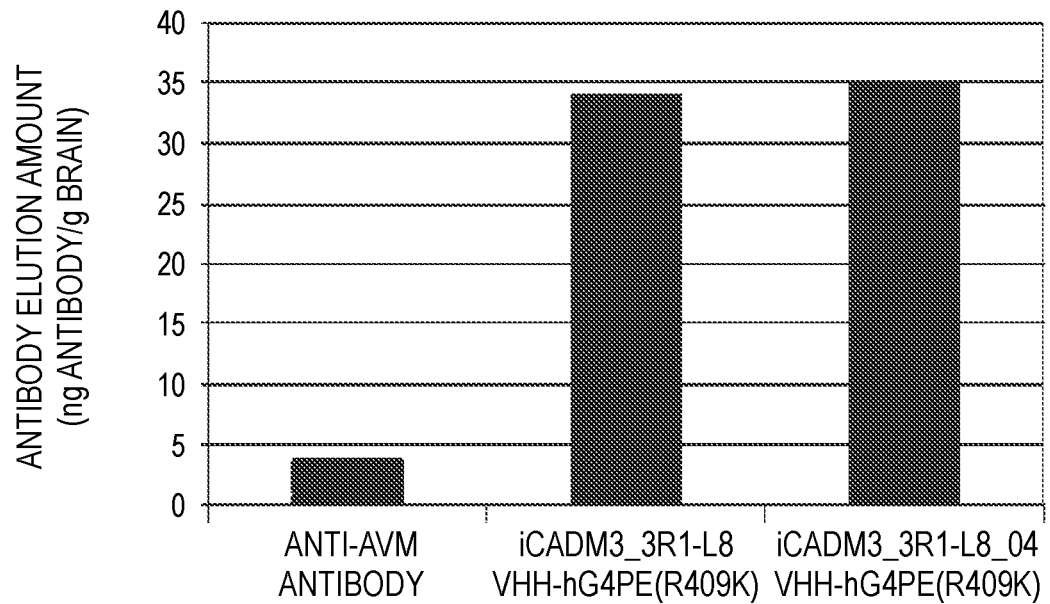

The antibody concentration in the serum 7 days after administering the antibody is shown in FIG. 7(A), and the antibody amount per unit brain weight in the brain tissue is shown in FIG. 7(B). As shown in FIGS. 7(A) and (B), there was no difference both in the antibody concentration in the serum and the antibody amount per unit brain weight in the brain tissue between iCADM3_3R1-L8 VHH-hG4PE (R409K) and iCADM3_3R1-L8_04 VHH-hG4PE(R409K), and it was demonstrated that the effect of increasing the antibody amount in the brain is maintained even after humanization of the antibody.

Figure 8:
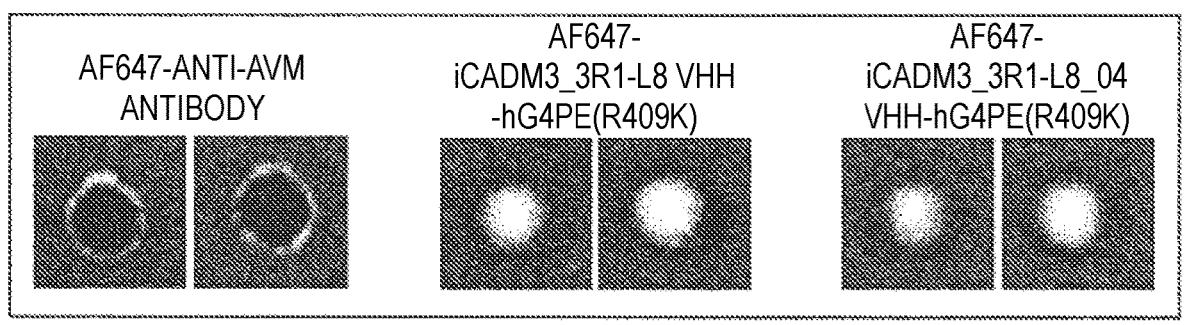
FIG. 8 shows the results of imaging evaluation of the migration ability into a mouse brain of each antibody.
Figure 8:
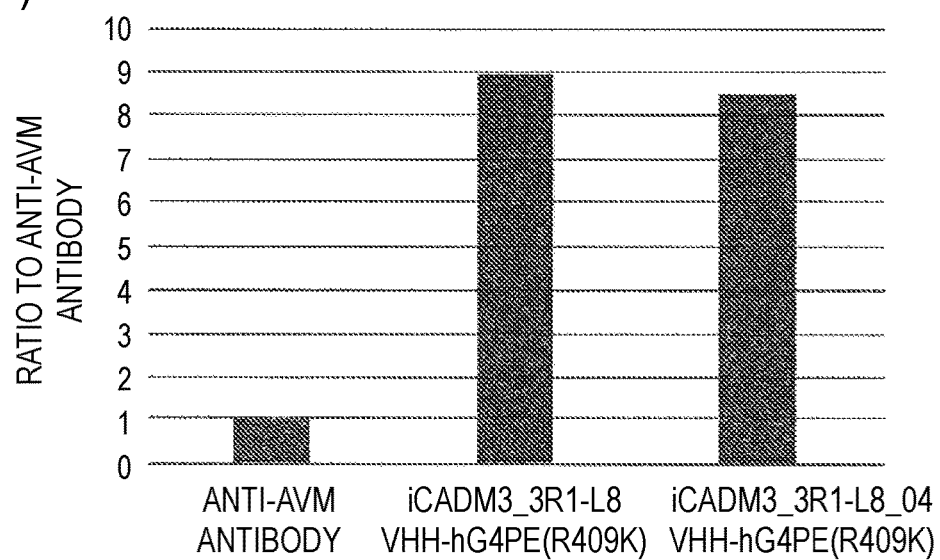

Imaging images of the brain 7 days after administering the antibody are shown in FIG. 8(A). The ratio of a value of the fluorescence amount in the brain corrected by the fluorescence intensity of the administered antibody to the negative control is shown in FIG. 8(B). As shown in FIGS. 8(A) and (B), the antibody amount in the brain of each of the anti-CADM3 VHH-Fc antibody and the humanized anti-CADM3 VHH-Fc antibody is increased by several times as compared with that of the negative control, and it was demonstrated that the distribution of the antibody spreads over the entire area of the brain. From the above results, humanized VHH that maintains an activity equivalent to that of the anti-CADM3 VHH antibody was produced.

The invention has been explained in detail using the specific aspects, but it is obvious for those skilled in the art that various changes and modifications can be made without departing from the spirit and scope of the invention. The present application is based on a Japanese Patent Application filed on Jun. 26, 2018 (Patent Application No. 2018-120477), which is incorporated by reference in its entirety.

SEQUENCE LISTING FREE TEXT

SEQ ID NO: 1—Description of artificial sequence: nucleotide sequence encoding VHH (excluding signal sequence) of iCADM3_3R1-L5

SEQ ID NO: 2—Description of artificial sequence: amino acid sequence of VHH (excluding signal sequence) of iCADM3_3R1-L5

SEQ ID NO: 3—Description of artificial sequence: amino acid sequence of CDR1 of iCADM3_3R1-L5

SEQ ID NO: 4—Description of artificial sequence: amino acid sequence of CDR2 of iCADM3_3R1-L5

SEQ ID NO: 5—Description of artificial sequence: amino acid sequence of CDR3 of iCADM3_3R1-L5

SEQ ID NO: 6—Description of artificial sequence: nucleotide sequence encoding VHH (excluding signal sequence) of iCADM3_3R1-L8

SEQ ID NO: 7—Description of artificial sequence: amino acid sequence of VHH (excluding signal sequence) of iCADM3_3R1-L8

SEQ ID NO: 8—Description of artificial sequence: amino acid sequence of CDR1 of iCADM3_3R1-L8

SEQ ID NO: 9—Description of artificial sequence: amino acid sequence of CDR2 of iCADM3_3R1-L8

SEQ ID NO: 10—Description of artificial sequence: amino acid sequence of CDR3 of iCADM3_3R1-L8

SEQ ID NO: 11—Description of artificial sequence: nucleotide sequence encoding VHH (excluding signal sequence) of iCADM3_3R1-L10

SEQ ID NO: 12—Description of artificial sequence: amino acid sequence of VHH (excluding signal sequence) of iCADM3_3R1-L10

SEQ ID NO: 13—Description of artificial sequence: amino acid sequence of CDR1 of iCADM3_3R1-L10

SEQ ID NO: 14—Description of artificial sequence: amino acid sequence of CDR2 of iCADM3_3R1-L10

SEQ ID NO: 15—Description of artificial sequence: amino acid sequence of CDR3 of iCADM3_3R1-L10

SEQ ID NO: 16—Description of artificial sequence: nucleotide sequence encoding VHH (excluding signal sequence) of iCADM3_3R1-L11

SEQ ID NO: 17—Description of artificial sequence: amino acid sequence of VHH (excluding signal sequence) of iCADM3_3R1-L11

SEQ ID NO: 18—Description of artificial sequence: amino acid sequence of CDR1 of iCADM3_3R1-L11

SEQ ID NO: 19—Description of artificial sequence: amino acid sequence of CDR2 of iCADM3_3R1-L11

SEQ ID NO: 20—Description of artificial sequence: amino acid sequence of CDR3 of iCADM3_3R1-L11

SEQ ID NO: 21—Description of artificial sequence: nucleotide sequence encoding VH (excluding signal sequence) of CADM301

SEQ ID NO: 22—Description of artificial sequence: amino acid sequence of VH (excluding signal sequence) of CADM301

SEQ ID NO: 23—Description of artificial sequence: amino acid sequence of HCDR1 of CADM301

SEQ ID NO: 24—Description of artificial sequence: amino acid sequence of HCDR2 of CADM301

SEQ ID NO: 25—Description of artificial sequence: amino acid sequence of HCDR3 of CADM301

SEQ ID NO: 26—Description of artificial sequence: nucleotide sequence encoding VL (excluding signal sequence) of CADM301

SEQ ID NO: 27—Description of artificial sequence: amino acid sequence of VL (excluding signal sequence) of CADM301

SEQ ID NO: 28—Description of artificial sequence: amino acid sequence of LCDR1 of CADM301

SEQ ID NO: 29—Description of artificial sequence: amino acid sequence of LCDR2 of CADM301

SEQ ID NO: 30—Description of artificial sequence: amino acid sequence of LCDR3 of CADM301

SEQ ID NO: 31—Description of artificial sequence: nucleotide sequence encoding VH (excluding signal sequence) of CADM3102

SEQ ID NO: 32—Description of artificial sequence: amino acid sequence of VH (excluding signal sequence) of CADM3102

SEQ ID NO: 33—Description of artificial sequence: amino acid sequence of HCDR1 of CADM3102

SEQ ID NO: 34—Description of artificial sequence: amino acid sequence of HCDR2 of CADM3102

SEQ ID NO: 35—Description of artificial sequence: amino acid sequence of HCDR3 of CADM3102

SEQ ID NO: 36—Description of artificial sequence: nucleotide sequence encoding VL (excluding signal sequence) of CADM3102

SEQ ID NO: 37—Description of artificial sequence: amino acid sequence of VL (excluding signal sequence) of CADM3102

SEQ ID NO: 38—Description of artificial sequence: amino acid sequence of LCDR1 of CADM3102

SEQ ID NO: 39—Description of artificial sequence: amino acid sequence of LCDR2 of CADM3102

SEQ ID NO: 40—Description of artificial sequence: amino acid sequence of LCDR3 of CADM3102

SEQ ID NO: 41—Description of artificial sequence: nucleotide sequence encoding light chain (excluding signal sequence) of anti-AVM antibody SEQ ID NO: 42—Description of artificial sequence: amino acid sequence of light chain (excluding signal sequence) of anti-AVM antibody SEQ ID NO: 43—Description of artificial sequence: nucleotide sequence encoding heavy chain (excluding signal sequence) of pCI_AVM-hLG4PE(R409K)-iCADM3_3R1-L5 VHH SEQ ID NO: 44—Description of artificial sequence: amino acid sequence of heavy chain (excluding signal sequence) of pCI_AVM-hLG4PE(R409K)-iCADM3_3R1-L5 VHH SEQ ID NO: 45—Description of artificial sequence: nucleotide sequence encoding heavy chain (excluding signal sequence) of pCI_AVM-hLG4PE(R409K)-iCADM3_3R1-L8 VHH SEQ ID NO: 46—Description of artificial sequence: amino acid sequence of heavy chain (excluding signal sequence) of pCI_AVM-hLG4PE(R409K)-iCADM3_3R1-L8 VHH SEQ ID NO: 47—Description of artificial sequence: nucleotide sequence encoding heavy chain (excluding signal sequence) of pCI_AVM-hLG4PE(R409K)-iCADM3_3R1-L10 VHH SEQ ID NO: 48—Description of artificial sequence: amino acid sequence of heavy chain (excluding signal sequence) of pCI_AVM-hLG4PE(R409K)-iCADM3_3R1-L10 VHH SEQ ID NO: 49—Description of artificial sequence: nucleotide sequence encoding heavy chain (excluding signal sequence) of pCI_AVM-hLG4PE(R409K)-iCADM3_3R1-L11 VHH SEQ ID NO: 50—Description of artificial sequence: amino acid sequence of heavy chain (excluding signal sequence) of pCI_AVM-hLG4PE(R409K)-iCADM3_3R1-L11 VHH SEQ ID NO: 51—Description of artificial sequence: nucleotide sequence encoding human CADM3 (comprising signal sequence) comprising signal sequence SEQ ID NO: 52—Description of artificial sequence: amino acid sequence of human CADM3 (comprising signal sequence) comprising signal sequence SEQ ID NO: 53—Description of artificial sequence: nucleotide sequence encoding mouse CADM3 (comprising signal sequence) comprising signal sequence SEQ ID NO: 54—Description of artificial sequence: amino acid sequence of mouse CADM3 (comprising signal sequence) comprising signal sequence SEQ ID NO: 55—Description of artificial sequence: nucleotide sequence encoding monkey CADM3 (comprising signal sequence) comprising signal sequence SEQ ID NO: 56—Description of artificial sequence: amino acid sequence of monkey CADM3 (comprising signal sequence) comprising signal sequence SEQ ID NO: 57—Description of artificial sequence: nucleotide sequence encoding hCADM3-FLAG_Fc (comprising signal sequence)

SEQ ID NO: 58—Description of artificial sequence: amino acid sequence of hCADM3-FLAG_Fc (comprising signal sequence)

SEQ ID NO: 59—Description of artificial sequence: nucleotide sequence encoding mCADM3-FLAG_Fc (comprising signal sequence)

SEQ ID NO: 60—Description of artificial sequence: amino acid sequence of mCADM3-FLAG_Fc (comprising signal sequence)

SEQ ID NO: 61—Description of artificial sequence: nucleotide sequence encoding rCADM3-FLAG_Fc (comprising signal sequence)

SEQ ID NO: 62—Description of artificial sequence: amino acid sequence of rCADM3-FLAG_Fc (comprising signal sequence)

SEQ ID NO: 63—Description of artificial sequence: nucleotide sequence encoding hCADM3-GST (comprising signal sequence)

SEQ ID NO: 64—Description of artificial sequence: amino acid sequence of hCADM3-GST (comprising signal sequence)

SEQ ID NO: 65—Description of artificial sequence: nucleotide sequence encoding mCADM3-GST (comprising signal sequence)

SEQ ID NO: 66—Description of artificial sequence: amino acid sequence of mCADM3-GST (comprising signal sequence)

SEQ ID NO: 67—Description of artificial sequence: nucleotide sequence encoding VHH (excluding signal sequence) of iCADM3_3R1-L8_01

SEQ ID NO: 68—Description of artificial sequence: amino acid sequence of VHH (excluding signal sequence) of iCADM3_3R1-L8_01

SEQ ID NO: 69—Description of artificial sequence: nucleotide sequence encoding VHH (excluding signal sequence) of iCADM3_3R1-L8_02

SEQ ID NO: 70—Description of artificial sequence: amino acid sequence of VHH (excluding signal sequence) of iCADM3_3R1-L8_02

SEQ ID NO: 71—Description of artificial sequence: nucleotide sequence encoding VHH (excluding signal sequence) of iCADM3_3R1-L8_03

SEQ ID NO: 72—Description of artificial sequence: amino acid sequence of VHH (excluding signal sequence) of iCADM3_3R1-L8_03

SEQ ID NO: 73—Description of artificial sequence: nucleotide sequence encoding VHH (excluding signal sequence) of iCADM3_3R1-L8_04

SEQ ID NO: 74—Description of artificial sequence: amino acid sequence of VHH (excluding signal sequence) of iCADM3_3R1-L8_04

SEQ ID NO: 75—Description of artificial sequence: nucleotide sequence encoding VHH (excluding signal sequence) of iCADM3_3R1-L11_01

SEQ ID NO: 76—Description of artificial sequence: amino acid sequence of VHH (excluding signal sequence) of iCADM3_3R1-L11_01

SEQ ID NO: 77—Description of artificial sequence: nucleotide sequence encoding VHH (excluding signal sequence) of iCADM3_3R1-L11_02

SEQ ID NO: 78—Description of artificial sequence: amino acid sequence of VHH (excluding signal sequence) of iCADM3_3R1-L11_02

SEQ ID NO: 79—Description of artificial sequence: nucleotide sequence encoding VHH (excluding signal sequence) of iCADM3_3R1-L11_03

SEQ ID NO: 80—Description of artificial sequence: amino acid sequence of VHH (excluding signal sequence) of iCADM3_3R1-L11_03

SEQ ID NO: 81—Description of artificial sequence: nucleotide sequence encoding VHH (excluding signal sequence) of iCADM3_3R1-L11_04

SEQ ID NO: 82—Description of artificial sequence: amino acid sequence of VHH (excluding signal sequence) of iCADM3_3R1-L11_04

SEQ ID NO: 83—Description of artificial sequence: nucleotide sequence encoding VHH (excluding signal sequence) of iCADM3_3R1-L11_05

SEQ ID NO: 84—Description of artificial sequence: amino acid sequence of VHH (excluding signal sequence) of iCADM3_3R1-L11_05

SEQ ID NO: 85—Description of artificial sequence: nucleotide sequence encoding VHH (excluding signal sequence) of iCADM3_3R1-L11_06

SEQ ID NO: 86—Description of artificial sequence: amino acid sequence of VHH (excluding signal sequence) of iCADM3_3R1-L11-_06

SEQ ID NO: 87—Description of artificial sequence: nucleotide sequence encoding VH (excluding signal sequence) of CADM3219

SEQ ID NO: 88—Description of artificial sequence: amino acid sequence of VH (excluding signal sequence) of CADM3219

SEQ ID NO: 89—Description of artificial sequence: amino acid sequence of HCDR1 of CADM3219

SEQ ID NO: 90—Description of artificial sequence: amino acid sequence of HCDR2 of CADM3219

SEQ ID NO: 91—Description of artificial sequence: amino acid sequence of HCDR3 of CADM3219

SEQ ID NO: 92—Description of artificial sequence: nucleotide sequence encoding VL (excluding signal sequence) of CADM3219

SEQ ID NO: 93—Description of artificial sequence: amino acid sequence of VL (excluding signal sequence) of CADM3219

SEQ ID NO: 94—Description of artificial sequence: amino acid sequence of LCDR1 of CADM3219

SEQ ID NO: 95—Description of artificial sequence: amino acid sequence of LCDR2 of CADM3219

SEQ ID NO: 96—Description of artificial sequence: amino acid sequence of LCDR3 of CADM3219

SEQ ID NO: 97—Description of artificial sequence: nucleotide sequence encoding VH (excluding signal sequence) of CADM3301

SEQ ID NO: 98—Description of artificial sequence: amino acid sequence of VH (excluding signal sequence) of CADM3301

SEQ ID NO: 99—Description of artificial sequence: amino acid sequence of HCDR1 of CADM3301

SEQ ID NO: 100—Description of artificial sequence; amino acid sequence of HCDR2 of CADM3301

SEQ ID NO: 101—Description of artificial sequence: amino acid sequence of HCDR3 of CADM3301

SEQ ID NO: 102—Description of artificial sequence: nucleotide sequence encoding VH (excluding signal sequence) of CADM3309

SEQ ID NO: 103—Description of artificial sequence: amino acid sequence of VH (excluding signal sequence) of CADM3309

SEQ ID NO: 104—Description of artificial sequence; amino acid sequence of HCDR1 of CADM3309

SEQ ID NO: 105—Description of artificial sequence: amino acid sequence of HCDR2 of CADM3309

SEQ ID NO: 106—Description of artificial sequence: amino acid sequence of HCDR3 of CADM3309

SEQ ID NO: 107—Description of artificial sequence: nucleotide sequence encoding VH (excluding signal sequence) of CADM3312

SEQ ID NO: 108—Description of artificial sequence: amino acid sequence of VH (excluding signal sequence) of CADM3312

SEQ ID NO: 109—Description of artificial sequence: amino acid sequence of HCDR1 of CADM3312

SEQ ID NO: 110—Description of artificial sequence: amino acid sequence of HCDR2 of CADM3312

SEQ ID NO: 111—Description of artificial sequence: amino acid sequence of HCDR3 of CADM3312

SEQ ID NO: 112—Description of artificial sequence: nucleotide sequence encoding VH (excluding signal sequence) of CADM3314

SEQ ID NO: 113—Description of artificial sequence: amino acid sequence of VH (excluding signal sequence) of CADM3314

SEQ ID NO: 114—Description of artificial sequence: amino acid sequence of HCDR1 of CADM3314

SEQ ID NO: 115—Description of artificial sequence: amino acid sequence of HCDR2 of CADM3314

SEQ ID NO: 116—Description of artificial sequence: amino acid sequence of HCDR3 of CADM3314

SEQ ID NO: 117—Description of artificial sequence: nucleotide sequence encoding VH (excluding signal sequence) of CADM3316

SEQ ID NO: 118—Description of artificial sequence: amino acid sequence of VH (excluding signal sequence) of CADM3316

SEQ ID NO: 119—Description of artificial sequence: amino acid sequence of HCDR1 of CADM3316

SEQ ID NO: 120—Description of artificial sequence: amino acid sequence of HCDR2 of CADM3316

SEQ ID NO: 121—Description of artificial sequence: amino acid sequence of HCDR3 of CADM3316

SEQ ID NO: 122—Description of artificial sequence: nucleotide sequence encoding VH (excluding signal sequence) of CADM3349

SEQ ID NO: 123—Description of artificial sequence: amino acid sequence of VH (excluding signal sequence) of CADM3349

SEQ ID NO: 124—Description of artificial sequence; amino acid sequence of HCDR1 of CADM3349

SEQ ID NO: 125—Description of artificial sequence: amino acid sequence of HCDR2 of CADM3349

SEQ ID NO: 126—Description of artificial sequence; amino acid sequence of HCDR3 of CADM3349

SEQ ID NO: 127—Description of artificial sequence: nucleotide sequence encoding VH (excluding signal sequence) of CADM3351

SEQ ID NO: 128—Description of artificial sequence: amino acid sequence of VH (excluding signal sequence) of CADM3351

SEQ ID NO: 129—Description of artificial sequence: amino acid sequence of HCDR1 of CADM3351

SEQ ID NO: 130—Description of artificial sequence: amino acid sequence of HCDR2 of CADM3351

SEQ ID NO: 131—Description of artificial sequence: amino acid sequence of HCDR3 of CADM3351

SEQ ID NO: 132—Description of artificial sequence: nucleotide sequence encoding VL (excluding signal sequence) of CADM3301, CADM3309, CADM3312, CADM3314, CADM3316, CADM3349, and CADM3351

SEQ ID NO: 133—Description of artificial sequence; amino acid sequence of VL (excluding signal sequence) of CADM3301, CADM3309, CADM3312, CADM3314, CADM3316, CADM3349, and CADM3351

SEQ ID NO: 134—Description of artificial sequence: amino acid sequence of LCDR1 of CADM3301, CADM3309, CADM3312, CADM3314, CADM3316, CADM3349, and CADM3351

SEQ ID NO: 135—Description of artificial sequence: amino acid sequence of LCDR2 of CADM3301, CADM3309, CADM3312, CADM3314, CADM3316, CADM3349, and CADM3351

SEQ ID NO: 136—Description of artificial sequence: amino acid sequence of LCDR3 of CADM3301, CADM3309, CADM3312, CADM3314, CADM3316, CADM3349, and CADM3351

SEQ ID NO: 137—Description of artificial sequence: nucleotide sequence encoding VH (excluding signal sequence) of CADM3402

SEQ ID NO: 138—Description of artificial sequence; amino acid sequence of VH (excluding signal sequence) of CADM3402

SEQ ID NO: 139—Description of artificial sequence: amino acid sequence of HCDR1 of CADM3402

SEQ ID NO: 140—Description of artificial sequence: amino acid sequence of HCDR2 of CADM3402

SEQ ID NO: 141—Description of artificial sequence: amino acid sequence of HCDR3 of CADM3402

SEQ ID NO: 142—Description of artificial sequence: nucleotide sequence encoding VH (excluding signal sequence) of CADM3404

SEQ ID NO: 143—Description of artificial sequence: amino acid sequence of VH (excluding signal sequence) of CADM3404

SEQ ID NO: 144—Description of artificial sequence: amino acid sequence of HCDR1 of CADM3404

SEQ ID NO: 145—Description of artificial sequence: amino acid sequence of HCDR2 of CADM3404

SEQ ID NO: 146—Description of artificial sequence: amino acid sequence of HCDR3 of CADM3404

SEQ ID NO: 147—Description of artificial sequence: nucleotide sequence encoding VH (excluding signal sequence) of CADM3432

SEQ ID NO: 148—Description of artificial sequence: amino acid sequence of VH (excluding signal sequence) of CADM3432

SEQ ID NO: 149—Description of artificial sequence: amino acid sequence of HCDR1 of CADM3432

SEQ ID NO: 150—Description of artificial sequence: amino acid sequence of HCDR2 of CADM3432

SEQ ID NO: 151—Description of artificial sequence; amino acid sequence of HCDR3 of CADM3432

SEQ ID NO: 152—Description of artificial sequence: nucleotide sequence encoding VH (excluding signal sequence) of CADM3448

SEQ ID NO: 153—Description of artificial sequence: amino acid sequence of VH (excluding signal sequence) of CADM3448

SEQ ID NO: 154—Description of artificial sequence: amino acid sequence of HCDR1 of CADM3448

SEQ ID NO: 155—Description of artificial sequence: amino acid sequence of HCDR2 of CADM3448

SEQ ID NO: 156—Description of artificial sequence: amino acid sequence of HCDR3 of CADM3448

SEQ ID NO: 157—Description of artificial sequence: nucleotide sequence encoding VH (excluding signal sequence) of CADM3458

SEQ ID NO: 158—Description of artificial sequence: amino acid sequence of VH (excluding signal sequence) of CADM3458

SEQ ID NO: 159—Description of artificial sequence: amino acid sequence of HCDR1 of CADM3458

SEQ ID NO: 160—Description of artificial sequence; amino acid sequence of HCDR2 of CADM3458

SEQ ID NO: 161—Description of artificial sequence: amino acid sequence of HCDR3 of CADM3458

SEQ ID NO: 162—Description of artificial sequence: nucleotide sequence encoding VL (excluding signal sequence) of CADM3402, CADM3404, CADM3432, CADM3448, and CADM3458

SEQ ID NO: 163—Description of artificial sequence; amino acid sequence of VL (excluding signal sequence) of CADM3402, CADM3404, CADM3432, CADM3448, and CADM3458

SEQ ID NO: 164—Description of artificial sequence: amino acid sequence of LCDR1 of CADM3402, CADM3404, CADM3432, CADM3448, and CADM3458

SEQ ID NO: 165—Description of artificial sequence: amino acid sequence of LCDR2 of CADM3402, CADM3404, CADM3432, CADM3448, and CADM3458

SEQ ID NO: 166—Description of artificial sequence: amino acid sequence of LCDR3 of CADM3402, CADM3404, CADM3432, CADM3448, and CADM3458

SEQ ID NO: 167—Description of artificial sequence: nucleotide sequence encoding VH (excluding signal sequence) of CADM3501

SEQ ID NO: 168—Description of artificial sequence: amino acid sequence of VH (excluding signal sequence) of CADM3501

SEQ ID NO: 169—Description of artificial sequence: amino acid sequence of HCDR1 of CADM3501

SEQ ID NO: 170—Description of artificial sequence; amino acid sequence of HCDR2 of CADM3501

SEQ ID NO: 171—Description of artificial sequence: amino acid sequence of HCDR3 of CADM3501

SEQ ID NO: 172—Description of artificial sequence: nucleotide sequence encoding VL (excluding signal sequence) of CADM3501

SEQ ID NO: 173—Description of artificial sequence: amino acid sequence of VL (excluding signal sequence) of CADM3501

SEQ ID NO: 174—Description of artificial sequence: amino acid sequence of LCDR1 of CADM3501

SEQ ID NO: 175—Description of artificial sequence: amino acid sequence of LCDR2 of CADM3501

SEQ ID NO: 176—Description of artificial sequence: amino acid sequence of LCDR3 of CADM3501

SEQ ID NO: 177—Description of artificial sequence: amino acid sequence of VHH (excluding signal sequence) of iCADM3_3R1-L8_00

SEQ ID NO: 178—Description of artificial sequence: amino acid sequence of VHH (excluding signal sequence) of iCADM3_3R1-L11_00

The invention claimed is:

1. An antibody which binds to cell adhesion molecule 3 (CADM3) or an antibody fragment thereof,
wherein the antibody or the antibody fragment thereof is selected from the group consisting of the following (a) to (t):
(a) an antibody in which the amino acid sequences of complementarity determining regions (CDRs) 1 to 3 of a variable domain of a heavy chain (VH) comprise the amino acid sequences represented by SEQ ID NOS: 23, 24, and 25, respectively, and in which the amino acid sequences of CDR1 to CDR3 of a variable domain of a light chain (VL) comprise the amino acid sequences represented by SEQ ID NOS: 28, 29, and 30, respectively;
(b) an antibody in which the amino acid sequences of CDR1 to CDR3 of VH comprise the amino acid sequences represented by SEQ ID NOS: 33, 34 and 35, respectively, and in which the amino acid sequences of CDR1 to CDR3 of VL comprise the amino acid sequences represented by SEQ ID NOS: 38, 39, and 40, respectively;
(c) an antibody fragment in which the amino acid sequences of CDR1 to CDR3 of a variable domain of a heavy chain of a heavy chain antibody (VHH) comprise the amino acid sequences represented by SEQ ID NOS: 3, 4, and 5, respectively;
(d) an antibody fragment in which the amino acid sequences of CDR1 to CDR3 of VHH comprise the amino acid sequences represented by SEQ ID NOS: 8, 9, and 10, respectively;
(e) an antibody fragment in which the amino acid sequences of CDR1 to CDR3 of VHH comprise the amino acid sequences represented by SEQ ID NOS: 13, 14, and 15, respectively;
(f) an antibody fragment in which the amino acid sequences of CDR1 to CDR3 of VHH comprise the amino acid sequences represented by SEQ ID NOS: 18, 19, and 20, respectively;
(g) an antibody in which the amino acid sequences of CDR1 to CDR3 of VH comprise the amino acid sequences represented by SEQ ID NOS: 89, 90, and 91, respectively, and in which the amino acid sequences of CDR1 to CDR3 of VL comprise the amino acid sequences represented by SEQ ID NOS: 94, 95, and 96, respectively;
(h) an antibody in which the amino acid sequences of CDR1 to CDR3 of VH comprise the amino acid sequences represented by SEQ ID NOS: 99, 100, and 101, respectively, and in which the amino acid sequences of CDR1 to CDR3 of VL comprise the amino acid sequences represented by SEQ ID NOS: 134, 135, and 136, respectively;
(i) an antibody in which the amino acid sequences of CDR1 to CDR3 of VH comprise the amino acid sequences represented by SEQ ID NOS: 104, 105, and 106, respectively, and in which the amino acid sequences of CDR1 to CDR3 of VL comprise the amino acid sequences represented by SEQ ID NOS: 134, 135, and 136, respectively;
(j) an antibody in which the amino acid sequences of CDR1 to CDR3 of VH comprise the amino acid sequences represented by SEQ ID NOS: 109, 110, and 111, respectively, and in which the amino acid sequences of CDR1 to CDR3 of VL comprise the amino acid sequences represented by SEQ ID NOS: 134, 135, and 136, respectively;

(k) an antibody in which the amino acid sequences of CDR1 to CDR3 of VH comprise the amino acid sequences represented by SEQ ID NOS: 114, 115, and, 116, respectively, and in which the amino acid sequences of CDR1 to CDR3 of VL comprise the amino acid sequences represented by SEQ ID NOS: 134, 135, and 136, respectively;

(l) an antibody in which the amino acid sequences of CDR1 to CDR3 of VH comprise the amino acid sequences represented by SEQ ID NOS: 119, 120, and 121, respectively, and in which the amino acid sequences of CDR1 to CDR3 of VL comprise the amino acid sequences represented by SEQ ID NOS: 134, 135, and 136, respectively;

(m) an antibody in which the amino acid sequences of CDR1 to CDR3 of VH comprise the amino acid sequences represented by SEQ ID NOS: 124, 125, and 126, respectively, and in which the amino acid sequences of CDR1 to CDR3 of VL comprise the amino acid sequences represented by SEQ ID NOS: 134, 135, and 136, respectively;

(n) an antibody in which the amino acid sequences of CDR1 to CDR3 of VH comprise the amino acid sequences represented by SEQ ID NOS: 129, 130, and 131, respectively, and in which the amino acid sequences of CDR1 to CDR3 of VL comprise the amino acid sequences represented by SEQ ID NOS: 134, 135, and 136, respectively;

(o) an antibody in which the amino acid sequences of CDR1 to CDR3 of VH comprise the amino acid sequences represented by SEQ ID NOS: 139, 140, and 141, respectively, and in which the amino acid sequences of CDR1 to CDR3 of VL comprise the amino acid sequences represented by SEQ ID NOS: 164, 165, and 166, respectively;

(p) an antibody in which the amino acid sequences of CDR1 to CDR3 of VH comprise the amino acid sequences represented by SEQ ID NOS: 144, 145, and 146, respectively, and in which the amino acid sequences of CDR1 to CDR3 of VL comprise the amino acid sequences represented by SEQ ID NOS: 164, 165, and 166, respectively;

(q) an antibody in which the amino acid sequences of CDR1 to CDR3 of VH comprise the amino acid sequences represented by SEQ ID NOS: 149, 150, and 151, respectively, and in which the amino acid sequences of CDR1 to CDR3 of VL comprise the amino acid sequences represented by SEQ ID NOS: 164, 165, and 166, respectively;

(r) an antibody in which the amino acid sequences of CDR1 to CDR3 of VH comprise the amino acid sequences represented by SEQ ID NOS: 154, 155, and 156, respectively, and in which the amino acid sequences of CDR1 to CDR3 of VL comprise the amino acid sequences represented by SEQ ID NOS: 164, 165, and 166, respectively;

(s) an antibody in which the amino acid sequences of CDR1 to CDR3 of VH comprise the amino acid sequences represented by SEQ ID NOS: 159, 160, and 161, respectively, and in which the amino acid sequences of CDR1 to CDR3 of VL comprise the amino acid sequences represented by SEQ ID NOS: 164, 165, and 166, respectively; and (t) an antibody in which the amino acid sequences of CDR1 to CDR3 of VH comprise the amino acid sequences represented by SEQ ID NOS: 169, 170, and 171, respectively, and in which the amino acid sequences of CDR1 to CDR3 of VL comprise the amino acid sequences represented by SEQ ID NOS: 174, 175, and 176, respectively.

2. The antibody or the antibody fragment thereof according to claim 1, wherein the antibody has a property of accumulating a brain.

3. The antibody or the antibody fragment thereof according to claim 1, wherein the antibody has an affinity for neurons and/or nerve tissues.

4. The antibody or the antibody fragment thereof according to claim 1, wherein the antibody or the antibody fragment thereof is selected from the group consisting of the following (1) to (30):

(1) an antibody in which the amino acid sequence of VH comprises the amino acid sequence represented by SEQ ID NO: 22 and in which the amino acid sequence of VL comprises the amino acid sequence represented by SEQ ID NO: 27;

(2) an antibody in which the amino acid sequence of VH comprises the amino acid sequence represented by SEQ ID NO: 32 and in which the amino acid sequence of VL comprises the amino acid sequence represented by SEQ ID NO: 37;

(3) an antibody fragment in which the amino acid sequence of VHH comprises the amino acid sequence represented by SEQ ID NO: 2;

(4) an antibody fragment in which the amino acid sequence of VHH comprises the amino acid sequence represented by SEQ ID NO: 7;

(5) an antibody fragment in which the amino acid sequence of VHH comprises the amino acid sequence represented by SEQ ID NO: 12;

(6) an antibody fragment in which the amino acid sequence of VHH comprises the amino acid sequence represented by SEQ ID NO: 17;

(7) an antibody fragment in which the amino acid sequence of VHH comprises the amino acid sequence represented by SEQ ID NO: 68;

(8) an antibody fragment in which the amino acid sequence of VHH comprises the amino acid sequence represented by SEQ ID NO: 70;

(9) an antibody fragment in which the amino acid sequence of VHH comprises the amino acid sequence represented by SEQ ID NO: 72;

(10) an antibody fragment in which the amino acid sequence of VHH comprises the amino acid sequence represented by SEQ ID NO: 74;

(11) an antibody fragment in which the amino acid sequence of VHH comprises the amino acid sequence represented by SEQ ID NO: 76;

(12) an antibody fragment in which the amino acid sequence of VHH comprises the amino acid sequence represented by SEQ ID NO: 78;

(13) an antibody fragment in which the amino acid sequence of VHH comprises the amino acid sequence represented by SEQ ID NO: 80;

(14) an antibody fragment in which the amino acid sequence of VHH comprises the amino acid sequence represented by SEQ ID NO: 82;

(15) an antibody fragment in which the amino acid sequence of VHH comprises the amino acid sequence represented by SEQ ID NO: 84;
(16) an antibody fragment in which the amino acid sequence of VHH comprises the amino acid sequence represented by SEQ ID NO: 86;
(17) an antibody in which the amino acid sequence of VH comprises the amino acid sequence represented by SEQ ID NO: 88 and in which the amino acid sequence of VL comprises the amino acid sequence represented by SEQ ID NO: 93;
(18) an antibody in which the amino acid sequence of VH comprises the amino acid sequence represented by SEQ ID NO: 98 and in which the amino acid sequence of VL comprises the amino acid sequence represented by SEQ ID NO: 133;
(19) an antibody in which the amino acid sequence of VH comprises the amino acid sequence represented by SEQ ID NO: 103 and in which the amino acid sequence of VL comprises the amino acid sequence represented by SEQ ID NO: 133;
(20) an antibody in which the amino acid sequence of VH comprises the amino acid sequence represented by SEQ ID NO: 108 and in which the amino acid sequence of VL comprises the amino acid sequence represented by SEQ ID NO: 133;
(21) an antibody in which the amino acid sequence of VH comprises the amino acid sequence represented by SEQ ID NO: 113 and in which the amino acid sequence of VL comprises the amino acid sequence represented by SEQ ID NO: 133;
(22) an antibody in which the amino acid sequence of VH comprises the amino acid sequence represented by SEQ ID NO: 118 and in which the amino acid sequence of VL comprises the amino acid sequence represented by SEQ ID NO: 133;
(23) an antibody in which the amino acid sequence of VH comprises the amino acid sequence represented by SEQ ID NO: 123 and in which the amino acid sequence of VL comprises the amino acid sequence represented by SEQ ID NO: 133;
(24) an antibody in which the amino acid sequence of VH comprises the amino acid sequence represented by SEQ ID NO: 128 and in which the amino acid sequence of VL comprises the amino acid sequence represented by SEQ ID NO: 133;
(25) an antibody in which the amino acid sequence of VH comprises the amino acid sequence represented by SEQ ID NO: 138 and in which the amino acid sequence of VL comprises the amino acid sequence represented by SEQ ID NO: 163;
(26) an antibody in which the amino acid sequence of VH comprises the amino acid sequence represented by SEQ ID NO: 143 and in which the amino acid sequence of VL comprises the amino acid sequence represented by SEQ ID NO: 163;
(27) an antibody in which the amino acid sequence of VH comprises the amino acid sequence represented by SEQ ID NO: 148 and in which the amino acid sequence of VL comprises the amino acid sequence represented by SEQ ID NO: 163;
(28) an antibody in which the amino acid sequence of VH comprises the amino acid sequence represented by SEQ ID NO: 153 and in which the amino acid sequence of VL comprises the amino acid sequence represented by SEQ ID NO: 163;
(29) an antibody in which the amino acid sequence of VH comprises the amino acid sequence represented by SEQ ID NO: 158 and in which the amino acid sequence of VL comprises the amino acid sequence represented by SEQ ID NO: 163; and
(30) an antibody in which the amino acid sequence of VH comprises the amino acid sequence represented by SEQ ID NO: 168 and in which the amino acid sequence of VL comprises the amino acid sequence represented by SEQ ID NO: 173.

5. The antibody or the antibody fragment thereof according to claim 1, wherein the antibody or the antibody fragment thereof is a bispecific antibody.

6. The antibody or the antibody fragment thereof according to claim 1, wherein the antibody or the antibody fragment thereof is a bispecific antibody, and wherein the bispecific antibody binds to CADM3 and to an antigen present in a brain.

7. The antibody or the antibody fragment thereof according to claim 1, wherein the antibody or the antibody fragment thereof is a bispecific antibody, and wherein the bispecific antibody comprises a first antigen-binding site which binds to CADM3 and a second antigen-binding site which binds to an antigen present in a brain.

8. The antibody fragment according to claim 1, wherein the antibody fragment is selected from the group consisting of Fab, Fab', F(ab')$_2$, a single chain antibody (scFv), a dimerized V region (diabody), a disulfide-stabilized V region (dsFv), a variable domain of a heavy chain of a heavy chain antibody (VHH), and a peptide comprising a plurality of CDRs.

9. The antibody or the antibody fragment thereof according to claim 1, wherein the antibody is a genetically recombinant antibody.

10. The antibody or the antibody fragment thereof according to claim 1, wherein the antibody is selected from the group consisting of an alpaca antibody, chimeric antibody, a humanized antibody, and a human antibody.

11. A fusion antibody or a fusion antibody fragment thereof, in which at least one selected from the group consisting of the following (i) to (iii) is linked to the antibody or the antibody fragment thereof which binds to CADM3 according to claim 1:
(i) a hydrophilic polymer;
(ii) an amphipathic polymer; and
(iii) a functional molecule.

12. A nucleic acid comprising a nucleotide sequence encoding the fusion antibody or the fusion antibody fragment thereof according to claim 11.

13. A transformant cell comprising a vector comprising the nucleic acid according to claim 12.

14. A method for producing the fusion antibody or the fusion antibody fragment thereof according to claim 11, comprising:
culturing a transformant cell comprising a vector comprising a nucleic acid encoding the fusion antibody or the fusion antibody fragment thereof, and
collecting the antibody or the antibody fragment thereof from a culture solution.

15. A composition comprising the fusion antibody or the fusion antibody fragment thereof according to claim 11 and one or more pharmacologically acceptable carriers.

16. A method for detecting or measuring an antigen present in a brain, comprising:
performing an immunological method on brain cells or tissue using the fusion antibody or the fusion antibody fragment thereof according to claim 11, wherein the brain cells or tissue are contacted with the fusion antibody or the fusion antibody fragment under conditions allowing the fusion antibody or the fusion antibody fragment to react with the brain cells or tissue, and detecting the reaction.

17. A method for diagnosing or treating a brain disease, comprising:
   administering the fusion antibody or the fusion antibody fragment thereof according to claim 11 to the periphery of the subject.

18. A method for enhancing accumulating of a fusion antibody or a fusion antibody fragment thereof in a brain of a subject, comprising:
   administering the fusion antibody or the fusion antibody fragment thereof according to claim 11 to the periphery of the subject.

19. A method for increasing the amount of a fusion antibody or a fusion antibody fragment thereof in a brain of a subject, comprising:
   administering the fusion antibody or the fusion antibody fragment thereof according to claim 11 to the periphery of the subject.

20. A hybridoma which produces the antibody or the antibody fragment thereof according to claim 1.

21. A nucleic acid, comprising a nucleotide sequence encoding the antibody or the antibody fragment thereof according to claim 1.

22. A transformant cell comprising a vector comprising the nucleic acid according to claim 21.

23. A method for producing the antibody or the antibody fragment thereof according to claim 1, comprising:
   culturing either (i) a hybridoma which produces the antibody or the antibody fragment thereof or (ii) a transformant cell comprising a vector comprising a nucleic acid encoding the antibody or antibody fragment thereof, and
   collecting the antibody or the antibody fragment thereof from a culture solution.

24. A composition comprising the antibody or the antibody fragment thereof according to claim 1 and one or more pharmacologically acceptable carriers.

25. A method for detecting or measuring an antigen present in a brain, comprising:
   performing an immunological method on brain cells or tissue using the antibody or the antibody fragment thereof according to claim 1, wherein the brain cells or tissue are contacted with the antibody or the antibody fragment under conditions allowing the antibody or the antibody fragment to react with the brain cells or tissue, and detecting the reaction.

26. A method for diagnosing or treating a brain disease, comprising:
   administering the antibody or the antibody fragment thereof according to claim 1 to the periphery of the subject.

27. A method for enhancing the property of accumulating an antibody or an antibody fragment thereof in a brain of a subject, comprising:
   administering the antibody or the antibody fragment thereof according to claim 1 to the periphery of the subject.

28. A method for increasing the amount of an antibody or an antibody fragment thereof in a brain of a subject, comprising:
   administering the antibody or the antibody fragment thereof according to claim 1 to the periphery of the subject.

29. A method for producing a fusion antibody or a fusion antibody fragment thereof, comprising:
   (a) culturing either (i) a hybridoma which produces the antibody or the antibody fragment thereof of claim 1 or (ii) a transformant cell comprising a vector comprising a nucleic acid encoding the antibody or the antibody fragment thereof of claim 1,
   (b) collecting the antibody or the antibody fragment thereof from a culture solution, and
   (c) linking at least one selected from the group consisting of the following (i) to (iii) to the antibody or the antibody fragment thereof collected in (b):
      (i) a hydrophilic polymer;
      (ii) an amphipathic polymer; and
      (iii) a functional molecule.

* * * * *

```
                            SEQUENCE LISTING

<160> NUMBER OF SEQ ID NOS: 178

<210> SEQ ID NO 1
<211> LENGTH: 372
<212> TYPE: DNA
<213> ORGANISM: Artificial Sequence
<220> FEATURE:
<223> OTHER INFORMATION: Description of the artificial sequence: base
      sequence of VHH of iCADM3_3R1-L5 excluding signal sequence

<400> SEQUENCE: 1
caggtgcagc tcgtggagtc tgggggaggc ttggtgcagg ctgggggtc tctgagactc      60 tcctgtgcag cctctggaag catcgtcagt gtcaatgcca tgggctggta ccgccaggct    120
ccagggaagc agcgcgagtt ggtcgcaact attactagtg ggggtagcac aaactatgca    180
gactccgcga agggccgatt caccatctcc agagacaacg ccaagaacac gatgtatctg    240
caaatgaaca gcctgaaacc tgaggacaca gccgtctatt actgtaacgg ggaattctgg    300
tcgcgccggg acacacgccc cccaggggtc gtaaactact ggggccaggg gacccaggtc    360
accgtctcct ca                                                       372

<210> SEQ ID NO 2
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L5 excluding signal sequence

<400> SEQUENCE: 2

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Val Ser Val Asn
            20                  25                  30

Ala Met Gly Trp Tyr Arg Gln Ala Pro Gly Lys Gln Arg Glu Leu Val
        35                  40                  45

Ala Thr Ile Thr Ser Gly Gly Ser Thr Asn Tyr Ala Asp Ser Ala Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Gly Glu Phe Trp Ser Arg Arg Asp Thr Arg Pro Pro Gly Val Val Asn
            100                 105                 110
```

Tyr Trp Gly Gln Gly Thr Gln Val Thr Val Ser Ser
        115                 120

<210> SEQ ID NO 3
<211> LENGTH: 5
<212> TYPE: PRT
<213> ORGANISM: Artificial Sequence
<220> FEATURE:
<223> OTHER INFORMATION: Description of the artificial sequence: amino
      acid sequence of CDR1 of iCADM3_3R1-L5

<400> SEQUENCE: 3

Val Asn Ala Met Gly
1               5

<210> SEQ ID NO 4
<211> LENGTH: 16
<212> TYPE: PRT
<213> ORGANISM: Artificial Sequence
<220> FEATURE:
<223> OTHER INFORMATION: Description of the artificial sequence: amino
      acid sequence of CDR2 of iCADM3_3R1-L5

<400> SEQUENCE: 4

Thr Ile Thr Ser Gly Gly Ser Thr Asn Tyr Ala Asp Ser Ala Lys Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of the artificial sequence: amino
      acid sequence of CDR3 of iCADM3_3R1-L5

<400> SEQUENCE: 5

Glu Phe Trp Ser Arg Arg Asp Thr Arg Pro Pro Gly Val Val Asn Tyr
1               5                   10                  15

<210> SEQ ID NO 6
<211> LENGTH: 372
<212> TYPE: DNA
<213> ORGANISM: Artificial Sequence
<220> FEATURE:
<223> OTHER INFORMATION: Description of the artificial sequence: base
      sequence of VHH of iCADM3_3R1-L8 excluding signal sequence

<400> SEQUENCE: 6
caggtgcagc tcgtggagtc tgggggaggc ttggtgcagc ctggggggtc tctgagactc      60
tcctgtgcag cctctggacg caccttcagt aattatgccc ggggctggtt ccgccaggct     120
ccagggaagg agcgtgagtt tgtagcagct attgactaca gtggtggtag cacaaactat     180
gcagactccg cgaagggccg attcaccatc tccagagaca cgccaagaa cacggtgtat      240 ctgcaaatga acagcctgaa acccggggac acggccgttt attactgtgc agcgcccgca     300
agccggcgtc ctagttggga tgctgatggg tatgactact ggggccaggg gacccaggtc     360
accgtctcct ca                                                         372

<210> SEQ ID NO 7
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L8 excluding signal sequence

```
<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Asn Tyr
            20                  25                  30

Ala Arg Gly Trp Phe Arg Gln Ala Pro Gly Lys Glu Arg Glu Phe Val
        35                  40                  45

Ala Ala Ile Asp Tyr Ser Gly Gly Ser Thr Asn Tyr Ala Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Gly Asp Thr Ala Val Tyr Tyr Cys
                85                  90                  95

Ala Ala Pro Ala Ser Arg Arg Pro Ser Trp Asp Ala Asp Gly Tyr Asp
            100                 105                 110

Tyr Trp Gly Gln Gly Thr Gln Val Thr Val Ser Ser
        115                 120

<210> SEQ ID NO 8
<211> LENGTH: 5
<212> TYPE: PRT
<213> ORGANISM: Artificial Sequence
<220> FEATURE:
<223> OTHER INFORMATION: Description of the artificial sequence: amino
      acid sequence of CDR1 of iCADM3_3R1-L8

<400> SEQUENCE: 8

Asn Tyr Ala Arg Gly
1               5

<210> SEQ ID NO 9
<211> LENGTH: 17
<212> TYPE: PRT
<213> ORGANISM: Artificial Sequence
<220> FEATURE:
<223> OTHER INFORMATION: Description of the artificial sequence: amino
      acid sequence of CDR2 of iCADM3_3R1-L8

<400> SEQUENCE: 9

Ala Ile Asp Tyr Ser Gly Gly Ser Thr Asn Tyr Ala Asp Ser Ala Lys
1               5                   10                  15

Gly

<210> SEQ ID NO 10
<211> LENGTH: 15
<212> TYPE: PRT
<213> ORGANISM: Artificial Sequence
<220> FEATURE:
<223> OTHER INFORMATION: Description of the artificial sequence: amino
      acid sequence of CDR3 of iCADM3_3R1-L8

<400> SEQUENCE: 10

Pro Ala Ser Arg Arg Pro Ser Trp Asp Ala Asp Gly Tyr Asp Tyr
1               5                   10                  15

<210> SEQ ID NO 11
<211> LENGTH: 363
<212> TYPE: DNA
<213> ORGANISM: Artificial Sequence
<220> FEATURE:
<223> OTHER INFORMATION: Description of the artificial sequence: base
      sequence of VHH of iCADM3_3R1-L10 excluding signal sequence
```

```
<400> SEQUENCE: 11
caggtgcagc tcgtggagtc tgggggaggc ttggtgcagg ctggggggtc tctgagactc      60
tcctgtgcag cctctggaag catcttcagt atacatgcca tgggctggta ccgtcaggct     120
ccagggaagc agcgcgagtt ggtcgcaact gttactagtg gtggtagcac aaactatgca     180
gactccgtga agggccgatt caccatctcc agagacaacg ccaagaacac ggtgtatctg     240
caaatgaaca gcctgaaacc tgaggacaca gccgtctatt actgtaatgc agaaaccccc     300
tactatagta gtacttacta cacgaactac tggggccagg ggacccaggt caccgtctcc     360
tca                                                                    363

<210> SEQ ID NO 12
<211> LENGTH: 121
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L10 excluding signal sequence

<400> SEQUENCE: 12

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile His
            20                  25                  30

Ala Met Gly Trp Tyr Arg Gln Ala Pro Gly Lys Gln Arg Glu Leu Val
        35                  40                  45

Ala Thr Val Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Thr Pro Tyr Tyr Ser Ser Thr Tyr Tyr Thr Asn Tyr Trp Gly
            100                 105                 110

Gln Gly Thr Gln Val Thr Val Ser Ser
        115                 120

<210> SEQ ID NO 13
<211> LENGTH: 5
<212> TYPE: PRT
<213> ORGANISM: Artificial Sequence
<220> FEATURE:
<223> OTHER INFORMATION: Description of the artificial sequence: amino
      acid sequence of CDR1 of iCADM3_3R1-L10

<400> SEQUENCE: 13

Ile His Ala Met Gly
1               5

<210> SEQ ID NO 14
<211> LENGTH: 16
<212> TYPE: PRT
<213> ORGANISM: Artificial Sequence
<220> FEATURE:
<223> OTHER INFORMATION: Description of the artificial sequence: amino
      acid sequence of CDR2 of iCADM3_3R1-L10

<400> SEQUENCE: 14

Thr Val Thr Ser Gly Gly Ser Thr Asn Tyr Ala Asp Ser Val Lys Gly
1               5                   10                  15
```

<210> SEQ ID NO 15
<211> LENGTH: 13
<212> TYPE: PRT
<213> ORGANISM: Artificial Sequence
<220> FEATURE:
<223> OTHER INFORMATION: Description of the artificial sequence: amino
      acid sequence of CDR3 of iCADM3_3R1-L10

<400> SEQUENCE: 15

Glu Thr Pro Tyr Tyr Ser Ser Thr Tyr Tyr Thr Asn Tyr
1               5                   10

<210> SEQ ID NO 16
<211> LENGTH: 360
<212> TYPE: DNA
<213> ORGANISM: Artificial Sequence
<220> FEATURE:
<223> OTHER INFORMATION: Description of the artificial sequence: base
      sequence of VHH of iCADM3_3R1-L11 excluding signal sequence

<400> SEQUENCE: 16
caggtgcagc tcgtggagtc tgggggaggc ttggtgcagg ctggggggtc tctgagactt      60
tcctgtgcag cctctggaag catcttcagc ttcaatgcca tgggctggta ccgccaggct     120
ccagggaagc agcgcgggtt ggtcgcagtt attactagtg gtggttacac aaactatgcg     180
gactccgtga aggccgatt caccatcacc agagacaacg ccaagaacac ggtgtatctg      240
caaatgaaca gcctgaaacc tgaggacaca gccgtctatt actgtaatgc agaaggagtc     300
tacagcgact atgtgatcat gaactactgg ggccagggga cccaggtcac cgtctcctca     360

<210> SEQ ID NO 17
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11 excluding signal sequence

<400> SEQUENCE: 17

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Asn
            20                  25                  30

Ala Met Gly Trp Tyr Arg Gln Ala Pro Gly Lys Gln Arg Gly Leu Val
        35                  40                  45

Ala Val Ile Thr Ser Gly Gly Tyr Thr Asn Tyr Ala Asp Ser Val Lys
    50                  55                  60

Gly Arg Phe Thr Ile Thr Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Val Tyr Ser Asp Tyr Val Ile Met Asn Tyr Trp Gly Gln
            100                 105                 110

Gly Thr Gln Val Thr Val Ser Ser
        115                 120

<210> SEQ ID NO 18
<211> LENGTH: 5
<212> TYPE: PRT
<213> ORGANISM: Artificial Sequence
<220> FEATURE:
<223> OTHER INFORMATION: Description of the artificial sequence: amino acid sequence of CDR1 of iCADM3_3R1-L11

<400> SEQUENCE: 18

Phe Asn Ala Met Gly
1               5

<210> SEQ ID NO 19
<211> LENGTH: 16
<212> TYPE: PRT
<213> ORGANISM: Artificial Sequence
<220> FEATURE:
<223> OTHER INFORMATION: Description of the artificial sequence: amino
      acid sequence of CDR2 of iCADM3_3R1-L11

<400> SEQUENCE: 19

Val Ile Thr Ser Gly Gly Tyr Thr Asn Tyr Ala Asp Ser Val Lys Gly
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Description of the artificial sequence: amino
      acid sequence of CDR3 of iCADM3_3R1-L11

<400> SEQUENCE: 20

Glu Gly Val Tyr Ser Asp Tyr Val Ile Met Asn Tyr
1               5                   10

<210> SEQ ID NO 21
<211> LENGTH: 369
<212> TYPE: DNA
<213> ORGANISM: Artificial Sequence
<220> FEATURE:
<223> OTHER INFORMATION: Description of the artificial sequence: base
      sequence of VH of CADM301 excluding signal sequence

<400> SEQUENCE: 21
caggtgcagc tggtgcaatc tggggctgag gtgaggaggc ctgggacctc agtgaaagtc    60
tcctgcaagg cttctggata cagcttcacc agttatgata ttaactgggt gcgcctggcc   120
actggacaag gcttgagtg gatggggtgg atgaacccta acactggtga tacaggctct    180
ccacagaagt tccaggacag agtcaccatg accagggaca tctccacagg cacagcctac   240
ttagaactga gaggcctgaa gtctgaggac acggccattt attattgtgc gagaggcttc   300
ctggtgacag catataccgc tgagttcttc ccgcactggg gccagggcac cctggtcacc   360
gtctcctca                                                          369

<210> SEQ ID NO 22
<211> LENGTH: 123
<212> TYPE: PRT
<213> ORGANISM: Artificial Sequence
<220> FEATURE:
<223> OTHER INFORMATION: Description of the artificial sequence: amino
      acid sequence of VH of CADM301 excluding signal sequence

<400> SEQUENCE: 22

Gln Val Gln Leu Val Gln Ser Gly Ala Glu Val Arg Arg Pro Gly Thr
1               5                   10                  15

Ser Val Lys Val Ser Cys Lys Ala Ser Gly Tyr Ser Phe Thr Ser Tyr
            20                  25                  30

Asp Ile Asn Trp Val Arg Leu Ala Thr Gly Gln Gly Leu Glu Trp Met
        35                  40                  45

```
Gly Trp Met Asn Pro Asn Thr Gly Asp Thr Gly Ser Pro Gln Lys Phe
        50                  55                  60

Gln Asp Arg Val Thr Met Thr Arg Asp Ile Ser Thr Gly Thr Ala Tyr
65                  70                  75                  80

Leu Glu Leu Arg Gly Leu Lys Ser Glu Asp Thr Ala Ile Tyr Tyr Cys
                85                  90                  95

Ala Arg Gly Phe Leu Val Thr Ala Tyr Thr Ala Glu Phe Phe Pro His
            100                 105                 110

Trp Gly Gln Gly Thr Leu Val Thr Val Ser Ser
        115                 120

<210> SEQ ID NO 23
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM301

<400> SEQUENCE: 23

Ser Tyr Asp Ile Asn
1               5

<210> SEQ ID NO 24
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CADM301

<400> SEQUENCE: 24

Trp Met Asn Pro Asn Thr Gly Asp Thr Gly Ser Pro Gln Lys Phe Gln
1               5                   10                  15

Asp

<210> SEQ ID NO 25
<211> LENGTH: 14
<212> TYPE: PRT
<213> ORGANISM: Artificial Sequence
<220> FEATURE:
<223> OTHER INFORMATION: Description of the artificial sequence: amino
      acid sequence of HCDR3 of CADM301

<400> SEQUENCE: 25

Gly Phe Leu Val Thr Ala Tyr Thr Ala Glu Phe Phe Pro His
1               5                   10

<210> SEQ ID NO 26
<211> LENGTH: 324
<212> TYPE: DNA
<213> ORGANISM: Artificial Sequence
<220> FEATURE:
<223> OTHER INFORMATION: Description of the artificial sequence: base
      sequence of VL of CADM301 excluding signal sequence

<400> SEQUENCE: 26
tcctatgtgc tgactcagcc accctcagtg tcagtggccc caggaaagac ggccaggctc      60
acctgtgggg gaaacaacat tggaagtaaa agtgttcact ggtaccagca gaggccaggc     120
caggcccctg tgctggtcat aaattatgat agtgaccggc cctctgggat ccctgagcga     180
ttctctggct ccaactctga gaacacggcc accctgacca tcagcagggt cgaagccggg     240
```

```
gatgaggccg actattactg tcaggtgtgg gatagtggta gtgatcatgt ggtattcggc      300
ggaggaaccc agctgatcat ttta                                             324
```

<210> SEQ ID NO 27
<211> LENGTH: 108
<212> TYPE: PRT
<213> ORGANISM: Artificial Sequence
<220> FEATURE:
<223> OTHER INFORMATION: Description of the artificial sequence: amino
      acid sequence of VL of CADM301 excluding signal sequence

<400> SEQUENCE: 27

Ser Tyr Val Leu Thr Gln Pro Pro Ser Val Ser Val Ala Pro Gly Lys
1               5                   10                  15

Thr Ala Arg Leu Thr Cys Gly Gly Asn Asn Ile Gly Ser Lys Ser Val
            20                  25                  30

His Trp Tyr Gln Gln Arg Pro Gly Gln Ala Pro Val Leu Val Ile Asn
        35                  40                  45

Tyr Asp Ser Asp Arg Pro Ser Gly Ile Pro Glu Arg Phe Ser Gly Ser
    50                  55                  60

Asn Ser Glu Asn Thr Ala Thr Leu Thr Ile Ser Arg Val Glu Ala Gly
65                  70                  75                  80

Asp Glu Ala Asp Tyr Tyr Cys Gln Val Trp Asp Ser Gly Ser Asp His
                85                  90                  95

Val Val Phe Gly Gly Gly Thr Gln Leu Ile Ile Leu
            100                 105

<210> SEQ ID NO 28
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR1 of CADM301

<400> SEQUENCE: 28

Gly Gly Asn Asn Ile Gly Ser Lys Ser Val His
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CADM301

<400> SEQUENCE: 29

Tyr Asp Ser Asp Arg Pro Ser
1               5

<210> SEQ ID NO 30
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR3 of CADM301

<400> SEQUENCE: 30

Gln Val Trp Asp Ser Gly Ser Asp His Val Val
1               5                   10

<210> SEQ ID NO 31
<211> LENGTH: 372
<212> TYPE: DNA
<213> ORGANISM: Artificial Sequence
<220> FEATURE:
<223> OTHER INFORMATION: Description of the artificial sequence: base
      sequence of VH of CADM3102 excluding signal sequence

<400> SEQUENCE: 31

```
cagatgcagc tagtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccota tgtctggcac agcaaactac     180
gcacagaaat tccagggcag agtcacgatt accgcggacg aatccacgag cacagcctac     240
atggagctga gcagcctgag atctgaggac acggccgtct actactgtgc gagagttgag     300
gaaagtggct ggtacgacca ctaccacggt atggacgtct ggggccaagg gaccacggtc     360
accgtctcct ca                                                        372
```

<210> SEQ ID NO 32
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VH of CADM3102 excluding signal sequence

<400> SEQUENCE: 32

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Met Ser Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Glu Glu Ser Gly Trp Tyr Asp His Tyr His Gly Met Asp
            100                 105                 110

Val Trp Gly Gln Gly Thr Thr Val Thr Val Ser Ser
        115                 120
```

<210> SEQ ID NO 33
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3102

<400> SEQUENCE: 33

```
Ser Tyr Ala Ile Ser
1               5
```

<210> SEQ ID NO 34
<211> LENGTH: 17
<212> TYPE: PRT
<213> ORGANISM: Artificial Sequence
<220> FEATURE:

<223> OTHER INFORMATION: Description of the artificial sequence: amino
      acid sequence of HCDR2 of CADM3102

<400> SEQUENCE: 34

Gly Ile Ile Pro Met Ser Gly Thr Ala Asn Tyr Ala Gln Lys Phe Gln
1               5                   10                  15

Gly

<210> SEQ ID NO 35
<211> LENGTH: 15
<212> TYPE: PRT
<213> ORGANISM: Artificial Sequence
<220> FEATURE:
<223> OTHER INFORMATION: Description of the artificial sequence: amino
      acid sequence of HCDR3 of CADM3102

<400> SEQUENCE: 35

Val Glu Glu Ser Gly Trp Tyr Asp His Tyr His Gly Met Asp Val
1               5                   10                  15

<210> SEQ ID NO 36
<211> LENGTH: 336
<212> TYPE: DNA
<213> ORGANISM: Artificial Sequence
<220> FEATURE:
<223> OTHER INFORMATION: Description of the artificial sequence: base
      sequence of VL of CADM3102 excluding signal sequence

<400> SEQUENCE: 36
gatgttgtga tgactcagtc tccactctcc ctgcccgtca cccctggaga gccggcctcc        60
atctcctgca cgtctagtca gagcctcctg tatagtaatg gattcaacta tttggattgg       120
tacctgcaga aaccagggca gtctccacag ctcctgatct atttgggttc taatcgggcc       180
tccggggtcc ctgacaggtt cagtggcagt ggatcaggca cagattttac actgaaaatc       240
agtagagtgg aggctgagga tgttggggtg tattactgca tgcaagctct aacaactcat       300 cccactttg gcggagggac caaagtggat atcaaa                                  336

<210> SEQ ID NO 37
<211> LENGTH: 112
<212> TYPE: PRT
<213> ORGANISM: Artificial Sequence
<220> FEATURE:
<223> OTHER INFORMATION: Description of the artificial sequence: amino
      acid sequence of VL of CADM3102 excluding signal sequence

<400> SEQUENCE: 37

Asp Val Val Met Thr Gln Ser Pro Leu Ser Leu Pro Val Thr Pro Gly
1               5                   10                  15

Glu Pro Ala Ser Ile Ser Cys Thr Ser Ser Gln Ser Leu Leu Tyr Ser
                20                  25                  30

Asn Gly Phe Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Thr Thr His Pro Thr Phe Gly Gly Gly Thr Lys Val Asp Ile Lys
            100                 105                 110

```
<210> SEQ ID NO 38
<211> LENGTH: 16
<212> TYPE: PRT
<213> ORGANISM: Artificial Sequence
<220> FEATURE:
<223> OTHER INFORMATION: Description of the artificial sequence: amino
      acid sequence of LCDR1 of CADM3102

<400> SEQUENCE: 38

Thr Ser Ser Gln Ser Leu Leu Tyr Ser Asn Gly Phe Asn Tyr Leu Asp
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CADM3102

<400> SEQUENCE: 39

Leu Gly Ser Asn Arg Ala Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CADM3102

<400> SEQUENCE: 40

Met Gln Ala Leu Thr Thr His Pro Thr
1               5

<210> SEQ ID NO 41
<211> LENGTH: 648
<212> TYPE: DNA
<213> ORGANISM: Artificial Sequence
<220> FEATURE:
<223> OTHER INFORMATION: base sequence of light chain antibody excluding
      signal sequence of pCI_AVM-hLG4PE(R409K)-iCADM3_3R1-L5 VHH,
      pCI_AVM-hLG4PE(R409K)-iCADM3_3R1-L8 VHH,
      pCI_AVM-hLG4PE(R409K)-iCADM3_3R1-L10 VHH,

<400> SEQUENCE: 41
cagtttgtgc tttctcagcc aaactctgtg tctacgaatc tcggaagcac agtcaaactg      60
tcttgcaagc gcagcactgg taacattgga agcaattatg tgagctggta ccagcagcat     120
gagggaagat ctcccaccac tatgatttat agggatgata agagaccaga tggagttcct     180
gacaggttct ctggctccat tgacagatct tccgactcag ccctcctgac aatcaataat     240
gtgcagactg aagatgaagc tgactacttc tgtcagtctt acagtagtgg tattaatatt     300
ttcggcggtg gaaccaagct cactgtccta ggtcagccca aggccgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac acctccaaa  caaagcaaca caagtacgc  ggccagcagc     540 tacctgagcc tgacgcctga gcagtggaag tcccacagaa gctacagctg ccaggtcacg     600
catgaaggga gcaccgtgga agacagtg   gcccctacag aatgttca                  648

<210> SEQ ID NO 42
```

<211> LENGTH: 216
<212> TYPE: PRT
<213> ORGANISM: Artificial Sequence
<220> FEATURE:
<223> OTHER INFORMATION: amino acid sequence of light chain antibody
excluding signal sequence of pCI_AVM-hLG4PE(R409K)-iCADM3_3R1-L5
VHH, pCI_AVM-hLG4PE(R409K)-iCADM3_3R1-L8 VHH,
pCI_AVM-hLG4PE(R409K)-iCADM3_3R1-L10 VHH,

<400> SEQUENCE: 42

Gln Phe Val Leu Ser Gln Pro Asn Ser Val Ser Thr Asn Leu Gly Ser
1               5                   10                  15

Thr Val Lys Leu Ser Cys Lys Arg Ser Thr Gly Asn Ile Gly Ser Asn
            20                  25                  30

Tyr Val Ser Trp Tyr Gln Gln His Glu Gly Arg Ser Pro Thr Thr Met
        35                  40                  45

Ile Tyr Arg Asp Asp Lys Arg Pro Asp Gly Val Pro Asp Arg Phe Ser
    50                  55                  60

Gly Ser Ile Asp Arg Ser Ser Asp Ser Ala Leu Leu Thr Ile Asn Asn
65                  70                  75                  80

Val Gln Thr Glu Asp Glu Ala Asp Tyr Phe Cys Gln Ser Tyr Ser Ser
                85                  90                  95

Gly Ile Asn Ile Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 43
<211> LENGTH: 1764
<212> TYPE: DNA
<213> ORGANISM: Artificial Sequence
<220> FEATURE:
<223> OTHER INFORMATION: Description of the artificial sequence: base
sequence of heavy chain antibody sequence of
pCI_AVM-hLG4PE(R409K)-iCADM3_3R1-L5 VHH excluding signal sequence

<400> SEQUENCE: 43
gaggtgcagc tggtggaatc tgggggaggc ttagtgcagc ctggaagatc cctgaaactc      60
tcctgtgcag cctcaggatt cactttcagt aactatgcca tggcttgggt ccgccgggct    120
ccaacgaagg gtctggagtg ggtcgcatcc attagtaatg gtggtggtaa cacttactat    180
cgcgactccg tgaagggccg attcactatc tccagagata tgcaaaaaa cacccctatac    240 ctgcaaatgg acagtctgag gtctgaggac acggccactt attactgtgc aagacacggg    300
aattatatat attatgggtc cttctttgat tactggggcc aaggagtcat ggtcacagtc    360
tcctcagcta gcaccaaggg gccatccgtc ttccccctgg cgccctgctc caggagcacc    420

```
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga ggggggacca    720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctacccag cgacatcgcc     1140 gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga ggagggtccg gaggaggagg gtccggtgga    1380
ggtgggtccc aggtgcagct cgtggagtct gggggaggct tggtgcaggc tgggggtct    1440 ctgagactct cctgtgcagc ctctggaagc atcgtcagtg tcaatgccat gggctggtac    1500
cgccaggctc cagggaagca gcgcgagttg gtcgcaacta ttactagtgg gggtagcaca    1560
aactatgcag actccgcgaa gggccgattc accatctcca gagacaacgc caagaacacg    1620
atgtatctgc aaatgaacag cctgaaacct gaggacacag ccgtctatta ctgtaacggg    1680
gaattctggt cgcgccggga cacacgcccc caggggtcg taaactactg gggccagggg    1740
acccaggtca ccgtctcctc atga                                           1764
```

<210> SEQ ID NO 44
<211> LENGTH: 587
<212> TYPE: PRT
<213> ORGANISM: Artificial Sequence
<220> FEATURE:
<223> OTHER INFORMATION: Description of the artificial sequence: amino
      acid sequence of heavy chain antibody sequence of
      pCI_AVM-hLG4PE(R409K)-iCADM3_3R1-L5 VHH excluding signal sequence

<400> SEQUENCE: 44

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110
```

-continued

Gly Gln Gly Val Met Val Thr Val Ser Ser Ala Ser Thr Lys Gly Pro
            115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
            165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
            195                 200                 205
His Lys Pro Ser Asn Thr Lys Val Asp Lys Arg Val Glu Ser Lys Tyr
            210                 215                 220
Gly Pro Pro Cys Pro Pro Cys Pro Ala Pro Glu Phe Glu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
            275                 280                 285
Ala Lys Thr Lys Pro Arg Glu Glu Gln Phe Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
            435                 440                 445
Gly Gly Gly Gly Ser Gly Gly Gly Ser Gly Gly Gly Gly Ser Gln
            450                 455                 460
Val Gln Leu Val Glu Ser Gly Gly Gly Leu Val Gln Ala Gly Gly Ser
465                 470                 475                 480
Leu Arg Leu Ser Cys Ala Ala Ser Gly Ser Ile Val Ser Val Asn Ala
            485                 490                 495
Met Gly Trp Tyr Arg Gln Ala Pro Gly Lys Gln Arg Glu Leu Val Ala
            500                 505                 510
Thr Ile Thr Ser Gly Gly Ser Thr Asn Tyr Ala Asp Ser Ala Lys Gly
            515                 520                 525
Arg Phe Thr Ile Ser Arg Asp Asn Ala Lys Asn Thr Met Tyr Leu Gln

|   |   |   |   |   |   |   |   |   |   |
|---|---|---|---|---|---|---|---|---|---|
|   | 530 |   |   | 535 |   |   | 540 |   |   |

Met Asn Ser Leu Lys Pro Glu Asp Thr Ala Val Tyr Tyr Cys Asn Gly
545                 550                 555                 560

Glu Phe Trp Ser Arg Arg Asp Thr Arg Pro Pro Gly Val Val Asn Tyr
                565                 570                 575

Trp Gly Gln Gly Thr Gln Val Thr Val Ser Ser
            580                 585

<210> SEQ ID NO 45
<211> LENGTH: 1764
<212> TYPE: DNA
<213> ORGANISM: Artificial Sequence
<220> FEATURE:
<223> OTHER INFORMATION: Description of the artificial sequence: base
      sequence of heavy chain antibody sequence of
      pCI_AVM-hLG4PE(R409K)-iCADM3_3R1-L8 VHH excluding signal sequence

<400> SEQUENCE: 45

| gaggtgcagc | tggtggaatc | tgggggaggc | ttagtgcagc | ctggaagatc | cctgaaactc | 60 |
| tcctgtgcag | cctcaggatt | cactttcagt | aactatgcca | tggcttgggt | ccgccgggct | 120 |
| ccaacgaagg | gtctggagtg | ggtcgcatcc | attagtaatg | gtggtggtaa | cacttactat | 180 |
| cgcgactccg | tgaagggccg | attcactatc | tccagagatg | atgcaaaaaa | caccctatac | 240 |
| ctgcaaatgg | acagtctgag | gtctgaggac | acggccactt | attactgtgc | aagacacggg | 300 |
| aattatatat | attatgggtc | cttctttgat | tactggggcc | aaggagtcat | ggtcacagtc | 360 |
| tcctcagcta | gcaccaaggg | gccatccgtc | ttccccctgg | cgccctgctc | caggagcacc | 420 |
| tccgagagca | cagccgccct | gggctgcctg | gtcaaggact | acttccccga | accggtgacg | 480 |
| gtgtcgtgga | actcaggcgc | cctgaccagc | ggcgtgcaca | ccttcccggc | tgtcctacag | 540 |
| tcctcaggac | tctactccct | cagcagcgtg | gtgaccgtgc | cctccagcag | cttgggcacg | 600 |
| aagacctaca | cctgcaacgt | agatcacaag | cccagcaaca | ccaaggtgga | caagagagtt | 660 |
| gagtccaaat | atggtccccc | atgcccacca | tgcccagcac | ctgagttcga | gggggaccca | 720 |
| tcagtcttcc | tgttcccccc | aaaacccaag | gacactctca | tgatctcccg | gacccctgag | 780 |
| gtcacgtgcg | tggtggtgga | cgtgagccag | gaagaccccg | aggtccagtt | caactggtac | 840 |
| gtggatggcg | tggaggtgca | taatgccaag | acaaagccgc | gggaggagca | gttcaacagc | 900 |
| acgtaccgtg | tggtcagcgt | cctcaccgtc | ctgcaccagg | actggctgaa | cggcaaggag | 960 |
| tacaagtgca | aggtctccaa | caaaggcctc | ccgtcctcca | tcgagaaaac | catctccaaa | 1020 |
| gccaaagggc | agccccgaga | gccacaggtg | tacaccctgc | ccccatccca | ggaggagatg | 1080 |
| accaagaacc | aggtcagcct | gacctgcctg | gtcaaaggct | tctaccccag | cgacatcgcc | 1140 |
| gtggagtggg | agagcaatgg | gcagccggag | aacaactaca | agaccacgcc | tcccgtgctg | 1200 |
| gactccgacg | gctccttctt | cctctacagc | aagctaaccg | tggacaagag | caggtggcag | 1260 |
| gaggggaatg | tcttctcatg | ctccgtgatg | catgaggctc | tgcacaacca | ctacacacag | 1320 |
| aagagcctct | ccctgtctct | gggtggagga | ggagggtccg | gaggaggagg | gtccggtgga | 1380 |
| ggtgggtccc | aggtgcagct | cgtggagtct | gggggaggct | tggtgcagcc | tggggggtct | 1440 |
| ctgagactct | cctgtgcagc | ctctggacgc | accttcagta | attatgcccg | ggctggttc | 1500 |
| cgccaggctc | cagggaagga | gcgtgagttt | gtagcagcta | ttgactacag | tggtggtagc | 1560 |
| acaaactatg | cagactccgc | gaagggccga | ttcaccatct | ccagagacaa | cgccaagaac | 1620 |
| acggtgtatc | tgcaaatgaa | cagcctgaaa | cccggggaca | cggccgttta | ttactgtgca | 1680 |

```
gcgcccgcaa gccggcgtcc tagttgggat gctgatgggt atgactactg gggccagggg    1740
acccaggtca ccgtctcctc atga                                            1764
```

<210> SEQ ID NO 46
<211> LENGTH: 587
<212> TYPE: PRT
<213> ORGANISM: Artificial Sequence
<220> FEATURE:
<223> OTHER INFORMATION: Description of the artificial sequence: amino
      acid sequence of heavy chain antibody sequence of
      pCI_AVM-hLG4PE(R409K)-iCADM3_3R1-L8 VHH excluding signal sequence

<400> SEQUENCE: 46

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335
```

```
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
                355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
            435                 440                 445
Gly Gly Gly Gly Ser Gly Gly Gly Ser Gly Gly Gly Gly Ser Gln
            450                 455                 460
Val Gln Leu Val Glu Ser Gly Gly Gly Leu Val Gln Pro Gly Gly Ser
465                 470                 475                 480
Leu Arg Leu Ser Cys Ala Ala Ser Gly Arg Thr Phe Ser Asn Tyr Ala
                485                 490                 495
Arg Gly Trp Phe Arg Gln Ala Pro Gly Lys Glu Arg Glu Phe Val Ala
            500                 505                 510
Ala Ile Asp Tyr Ser Gly Gly Ser Thr Asn Tyr Ala Asp Ser Ala Lys
            515                 520                 525
Gly Arg Phe Thr Ile Ser Arg Asp Asn Ala Lys Asn Thr Val Tyr Leu
            530                 535                 540
Gln Met Asn Ser Leu Lys Pro Gly Asp Thr Ala Val Tyr Tyr Cys Ala
545                 550                 555                 560
Ala Pro Ala Ser Arg Arg Pro Ser Trp Asp Ala Asp Gly Tyr Asp Tyr
                565                 570                 575
Trp Gly Gln Gly Thr Gln Val Thr Val Ser Ser
            580                 585

<210> SEQ ID NO 47
<211> LENGTH: 1755
<212> TYPE: DNA
<213> ORGANISM: Artificial Sequence
<220> FEATURE:
<223> OTHER INFORMATION: Description of the artificial sequence: base
      sequence of heavy chain antibody sequence of
      pCI_AVM-hLG4PE(R409K)-iCADM3_3R1-L10 VHH excluding signal sequence

<400> SEQUENCE: 47
gaggtgcagc tggtggaatc tggggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactgggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
```

```
aagacctaca cctgcaacgt agatcacaag cccagcaaca ccaaggtgga caagagagtt    660
gagtccaaat atggtccccc atgcccacca tgcccagcac ctgagttcga gggggggacca   720 tcagtcttcc tgttcccccc aaaacccaag acactctca tgatctcccg accccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc    1140 gtggagtggg agagcaatgg gcagccggag aacaactaca agaccacgcc tcccgtgctg   1200
gactccgacg gctccttctt cctctacagc aagctaaccg tggacaagag caggtggcag   1260 gagggggaatg tcttctcatg ctccgtgatg catgaggctc tgcacaacca ctacacacag   1320
aagagcctct ccctgtctct gggtggagga ggagggtccg gaggaggagg gtccggtgga   1380
ggtgggtccc aggtgcagct cgtggagtct gggggaggct tggtgcaggc tggggggtct   1440
ctgagactct cctgtgcagc ctctggaagc atcttcagta tacatgccat gggctggtac   1500
cgtcaggctc cagggaagca gcgcgagttg gtcgcaactg ttactagtgg tggtagcaca   1560
aactatgcag actccgtgaa gggccgattc accatctcca gagacaacgc caagaacacg   1620
gtgtatctgc aaatgaacag cctgaaacct gaggacacag ccgtctatta ctgtaatgca   1680 gaaacccct actatagtag tacttactac acgaactact ggggccaggg gacccaggtc    1740
accgtctcct catga                                                    1755
```

<210> SEQ ID NO 48
<211> LENGTH: 584
<212> TYPE: PRT
<213> ORGANISM: Artificial Sequence
<220> FEATURE:
<223> OTHER INFORMATION: Description of the artificial sequence: amino
      acid sequence of heavy chain antibody sequence of
      pCI_AVM-hLG4PE(R409K)-iCADM3_3R1-L10 VHH excluding signal
      sequence

<400> SEQUENCE: 48

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
```

```
                130             135             140
Ala Ala Leu Gly Cys Leu Val Lys Asp Tyr Phe Pro Glu Pro Val Thr
145             150             155             160
Val Ser Trp Asn Ser Gly Ala Leu Thr Ser Gly Val His Thr Phe Pro
                165             170             175
Ala Val Leu Gln Ser Ser Gly Leu Tyr Ser Leu Ser Ser Val Val Thr
            180             185             190
Val Pro Ser Ser Ser Leu Gly Thr Lys Thr Tyr Thr Cys Asn Val Asp
            195             200             205
His Lys Pro Ser Asn Thr Lys Val Asp Lys Arg Val Glu Ser Lys Tyr
        210             215             220
Gly Pro Pro Cys Pro Pro Cys Pro Ala Pro Glu Phe Glu Gly Gly Pro
225             230             235             240
Ser Val Phe Leu Phe Pro Pro Lys Pro Lys Asp Thr Leu Met Ile Ser
                245             250             255
Arg Thr Pro Glu Val Thr Cys Val Val Val Asp Val Ser Gln Glu Asp
            260             265             270
Pro Glu Val Gln Phe Asn Trp Tyr Val Asp Gly Val Glu Val His Asn
            275             280             285
Ala Lys Thr Lys Pro Arg Glu Glu Gln Phe Asn Ser Thr Tyr Arg Val
290             295             300
Val Ser Val Leu Thr Val Leu His Gln Asp Trp Leu Asn Gly Lys Glu
305             310             315             320
Tyr Lys Cys Lys Val Ser Asn Lys Gly Leu Pro Ser Ser Ile Glu Lys
            325             330             335
Thr Ile Ser Lys Ala Lys Gly Gln Pro Arg Glu Pro Gln Val Tyr Thr
            340             345             350
Leu Pro Pro Ser Gln Glu Glu Met Thr Lys Asn Gln Val Ser Leu Thr
            355             360             365
Cys Leu Val Lys Gly Phe Tyr Pro Ser Asp Ile Ala Val Glu Trp Glu
        370             375             380
Ser Asn Gly Gln Pro Glu Asn Asn Tyr Lys Thr Thr Pro Pro Val Leu
385             390             395             400
Asp Ser Asp Gly Ser Phe Phe Leu Tyr Ser Lys Leu Thr Val Asp Lys
                405             410             415
Ser Arg Trp Gln Glu Gly Asn Val Phe Ser Cys Ser Val Met His Glu
            420             425             430
Ala Leu His Asn His Tyr Thr Gln Lys Ser Leu Ser Leu Ser Leu Gly
            435             440             445
Gly Gly Gly Gly Ser Gly Gly Gly Gly Ser Gly Gly Gly Gly Ser Gln
        450             455             460
Val Gln Leu Val Glu Ser Gly Gly Gly Leu Val Gln Ala Gly Gly Ser
465             470             475             480
Leu Arg Leu Ser Cys Ala Ala Ser Gly Ser Ile Phe Ser Ile His Ala
                485             490             495
Met Gly Trp Tyr Arg Gln Ala Pro Gly Lys Gln Arg Glu Leu Val Ala
            500             505             510
Thr Val Thr Ser Gly Gly Ser Thr Asn Tyr Ala Asp Ser Val Lys Gly
            515             520             525
Arg Phe Thr Ile Ser Arg Asp Asn Ala Lys Asn Thr Val Tyr Leu Gln
        530             535             540
Met Asn Ser Leu Lys Pro Glu Asp Thr Ala Val Tyr Tyr Cys Asn Ala
545             550             555             560
```

Glu Thr Pro Tyr Tyr Ser Ser Thr Tyr Thr Asn Tyr Trp Gly Gln
            565                 570                 575

Gly Thr Gln Val Thr Val Ser Ser
            580

<210> SEQ ID NO 49
<211> LENGTH: 1752
<212> TYPE: DNA
<213> ORGANISM: Artificial Sequence
<220> FEATURE:
<223> OTHER INFORMATION: Description of the artificial sequence: base
      sequence of heavy chain antibody sequence of
      pCI_AVM-hLG4PE(R409K)-iCADM3_3R1-L11 VHH excluding signal sequence

<400> SEQUENCE: 49

| | | | |
|---|---|---|---|
| gaggtgcagc tggtggaatc tgggggaggc ttagtgcagc ctggaagatc cctgaaactc | 60 |
| tcctgtgcag cctcaggatt cactttcagt aactatgcca tggcttgggt ccgccgggct | 120 |
| ccaacgaagg gtctggagtg gtcgcatcc attagtaatg gtggtggtaa cacttactat | 180 |
| cgcgactccg tgaagggccg attcactatc tccagagatg atgcaaaaaa caccctatac | 240 |
| ctgcaaatgg acagtctgag gtctgaggac acggccactt attactgtgc aagacacggg | 300 |
| aattatatat attatgggtc cttctttgat tactggggcc aaggagtcat ggtcacagtc | 360 |
| tcctcagcta gcaccaaggg gccatccgtc ttccccctgg cgccctgctc caggagcacc | 420 |
| tccgagagca gccgcccct gggctgcctg gtcaaggact acttccccga accggtgacg | 480 |
| gtgtcgtgga actcaggcgc cctgaccagc ggcgtgcaca ccttcccggc tgtcctacag | 540 |
| tcctcaggac tctactccct cagcagcgtg gtgaccgtgc cctccagcag cttgggcacg | 600 |
| aagacctaca cctgcaacgt agatcacaag cccagcaaca ccaaggtgga caagagagtt | 660 |
| gagtccaaat atggtccccc atgcccacca tgcccagcac ctgagttcga gggggaccca | 720 |
| tcagtcttcc tgttcccccc aaaacccaag gacactctca tgatctcccg gacccctgag | 780 |
| gtcacgtgcg tggtggtgga cgtgagccag gaagaccccg aggtccagtt caactggtac | 840 |
| gtggatggcg tggaggtgca taatgccaag acaaagccgc gggaggagca gttcaacagc | 900 |
| acgtaccgtg tggtcagcgt cctcaccgtc ctgcaccagg actggctgaa cggcaaggag | 960 |
| tacaagtgca aggtctccaa caaaggcctc ccgtcctcca tcgagaaaac catctccaaa | 1020 |
| gccaaagggc agccccgaga gccacaggtg tacaccctgc ccccatccca ggaggagatg | 1080 |
| accaagaacc aggtcagcct gacctgcctg gtcaaaggct tctaccccag cgacatcgcc | 1140 |
| gtggagtggg agagcaatgg gcagccggag aacaactaca agaccacgcc tcccgtgctg | 1200 |
| gactccgacg gctccttctt cctctacagc aagctaaccg tggacaagag caggtggcag | 1260 |
| gaggggaatg tcttctcatg ctccgtgatg catgaggctc tgcacaacca ctacacacag | 1320 |
| aagagcctct ccctgtctct gggtggagga ggagggtccg gaggaggagg gtccggtgga | 1380 |
| ggtgggtccc aggtgcagct cgtggagtct gggggaggct tggtgcaggc tggggggtct | 1440 |
| ctgagacttt cctgtgcagc ctctggaagc atcttcagct tcaatgccat gggctggtac | 1500 |
| cgccaggctc cagggaagca gcgcgggttg gtcgcagtta ttactagtgg tggttacaca | 1560 |
| aactatgcgg actccgtgaa gggccgattc accatcacca gagacaacgc caagaacacg | 1620 |
| gtgtatctgc aaatgaacag cctgaaacct gaggacacag ccgtctatta ctgtaatgca | 1680 |
| gaaggagtct acagcgacta tgtgatcatg aactactggg gccaggggac ccaggtcacc | 1740 |
| gtctcctcat ga | 1752 |

<210> SEQ ID NO 50
<211> LENGTH: 583
<212> TYPE: PRT
<213> ORGANISM: Artificial Sequence
<220> FEATURE:
<223> OTHER INFORMATION: Description of the artificial sequence: amino
acid sequence of heavy chain antibody sequence of
pCI_AVM-hLG4PE(R409K)-iCADM3_3R1-L11 VHH excluding signal
sequence

<400> SEQUENCE: 50

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350
```

| | | | | | | | | | | |
|---|---|---|---|---|---|---|---|---|---|---|
| Leu | Pro | Pro | Ser | Gln | Glu | Glu | Met | Thr | Lys | Asn | Gln | Val | Ser | Leu | Thr |
| | 355 | | | | | 360 | | | | | 365 | | | | |
| Cys | Leu | Val | Lys | Gly | Phe | Tyr | Pro | Ser | Asp | Ile | Ala | Val | Glu | Trp | Glu |
| 370 | | | | | 375 | | | | | 380 | | | | | |
| Ser | Asn | Gly | Gln | Pro | Glu | Asn | Asn | Tyr | Lys | Thr | Thr | Pro | Pro | Val | Leu |
| 385 | | | | | 390 | | | | | 395 | | | | | 400 |
| Asp | Ser | Asp | Gly | Ser | Phe | Phe | Leu | Tyr | Ser | Lys | Leu | Thr | Val | Asp | Lys |
| | | | 405 | | | | | 410 | | | | | 415 | | |
| Ser | Arg | Trp | Gln | Glu | Gly | Asn | Val | Phe | Ser | Cys | Ser | Val | Met | His | Glu |
| | | | 420 | | | | | 425 | | | | | 430 | | |
| Ala | Leu | His | Asn | His | Tyr | Thr | Gln | Lys | Ser | Leu | Ser | Leu | Ser | Leu | Gly |
| | | 435 | | | | | 440 | | | | | 445 | | | |
| Gly | Gly | Gly | Gly | Ser | Gly | Gly | Gly | Ser | Gly | Gly | Gly | Ser | Gln |
| | 450 | | | | | 455 | | | | | 460 | | |
| Val | Gln | Leu | Val | Glu | Ser | Gly | Gly | Gly | Leu | Val | Gln | Ala | Gly | Gly | Ser |
| 465 | | | | | 470 | | | | | 475 | | | | | 480 |
| Leu | Arg | Leu | Ser | Cys | Ala | Ala | Ser | Gly | Ser | Ile | Phe | Ser | Phe | Asn | Ala |
| | | | | 485 | | | | | 490 | | | | | 495 | |
| Met | Gly | Trp | Tyr | Arg | Gln | Ala | Pro | Gly | Lys | Gln | Arg | Gly | Leu | Val | Ala |
| | | | | 500 | | | | | 505 | | | | | 510 | |
| Val | Ile | Thr | Ser | Gly | Gly | Tyr | Thr | Asn | Tyr | Ala | Asp | Ser | Val | Lys | Gly |
| | | | 515 | | | | | 520 | | | | | 525 | | |
| Arg | Phe | Thr | Ile | Thr | Arg | Asp | Asn | Ala | Lys | Asn | Thr | Val | Tyr | Leu | Gln |
| | | | 530 | | | | | 535 | | | | | 540 | | |
| Met | Asn | Ser | Leu | Lys | Pro | Glu | Asp | Thr | Ala | Val | Tyr | Tyr | Cys | Asn | Ala |
| 545 | | | | | 550 | | | | | 555 | | | | | 560 |
| Glu | Gly | Val | Tyr | Ser | Asp | Tyr | Val | Ile | Met | Asn | Tyr | Trp | Gly | Gln | Gly |
| | | | | 565 | | | | | 570 | | | | | 575 | |
| Thr | Gln | Val | Thr | Val | Ser | Ser |
| | | | 580 | | | |

```
<210> SEQ ID NO 51
<211> LENGTH: 1197
<212> TYPE: DNA
<213> ORGANISM: Artificial Sequence
<220> FEATURE:
<223> OTHER INFORMATION: Description of the artificial sequence: base
      sequence of human CADM3 including signal sequence

<400> SEQUENCE: 51 atggggggccc cagccgcctc gctcctgctc ctgctcctgc tgttcgcctg ctgctgggcg     60
cccggcgggg ccaacctctc ccaggacgac agccagcccct ggacatctga tgaaacagtg    120
gtggctggtg gcaccgtggt gctcaagtgc caagtgaaag atcacgagga ctcatccctg    180
caatggtcta accctgctca gcagactctc tactttgggg agaagagagc ccttcgagat    240
aatcgaattc agctggttac ctctacgccc acgagctca gcatcagcat cagcaatgtg    300
gccctggcag acgagggcga gtacacctgc tcaatcttca ctatgcctgt gcgaactgcc    360
aagtccctcg tcactgtgct aggaattcca cagaagccca tcatcactgg ttataaatct    420
tcattacggg aaaaagacac agccacccta aactgtcagt cttctgggag caagcctgca    480
gcccggctca cctggagaaa gggtgaccaa gaactccacg agaaccaac ccgcatacag    540 gaagatccca atggtaaaac cttcactgtc agcagctcgg tgacattcca ggttacccgg    600
gaggatgatg gggcgagcat cgtgtgctct gtgaaccatg aatctctaaa gggagctgac    660
agatccacct ctcaacgcat tgaagtttta tacacaccaa ctgcgatgat taggccagac    720
```

```
cctccccatc ctcgtgaggg ccagaagctg ttgctacact gtgagggtcg cggcaatcca    780
gtcccccagc agtacctatg ggagaaggag ggcagtgtgc caccccctgaa gatgacccag   840 gagagtgccc tgatcttccc tttcctcaac aagagtgaca gtggcaccta cggctgcaca   900
gccaccagca acatgggcag ctacaaggcc tactacaccc tcaatgttaa tgaccccagt   960
ccggtgccct cctcctccag cacctaccac gccatcatcg gtgggatcgt ggctttcatt  1020
gtcttcctgc tgctcatcat gctcatcttc cttggccact acttgatccg cacaaagga   1080 acctacctga cacatgaggc aaaaggctcc gacgatgctc cagacgcgga cacggccatc  1140
atcaatgcag aaggcgggca gtcaggaggg gacgacaaga aggaatattt catctag      1197

<210> SEQ ID NO 52
<211> LENGTH: 398
<212> TYPE: PRT
<213> ORGANISM: Artificial Sequence
<220> FEATURE:
<223> OTHER INFORMATION: Description of the artificial sequence: amino
      acid sequence of human CADM3 including signal sequence

<400> SEQUENCE: 52

Met Gly Ala Pro Ala Ala Ser Leu Leu Leu Leu Leu Leu Phe Ala
1               5                   10                  15

Cys Cys Trp Ala Pro Gly Gly Ala Asn Leu Ser Gln Asp Asp Ser Gln
            20                  25                  30

Pro Trp Thr Ser Asp Glu Thr Val Val Ala Gly Gly Thr Val Val Leu
        35                  40                  45

Lys Cys Gln Val Lys Asp His Glu Asp Ser Ser Leu Gln Trp Ser Asn
    50                  55                  60

Pro Ala Gln Gln Thr Leu Tyr Phe Gly Glu Lys Arg Ala Leu Arg Asp
65                  70                  75                  80

Asn Arg Ile Gln Leu Val Thr Ser Thr Pro His Glu Leu Ser Ile Ser
                85                  90                  95

Ile Ser Asn Val Ala Leu Ala Asp Glu Gly Glu Tyr Thr Cys Ser Ile
            100                 105                 110

Phe Thr Met Pro Val Arg Thr Ala Lys Ser Leu Val Thr Val Leu Gly
        115                 120                 125

Ile Pro Gln Lys Pro Ile Ile Thr Gly Tyr Lys Ser Ser Leu Arg Glu
    130                 135                 140

Lys Asp Thr Ala Thr Leu Asn Cys Gln Ser Ser Gly Ser Lys Pro Ala
145                 150                 155                 160

Ala Arg Leu Thr Trp Arg Lys Gly Asp Gln Glu Leu His Gly Glu Pro
                165                 170                 175

Thr Arg Ile Gln Glu Asp Pro Asn Gly Lys Thr Phe Thr Val Ser Ser
            180                 185                 190

Ser Val Thr Phe Gln Val Thr Arg Glu Asp Asp Gly Ala Ser Ile Val
        195                 200                 205

Cys Ser Val Asn His Glu Ser Leu Lys Gly Ala Asp Arg Ser Thr Ser
    210                 215                 220

Gln Arg Ile Glu Val Leu Tyr Thr Pro Thr Ala Met Ile Arg Pro Asp
225                 230                 235                 240

Pro Pro His Pro Arg Glu Gly Gln Lys Leu Leu Leu His Cys Glu Gly
                245                 250                 255

Arg Gly Asn Pro Val Pro Gln Gln Tyr Leu Trp Glu Lys Glu Gly Ser
            260                 265                 270
```

| | | | | | | | | | | | | |
|---|---|---|---|---|---|---|---|---|---|---|---|---|
| Val | Pro | Pro | Leu | Lys | Met | Thr | Gln | Glu | Ser | Ala | Leu | Ile | Phe | Pro | Phe |
| | | 275 | | | | 280 | | | | 285 | | |

Val Pro Pro Leu Lys Met Thr Gln Glu Ser Ala Leu Ile Phe Pro Phe
            275                 280                 285

Leu Asn Lys Ser Asp Ser Gly Thr Tyr Gly Cys Thr Ala Thr Ser Asn
    290                 295                 300

Met Gly Ser Tyr Lys Ala Tyr Tyr Thr Leu Asn Val Asn Asp Pro Ser
305                 310                 315                 320

Pro Val Pro Ser Ser Ser Thr Tyr His Ala Ile Ile Gly Gly Ile
                325                 330                 335

Val Ala Phe Ile Val Phe Leu Leu Leu Ile Met Leu Ile Phe Leu Gly
                340                 345                 350

His Tyr Leu Ile Arg His Lys Gly Thr Tyr Leu Thr His Glu Ala Lys
                355                 360                 365

Gly Ser Asp Asp Ala Pro Asp Ala Asp Thr Ala Ile Ile Asn Ala Glu
            370                 375                 380

Gly Gly Gln Ser Gly Gly Asp Asp Lys Lys Glu Tyr Phe Ile
385                 390                 395

<210> SEQ ID NO 53
<211> LENGTH: 1191
<212> TYPE: DNA
<213> ORGANISM: Artificial Sequence
<220> FEATURE:
<223> OTHER INFORMATION: Description of the artificial sequence: base
      sequence of mouse CADM3 including signal sequence

<400> SEQUENCE: 53

```
atgggggccc cttccgccct gcccctgctc ctgctcctcg cctgctcctg ggcgcccggc    60
ggggccaatc tttcccagga cgatagccag ccctggacat ctgatgaaac agttgtggct   120
ggtggcacag tggttctcaa gtgtcaagta aaagaccatg aagactcatc tctgcagtgg   180
tctaaccctg ctcagcagac cctatacttc ggggagaaga gagcccttcg agataatcgg   240
attcagctgg ttagctctac tccccatgag ctcagcatca gcatcagcaa tgtggcgctg   300
gccgatgagg gggagtacac gtgctccatc ttcactatgc ctgtgcgaac cgccaagtcc   360
cttgtcactg tgctcggaat cccacagaaa cccataatca tggttataaa gtcatcattg   420
cgggaaaagg agacagccac tctaaattgt cagtcttctg ggagcaaacc tgcagcccag   480
ctcacctgga ggaaaggtga ccaagaactc cacggggacc aaacacgaat ccaggaagat   540
cccaacggga aaaccttcac tgtgagcagc tcagtgtcat tccaggttac ccgggaggat   600
gatggagcaa acatcgtgtg ctctgtgaac catgaatctc tgaagggagc cgacagatcc   660
acttctcagc gcattgaagt gttatacaca ccaacagcca tgattaggcc agaacctgct   720
catcctcgag aaggccagaa gctgttgtta cattgtgagg ggcgtggcaa tccagtcccc   780
cagcagtacg tgtgggtaaa ggaaggcagt gagccacccc tcaagatgac ccaagagagt   840
gctctcatct tccccttttt gaataagagt gacagtggca cttatggctg tacagccaca   900
agcaacatgg gcagctatac agcctacttc accctcaatg tcaacgaccc cagtccagtg   960
ccctcgtcct ccagtaccta ccacgccatc attggaggga ttgtggcttt cattgtcttc  1020
ctgctgctca ttctgctcat tttccttgga cactatttga tccggcacaa aggaacctac  1080
ctgacacacg aagcgaaggg ttccgacgat gctccagatg cggatacggc catcatcaac  1140
gcagaaggcg ggcagtcagg cggggatgac aagaaggaat atttcatcta g            1191
```

<210> SEQ ID NO 54
<211> LENGTH: 396
<212> TYPE: PRT

```
<213> ORGANISM: Artificial Sequence
<220> FEATURE:
<223> OTHER INFORMATION: Description of the artificial sequence: amino
      acid sequence of mouse CADM3 including signal sequence

<400> SEQUENCE: 54
```

| | | | | | | | | | | | | | | | |
|---|---|---|---|---|---|---|---|---|---|---|---|---|---|---|---|
| Met | Gly | Ala | Pro | Ser | Ala | Leu | Pro | Leu | Leu | Leu | Leu | Ala | Cys | Ser | |
| 1 | | | | 5 | | | | | 10 | | | | | 15 | |
| Trp | Ala | Pro | Gly | Gly | Ala | Asn | Leu | Ser | Gln | Asp | Asp | Ser | Gln | Pro | Trp |
| | | | 20 | | | | | 25 | | | | | 30 | | |
| Thr | Ser | Asp | Glu | Thr | Val | Val | Ala | Gly | Gly | Thr | Val | Val | Leu | Lys | Cys |
| | | | 35 | | | | | 40 | | | | | 45 | | |
| Gln | Val | Lys | Asp | His | Glu | Asp | Ser | Ser | Leu | Gln | Trp | Ser | Asn | Pro | Ala |
| | 50 | | | | | 55 | | | | | 60 | | | | |
| Gln | Gln | Thr | Leu | Tyr | Phe | Gly | Lys | Arg | Ala | Leu | Arg | Asp | Asn | Arg | |
| 65 | | | | | 70 | | | | | 75 | | | | | 80 |
| Ile | Gln | Leu | Val | Ser | Ser | Thr | Pro | His | Glu | Leu | Ser | Ile | Ser | Ile | Ser |
| | | | | 85 | | | | | 90 | | | | | 95 | |
| Asn | Val | Ala | Leu | Ala | Asp | Glu | Gly | Glu | Tyr | Thr | Cys | Ser | Ile | Phe | Thr |
| | | | 100 | | | | | 105 | | | | | 110 | | |
| Met | Pro | Val | Arg | Thr | Ala | Lys | Ser | Leu | Val | Thr | Val | Leu | Gly | Ile | Pro |
| | | | 115 | | | | | 120 | | | | | 125 | | |
| Gln | Lys | Pro | Ile | Ile | Thr | Gly | Tyr | Lys | Ser | Ser | Leu | Arg | Glu | Lys | Glu |
| | 130 | | | | | 135 | | | | | 140 | | | | |
| Thr | Ala | Thr | Leu | Asn | Cys | Gln | Ser | Ser | Gly | Ser | Lys | Pro | Ala | Ala | Gln |
| 145 | | | | | 150 | | | | | 155 | | | | | 160 |
| Leu | Thr | Trp | Arg | Lys | Gly | Asp | Gln | Glu | Leu | His | Gly | Asp | Gln | Thr | Arg |
| | | | | 165 | | | | | 170 | | | | | 175 | |
| Ile | Gln | Glu | Asp | Pro | Asn | Gly | Lys | Thr | Phe | Thr | Val | Ser | Ser | Ser | Val |
| | | | 180 | | | | | 185 | | | | | 190 | | |
| Ser | Phe | Gln | Val | Thr | Arg | Glu | Asp | Asp | Gly | Ala | Asn | Ile | Val | Cys | Ser |
| | | | 195 | | | | | 200 | | | | | 205 | | |
| Val | Asn | His | Glu | Ser | Leu | Lys | Gly | Ala | Asp | Arg | Ser | Thr | Ser | Gln | Arg |
| | 210 | | | | | 215 | | | | | 220 | | | | |
| Ile | Glu | Val | Leu | Tyr | Thr | Pro | Thr | Ala | Met | Ile | Arg | Pro | Glu | Pro | Ala |
| 225 | | | | | 230 | | | | | 235 | | | | | 240 |
| His | Pro | Arg | Glu | Gly | Gln | Lys | Leu | Leu | Leu | His | Cys | Glu | Gly | Arg | Gly |
| | | | | 245 | | | | | 250 | | | | | 255 | |
| Asn | Pro | Val | Pro | Gln | Gln | Tyr | Val | Trp | Val | Lys | Glu | Gly | Ser | Glu | Pro |
| | | | 260 | | | | | 265 | | | | | 270 | | |
| Pro | Leu | Lys | Met | Thr | Gln | Glu | Ser | Ala | Leu | Ile | Phe | Pro | Phe | Leu | Asn |
| | | | 275 | | | | | 280 | | | | | 285 | | |
| Lys | Ser | Asp | Ser | Gly | Thr | Tyr | Gly | Cys | Thr | Ala | Thr | Ser | Asn | Met | Gly |
| | 290 | | | | | 295 | | | | | 300 | | | | |
| Ser | Tyr | Thr | Ala | Tyr | Phe | Thr | Leu | Asn | Val | Asn | Asp | Pro | Ser | Pro | Val |
| 305 | | | | | 310 | | | | | 315 | | | | | 320 |
| Pro | Ser | Ser | Ser | Thr | Tyr | His | Ala | Ile | Ile | Gly | Gly | Ile | Val | Ala | |
| | | | | 325 | | | | | 330 | | | | | 335 | |
| Phe | Ile | Val | Phe | Leu | Leu | Leu | Ile | Leu | Leu | Ile | Phe | Leu | Gly | His | Tyr |
| | | | 340 | | | | | 345 | | | | | 350 | | |
| Leu | Ile | Arg | His | Lys | Gly | Thr | Tyr | Leu | Thr | His | Glu | Ala | Lys | Gly | Ser |
| | | | 355 | | | | | 360 | | | | | 365 | | |
| Asp | Asp | Ala | Pro | Asp | Ala | Asp | Thr | Ala | Ile | Ile | Asn | Ala | Glu | Gly | Gly |
| | 370 | | | | | 375 | | | | | 380 | | | | |

```
Gln Ser Gly Gly Asp Asp Lys Lys Glu Tyr Phe Ile
385                 390                 395
```

<210> SEQ ID NO 55
<211> LENGTH: 1191
<212> TYPE: DNA
<213> ORGANISM: Artificial Sequence
<220> FEATURE:
<223> OTHER INFORMATION: Description of the artificial sequence: base
      sequence of cynomolgus monkey CADM3 including signal sequence

<400> SEQUENCE: 55

```
atgggggccc cagtcgcctt gctcctgctc ctgctgttcg cctgctgctg ggcgcccagt     60
ggggccaacc tctcccagga cgacagccag ccctggacat ctgatgaaac agtggtggct   120
ggtggcaccg tggtgctcaa gtgccaagtg aaagatcacg aggactcatc cctgcaatgg   180
tctaaccctg ctcagcagac tctctacttt ggggagaaga gagcccttcg agataatcga   240
attcagctgg ttacctctac tccccacgag ctcagcatca gcatcagcaa tgtggccctg   300
gcagacgagg gcgagtacac ctgctcaatc ttcactatgc ctgtacgaac tgccaagtcc   360
ctcgtcactg tgctaggaat tccacagaag cccatcatca ctggttataa atcttcatta   420
cgggaaaagg acacagccac cctaaactgt cagtcttctg ggagcaagcc tgcagcccgg   480
ctcacctgga gaaagggtga ccaagaactc acggagaac caactcgcat acaggaagat   540
cccaatggta aaaccttcac tgtcagcagc tcggtgacat ccaggttac ccgggaggat   600
gatggggcga acatcgtgtg ctctgtgaac catgaatctc taaagggagc tgacagatcc   660
acctctcaac gcattgaagt tttatacaca ccgactgcga tgattaggcc agaccctccc   720
catcctcgtg agggccagaa gctgttgcta cactgtgagg gtcgtggcaa tccagtcccc   780
cagcagtacc tatgggagaa ggagggcagt gtgccacccc tgaagatgac caagagagt   840
gccctgatct tccccttcct caacaagagt gacagcggca cctacggctg cacggccacc   900
agcaacatgg gcagctacaa ggcctactac actctcaacg ttaatgaccc cagtccggtg   960
ccctcctcct ccagcaccta ccacgccatc atcggcggga tcgtggcttt cattgtcttc  1020
ctgctgctca tcatgctcat cttccttgga cattacttga tccggcacaa aggaacctac  1080
ctgacacatg aggcgaaagg ctccgacgat gccccagatg cggacacggc catcatcaat  1140
gcagaaggcg ggcagtcggg agggacgac aagaaggaat atttcatcta g            1191
```

<210> SEQ ID NO 56
<211> LENGTH: 396
<212> TYPE: PRT
<213> ORGANISM: Artificial Sequence
<220> FEATURE:
<223> OTHER INFORMATION: Description of the artificial sequence: amino
      acid sequence of cynomolgus monkey CADM3 including signal sequence

<400> SEQUENCE: 56

```
Met Gly Ala Pro Val Ala Leu Leu Leu Leu Leu Phe Ala Cys Cys
1               5                   10                  15

Trp Ala Pro Ser Gly Ala Asn Leu Ser Gln Asp Asp Ser Gln Pro Trp
                20                  25                  30

Thr Ser Asp Glu Thr Val Val Ala Gly Gly Thr Val Val Leu Lys Cys
            35                  40                  45

Gln Val Lys Asp His Glu Asp Ser Ser Leu Gln Trp Ser Asn Pro Ala
        50                  55                  60

Gln Gln Thr Leu Tyr Phe Gly Glu Lys Arg Ala Leu Arg Asp Asn Arg
65                  70                  75                  80
```

Ile Gln Leu Val Thr Ser Thr Pro His Glu Leu Ser Ile Ser
                85                  90                  95

Asn Val Ala Leu Ala Asp Glu Gly Glu Tyr Thr Cys Ser Ile Phe Thr
            100                 105                 110

Met Pro Val Arg Thr Ala Lys Ser Leu Val Thr Val Leu Gly Ile Pro
        115                 120                 125

Gln Lys Pro Ile Ile Thr Gly Tyr Lys Ser Ser Leu Arg Glu Lys Asp
    130                 135                 140

Thr Ala Thr Leu Asn Cys Gln Ser Ser Gly Ser Lys Pro Ala Ala Arg
145                 150                 155                 160

Leu Thr Trp Arg Lys Gly Asp Gln Glu Leu His Gly Glu Pro Thr Arg
                165                 170                 175

Ile Gln Glu Asp Pro Asn Gly Lys Thr Phe Thr Val Ser Ser Ser Val
            180                 185                 190

Thr Phe Gln Val Thr Arg Glu Asp Asp Gly Ala Asn Ile Val Cys Ser
        195                 200                 205

Val Asn His Glu Ser Leu Lys Gly Ala Asp Arg Ser Thr Ser Gln Arg
    210                 215                 220

Ile Glu Val Leu Tyr Thr Pro Thr Ala Met Ile Arg Pro Asp Pro Pro
225                 230                 235                 240

His Pro Arg Glu Gly Gln Lys Leu Leu Leu His Cys Glu Gly Arg Gly
                245                 250                 255

Asn Pro Val Pro Gln Gln Tyr Leu Trp Glu Lys Glu Gly Ser Val Pro
            260                 265                 270

Pro Leu Lys Met Thr Gln Glu Ser Ala Leu Ile Phe Pro Phe Leu Asn
        275                 280                 285

Lys Ser Asp Ser Gly Thr Tyr Gly Cys Thr Ala Thr Ser Asn Met Gly
    290                 295                 300

Ser Tyr Lys Ala Tyr Tyr Thr Leu Asn Val Asn Asp Pro Ser Pro Val
305                 310                 315                 320

Pro Ser Ser Ser Ser Thr Tyr His Ala Ile Ile Gly Gly Ile Val Ala
                325                 330                 335

Phe Ile Val Phe Leu Leu Leu Ile Met Leu Ile Phe Leu Gly His Tyr
            340                 345                 350

Leu Ile Arg His Lys Gly Thr Tyr Leu Thr His Glu Ala Lys Gly Ser
        355                 360                 365

Asp Asp Ala Pro Asp Ala Asp Thr Ala Ile Ile Asn Ala Glu Gly Gly
    370                 375                 380

Gln Ser Gly Gly Asp Asp Lys Lys Glu Tyr Phe Ile
385                 390                 395

<210> SEQ ID NO 57
<211> LENGTH: 1713
<212> TYPE: DNA
<213> ORGANISM: Artificial Sequence
<220> FEATURE:
<223> OTHER INFORMATION: Description of the artificial sequence: base
      sequence of hCADM3-FLAG_Fc including signal sequence

<400> SEQUENCE: 57 atggggccc cagccgcctc gctcctgctc ctgctcctgc tgttcgcctg ctgctgggcg      60
cccggcgggg ccaacctctc ccaggacgac agccagccct ggacatctga tgaaacagtg     120
gtggctggtg gcaccgtggt gctcaagtgc aagtgaaag atcacgagga ctcatccctg      180
caatggtcta accctgctca gcagactctc tactttgggg agaagagagc ccttcgagat     240

```
aatcgaattc agctggttac ctctacgccc cacgagctca gcatcagcat cagcaatgtg    300
gccctggcag acgagggcga gtacacctgc tcaatcttca ctatgcctgt gcgaactgcc    360
aagtccctcg tcactgtgct aggaattcca cagaagccca tcatcactgg ttataaatct    420
tcattacggg aaaaagacac agccacccta aactgtcagt cttctgggag caagcctgca    480
gcccggctca cctggagaaa gggtgaccaa gaactccacg agaaccaac ccgcatacag     540 gaagatccca tggtaaaac cttcactgtc agcagctcgg tgacattcca ggttacccgg     600
gaggatgatg gggcgagcat cgtgtgctct gtgaaccatg aatctctaaa gggagctgac    660
agatccacct ctcaacgcat tgaagtttta tacacaccaa ctgcgatgat taggccagac    720 cctcccatc ctcgtgaggg ccagaagctg ttgctacact gtgagggtcg cggcaatcca    780
gtcccccagc agtacctatg ggagaaggag ggcagtgtgc caccctgaa gatgacccag     840 gagagtgccc tgatcttccc tttcctcaac aagagtgaca gtggcaccta cggctgcaca    900
gccaccagca acatgggcag ctacaaggcc tactacaccc tcaatgttaa tgaccccagt    960
ccggtgccct cctcctccag cacctaccac tctagagcag actacaagga cgacgatgac   1020
aagactagtg acaaaactca cacatgccca ccgtgcccag cacctgaact cctgggggga   1080
ccgtcagtct tcctcttccc cccaaaaccc aaggacaccc tcatgatctc ccggacccct   1140
gaggtcacat gcgtggtggt ggacgtgagc cacgaagacc ctgaggtcaa gttcaactgg   1200
tacgtggacg gcgtggaggt gcataatgcc aagacaaagc cgcgggagga gcagtacaac   1260
agcacgtacc gtgtggtcag cgtcctcacc gtcctgcacc aggactggct gaatggcaag   1320
gagtacaagt gcaaggtctc caacaaagcc ctcccagccc catcgagaa aaccatctcc    1380 aaagccaaag gcagccccg agaaccacag gtgtacaccc tgcccccatc ccgggatgag   1440
ctgaccaaga accaggtcag cctgacctgc ctggtcaaag gcttctatcc cagcgacatc   1500
gccgtggagt gggagagcaa tgggcagccg gagaacaact acaagaccac gcctcccgtg   1560
ctggactccg acggctcctt cttcctctac agcaagctca ccgtggacaa gagcaggtgg   1620
cagcagggga acgtcttctc atgctccgtg atgcatgagg ctctgcacaa ccactacacg   1680
cagaagagcc tctccctgtc tccgggtaaa tga                                1713

<210> SEQ ID NO 58
<211> LENGTH: 570
<212> TYPE: PRT
<213> ORGANISM: Artificial Sequence
<220> FEATURE:
<223> OTHER INFORMATION: Description of the artificial sequence: amino
      acid sequence of hCADM3-FLAG_Fc including signal sequence

<400> SEQUENCE: 58

Met Gly Ala Pro Ala Ala Ser Leu Leu Leu Leu Leu Leu Leu Phe Ala
1               5                   10                  15

Cys Cys Trp Ala Pro Gly Gly Ala Asn Leu Ser Gln Asp Asp Ser Gln
                20                  25                  30

Pro Trp Thr Ser Asp Glu Thr Val Val Ala Gly Gly Thr Val Val Leu
            35                  40                  45

Lys Cys Gln Val Lys Asp His Glu Asp Ser Ser Leu Gln Trp Ser Asn
        50                  55                  60

Pro Ala Gln Gln Thr Leu Tyr Phe Gly Glu Lys Arg Ala Leu Arg Asp
65                  70                  75                  80

Asn Arg Ile Gln Leu Val Thr Ser Thr Pro His Glu Leu Ser Ile Ser
                85                  90                  95
```

-continued

```
Ile Ser Asn Val Ala Leu Ala Asp Glu Gly Glu Tyr Thr Cys Ser Ile
            100                 105                 110
Phe Thr Met Pro Val Arg Thr Ala Lys Ser Leu Val Thr Val Leu Gly
        115                 120                 125
Ile Pro Gln Lys Pro Ile Ile Thr Gly Tyr Lys Ser Ser Leu Arg Glu
    130                 135                 140
Lys Asp Thr Ala Thr Leu Asn Cys Gln Ser Ser Gly Ser Lys Pro Ala
145                 150                 155                 160
Ala Arg Leu Thr Trp Arg Lys Gly Asp Gln Glu Leu His Gly Glu Pro
                165                 170                 175
Thr Arg Ile Gln Glu Asp Pro Asn Gly Lys Thr Phe Thr Val Ser Ser
            180                 185                 190
Ser Val Thr Phe Gln Val Thr Arg Glu Asp Asp Gly Ala Ser Ile Val
        195                 200                 205
Cys Ser Val Asn His Glu Ser Leu Lys Gly Ala Asp Arg Ser Thr Ser
    210                 215                 220
Gln Arg Ile Glu Val Leu Tyr Thr Pro Thr Ala Met Ile Arg Pro Asp
225                 230                 235                 240
Pro Pro His Pro Arg Glu Gly Gln Lys Leu Leu Leu His Cys Glu Gly
                245                 250                 255
Arg Gly Asn Pro Val Pro Gln Gln Tyr Leu Trp Glu Lys Glu Gly Ser
            260                 265                 270
Val Pro Pro Leu Lys Met Thr Gln Glu Ser Ala Leu Ile Phe Pro Phe
        275                 280                 285
Leu Asn Lys Ser Asp Ser Gly Thr Tyr Gly Cys Thr Ala Thr Ser Asn
    290                 295                 300
Met Gly Ser Tyr Lys Ala Tyr Tyr Thr Leu Asn Val Asn Asp Pro Ser
305                 310                 315                 320
Pro Val Pro Ser Ser Ser Thr Tyr His Ser Arg Ala Asp Tyr Lys
                325                 330                 335
Asp Asp Asp Asp Lys Thr Ser Asp Lys Thr His Thr Cys Pro Pro Cys
            340                 345                 350
Pro Ala Pro Glu Leu Leu Gly Gly Pro Ser Val Phe Leu Phe Pro Pro
        355                 360                 365
Lys Pro Lys Asp Thr Leu Met Ile Ser Arg Thr Pro Glu Val Thr Cys
    370                 375                 380
Val Val Val Asp Val Ser His Glu Asp Pro Glu Val Lys Phe Asn Trp
385                 390                 395                 400
Tyr Val Asp Gly Val Glu Val His Asn Ala Lys Thr Lys Pro Arg Glu
                405                 410                 415
Glu Gln Tyr Asn Ser Thr Tyr Arg Val Val Ser Val Leu Thr Val Leu
            420                 425                 430
His Gln Asp Trp Leu Asn Gly Lys Glu Tyr Lys Cys Lys Val Ser Asn
        435                 440                 445
Lys Ala Leu Pro Ala Pro Ile Glu Lys Thr Ile Ser Lys Ala Lys Gly
    450                 455                 460
Gln Pro Arg Glu Pro Gln Val Tyr Thr Leu Pro Pro Ser Arg Asp Glu
465                 470                 475                 480
Leu Thr Lys Asn Gln Val Ser Leu Thr Cys Leu Val Lys Gly Phe Tyr
                485                 490                 495
Pro Ser Asp Ile Ala Val Glu Trp Glu Ser Asn Gly Gln Pro Glu Asn
            500                 505                 510
```

|     |     |     |     |     |     |     |     |     |     |     |     |     |
| --- | --- | --- | --- | --- | --- | --- | --- | --- | --- | --- | --- | --- |
| Asn | Tyr | Lys | Thr | Thr | Pro | Pro | Val | Leu | Asp | Ser | Asp | Gly | Ser | Phe | Phe |
|     |     | 515 |     |     |     | 520 |     |     |     | 525 |     |     |

| Leu | Tyr | Ser | Lys | Leu | Thr | Val | Asp | Lys | Ser | Arg | Trp | Gln | Gln | Gly | Asn |
|     | 530 |     |     |     |     | 535 |     |     |     |     | 540 |

| Val | Phe | Ser | Cys | Ser | Val | Met | His | Glu | Ala | Leu | His | Asn | His | Tyr | Thr |
| 545 |     |     |     |     | 550 |     |     |     |     | 555 |     |     |     |     | 560 |

| Gln | Lys | Ser | Leu | Ser | Leu | Ser | Pro | Gly | Lys |
|     |     |     | 565 |     |     |     |     | 570 |

<210> SEQ ID NO 59
<211> LENGTH: 1707
<212> TYPE: DNA
<213> ORGANISM: Artificial Sequence
<220> FEATURE:
<223> OTHER INFORMATION: Description of the artificial sequence: base
      sequence of mCADM3-FLAG_Fc including signal sequence

<400> SEQUENCE: 59

| | | | |
|---|---|---|---|
| atgggggccc cttccgccct gcccctgctc ctgctcctcg cctgctcctg ggcgcccggc | 60 |
| ggggccaatc tttcccagga cgatagccag ccctggacat ctgatgaaac agttgtggct | 120 |
| ggtggcacag tggttctcaa gtgtcaagta aaagaccatg aagactcatc tctgcagtgg | 180 |
| tctaaccctg ctcagcagac cctatacttc ggggagaaga gagcccttcg agataatcgg | 240 |
| attcagctgg ttagctctac tccccatgag ctcagcatca gcatcagcaa tgtggcgctg | 300 |
| gccgatgagg gggagtacac gtgctccatc ttcactatgc ctgtgcgaac cgccaagtcc | 360 |
| cttgtcactg tgctcggaat cccacagaaa cccataatca ctggttataa gtcatcattg | 420 |
| cgggaaaagg agacagccac tctaaattgt cagtcttctg ggagcaaacc tgcagcccag | 480 |
| ctcacctgga ggaaaggtga ccaagaactc acgggggacc aaacacgaat ccaggaagat | 540 |
| cccaacggga aaaccttcac tgtgagcagc tcagtgtcat tccaggttac ccgggaggat | 600 |
| gatgagcaa acatcgtgtg ctctgtgaac catgaatctc tgaagggagc cgacagatcc | 660 |
| acttctcagc gcattgaagt gttatacaca ccaacagcca tgattaggcc agaacctgct | 720 |
| catcctcgag aaggccagaa gctgttgtta cattgtgagg ggcgtggcaa tccagtcccc | 780 |
| cagcagtacg tgtgggtaaa ggaaggcagt gagccacccc tcaagatgac caagagagt | 840 |
| gctctcatct tcccctttt gaataagagt gacagtggca cttatggctg tacagccaca | 900 |
| agcaacatgg gcagctatac agcctacttc acccctcaatg tcaacgaccc cagtccagtg | 960 |
| ccctcgtcct ccagtaccta ccactctaga gcagactaca aggacgacga tgacaagact | 1020 |
| agtgacaaaa ctcacacatg cccaccgtgc ccagcacctg aactcctggg gggaccgtca | 1080 |
| gtcttcctct tccccccaaa acccaaggac accctcatga tctcccggac ccctgaggtc | 1140 |
| acatgcgtgt ggtggacgt gagccacgaa gaccctgagg tcaagttcaa ctggtacgtg | 1200 |
| gacggcgtgg aggtgcataa tgccaagaca aagccgcggg aggagcagta caacagcacg | 1260 |
| taccgtgtgg tcagcgtcct caccgtcctg caccaggact ggctgaatgg caaggagtac | 1320 |
| aagtgcaagg tctccaacaa agccctccca gcccccatcg agaaaaccat ctccaaagcc | 1380 |
| aaagggcagc cccgagaacc acaggtgtac accctgcccc catcccggga tgagctgacc | 1440 |
| aagaaccagg tcagcctgac ctgcctggtc aaaggcttct atcccagcga catcgccgtg | 1500 |
| gagtgggaga gcaatgggca gccggagaac aactacaaga ccacgcctcc cgtgctggac | 1560 |
| tccgacggct ccttcttcct ctacagcaag ctcaccgtgg acaagagcag gtggcagcag | 1620 |
| gggaacgtct tctcatgctc cgtgatgcat gaggctctgc acaaccacta cacgcagaag | 1680 | agcctctccc tgtctccggg taaatga                                    1707

<210> SEQ ID NO 60
<211> LENGTH: 568
<212> TYPE: PRT
<213> ORGANISM: Artificial Sequence
<220> FEATURE:
<223> OTHER INFORMATION: Description of the artificial sequence: amino
      acid sequence of mCADM3-FLAG_Fc including signal sequence

<400> SEQUENCE: 60

```
Met Gly Ala Pro Ser Ala Leu Pro Leu Leu Leu Leu Ala Cys Ser
1               5                   10                  15

Trp Ala Pro Gly Gly Ala Asn Leu Ser Gln Asp Asp Ser Gln Pro Trp
            20                  25                  30

Thr Ser Asp Glu Thr Val Val Ala Gly Gly Thr Val Val Leu Lys Cys
        35                  40                  45

Gln Val Lys Asp His Glu Asp Ser Ser Leu Gln Trp Ser Asn Pro Ala
    50                  55                  60

Gln Gln Thr Leu Tyr Phe Gly Glu Lys Arg Ala Leu Arg Asp Asn Arg
65                  70                  75                  80

Ile Gln Leu Val Ser Ser Thr Pro His Glu Leu Ser Ile Ser Ile Ser
                85                  90                  95

Asn Val Ala Leu Ala Asp Glu Gly Glu Tyr Thr Cys Ser Ile Phe Thr
            100                 105                 110

Met Pro Val Arg Thr Ala Lys Ser Leu Val Thr Val Leu Gly Ile Pro
        115                 120                 125

Gln Lys Pro Ile Ile Thr Gly Tyr Lys Ser Ser Leu Arg Glu Lys Glu
    130                 135                 140

Thr Ala Thr Leu Asn Cys Gln Ser Ser Gly Ser Lys Pro Ala Ala Gln
145                 150                 155                 160

Leu Thr Trp Arg Lys Gly Asp Gln Glu Leu His Gly Asp Gln Thr Arg
                165                 170                 175

Ile Gln Glu Asp Pro Asn Gly Lys Thr Phe Thr Val Ser Ser Ser Val
            180                 185                 190

Ser Phe Gln Val Thr Arg Glu Asp Asp Gly Ala Asn Ile Val Cys Ser
        195                 200                 205

Val Asn His Glu Ser Leu Lys Gly Ala Asp Arg Ser Thr Ser Gln Arg
    210                 215                 220

Ile Glu Val Leu Tyr Thr Pro Thr Ala Met Ile Arg Pro Glu Pro Ala
225                 230                 235                 240

His Pro Arg Glu Gly Gln Lys Leu Leu Leu His Cys Glu Gly Arg Gly
                245                 250                 255

Asn Pro Val Pro Gln Gln Tyr Val Trp Val Lys Glu Gly Ser Glu Pro
            260                 265                 270

Pro Leu Lys Met Thr Gln Glu Ser Ala Leu Ile Phe Pro Phe Leu Asn
        275                 280                 285

Lys Ser Asp Ser Gly Thr Tyr Gly Cys Thr Ala Thr Ser Asn Met Gly
    290                 295                 300

Ser Tyr Thr Ala Tyr Phe Thr Leu Asn Val Asn Asp Pro Ser Pro Val
305                 310                 315                 320

Pro Ser Ser Ser Ser Thr Tyr His Ser Arg Ala Asp Tyr Lys Asp Asp
                325                 330                 335

Asp Asp Lys Thr Ser Asp Lys Thr His Thr Cys Pro Pro Cys Pro Ala
            340                 345                 350
```

```
Pro Glu Leu Leu Gly Gly Pro Ser Val Phe Leu Phe Pro Lys Pro
            355                 360                 365

Lys Asp Thr Leu Met Ile Ser Arg Thr Pro Glu Val Thr Cys Val Val
    370                 375                 380

Val Asp Val Ser His Glu Asp Pro Glu Val Lys Phe Asn Trp Tyr Val
385                 390                 395                 400

Asp Gly Val Glu Val His Asn Ala Lys Thr Lys Pro Arg Glu Glu Gln
                405                 410                 415

Tyr Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Ala
        435                 440                 445

Leu Pro Ala Pro Ile Glu Lys Thr Ile Ser Lys Ala Lys Gly Gln Pro
    450                 455                 460

Arg Glu Pro Gln Val Tyr Thr Leu Pro Pro Ser Arg Asp Glu Leu Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Lys Leu Thr Val Asp Lys Ser Arg Trp Gln Gln Gly Asn Val Phe
    530                 535                 540

Ser Cys Ser Val Met His Glu Ala Leu His Asn His Tyr Thr Gln Lys
545                 550                 555                 560

Ser Leu Ser Leu Ser Pro Gly Lys
                565

<210> SEQ ID NO 61
<211> LENGTH: 1707
<212> TYPE: DNA
<213> ORGANISM: Artificial Sequence
<220> FEATURE:
<223> OTHER INFORMATION: Description of the artificial sequence: base
      sequence of rCADM3-FLAG_Fc including signal sequence

<400> SEQUENCE: 61
atgggggccc cttccgccct gcccctgctc ctgctcctcg cctgctcctg ggcgcccggc      60
ggggccaatc tttcccagga cgatagccag ccctggacgt ctgatgaaac agtggtggct     120
ggtggcacag tagtgctcaa gtgccaagtg aaagaccatg aagactcatc tctgcagtgg     180
tctaaccctg cccagcagac tctatacttt ggggagaaaa gagcccttcg agataatcgg     240
attcagctgg ttagctccac cccgcatgag ctcagcatca gcatcagcaa cgtggcactg     300
gccgacgagg gcgagtacac atgctccatc ttcactatgc ctgtgcggac cgccaagtcc     360
ctcgtcactg tgctcggaat cccacagaaa cccataatca ctggttataa gtcatcgttg     420
cgggaaaagg agacagccac tctaaattgt cagtcttctg ggagcaaacc tgcagcccag     480
ctcgcctgga aaaaggtga ccaagaactc acgggggacc agacgcgaat ccaggaagat     540
cccaatggga aaaccttcac tgtgagcagc tcggtgtcat tccaggttac ccgggatgat     600
gatggagcaa acgtcgtgtg ctctgtgaac catgaatctc tgaagggagc tgacagatcc     660
acctctcagc gcattgaagt gttatacaca ccaacagcca tgattaggcc agaacctgct     720
catcctcgtg aaggccagaa gctgttgtta cattgtgagg ggcgtggcaa tccagtccct     780
```

```
cagcagtacg tgtgggtaaa agaaggcagc gagccacccc tcaagatgac ccaagagagt    840
gcactcatct tcccattttt gaacaaaagt gacagtggca cctatggctg tacagccacg    900
agcaacatgg gcagctatac agcctacttc actctcaatg tcaacgaccc tagtccagtg    960
ccctcatcct ccagtactta ccactctaga gcagactaca aggacgacga tgacaagact   1020
agtgacaaaa ctcacacatg cccaccgtgc ccagcacctg aactcctggg gggaccgtca   1080
gtcttcctct tccccccaaa acccaaggac accctcatga tctcccggac ccctgaggtc   1140
acatgcgtgg tggtggacgt gagccacgaa gaccctgagg tcaagttcaa ctggtacgtg   1200
gacggcgtgg aggtgcataa tgccaagaca aagccgcggg aggagcagta caacagcacg   1260
taccgtgtgg tcagcgtcct caccgtcctg caccaggact ggctgaatgg caaggagtac   1320
aagtgcaagg tctccaacaa agccctccca gcccccatcg agaaaaccat ctccaaagcc   1380
aaagggcagc cccgagaacc acaggtgtac accctgcccc catcccggga tgagctgacc   1440
aagaaccagg tcagcctgac ctgcctggtc aaaggcttct atcccagcga catcgccgtg   1500
gagtgggaga gcaatgggca gccggagaac aactacaaga ccacgcctcc cgtgctggac   1560
tccgacggct ccttcttcct ctacagcaag ctcaccgtgg acaagagcag gtggcagcag   1620
gggaacgtct tctcatgctc cgtgatgcat gaggctctgc acaaccacta cacgcagaag   1680
agcctctccc tgtctccggg taaatga                                       1707

<210> SEQ ID NO 62
<211> LENGTH: 568
<212> TYPE: PRT
<213> ORGANISM: Artificial Sequence
<220> FEATURE:
<223> OTHER INFORMATION: Description of the artificial sequence: amino
      acid sequence of rCADM3-FLAG_Fc including signal sequence

<400> SEQUENCE: 62

Met Gly Ala Pro Ser Ala Leu Pro Leu Leu Leu Leu Ala Cys Ser
1               5                   10                  15

Trp Ala Pro Gly Gly Ala Asn Leu Ser Gln Asp Asp Ser Gln Pro Trp
                20                  25                  30

Thr Ser Asp Glu Thr Val Val Ala Gly Gly Thr Val Val Leu Lys Cys
            35                  40                  45

Gln Val Lys Asp His Glu Asp Ser Ser Leu Gln Trp Ser Asn Pro Ala
        50                  55                  60

Gln Gln Thr Leu Tyr Phe Gly Glu Lys Arg Ala Leu Arg Asp Asn Arg
65                  70                  75                  80

Ile Gln Leu Val Ser Ser Thr Pro His Glu Leu Ser Ile Ser Ile Ser
                85                  90                  95

Asn Val Ala Leu Ala Asp Glu Gly Glu Tyr Thr Cys Ser Ile Phe Thr
            100                 105                 110

Met Pro Val Arg Thr Ala Lys Ser Leu Val Thr Val Leu Gly Ile Pro
        115                 120                 125

Gln Lys Pro Ile Ile Thr Gly Tyr Lys Ser Ser Leu Arg Glu Lys Glu
    130                 135                 140

Thr Ala Thr Leu Asn Cys Gln Ser Ser Gly Ser Lys Pro Ala Ala Gln
145                 150                 155                 160

Leu Ala Trp Arg Lys Gly Asp Gln Glu Leu His Gly Asp Gln Thr Arg
                165                 170                 175

Ile Gln Glu Asp Pro Asn Gly Lys Thr Phe Thr Val Ser Ser Ser Val
            180                 185                 190
```

```
Ser Phe Gln Val Thr Arg Asp Asp Gly Ala Asn Val Val Cys Ser
            195                 200                 205

Val Asn His Glu Ser Leu Lys Gly Ala Asp Arg Ser Thr Ser Gln Arg
    210                 215                 220

Ile Glu Val Leu Tyr Thr Pro Thr Ala Met Ile Arg Pro Glu Pro Ala
225                 230                 235                 240

His Pro Arg Glu Gly Gln Lys Leu Leu Leu His Cys Glu Gly Arg Gly
                245                 250                 255

Asn Pro Val Pro Gln Gln Tyr Val Trp Val Lys Glu Gly Ser Glu Pro
            260                 265                 270

Pro Leu Lys Met Thr Gln Glu Ser Ala Leu Ile Phe Pro Phe Leu Asn
        275                 280                 285

Lys Ser Asp Ser Gly Thr Tyr Gly Cys Thr Ala Thr Ser Asn Met Gly
290                 295                 300

Ser Tyr Thr Ala Tyr Phe Thr Leu Asn Val Asn Asp Pro Ser Pro Val
305                 310                 315                 320

Pro Ser Ser Ser Ser Thr Tyr His Ser Arg Ala Asp Tyr Lys Asp Asp
                325                 330                 335

Asp Asp Lys Thr Ser Asp Lys Thr His Thr Cys Pro Pro Cys Pro Ala
            340                 345                 350

Pro Glu Leu Leu Gly Gly Pro Ser Val Phe Leu Phe Pro Pro Lys Pro
        355                 360                 365

Lys Asp Thr Leu Met Ile Ser Arg Thr Pro Glu Val Thr Cys Val Val
370                 375                 380

Val Asp Val Ser His Glu Asp Pro Glu Val Lys Phe Asn Trp Tyr Val
385                 390                 395                 400

Asp Gly Val Glu Val His Asn Ala Lys Thr Lys Pro Arg Glu Glu Gln
                405                 410                 415

Tyr Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Ala
        435                 440                 445

Leu Pro Ala Pro Ile Glu Lys Thr Ile Ser Lys Ala Lys Gly Gln Pro
450                 455                 460

Arg Glu Pro Gln Val Tyr Thr Leu Pro Pro Ser Arg Asp Glu Leu Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Lys Leu Thr Val Asp Lys Ser Arg Trp Gln Gln Gly Asn Val Phe
530                 535                 540

Ser Cys Ser Val Met His Glu Ala Leu His Asn His Tyr Thr Gln Lys
545                 550                 555                 560

Ser Leu Ser Leu Ser Pro Gly Lys
                565

<210> SEQ ID NO 63
<211> LENGTH: 1683
<212> TYPE: DNA
<213> ORGANISM: Artificial Sequence
<220> FEATURE:
<223> OTHER INFORMATION: Description of the artificial sequence: base
``` sequence of hCADM3-GST including signal sequence

<400> SEQUENCE: 63

```
atgggggccc cagccgcctc gctcctgctc ctgctcctgc tgttcgcctg ctgctgggcg      60
cccggcgggg ccaacctctc ccaggacgac agccagccct ggacatctga tgaaacagtg     120
gtggctggtg gcaccgtggt gctcaagtgc aagtgaaag  atcacgagga ctcatccctg     180
caatggtcta accctgctca gcagactctc tactttgggg agaagagagc ccttcgagat     240
aatcgaattc agctggttac ctctacgccc acgagctca  gcatcagcat cagcaatgtg     300
gccctggcag acgagggcga gtacacctgc tcaatcttca ctatgcctgt gcgaactgcc     360
aagtccctcg tcactgtgct aggaattcca cagaagccca tcatcactgg ttataaatct     420
tcattacggg aaaaagacac agccacccta aactgtcagt cttctgggag caagcctgca     480
gcccggctca cctggagaaa gggtgaccaa gaactccacg agaaccaac  ccgcatacag     540
gaagatccca atggtaaaac cttcactgtc agcagctcgg tgacattcca ggttacccgg     600
gaggatgatg gggcgagcat cgtgtgctct gtgaaccatg aatctctaaa gggagctgac     660
agatccacct ctcaacgcat tgaagtttta tacacaccaa ctgcgatgat taggccagac     720
cctccccatc ctcgtgaggg ccagaagctg ttgctacact gtgagggtcg cggcaatcca     780
gtcccccagc agtacctatg ggagaaggag ggcagtgtgc acccctgaa  gatgacccag     840
gagagtgccc tgatcttccc tttcctcaac aagagtgaca gtggcaccta cggctgcaca     900
gccaccagca acatgggcag ctacaaggcc tactacaccc tcaatgttaa tgaccccagt     960
ccggtgccct cctcctccag cacctaccac ggtaccctgg aagttctgtt ccaggggccc    1020
atgtcccta  tactaggtta ttggaaaatt aagggccttg tgcaacccac tcgacttctt    1080
ttggaatatc ttgaagaaaa atatgaagag catttgtatg agcgcgatga aggtgataaa    1140
tggcgaaaca aaaagtttga attgggtttg gagtttccca atcttcctta ttatattgat    1200
ggtgatgtta aattaacaca gtctatggcc atcatacgtt atatagctga caagcacaac    1260
atgttgggtg gttgtccaaa agagcgtgca gagatttcaa tgcttgaagg agcggttttg    1320
gatattagat acggtgtttc gagaattgca tatagtaaag actttgaaac tctcaaagtt    1380
gattttctta gcaagctacc tgaaatgctg aaaatgttcg aagatcgttt atgtcataaa    1440
acatatttaa atggtgatca tgtaacccat cctgacttca tgttgtatga cgctcttgat    1500
gttgttttat acatggaccc aatgtgcctg gatgcgttcc caaaattagt ttgttttaaa    1560
aaacgtattg aagctatccc acaaattgat aagtacttga atccagcaa  gtatatagca    1620
tggcctttgc agggctggca agccacgttt ggtggtggcg accatcctcc aaaatcggat    1680
tga                                                                 1683
```

<210> SEQ ID NO 64
<211> LENGTH: 560
<212> TYPE: PRT
<213> ORGANISM: Artificial Sequence
<220> FEATURE:
<223> OTHER INFORMATION: Description of the artificial sequence: amino
      acid sequence of hCADM3-GST including signal sequence

<400> SEQUENCE: 64

```
Met Gly Ala Pro Ala Ala Ser Leu Leu Leu Leu Leu Leu Leu Phe Ala
1               5                   10                  15

Cys Cys Trp Ala Pro Gly Gly Ala Asn Leu Ser Gln Asp Asp Ser Gln
            20                  25                  30
```

```
Pro Trp Thr Ser Asp Glu Thr Val Ala Gly Gly Thr Val Val Leu
         35                  40                  45
Lys Cys Gln Val Lys Asp His Glu Asp Ser Ser Leu Gln Trp Ser Asn
 50                  55                  60
Pro Ala Gln Gln Thr Leu Tyr Phe Gly Glu Lys Arg Ala Leu Arg Asp
 65                  70                  75                  80
Asn Arg Ile Gln Leu Val Thr Ser Thr Pro His Glu Leu Ser Ile Ser
                 85                  90                  95
Ile Ser Asn Val Ala Leu Ala Asp Glu Gly Tyr Thr Cys Ser Ile
                100                 105                 110
Phe Thr Met Pro Val Arg Thr Ala Lys Ser Leu Val Thr Val Leu Gly
                115                 120                 125
Ile Pro Gln Lys Pro Ile Ile Thr Gly Tyr Lys Ser Ser Leu Arg Glu
                130                 135                 140
Lys Asp Thr Ala Thr Leu Asn Cys Gln Ser Ser Gly Ser Lys Pro Ala
145                 150                 155                 160
Ala Arg Leu Thr Trp Arg Lys Gly Asp Gln Glu Leu His Gly Glu Pro
                165                 170                 175
Thr Arg Ile Gln Glu Asp Pro Asn Gly Lys Thr Phe Thr Val Ser Ser
                180                 185                 190
Ser Val Thr Phe Gln Val Thr Arg Glu Asp Asp Gly Ala Ser Ile Val
                195                 200                 205
Cys Ser Val Asn His Glu Ser Leu Lys Gly Ala Asp Arg Ser Thr Ser
                210                 215                 220
Gln Arg Ile Glu Val Leu Tyr Thr Pro Thr Ala Met Ile Arg Pro Asp
225                 230                 235                 240
Pro Pro His Pro Arg Glu Gly Gln Lys Leu Leu Leu His Cys Glu Gly
                245                 250                 255
Arg Gly Asn Pro Val Pro Gln Gln Tyr Leu Trp Glu Lys Glu Gly Ser
                260                 265                 270
Val Pro Pro Leu Lys Met Thr Gln Glu Ser Ala Leu Ile Phe Pro Phe
                275                 280                 285
Leu Asn Lys Ser Asp Ser Gly Thr Tyr Gly Cys Thr Ala Thr Ser Asn
                290                 295                 300
Met Gly Ser Tyr Lys Ala Tyr Tyr Thr Leu Asn Val Asn Asp Pro Ser
305                 310                 315                 320
Pro Val Pro Ser Ser Ser Thr Tyr His Gly Thr Leu Glu Val Leu
                325                 330                 335
Phe Gln Gly Pro Met Ser Pro Ile Leu Gly Tyr Trp Lys Ile Lys Gly
                340                 345                 350
Leu Val Gln Pro Thr Arg Leu Leu Leu Glu Tyr Leu Glu Glu Lys Tyr
                355                 360                 365
Glu Glu His Leu Tyr Glu Arg Asp Glu Gly Asp Lys Trp Arg Asn Lys
                370                 375                 380
Lys Phe Glu Leu Gly Leu Glu Phe Pro Asn Leu Pro Tyr Tyr Ile Asp
385                 390                 395                 400
Gly Asp Val Lys Leu Thr Gln Ser Met Ala Ile Ile Arg Tyr Ile Ala
                405                 410                 415
Asp Lys His Asn Met Leu Gly Gly Cys Pro Lys Glu Arg Ala Glu Ile
                420                 425                 430
Ser Met Leu Glu Gly Ala Val Leu Asp Ile Arg Tyr Gly Val Ser Arg
                435                 440                 445
Ile Ala Tyr Ser Lys Asp Phe Glu Thr Leu Lys Val Asp Phe Leu Ser
```

```
                  450             455             460
Lys Leu Pro Glu Met Leu Lys Met Phe Glu Asp Arg Leu Cys His Lys
465                 470                 475                 480

Thr Tyr Leu Asn Gly Asp His Val Thr His Pro Asp Phe Met Leu Tyr
                485                 490                 495

Asp Ala Leu Asp Val Val Leu Tyr Met Asp Pro Met Cys Leu Asp Ala
                500                 505                 510

Phe Pro Lys Leu Val Cys Phe Lys Lys Arg Ile Glu Ala Ile Pro Gln
            515                 520                 525

Ile Asp Lys Tyr Leu Lys Ser Ser Lys Tyr Ile Ala Trp Pro Leu Gln
        530                 535                 540

Gly Trp Gln Ala Thr Phe Gly Gly Gly Asp His Pro Pro Lys Ser Asp
545                 550                 555                 560

<210> SEQ ID NO 65
<211> LENGTH: 1677
<212> TYPE: DNA
<213> ORGANISM: Artificial Sequence
<220> FEATURE:
<223> OTHER INFORMATION: Description of the artificial sequence: base
      sequence of mCADM3-GST including signal sequence

<400> SEQUENCE: 65
atgggggccc cttccgccct gcccctgctc ctgctcctcg cctgctcctg ggcgcccggc       60
ggggccaatc tttcccagga cgatagccag ccctggacat ctgatgaaac agttgtggct      120
ggtggcacag tggttctcaa gtgtcaagta aaagaccatg aagactcatc tctgcagtgg      180
tctaaccctg ctcagcagac cctatacttc ggggagaaga gagcccttcg agataatcgg      240
attcagctgg ttagctctac tccccatgag ctcagcatca gcatcagcaa tgtggcgctg      300
gccgatgagg gggagtacac gtgctccatc ttcactatgc ctgtgcgaac cgccaagtcc      360
cttgtcactg tgctcggaat cccacagaaa cccataatca ctggttataa gtcatcattg      420
cgggaaaagg agacagccac tctaaattgt cagtcttctg ggagcaaacc tgcagcccag      480
ctcacctgga ggaaaggtga ccaagaactc acgggggacc aaacacgaat ccaggaagat      540
cccaacggga aaaccttcac tgtgagcagc tcagtgtcat ccaggttac ccgggaggat      600 gatggagcaa acatcgtgtg ctctgtgaac catgaatctc tgaagggagc cgacagatcc      660
acttctcagc gcattgaagt gttatacaca ccaacagcca tgattaggcc agaacctgct      720
catcctcgag aaggccagaa gctgttgtta cattgtgagg ggcgtggcaa tccagtcccc      780
cagcagtacg tgtgggtaaa ggaaggcagt gagccacccc tcaagatgac caagagagt      840 gctctcatct tcccctttt gaataagagt gacagtggca cttatggctg tacagccaca      900
agcaacatgg gcagctatac agcctacttc acccttcaatg tcaacgaccc cagtccagtg      960
ccctcgtcct ccagtaccta ccacggtacc ctggaagttc tgttccaggg gcccatgtcc     1020
cctatactag gttattggaa aattaagggc cttgtgcaac ccactcgact tcttttggaa     1080
tatcttgaag aaaaatatga agagcatttg tatgagcgcg atgaaggtga taatggcga     1140 aacaaaaagt tgaattggg tttggagttt cccaatcttc cttattatat tgatggtgat     1200
gttaaattaa cacagtctat ggccatcata cgttatatag ctgacaagca aaacatgttg     1260
ggtggttgtc caaaagagcg tgcagagatt tcaatgcttg aaggagcggt tttggatatt     1320
agatacggtg tttcgagaat tgcatatagt aaagactttg aaactctcaa agttgatttt     1380
cttagcaagc tacctgaaat gctgaaaatg ttcgaagatc gtttatgtca taaaacatat     1440
```

```
ttaaatggtg atcatgtaac ccatcctgac ttcatgttgt atgacgctct tgatgttgtt    1500
ttatacatgg acccaatgtg cctggatgcg ttcccaaaat tagtttgttt taaaaaacgt    1560
attgaagcta tcccacaaat tgataagtac ttgaaatcca gcaagtatat agcatggcct    1620
ttgcagggct ggcaagccac gtttggtggt ggcgaccatc ctccaaaatc ggattga       1677

<210> SEQ ID NO 66
<211> LENGTH: 558
<212> TYPE: PRT
<213> ORGANISM: Artificial Sequence
<220> FEATURE:
<223> OTHER INFORMATION: Description of the artificial sequence: amino
      acid sequence of mCADM3-GST including signal sequence

<400> SEQUENCE: 66
```

Met Gly Ala Pro Ser Ala Leu Pro Leu Leu Leu Leu Ala Cys Ser
1               5                   10                  15

Trp Ala Pro Gly Gly Ala Asn Leu Ser Gln Asp Asp Ser Gln Pro Trp
            20                  25                  30

Thr Ser Asp Glu Thr Val Val Ala Gly Gly Thr Val Val Leu Lys Cys
        35                  40                  45

Gln Val Lys Asp His Glu Asp Ser Ser Leu Gln Trp Ser Asn Pro Ala
    50                  55                  60

Gln Gln Thr Leu Tyr Phe Gly Glu Lys Arg Ala Leu Arg Asp Asn Arg
65                  70                  75                  80

Ile Gln Leu Val Ser Ser Thr Pro His Glu Leu Ser Ile Ser Ile Ser
                85                  90                  95

Asn Val Ala Leu Ala Asp Glu Gly Glu Tyr Thr Cys Ser Ile Phe Thr
            100                 105                 110

Met Pro Val Arg Thr Ala Lys Ser Leu Val Thr Val Leu Gly Ile Pro
        115                 120                 125

Gln Lys Pro Ile Ile Thr Gly Tyr Lys Ser Ser Leu Arg Glu Lys Glu
    130                 135                 140

Thr Ala Thr Leu Asn Cys Gln Ser Ser Gly Ser Lys Pro Ala Ala Gln
145                 150                 155                 160

Leu Thr Trp Arg Lys Gly Asp Gln Glu Leu His Gly Asp Gln Thr Arg
                165                 170                 175

Ile Gln Glu Asp Pro Asn Gly Lys Thr Phe Thr Val Ser Ser Ser Val
            180                 185                 190

Ser Phe Gln Val Thr Arg Glu Asp Asp Gly Ala Asn Ile Val Cys Ser
        195                 200                 205

Val Asn His Glu Ser Leu Lys Gly Ala Asp Arg Ser Thr Ser Gln Arg
    210                 215                 220

Ile Glu Val Leu Tyr Thr Pro Thr Ala Met Ile Arg Pro Glu Pro Ala
225                 230                 235                 240

His Pro Arg Glu Gly Gln Lys Leu Leu Leu His Cys Glu Gly Arg Gly
                245                 250                 255

Asn Pro Val Pro Gln Gln Tyr Val Trp Val Lys Glu Gly Ser Glu Pro
            260                 265                 270

Pro Leu Lys Met Thr Gln Glu Ser Ala Leu Ile Phe Pro Phe Leu Asn
        275                 280                 285

Lys Ser Asp Ser Gly Thr Tyr Gly Cys Thr Ala Thr Ser Asn Met Gly
    290                 295                 300

Ser Tyr Thr Ala Tyr Phe Thr Leu Asn Val Asn Asp Pro Ser Pro Val
305                 310                 315                 320

```
Pro Ser Ser Ser Ser Thr Tyr His Gly Thr Leu Glu Val Leu Phe Gln
                325                 330                 335

Gly Pro Met Ser Pro Ile Leu Gly Tyr Trp Lys Ile Lys Gly Leu Val
            340                 345                 350

Gln Pro Thr Arg Leu Leu Leu Glu Tyr Leu Glu Glu Lys Tyr Glu Glu
            355                 360                 365

His Leu Tyr Glu Arg Asp Glu Gly Asp Lys Trp Arg Asn Lys Lys Phe
        370                 375                 380

Glu Leu Gly Leu Glu Phe Pro Asn Leu Pro Tyr Tyr Ile Asp Gly Asp
385                 390                 395                 400

Val Lys Leu Thr Gln Ser Met Ala Ile Ile Arg Tyr Ile Ala Asp Lys
                405                 410                 415

His Asn Met Leu Gly Gly Cys Pro Lys Glu Arg Ala Glu Ile Ser Met
            420                 425                 430

Leu Glu Gly Ala Val Leu Asp Ile Arg Tyr Gly Val Ser Arg Ile Ala
        435                 440                 445

Tyr Ser Lys Asp Phe Glu Thr Leu Lys Val Asp Phe Leu Ser Lys Leu
450                 455                 460

Pro Glu Met Leu Lys Met Phe Glu Asp Arg Leu Cys His Lys Thr Tyr
465                 470                 475                 480

Leu Asn Gly Asp His Val Thr His Pro Asp Phe Met Leu Tyr Asp Ala
                485                 490                 495

Leu Asp Val Val Leu Tyr Met Asp Pro Met Cys Leu Asp Ala Phe Pro
            500                 505                 510

Lys Leu Val Cys Phe Lys Lys Arg Ile Glu Ala Ile Pro Gln Ile Asp
        515                 520                 525

Lys Tyr Leu Lys Ser Ser Lys Tyr Ile Ala Trp Pro Leu Gln Gly Trp
530                 535                 540

Gln Ala Thr Phe Gly Gly Gly Asp His Pro Pro Lys Ser Asp
545                 550                 555

<210> SEQ ID NO 67
<211> LENGTH: 372
<212> TYPE: DNA
<213> ORGANISM: Artificial Sequence
<220> FEATURE:
<223> OTHER INFORMATION: Description of the artificial sequence: base
      sequence of VHH of iCADM3_3R1-L8_01 excluding signal sequence

<400> SEQUENCE: 67
caggtgcaac ttgttcagag cggaggtggt ctcgtccaac ctggcggcag cctcagactc      60
tcttgtgctg cttcaggacg aactttcagt aattacgcac gaggatggtt cagacaggca    120
cccgggaagg ggcgcgagtt tgtggcagca atagattatt ctggtggaag caccaactac    180
gctgattctg ccaagggcag gtttaccata agtagagaca actccaagaa tactctttat    240
ttgcaaatga actcactgag agcagaggat acagccgtgt attactgcgc tgcccctgct    300
tcacgtcgtc catcttggga tgctgatgga tatgattact ggggtcaagg tactctggta    360
actgttagtt cc                                                        372

<210> SEQ ID NO 68
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L8_01 excluding signal sequence
```

<400> SEQUENCE: 68

Gln Val Gln Leu Val Gln Ser Gly Gly Gly Leu Val Gln Pro Gly Gly
1               5                   10                  15

Ser Leu Arg Leu Ser Cys Ala Ala Ser Gly Arg Thr Phe Ser Asn Tyr
            20                  25                  30

Ala Arg Gly Trp Phe Arg Gln Ala Pro Gly Lys Gly Arg Glu Phe Val
        35                  40                  45

Ala Ala Ile Asp Tyr Ser Gly Ser Thr Asn Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Pro Ala Ser Arg Arg Pro Ser Trp Asp Ala Asp Gly Tyr Asp
            100                 105                 110

Tyr Trp Gly Gln Gly Thr Leu Val Thr Val Ser Ser
        115                 120

<210> SEQ ID NO 69
<211> LENGTH: 372
<212> TYPE: DNA
<213> ORGANISM: Artificial Sequence
<220> FEATURE:
<223> OTHER INFORMATION: Description of the artificial sequence: base
      sequence of VHH of iCADM3_3R1-L8_02 excluding signal sequence

<400> SEQUENCE: 69
caagtccaac ttgtccaaag tggcggtggg ttggtccagc ccggcggttc tttgaggttg      60
tcatgcgccg cctccggcag gaccttctca aattacgccc gtggttggtt ccgtcaggca     120
cctgggaaag aacgggagtt cgtagctgca atagattaca cgcgtgggtc aactaattac     180
gctgattctg ccaaaggaag attcaccatc tcaagacaca attctaagaa cacactttac     240
cttcagatga actctctgag agctgaagac accgctgtgt attactgtgc tgcacccgca     300
tcacggcgac cctcatggga tgctgatggg tacgactatt ggggggcaagg tacacttgtt     360 actgtatcta gt                                                         372

<210> SEQ ID NO 70
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L8_02 excluding signal sequence

<400> SEQUENCE: 70

Gln Val Gln Leu Val Gln Ser Gly Gly Gly Leu Val Gln Pro Gly Gly
1               5                   10                  15

Ser Leu Arg Leu Ser Cys Ala Ala Ser Gly Arg Thr Phe Ser Asn Tyr
            20                  25                  30

Ala Arg Gly Trp Phe Arg Gln Ala Pro Gly Lys Glu Arg Glu Phe Val
        35                  40                  45

Ala Ala Ile Asp Tyr Ser Gly Ser Thr Asn Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Pro Ala Ser Arg Arg Pro Ser Trp Asp Ala Asp Gly Tyr Asp
            100                 105                 110

Tyr Trp Gly Gln Gly Thr Leu Val Thr Val Ser Ser
        115                 120

<210> SEQ ID NO 71
<211> LENGTH: 372
<212> TYPE: DNA
<213> ORGANISM: Artificial Sequence
<220> FEATURE:
<223> OTHER INFORMATION: Description of the artificial sequence: base
      sequence of VHH of iCADM3_3R1-L8_03 excluding signal sequence

<400> SEQUENCE: 71
caagttcaac ttgtagagtc tggaggcggt ctggttcaac tggtgggtc cctccgcctt    60 tcctgcgctg ctagcgggag aacctttagt aattatgcac gtggctggtt taggcaggca   120
ccagggaaag gcgtgagtt cgtcgcagca atagattata gcggcggatc taccaactac   180
gccgattcag ctaagggacg atttacaatt tcacgagaca attccaagaa taccgtttac   240
ctgcaaatga atagtctccg ggccgaagat accgctgtgt attattgtgc agcccctgct   300
tcccgccgtc ccagttggga cgcagacggg tatgactatt ggggccaggg aacttggta   360 accgtttcat ca                                                       372

<210> SEQ ID NO 72
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L8_03 excluding signal sequence

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Asn Tyr
            20                  25                  30

Ala Arg Gly Trp Phe Arg Gln Ala Pro Gly Lys Gly Arg Glu Phe Val
        35                  40                  45

Ala Ala Ile Asp Tyr Ser Gly Gly Ser Thr Asn Tyr Ala Asp Ser Ala
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Pro Ala Ser Arg Arg Pro Ser Trp Asp Ala Asp Gly Tyr Asp
            100                 105                 110

Tyr Trp Gly Gln Gly Thr Leu Val Thr Val Ser Ser
        115                 120

<210> SEQ ID NO 73
<211> LENGTH: 372
<212> TYPE: DNA
<213> ORGANISM: Artificial Sequence
<220> FEATURE:
<223> OTHER INFORMATION: Description of the artificial sequence: base
      sequence of VHH of iCADM3_3R1-L8_04 excluding signal sequence

<400> SEQUENCE: 73
caggttcagt tggttgagag cggtggtggt ctggtacagc ccggcggtag cttgcgactt    60

```
tcctgtgcag ccagtggtcg gacattttct aactatgccc gaggctggtt tcgccaggcc    120
cccggaaagg aacgtgagtt cgttgcagct atagattact ccggaggatc aaccaattat    180
gccgattctg caaaggacg ctttaccatc tcccgtgaca atagtaaaaa taccgtgtac     240
ttgcaaatga acagcttgag ggcagaggat accgctgttt attactgcgc cgctcccgct    300
agtcgcaggc catcctggga cgcagatggg tatgattact ggggccaagg caccctcgta    360
actgtttcct cc                                                        372
```

<210> SEQ ID NO 74
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L8_04 excluding signal sequence

<400> SEQUENCE: 74

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Asn Tyr
            20                  25                  30

Ala Arg Gly Trp Phe Arg Gln Ala Pro Gly Lys Glu Arg Glu Phe Val
        35                  40                  45

Ala Ala Ile Asp Tyr Ser Gly Gly Ser Thr Asn Tyr Ala Asp Ser Ala
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Pro Ala Ser Arg Arg Pro Ser Trp Asp Ala Asp Gly Tyr Asp
            100                 105                 110

Tyr Trp Gly Gln Gly Thr Leu Val Thr Val Ser Ser
        115                 120

<210> SEQ ID NO 75
<211> LENGTH: 360
<212> TYPE: DNA
<213> ORGANISM: Artificial Sequence
<220> FEATURE:
<223> OTHER INFORMATION: Description of the artificial sequence: base
      sequence of VHH of iCADM3_3R1-L11_01 excluding signal sequence

<400> SEQUENCE: 75

```
gaggtccaac ttgtagagtc tggaggggga ttgattcaac ccggcgggag tcttagactt    60
agctgtgccg catcagggag cacagtgtca ttcaatgcta tggggtggta tagacaagca    120
cctgggaaag gtcttggtct ggtagccgtc atcacttctg gtgggtacac caattatgcc    180
gacagcgtca aaggccgttt taccattagt cgtgacaaca gcaagaatac cctctttctg    240
caaatgaaca gccttagagc tgaagacaca gccgtatact attgtaatgc cgaggggggta   300 tattcagact atgttattat gaattattgg ggtcaaggca ctctcgttac cgtaagttca    360
```

<210> SEQ ID NO 76
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11_01 excluding signal sequence

<400> SEQUENCE: 76

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Ser Thr Val Ser Phe Asn
            20                  25                  30

Ala Met Gly Trp Tyr Arg Gln Ala Pro Gly Lys Gly Leu Gly Leu Val
        35                  40                  45

Ala Val Ile Thr Ser Gly Gly Tyr Thr Asn Tyr Ala Asp Ser Val Lys
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Asn
                85                  90                  95

Ala Glu Gly Val Tyr Ser Asp Tyr Val Ile Met Asn Tyr Trp Gly Gln
            100                 105                 110

Gly Thr Leu Val Thr Val Ser Ser
        115                 120
```

<210> SEQ ID NO 77
<211> LENGTH: 360
<212> TYPE: DNA
<213> ORGANISM: Artificial Sequence
<220> FEATURE:
<223> OTHER INFORMATION: Description of the artificial sequence: base
      sequence of VHH of iCADM3_3R1-L11_02 excluding signal sequence

<400> SEQUENCE: 77

```
gaggtacagt tggtggagag tggtggcgga ttgatccaac caggggggag cctgcgactc      60
tcctgtgctg ccagcggatc tacagtctct tttaatgcca tgggttggta tcgacaggct     120
ccaggtaaag acgggtttt ggtcgcagta attactagcg gaggatacac aaactacgca      180
gactctgtca agggccggtt tacaatatct cgggataact ccaagaacac cgtctatctt     240
caaatgaata gtttgcgggc cgaagatact gctgtctatt actgcaatgc tgaaggtgtg     300
tattccgatt atgttataat gaactattgg ggccagggca ccctggtcac agttagcagc     360
```

<210> SEQ ID NO 78
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11_02 excluding signal
      sequence

<400> SEQUENCE: 78

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Ser Thr Val Ser Phe Asn
            20                  25                  30

Ala Met Gly Trp Tyr Arg Gln Ala Pro Gly Lys Gly Arg Val Leu Val
        35                  40                  45

Ala Val Ile Thr Ser Gly Gly Tyr Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Asn
```

```
                  85                  90                  95
Ala Glu Gly Val Tyr Ser Asp Tyr Val Ile Met Asn Tyr Trp Gly Gln
            100                 105                 110

Gly Thr Leu Val Thr Val Ser Ser
        115                 120
```

<210> SEQ ID NO 79
<211> LENGTH: 360
<212> TYPE: DNA
<213> ORGANISM: Artificial Sequence
<220> FEATURE:
<223> OTHER INFORMATION: Description of the artificial sequence: base
      sequence of VHH of iCADM3_3R1-L11_03 excluding signal sequence

<400> SEQUENCE: 79

```
gaagttcagt tggtagaatc cggggggaggt ttgattcaac ccggtgggag ccttagattg    60
agctgtgcag ccagcggctc aaccgtatct tttaacgcta tgggttggta tcggcaagcc   120
ccaggcaaac aaaggggttt ggtcagcgtc attaccagtg gtggttacac aaactacgca   180
gattcagtta agggccgctt cacaatctcc cgcgacaatt ccaaaaacac tgtgtatttg   240
caaatgaata gcttgagggc tgaagacaca gcagtatatt actgcaatgc tgagggtgta   300
tattctgact acgtaatcat gaactactgg ggacaaggca ctctggtgac cgtgagtagt   360
```

<210> SEQ ID NO 80
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11_03 excluding signal
      sequence

<400> SEQUENCE: 80

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Ser Thr Val Ser Phe Asn
            20                  25                  30

Ala Met Gly Trp Tyr Arg Gln Ala Pro Gly Lys Gln Arg Gly Leu Val
        35                  40                  45

Ser Val Ile Thr Ser Gly Gly Tyr Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Asn
                85                  90                  95

Ala Glu Gly Val Tyr Ser Asp Tyr Val Ile Met Asn Tyr Trp Gly Gln
            100                 105                 110

Gly Thr Leu Val Thr Val Ser Ser
        115                 120
```

<210> SEQ ID NO 81
<211> LENGTH: 360
<212> TYPE: DNA
<213> ORGANISM: Artificial Sequence
<220> FEATURE:
<223> OTHER INFORMATION: Description of the artificial sequence: base
      sequence of VHH of iCADM3_3R1-L11_04 excluding signal sequence

<400> SEQUENCE: 81

```
gaagtccaac tggtagagag cggtgggggc cttattcagg caggaggctc tcttcgtctt    60
```

```
tcttgcgccg ccagcggcag tatcgttagc tttaatgcca tgggttggta tcgacaggcc    120
cctgggaaac aaaggggg tt ggtcgcagta ataaccagtg agggtacac caattatgca    180 gattctgtca agggaagatt caccatatca agggacaaca gtaagaacac attgtttctt    240
caaatgaata gtttgcgtgc agaagacaca gcagtgtact attgtaacgc tgagggcgtg    300
tactccgact atgttattat gaattactgg ggtcaaggta cactggtcac agttagcagc    360
```

<210> SEQ ID NO 82
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11_04 excluding signal
      sequence

<400> SEQUENCE: 82

```
Glu Val Gln Leu Val Glu Ser Gly Gly Gly Leu Ile Gln Ala Gly Gly
1               5                   10                  15

Ser Leu Arg Leu Ser Cys Ala Ala Ser Gly Ser Ile Val Ser Phe Asn
            20                  25                  30

Ala Met Gly Trp Tyr Arg Gln Ala Pro Gly Lys Gln Arg Gly Leu Val
        35                  40                  45

Ala Val Ile Thr Ser Gly Gly Tyr Thr Asn Tyr Ala Asp Ser Val Lys
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Asn
                85                  90                  95

Ala Glu Gly Val Tyr Ser Asp Tyr Val Ile Met Asn Tyr Trp Gly Gln
            100                 105                 110

Gly Thr Leu Val Thr Val Ser Ser
        115                 120
```

<210> SEQ ID NO 83
<211> LENGTH: 360
<212> TYPE: DNA
<213> ORGANISM: Artificial Sequence
<220> FEATURE:
<223> OTHER INFORMATION: Description of the artificial sequence: base
      sequence of VHH of iCADM3_3R1-L11_05 excluding signal sequence

<400> SEQUENCE: 83

```
gaggttcagc tcgtagaaag tggggggggc ctgatacagc caggcgggag ccttagattg    60
agttgtgccg catccgggtc catattttca tttaacgcca tgggttggta cagacaagca    120
ccaggcaaag ggcgcgtatt ggtagctgtt atcaccagtg gtgggtacac aaactacgcc    180
gatagtgtta aagggcgatt tacaatatcc agagacaatt ccaaaaatac cgtttacctc    240
caaatgaata gccttagagc tgaggacact gctgtatact attgcaacgc tgagggcgta    300
tactccgatt acgtgataat gaactactgg ggccaaggca ctctggtcac cgtgtcatcc    360
```

<210> SEQ ID NO 84
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11_05 excluding signal
      sequence

<400> SEQUENCE: 84

Glu Val Gln Leu Val Glu Ser Gly Gly Gly Leu Ile Gln Pro Gly Gly
1               5                   10                  15

Ser Leu Arg Leu Ser Cys Ala Ala Ser Gly Ser Ile Phe Ser Phe Asn
            20                  25                  30

Ala Met Gly Trp Tyr Arg Gln Ala Pro Gly Lys Gly Arg Val Leu Val
        35                  40                  45

Ala Val Ile Thr Ser Gly Gly Tyr Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Asn
                85                  90                  95

Ala Glu Gly Val Tyr Ser Asp Tyr Val Ile Met Asn Tyr Trp Gly Gln
            100                 105                 110

Gly Thr Leu Val Thr Val Ser Ser
        115                 120

<210> SEQ ID NO 85
<211> LENGTH: 360
<212> TYPE: DNA
<213> ORGANISM: Artificial Sequence
<220> FEATURE:
<223> OTHER INFORMATION: Description of the artificial sequence: base
      sequence of VHH of iCADM3_3R1-L11_06 excluding signal sequence

<400> SEQUENCE: 85
caggttcaac tcgttgaatc tggtggaggg ttggtccagg caggggggcag tttgagactg      60 agctgcgccg catccggctc tatttttctca tttaacgcca tggggtggta tcgacaggca     120
ccaggtaagc aacgcggtct cgttgcagtg ataaccagtg ggggctatac aaactatgct     180
gatagtgtta aaggcaggtt caccatcagt cgggacaaca gcaagaacac cgtcttcttg     240
caaatgaatt ctcttagagc tgaagatact gctgtatatt attgcaacgc cgagggtgtg     300
tattccgatt acgtgataat gaactactgg gggcagggga cacttgtgac cgttagttca     360

<210> SEQ ID NO 86
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11_06 excluding signal
      sequence

<400> SEQUENCE: 86

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Asn
            20                  25                  30

Ala Met Gly Trp Tyr Arg Gln Ala Pro Gly Lys Gln Arg Gly Leu Val
        35                  40                  45

Ala Val Ile Thr Ser Gly Gly Tyr Thr Asn Tyr Ala Asp Ser Val Lys
    50                  55                  60

Gly Arg Phe Thr Ile Ser Arg Asp Asn Ser Lys Asn Thr Val Phe Leu
65                  70                  75                  80

Gln Met Asn Ser Leu Arg Ala Glu Asp Thr Ala Val Tyr Tyr Cys Asn
                85                  90                  95

Ala Glu Gly Val Tyr Ser Asp Tyr Val Ile Met Asn Tyr Trp Gly Gln
            100                 105                 110

Gly Thr Leu Val Thr Val Ser Ser
        115                 120

<210> SEQ ID NO 87
<211> LENGTH: 375
<212> TYPE: DNA
<213> ORGANISM: Artificial Sequence
<220> FEATURE:
<223> OTHER INFORMATION: Description of the artificial sequence: base
      sequence of VH of CADM 3219 excluding signal sequence

<400> SEQUENCE: 87
caggtgcagc tggtgcagtc tggggctgag gtgaagaagc ctggggcctc agtgaaggtc      60
tcctgcaagg cctctggata cagcttcacc ggctactata tacactgggt gcgacaggcc     120
cctggacaag gacttgagtg gatgggacgg atcaacccta acagtggtgg cacaacttat     180
gcaccgaagt tcagggcag gttcaccatg accagagaca cgtccacgac cacagtgtac      240
ttggaactga gcggcctgag atctgaggac acggccgtgt attactgtgc gagagttctg     300
gaacgacagg gcaggccctt cgaggctgat gcttttgata tctggggcca agggacaatg     360
gtcaccgtct cttca                                                     375

<210> SEQ ID NO 88
<211> LENGTH: 125
<212> TYPE: PRT
<213> ORGANISM: Artificial Sequence
<220> FEATURE:
<223> OTHER INFORMATION: Description of the artificial sequence: amino
      acid sequence of VH of CADM 3219 excluding signal sequence

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Met
        35                  40                  45

Gly Arg Ile Asn Pro Asn Ser Gly Gly Thr Thr Tyr Ala Pro Lys Phe
    50                  55                  60

Gln Gly Arg Phe Thr Met Thr Arg Asp Thr Ser Thr Thr Thr Val Tyr
65                  70                  75                  80

Leu Glu Leu Ser Gly Leu Arg Ser Glu Asp Thr Ala Val Tyr Tyr Cys
                85                  90                  95

Ala Arg Val Leu Glu Arg Gln Gly Arg Pro Phe Glu Ala Asp Ala Phe
            100                 105                 110

Asp Ile Trp Gly Gln Gly Thr Met Val Thr Val Ser Ser
        115                 120                 125

<210> SEQ ID NO 89
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3219

<400> SEQUENCE: 89

Gly Tyr Tyr Ile His

<210> SEQ ID NO 90
<211> LENGTH: 17
<212> TYPE: PRT
<213> ORGANISM: Artificial Sequence
<220> FEATURE:
<223> OTHER INFORMATION: Description of the artificial sequence: amino acid sequence of HCDR2 of CADM3219

<400> SEQUENCE: 90

Arg Ile Asn Pro Asn Ser Gly Gly Thr Thr Tyr Ala Pro Lys Phe Gln
1               5                   10                  15
Gly

<210> SEQ ID NO 91
<211> LENGTH: 16
<212> TYPE: PRT
<213> ORGANISM: Artificial Sequence
<220> FEATURE:
<223> OTHER INFORMATION: Description of the artificial sequence: amino acid sequence of HCDR3 of CADM3219

<400> SEQUENCE: 91

Val Leu Glu Arg Gln Gly Arg Pro Phe Glu Ala Asp Ala Phe Asp Ile
1               5                   10                  15

<210> SEQ ID NO 92
<211> LENGTH: 327
<212> TYPE: DNA
<213> ORGANISM: Artificial Sequence
<220> FEATURE:
<223> OTHER INFORMATION: Description of the artificial sequence: base sequence of VL of CADM3219 excluding signal sequence

<400> SEQUENCE: 92
gaaatagtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcc gtggacgttc     300
ggccaaggga ccaaggtgga aataaaa                                          327

<210> SEQ ID NO 93
<211> LENGTH: 109
<212> TYPE: PRT
<213> ORGANISM: Artificial Sequence
<220> FEATURE:
<223> OTHER INFORMATION: Description of the artificial sequence: amino acid sequence of VL of CADM3219 excluding signal sequence

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu

<210> SEQ ID NO 94
<211> LENGTH: 12
<212> TYPE: PRT
<213> ORGANISM: Artificial Sequence
<220> FEATURE:
<223> OTHER INFORMATION: Description of the artificial sequence: amino acid sequence of LCDR1 of CADM3219

<400> SEQUENCE: 94

Arg Ala Ser Gln Ser Val Ser Ser Ser Tyr Leu Ala
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Description of the artificial sequence: amino acid sequence of LCDR2 of CADM3219

<400> SEQUENCE: 95

Gly Ala Ser Ser Arg Ala Thr
1               5

<210> SEQ ID NO 96
<211> LENGTH: 10
<212> TYPE: PRT
<213> ORGANISM: Artificial Sequence
<220> FEATURE:
<223> OTHER INFORMATION: Description of the artificial sequence: amino acid sequence of LCDR3 of CADM3219

<400> SEQUENCE: 96

Gln Gln Tyr Gly Ser Ser Pro Pro Trp Thr
1               5                   10

<210> SEQ ID NO 97
<211> LENGTH: 378
<212> TYPE: DNA
<213> ORGANISM: Artificial Sequence
<220> FEATURE:
<223> OTHER INFORMATION: Description of the artificial sequence: base sequence of VH of CADM3301 excluding signal sequence

<400> SEQUENCE: 97
cagatgcagc tggtgcaatc tggggctgag gtgaagaagc ctgggtcctc ggtgaaggtc      60
tcctgcaagg cttctggagg caccttcaac aactatgcta tcagctgggt gcgacaggcc     120
cctggacaag gcttgagtg gatgggaggg aatattcctc tttctggaac accaaagtac      180
gcacagaagt tcagggcag aatcacgatg accgcggaca atccacgag cacagagtac       240 atggaactga gcagcctgac atctgaggac acggccgtat actactgtgc gagagatacc    300
ccgagtggct acaattcccc ctactactat aaaggaatgg acgtctgggg ccaagggacc     360
atggtcaccg tctcttca                                                  378

<210> SEQ ID NO 98
<211> LENGTH: 126
<212> TYPE: PRT

```
<213> ORGANISM: Artificial Sequence
<220> FEATURE:
<223> OTHER INFORMATION: Description of the artificial sequence: amino
      acid sequence of VH of CADM3301 excluding signal sequence

<400> SEQUENCE: 98

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Ile Ser Trp Val Arg Gln Ala Pro Gly Gln Gly Leu Glu Trp Met
        35                  40                  45

Gly Gly Asn Ile Pro Leu Ser Gly Thr Pro Lys Tyr Ala Gln Lys Phe
    50                  55                  60

Gln Gly Arg Ile Thr Met Thr Ala Asp Lys Ser Thr Ser Thr Glu Tyr
65                  70                  75                  80

Met Glu Leu Ser Ser Leu Thr Ser Glu Asp Thr Ala Val Tyr Tyr Cys
                85                  90                  95

Ala Arg Asp Thr Pro Ser Gly Tyr Asn Ser Pro Tyr Tyr Lys Gly
            100                 105                 110

Met Asp Val Trp Gly Gln Gly Thr Met Val Thr Val Ser Ser
        115                 120                 125

<210> SEQ ID NO 99
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3301

<400> SEQUENCE: 99

Asn Tyr Ala Ile Ser
1               5

<210> SEQ ID NO 100
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CADM3301

<400> SEQUENCE: 100

Gly Asn Ile Pro Leu Ser Gly Thr Pro Lys Tyr Ala Gln Lys Phe Gln
1               5                   10                  15

Gly

<210> SEQ ID NO 101
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR3 of CADM3301

<400> SEQUENCE: 101

Asp Thr Pro Ser Gly Tyr Asn Ser Pro Tyr Tyr Lys Gly Met Asp
1               5                   10                  15

Val

<210> SEQ ID NO 102
```

```
<211> LENGTH: 378
<212> TYPE: DNA
<213> ORGANISM: Artificial Sequence
<220> FEATURE:
<223> OTHER INFORMATION: Description of the artificial sequence: base
      sequence of VH of CADM3309 excluding signal sequence

<400> SEQUENCE: 102
gaggtgcagc tggtgcagtc tggggctgag atgaagaagc ctgggtcctc ggtgaagctc    60
tcctgcaaat tttctggagg cgacttcagg agttatccta tcagctgggt gcgacaggcc   120
cctggacaag gcttgagtg gatgggcggc atcatcccga ttttagtcg agtaaactat    180 gcacagagat tcctgggcag aatcacgatt accgcggacg aatccacgag cacagcctac   240
atggaattga agcctgac gtctgacgac acggccgtct attactgtgc gacagatacc    300
ccgagtggct acaactcccc ctactactat aaaggaatgg acgtctgggg ccaggggacc   360
ctggtcaccg tctcctca                                                 378

<210> SEQ ID NO 103
<211> LENGTH: 126
<212> TYPE: PRT
<213> ORGANISM: Artificial Sequence
<220> FEATURE:
<223> OTHER INFORMATION: Description of the artificial sequence: amino
      acid sequence of VH of CADM3309 excluding signal sequence

<400> SEQUENCE: 103

Glu Val Gln Leu Val Gln Ser Gly Ala Glu Met Lys Lys Pro Gly Ser
1               5                   10                  15

Ser Val Lys Leu Ser Cys Lys Phe Ser Gly Gly Asp Phe Arg Ser Tyr
            20                  25                  30

Pro Ile Ser Trp Val Arg Gln Ala Pro Gly Gln Gly Leu Glu Trp Met
        35                  40                  45

Gly Gly Ile Ile Pro Ile Phe Ser Arg Val Asn Tyr Ala Gln Arg Phe
    50                  55                  60

Leu Gly Arg Ile Thr Ile Thr Ala Asp Glu Ser Thr Ser Thr Ala Tyr
65                  70                  75                  80

Met Glu Leu Arg Ser Leu Thr Ser Asp Asp Thr Ala Val Tyr Tyr Cys
                85                  90                  95

Ala Thr Asp Thr Pro Ser Gly Tyr Asn Ser Pro Tyr Tyr Tyr Lys Gly
            100                 105                 110

Met Asp Val Trp Gly Gln Gly Thr Leu Val Thr Val Ser Ser
        115                 120                 125

<210> SEQ ID NO 104
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3309

<400> SEQUENCE: 104

Ser Tyr Pro Ile Ser
1               5

<210> SEQ ID NO 105
<211> LENGTH: 17
<212> TYPE: PRT
<213> ORGANISM: Artificial Sequence
<220> FEATURE:
<223> OTHER INFORMATION: Description of the artificial sequence: amino
``` acid sequence of HCDR2 of CADM3309

<400> SEQUENCE: 105

Gly Ile Ile Pro Ile Phe Ser Arg Val Asn Tyr Ala Gln Arg Phe Leu
1               5                   10                  15

Gly

<210> SEQ ID NO 106
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR3 of CADM3309

<400> SEQUENCE: 106

Asp Thr Pro Ser Gly Tyr Asn Ser Pro Tyr Tyr Lys Gly Met Asp
1               5                   10                  15

Val

<210> SEQ ID NO 107
<211> LENGTH: 351
<212> TYPE: DNA
<213> ORGANISM: Artificial Sequence
<220> FEATURE:
<223> OTHER INFORMATION: Description of the artificial sequence: base
      sequence of VH of CADM3312 excluding signal sequence

<400> SEQUENCE: 107
cagctgcagc tgcaggagtc gggcccagga ctggtgaagc cttcggagac cctgtccctc      60
acctgcagtg tctctggtgg ctccatcaga ggacactatt ggagttggat ccggcagccc    120
ccagggaagg gactggagtg gatgggttac atcaaccaca ttgggagcgc cgcctacaac    180
ccctccctca agagtcgagt caccatatca gtagacacgt ccaagaacca gttctccctg    240
aagctgagct ctgtgaccgc cgcagacacg gccgtgtatt actgtgcgag aatgggccca    300
tggtgggagc ttgactactg gggccaggga accctggtca ccgtctcctc a             351

<210> SEQ ID NO 108
<211> LENGTH: 117
<212> TYPE: PRT
<213> ORGANISM: Artificial Sequence
<220> FEATURE:
<223> OTHER INFORMATION: Description of the artificial sequence: amino
      acid sequence of VH of CADM3312 excluding signal sequence

<400> SEQUENCE: 108

Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Arg Gly His
            20                  25                  30

Tyr Trp Ser Trp Ile Arg Gln Pro Pro Gly Lys Gly Leu Glu Trp Met
        35                  40                  45

Gly Tyr Ile Asn His Ile Gly Ser Ala Ala Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Gly Pro Trp Trp Glu Leu Asp Tyr Trp Gly Gln Gly Thr Leu
            100                 105                 110

-continued

Val Thr Val Ser Ser
        115

<210> SEQ ID NO 109
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3312

<400> SEQUENCE: 109

Gly His Tyr Trp Ser
1               5

<210> SEQ ID NO 110
<211> LENGTH: 16
<212> TYPE: PRT
<213> ORGANISM: Artificial Sequence
<220> FEATURE:
<223> OTHER INFORMATION: Description of the artificial sequence: amino
      acid sequence of HCDR2 of CADM3312

<400> SEQUENCE: 110

Tyr Ile Asn His Ile Gly Ser Ala Ala Tyr Asn Pro Ser Leu Lys Ser
1               5                   10                  15

<210> SEQ ID NO 111
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CADM3312

<400> SEQUENCE: 111

Met Gly Pro Trp Trp Glu Leu Asp Tyr
1               5

<210> SEQ ID NO 112
<211> LENGTH: 354
<212> TYPE: DNA
<213> ORGANISM: Artificial Sequence
<220> FEATURE:
<223> OTHER INFORMATION: Description of the artificial sequence: base
      sequence of VH of CADM3314 excluding signal sequence excluding
      signal sequence

<400> SEQUENCE: 112
caggtgcagc tggtggagtc tgggggaggc gtggtccagc ctggggggtc cctgagactt      60
tcctgtgcag cgtctggatt cagtttcaat aatcatggca tgcactgggt ccgccaggct     120
ccaggcaagg ggctggagtg ggtgacattt atccggtttg atggaagtag taaatactat     180
gcagactccg tgaagggccg attcaccatc tccagagaca attccaagaa caccgtgtat     240
ctggaaatga acagcctgag agcagaggac acgggtgtgt attactgtgt gaatacgcca     300 agggggttggt ccttcgatat ctggggccgt ggcaccctgg tcactgtctc ctca           354

<210> SEQ ID NO 113
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CADM3314 excluding signal sequence
      excluding signal sequence

<400> SEQUENCE: 113

Gln Val Gln Leu Val Glu Ser Gly Gly Val Val Gln Pro Gly Gly
1               5                   10                  15

Ser Leu Arg Leu Ser Cys Ala Ala Ser Gly Phe Ser Phe Asn Asn His
            20                  25                  30

Gly Met His Trp Val Arg Gln Ala Pro Gly Lys Gly Leu Glu Trp Val
        35                  40                  45

Thr Phe Ile Arg Phe Asp Gly Ser Ser Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Glu Met Asn Ser Leu Arg Ala Glu Asp Thr Gly Val Tyr Tyr Cys
                85                  90                  95

Val Asn Thr Pro Arg Gly Trp Ser Phe Asp Ile Trp Gly Arg Gly Thr
            100                 105                 110

Leu Val Thr Val Ser Ser
        115

<210> SEQ ID NO 114
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3314

<400> SEQUENCE: 114

Asn His Gly Met His
1               5

<210> SEQ ID NO 115
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CADM3314

<400> SEQUENCE: 115

Phe Ile Arg Phe Asp Gly Ser Ser Lys Tyr Tyr Ala Asp Ser Val Lys
1               5                   10                  15

Gly

<210> SEQ ID NO 116
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CADM3314

<400> SEQUENCE: 116

Thr Pro Arg Gly Trp Ser Phe Asp Ile
1               5

<210> SEQ ID NO 117
<211> LENGTH: 384
<212> TYPE: DNA
<213> ORGANISM: Artificial Sequence
<220> FEATURE:
<223> OTHER INFORMATION: Description of the artificial sequence: base
      sequence of VH of CADM3316 excluding signal sequence

<400> SEQUENCE: 117

```
gaggtgcagc tggtggagac tggggggagcc ttggtacagc ctggggggtc cctaagactc    60
tcctgtgcag cctctggatt cacctttagc agctattcca tgaactgggt ccgccaggct   120
ccagggaagg gctggagtg gctctcaggt attagtggtg gtgcttttag cacacactac   180
gcagactccg tgaagggccg gttcaccatc tccagagaca attccaagaa cacgctgtat   240
ctgcaaatga acagcctgag agctgaggac acggctgtgt attactgtgc gagagtaggt   300
cggttgagtg ggagctacaa cagatactac tactactacg gtatggacgt ctggggccaa   360
gggaccctgg tcaccgtctc ctca                                          384
```

<210> SEQ ID NO 118
<211> LENGTH: 128
<212> TYPE: PRT
<213> ORGANISM: Artificial Sequence
<220> FEATURE:
<223> OTHER INFORMATION: Description of the artificial sequence: amino acid sequence of VH of CADM3316 excluding signal sequence

<400> SEQUENCE: 118

```
Glu Val Gln Leu Val Glu Thr Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Leu
        35                  40                  45

Ser Gly Ile Ser Gly Gly Ala Phe Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Arg Leu Ser Gly Ser Tyr Asn Arg Tyr Tyr Tyr Tyr
            100                 105                 110

Tyr Gly Met Asp Val Trp Gly Gln Gly Thr Leu Val Thr Val Ser Ser
        115                 120                 125
```

<210> SEQ ID NO 119
<211> LENGTH: 5
<212> TYPE: PRT
<213> ORGANISM: Artificial Sequence
<220> FEATURE:
<223> OTHER INFORMATION: Description of the artificial sequence: amino acid sequence of HCDR1 of CADM3316

<400> SEQUENCE: 119

```
Ser Tyr Ser Met Asn
1               5
```

<210> SEQ ID NO 120
<211> LENGTH: 17
<212> TYPE: PRT
<213> ORGANISM: Artificial Sequence
<220> FEATURE:
<223> OTHER INFORMATION: Description of the artificial sequence: amino acid sequence of HCDR2 of CADM3316

<400> SEQUENCE: 120

```
Gly Ile Ser Gly Gly Ala Phe Ser Thr His Tyr Ala Asp Ser Val Lys
1               5                   10                  15
```

Gly

<210> SEQ ID NO 121
<211> LENGTH: 19
<212> TYPE: PRT
<213> ORGANISM: Artificial Sequence
<220> FEATURE:
<223> OTHER INFORMATION: Description of the artificial sequence: amino
      acid sequence of HCDR3 of CADM3316

<400> SEQUENCE: 121

Val Gly Arg Leu Ser Gly Ser Tyr Asn Arg Tyr Tyr Tyr Tyr Gly
1               5                   10                  15

Met Asp Val

<210> SEQ ID NO 122
<211> LENGTH: 357
<212> TYPE: DNA
<213> ORGANISM: Artificial Sequence
<220> FEATURE:
<223> OTHER INFORMATION: Description of the artificial sequence: base
      sequence of VH of CADM3349 excluding signal sequence

<400> SEQUENCE: 122
caggtgcagc tacagcagtg gggcggaggt ctgttgacgc cttcggagac cctgtccctc      60
agctgcgatg tctctggtgg ggccttcact aattaccact ggacctggat ccgccagccc     120
ccaggaaagg gactggaatg gattggagaa atctttcata ctgggaccac caactacaac     180
ccgtccctcc agggtcgagt cgccatgtct attgacacca ccaagcggca gttcttcctg     240
aggctgacgt ctctgaccgc cgcggacacg gctgtatatt actgtgcgag agttggtaaa     300
tatggctggt acgtaggtga cttttggggc cagggaacca cggtcaccgt ctcctca       357

<210> SEQ ID NO 123
<211> LENGTH: 119
<212> TYPE: PRT
<213> ORGANISM: Artificial Sequence
<220> FEATURE:
<223> OTHER INFORMATION: Description of the artificial sequence: amino
      acid sequence of VH of CADM3349 excluding signal sequence

<400> SEQUENCE: 123

Gln Val Gln Leu Gln Gln Trp Gly Gly Gly Leu Leu Thr Pro Ser Glu
1               5                   10                  15

Thr Leu Ser Leu Ser Cys Asp Val Ser Gly Gly Ala Phe Thr Asn Tyr
            20                  25                  30

His Trp Thr Trp Ile Arg Gln Pro Pro Gly Lys Gly Leu Glu Trp Ile
        35                  40                  45

Gly Glu Ile Phe His Thr Gly Thr Thr Asn Tyr Asn Pro Ser Leu Gln
    50                  55                  60

Gly Arg Val Ala Met Ser Ile Asp Thr Thr Lys Arg Gln Phe Phe Leu
65                  70                  75                  80

Arg Leu Thr Ser Leu Thr Ala Ala Asp Thr Ala Val Tyr Tyr Cys Ala
                85                  90                  95

Arg Val Gly Lys Tyr Gly Trp Tyr Val Gly Asp Phe Trp Gly Gln Gly
            100                 105                 110

Thr Thr Val Thr Val Ser Ser
        115

<210> SEQ ID NO 124

```
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3349

<400> SEQUENCE: 124

Asn Tyr His Trp Thr
1               5

<210> SEQ ID NO 125
<211> LENGTH: 16
<212> TYPE: PRT
<213> ORGANISM: Artificial Sequence
<220> FEATURE:
<223> OTHER INFORMATION: Description of the artificial sequence: amino
      acid sequence of HCDR2 of CADM3349

<400> SEQUENCE: 125

Glu Ile Phe His Thr Gly Thr Thr Asn Tyr Asn Pro Ser Leu Gln Gly
1               5                   10                  15

<210> SEQ ID NO 126
<211> LENGTH: 11
<212> TYPE: PRT
<213> ORGANISM: Artificial Sequence
<220> FEATURE:
<223> OTHER INFORMATION: Description of the artificial sequence: amino
      acid sequence of HCDR3 of CADM3349

<400> SEQUENCE: 126

Val Gly Lys Tyr Gly Trp Tyr Val Gly Asp Phe
1               5                   10

<210> SEQ ID NO 127
<211> LENGTH: 372
<212> TYPE: DNA
<213> ORGANISM: Artificial Sequence
<220> FEATURE:
<223> OTHER INFORMATION: Description of the artificial sequence: base
      sequence of VH of CADM3351 excluding signal sequence

<400> SEQUENCE: 127
gaagtgcagc tgttgcagtc tgggggaggc ttggtccagc ctggagggtc cctgagactc      60
tcctgtgcag cctccggact catcttcagt gaccactaca tggactgggt ccgccaggct     120
ccagggaagg gactggagtg ggtcggctct attagaaata acgtaacgg tggctccaca      180 gaatacgccg cctctgtgaa aggcagattc agcatctcaa gagatgattc aaagaattca     240
ctgtatctgc aaatgaacag cctgaaaacc gaggacacgg ccatgtattt ctgtgccaca     300
acgcgtactg gttatcaagg cttctacggc atggacgtct ggggccaagg gaccacggtc     360
accgtctcct ca                                                         372

<210> SEQ ID NO 128
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VH of CADM3351 excluding signal sequence

<400> SEQUENCE: 128

Glu Val Gln Leu Leu Gln Ser Gly Gly Gly Leu Val Gln Pro Gly Gly
1               5                   10                  15
```

```
Ser Leu Arg Leu Ser Cys Ala Ala Ser Gly Leu Ile Phe Ser Asp His
            20                  25                  30

Tyr Met Asp Trp Val Arg Gln Ala Pro Gly Lys Gly Leu Glu Trp Val
        35                  40                  45

Gly Ser Ile Arg Asn Lys Arg Asn Gly Gly Ser Thr Glu Tyr Ala Ala
    50                  55                  60

Ser Val Lys Gly Arg Phe Ser Ile Ser Arg Asp Asp Ser Lys Asn Ser
65                  70                  75                  80

Leu Tyr Leu Gln Met Asn Ser Leu Lys Thr Glu Asp Thr Ala Met Tyr
                85                  90                  95

Phe Cys Ala Thr Thr Arg Thr Gly Tyr Gln Gly Phe Tyr Gly Met Asp
            100                 105                 110

Val Trp Gly Gln Gly Thr Thr Val Thr Val Ser Ser
        115                 120

<210> SEQ ID NO 129
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3351

<400> SEQUENCE: 129

Asp His Tyr Met Asp
1               5

<210> SEQ ID NO 130
<211> LENGTH: 19
<212> TYPE: PRT
<213> ORGANISM: Artificial Sequence
<220> FEATURE:
<223> OTHER INFORMATION: Description of the artificial sequence: amino
      acid sequence of HCDR2 of CADM3351

<400> SEQUENCE: 130

Ser Ile Arg Asn Lys Arg Asn Gly Gly Ser Thr Glu Tyr Ala Ala Ser
1               5                   10                  15

Val Lys Gly

<210> SEQ ID NO 131
<211> LENGTH: 13
<212> TYPE: PRT
<213> ORGANISM: Artificial Sequence
<220> FEATURE:
<223> OTHER INFORMATION: Description of the artificial sequence: amino
      acid sequence of HCDR3 of CADM3351

<400> SEQUENCE: 131

Thr Arg Thr Gly Tyr Gln Gly Phe Tyr Gly Met Asp Val
1               5                   10

<210> SEQ ID NO 132
<211> LENGTH: 321
<212> TYPE: DNA
<213> ORGANISM: Artificial Sequence
<220> FEATURE:
<223> OTHER INFORMATION: Description of the artificial sequence: base
      sequence of VL of CADM3301, CADM3309, CADM3312, CADM3314,
      CADM3316, CADM3349 and CADM3351 excluding signal sequence

<400> SEQUENCE: 132
gaaatagtgt tgacgcagtc tccagccacc ctgtctttgt ctccagggga aagagccacc      60
```

```
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgac gttcggccaa    300
gggaccaagg tggaaatcaa a                                              321
```

<210> SEQ ID NO 133
<211> LENGTH: 107
<212> TYPE: PRT
<213> ORGANISM: Artificial Sequence
<220> FEATURE:
<223> OTHER INFORMATION: Description of the artificial sequence: amino
      acid sequence of VL of CADM3301, CADM3309, CADM3312, CADM3314,
      CADM3316, CADM3349 and CADM3351 excluding signal sequence

<400> SEQUENCE: 133

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 134
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR1 of CADM3301, CADM3309?ACADM3312, CADM3314,
      CADM3316, CADM3349 and CADM3351

<400> SEQUENCE: 134

```
Arg Ala Ser Gln Ser Val Ser Ser Tyr Leu Ala
1               5                   10
```

<210> SEQ ID NO 135
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CADM3301, CADM3309?ACADM3312, CADM3314,
      CADM3316, CADM3349 and CADM3351

<400> SEQUENCE: 135

```
Asp Ala Ser Asn Arg Ala Thr
1               5
```

<210> SEQ ID NO 136
<211> LENGTH: 9
<212> TYPE: PRT
<213> ORGANISM: Artificial Sequence
<220> FEATURE:

<223> OTHER INFORMATION: Description of the artificial sequence: amino
acid sequence of LCDR3 of CADM3301, CADM3309?ACADM3312, CADM3314,
CADM3316, CADM3349 and CADM3351

<400> SEQUENCE: 136

Gln Gln Arg Ser Asn Trp Pro Pro Thr
1               5

<210> SEQ ID NO 137
<211> LENGTH: 363
<212> TYPE: DNA
<213> ORGANISM: Artificial Sequence
<220> FEATURE:
<223> OTHER INFORMATION: Description of the artificial sequence: base
sequence of VH of CADM3402 excluding signal sequence

<400> SEQUENCE: 137

```
gaggtgcagc tggtggagtc tgggggaggc ttggtccagc cggggggggtc cctgagactc      60 tcctgtgcaa cctctggatt caggttcagt atgtatggca tgcactgggt ccgccagtct     120
ccagggaagg ggctggagtg ggtctcagtt atttatagcg gtggaaacac agactacgca     180
gactccgtga agggccgatt cacaatctcc agagacaatt ccaagaacac ggtgtatctt     240
caaatgaaca gcctgagagc cgaggacacg gccgtgtatt actgtgcgag tcgtcgagta     300
gttccaggtg ttatagacta ctttgactcc tggggccagg gaaccctggt caccgtctcc     360
tca                                                                   363
```

<210> SEQ ID NO 138
<211> LENGTH: 121
<212> TYPE: PRT
<213> ORGANISM: Artificial Sequence
<220> FEATURE:
<223> OTHER INFORMATION: Description of the artificial sequence: amino
acid sequence of VH of CADM3402 excluding signal sequence

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Arg Phe Ser Met Tyr
            20                  25                  30

Gly Met His Trp Val Arg Gln Ser Pro Gly Lys Gly Leu Glu Trp Val
        35                  40                  45

Ser Val Ile Tyr Ser Gly Gly Asn Thr Asp Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Ser Arg Arg Val Val Pro Gly Val Ile Asp Tyr Phe Asp Ser Trp Gly
            100                 105                 110

Gln Gly Thr Leu Val Thr Val Ser Ser
        115                 120

<210> SEQ ID NO 139
<211> LENGTH: 5
<212> TYPE: PRT
<213> ORGANISM: Artificial Sequence
<220> FEATURE:
<223> OTHER INFORMATION: Description of the artificial sequence: amino
acid sequence of HCDR1 of CADM3402

<400> SEQUENCE: 139

```
Met Tyr Gly Met His
1               5
```

<210> SEQ ID NO 140
<211> LENGTH: 16
<212> TYPE: PRT
<213> ORGANISM: Artificial Sequence
<220> FEATURE:
<223> OTHER INFORMATION: Description of the artificial sequence: amino
      acid sequence of HCDR2 of CADM3402

<400> SEQUENCE: 140

```
Val Ile Tyr Ser Gly Gly Asn Thr Asp Tyr Ala Asp Ser Val Lys Gly
1               5                   10                  15
```

<210> SEQ ID NO 141
<211> LENGTH: 13
<212> TYPE: PRT
<213> ORGANISM: Artificial Sequence
<220> FEATURE:
<223> OTHER INFORMATION: Description of the artificial sequence: amino
      acid sequence of HCDR3 of CADM3402

<400> SEQUENCE: 141

```
Arg Arg Val Val Pro Gly Val Ile Asp Tyr Phe Asp Ser
1               5                   10
```

<210> SEQ ID NO 142
<211> LENGTH: 363
<212> TYPE: DNA
<213> ORGANISM: Artificial Sequence
<220> FEATURE:
<223> OTHER INFORMATION: Description of the artificial sequence: base
      sequence of VH of CADM3404 excluding signal sequence

<400> SEQUENCE: 142

```
gaggtgcagc tggtggagac cggggggggc gtggtccagc ctggggaggtc cctgagactc    60 tcctgtgcag cctctggatt cgccttcagt aactatggca tgcactgggt ccgccaggct   120
ccaggcaagg ggctggagtg ggtctcagtt atttatagcg gtggaaacac agactacgca   180
gactccgtga agggccgatt cacaatctcc agagacaatt ccaagaacac ggtgtatctt   240
caaatgaaca gcctgagagc cgaggacacg gccgtgtatt actgtgcgag tcgtcgagta   300
gttccaggtg ttatagacta ctttgactcc tggggccagg gaaccctggt cactgtctcc   360
tca                                                                 363
```

<210> SEQ ID NO 143
<211> LENGTH: 121
<212> TYPE: PRT
<213> ORGANISM: Artificial Sequence
<220> FEATURE:
<223> OTHER INFORMATION: Description of the artificial sequence: amino
      acid sequence of VH of CADM3404 excluding signal sequence

<400> SEQUENCE: 143

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Ala Phe Ser Asn Tyr
                20                  25                  30

Gly Met His Trp Val Arg Gln Ala Pro Gly Lys Gly Leu Glu Trp Val
            35                  40                  45

Ser Val Ile Tyr Ser Gly Gly Asn Thr Asp Tyr Ala Asp Ser Val Lys
        50                  55                  60
```

```
Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
             85                  90                  95

Ser Arg Arg Val Val Pro Gly Val Ile Asp Tyr Phe Asp Ser Trp Gly
        100                 105                 110

Gln Gly Thr Leu Val Thr Val Ser Ser
        115                 120
```

<210> SEQ ID NO 144
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3404

<400> SEQUENCE: 144

```
Asn Tyr Gly Met His
1               5
```

<210> SEQ ID NO 145
<211> LENGTH: 16
<212> TYPE: PRT
<213> ORGANISM: Artificial Sequence
<220> FEATURE:
<223> OTHER INFORMATION: Description of the artificial sequence: amino
      acid sequence of HCDR2 of CADM3404

<400> SEQUENCE: 145

```
Val Ile Tyr Ser Gly Gly Asn Thr Asp Tyr Ala Asp Ser Val Lys Gly
1               5                   10                  15
```

<210> SEQ ID NO 146
<211> LENGTH: 13
<212> TYPE: PRT
<213> ORGANISM: Artificial Sequence
<220> FEATURE:
<223> OTHER INFORMATION: Description of the artificial sequence: amino
      acid sequence of HCDR3 of CADM3404

<400> SEQUENCE: 146

```
Arg Arg Val Val Pro Gly Val Ile Asp Tyr Phe Asp Ser
1               5                   10
```

<210> SEQ ID NO 147
<211> LENGTH: 390
<212> TYPE: DNA
<213> ORGANISM: Artificial Sequence
<220> FEATURE:
<223> OTHER INFORMATION: Description of the artificial sequence: base
      sequence of VH of CADM3432 excluding signal sequence

<400> SEQUENCE: 147

```
caggtacagc tgcagcagtc aggtccagga ctggtgaagg cctcgcagac cctctcactc    60
acctgtgcca tctccgggga cagtgtctct agcaggagtg ctgcttggga ctggataagg   120
cagtccccat cgagaggcct tgagtggctg ggaaggacat actacaggtc cacgtggtat   180
aatgactatg catcatctgt gagaagtcga ataagcatca accccgacac atccaagaac   240
cagttctccc tgcagctgaa ctctgtgact cccgaggaca cggctgtata ttattgtgtg   300
agagcaaata ggaagcttcc agcacctgga cagcactttt attatggtat ggacgtctgg   360
ggccaaggga ccacggtcac cgtctcctca                                    390
```

<210> SEQ ID NO 148
<211> LENGTH: 130
<212> TYPE: PRT
<213> ORGANISM: Artificial Sequence
<220> FEATURE:
<223> OTHER INFORMATION: Description of the artificial sequence: amino
      acid sequence of VH of CADM3432 excluding signal sequence

<400> SEQUENCE: 148

Gln Val Gln Leu Gln Gln Ser Gly Pro Gly Leu Val Lys Ala Ser Gln
1               5                   10                  15

Thr Leu Ser Leu Thr Cys Ala Ile Ser Gly Asp Ser Val Ser Ser Arg
            20                  25                  30

Ser Ala Ala Trp Asp Trp Ile Arg Gln Ser Pro Ser Arg Gly Leu Glu
        35                  40                  45

Trp Leu Gly Arg Thr Tyr Tyr Arg Ser Thr Trp Tyr Asn Asp Tyr Ala
    50                  55                  60

Ser Ser Val Arg Ser Arg Ile Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Val Arg Ala Asn Arg Lys Leu Pro Ala Pro Gly Gln His
            100                 105                 110

Phe Tyr Tyr Gly Met Asp Val Trp Gly Gln Gly Thr Thr Val Thr Val
        115                 120                 125

Ser Ser
    130

<210> SEQ ID NO 149
<211> LENGTH: 7
<212> TYPE: PRT
<213> ORGANISM: Artificial Sequence
<220> FEATURE:
<223> OTHER INFORMATION: Description of the artificial sequence: amino
      acid sequence of HCDR1 of CADM3432

<400> SEQUENCE: 149

Ser Arg Ser Ala Ala Trp Asp
1               5

<210> SEQ ID NO 150
<211> LENGTH: 18
<212> TYPE: PRT
<213> ORGANISM: Artificial Sequence
<220> FEATURE:
<223> OTHER INFORMATION: Description of the artificial sequence: amino
      acid sequence of HCDR2 of CADM3432

<400> SEQUENCE: 150

Arg Thr Tyr Tyr Arg Ser Thr Trp Tyr Asn Asp Tyr Ala Ser Ser Val
1               5                   10                  15

Arg Ser

<210> SEQ ID NO 151
<211> LENGTH: 18
<212> TYPE: PRT
<213> ORGANISM: Artificial Sequence
<220> FEATURE:
<223> OTHER INFORMATION: Description of the artificial sequence: amino
      acid sequence of HCDR3 of CADM3432

<400> SEQUENCE: 151

Ala Asn Arg Lys Leu Pro Ala Pro Gly Gln His Phe Tyr Tyr Gly Met
1               5                   10                  15

Asp Val

<210> SEQ ID NO 152
<211> LENGTH: 390
<212> TYPE: DNA
<213> ORGANISM: Artificial Sequence
<220> FEATURE:
<223> OTHER INFORMATION: Description of the artificial sequence: base
      sequence of VH of CADM3448 excluding signal sequence

<400> SEQUENCE: 152
caggtacagc tgcagcagtc aggtccagga ctggtgaagc ccgcgcagac cctctcactc      60
acctgtgcca tctccggaga cagtgtctcc agcaacagtg ttgcttggaa ctgggtcagg     120
cagtccccat cgagaggcct tgagtggctg ggaaggacat attacaggtc ccagtggtat     180
aacgattatg caggatctgt gagaagtcga ataaccatca gcgcagacac atctaagaac     240
cagttctccc tgcaactgaa ctctgtgact cccgaggaca cggctcttta ttattgtgtg     300
agagcaaata ggaagcttcc agcacctgga cagcactttt attatggtat ggacgtctgg     360
ggccaaggga ccacggtcac cgtctcctca                                      390

<210> SEQ ID NO 153
<211> LENGTH: 130
<212> TYPE: PRT
<213> ORGANISM: Artificial Sequence
<220> FEATURE:
<223> OTHER INFORMATION: Description of the artificial sequence: amino
      acid sequence of VH of CADM3448 excluding signal sequence

<400> SEQUENCE: 153

Gln Val Gln Leu Gln Gln Ser Gly Pro Gly Leu Val Lys Pro Ala Gln
1               5                   10                  15

Thr Leu Ser Leu Thr Cys Ala Ile Ser Gly Asp Ser Val Ser Ser Asn
            20                  25                  30

Ser Val Ala Trp Asn Trp Val Arg Gln Ser Pro Ser Arg Gly Leu Glu
        35                  40                  45

Trp Leu Gly Arg Thr Tyr Tyr Arg Ser Gln Trp Tyr Asn Asp Tyr Ala
    50                  55                  60

Gly Ser Val Arg Ser Arg Ile Thr Ile Ser Ala Asp Thr Ser Lys Asn
65                  70                  75                  80

Gln Phe Ser Leu Gln Leu Asn Ser Val Thr Pro Glu Asp Thr Ala Leu
                85                  90                  95

Tyr Tyr Cys Val Arg Ala Asn Arg Lys Leu Pro Ala Pro Gly Gln His
            100                 105                 110

Phe Tyr Tyr Gly Met Asp Val Trp Gly Gln Gly Thr Thr Val Thr Val
        115                 120                 125

Ser Ser
    130

<210> SEQ ID NO 154
<211> LENGTH: 7
<212> TYPE: PRT
<213> ORGANISM: Artificial Sequence
<220> FEATURE:
<223> OTHER INFORMATION: Description of the artificial sequence: amino
      acid sequence of HCDR1 of CADM3448

<400> SEQUENCE: 154

```
<210> SEQ ID NO 155
<211> LENGTH: 18
<212> TYPE: PRT
<213> ORGANISM: Artificial Sequence
<220> FEATURE:
<223> OTHER INFORMATION: Description of the artificial sequence: amino
      acid sequence of HCDR2 of CADM3448

<400> SEQUENCE: 155

Arg Thr Tyr Tyr Arg Ser Gln Trp Tyr Asn Asp Tyr Ala Gly Ser Val
1               5                   10                  15

Arg Ser

<210> SEQ ID NO 156
<211> LENGTH: 18
<212> TYPE: PRT
<213> ORGANISM: Artificial Sequence
<220> FEATURE:
<223> OTHER INFORMATION: Description of the artificial sequence: amino
      acid sequence of HCDR3 of CADM3448

<400> SEQUENCE: 156

Ala Asn Arg Lys Leu Pro Ala Pro Gly Gln His Phe Tyr Tyr Gly Met
1               5                   10                  15

Asp Val

<210> SEQ ID NO 157
<211> LENGTH: 363
<212> TYPE: DNA
<213> ORGANISM: Artificial Sequence
<220> FEATURE:
<223> OTHER INFORMATION: Description of the artificial sequence: base
      sequence of VH of CADM3458 excluding signal sequence

<400> SEQUENCE: 157
gaggtgcagc tggtggagtc cggggggaggc gtggtccagc ctggggaggtc cctgagactc        60 tcctgtgcag cctctggatt caccttcagt agatatggca tacactgggt ccgccaggct       120
ccaggcaagg ggctggagtg gtggcagtt atttatagcg gtggaaacac agactacgca       180
gactccgtga agggccgatt cacaatctcc agagacaatt ccaagaacac ggtgtatctt       240
caaatgaaca gcctgagagc cgaggacacg gccgtgtatt actgtgcgag tcgtcgagta       300
gttccaggtg ttatagacta ctttgactcc tgggggccagg gaaccctggt caccgtctcc       360
tca                                                                      363

<210> SEQ ID NO 158
<211> LENGTH: 121
<212> TYPE: PRT
<213> ORGANISM: Artificial Sequence
<220> FEATURE:
<223> OTHER INFORMATION: Description of the artificial sequence: amino
      acid sequence of VH of CADM3458 excluding signal sequence

<400> SEQUENCE: 158

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Ile His Trp Val Arg Gln Ala Pro Gly Lys Gly Leu Glu Trp Val
```

Ser Asn Ser Val Ala Trp Asn
1               5

```
              35                  40                  45

Ala Val Ile Tyr Ser Gly Gly Asn Thr Asp Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Ser Arg Arg Val Val Pro Gly Val Ile Asp Tyr Phe Asp Ser Trp Gly
            100                 105                 110

Gln Gly Thr Leu Val Thr Val Ser Ser
        115                 120

<210> SEQ ID NO 159
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3458

<400> SEQUENCE: 159

Arg Tyr Gly Ile His
1               5

<210> SEQ ID NO 160
<211> LENGTH: 16
<212> TYPE: PRT
<213> ORGANISM: Artificial Sequence
<220> FEATURE:
<223> OTHER INFORMATION: Description of the artificial sequence: amino
      acid sequence of HCDR2 of CADM3458

<400> SEQUENCE: 160

Val Ile Tyr Ser Gly Gly Asn Thr Asp Tyr Ala Asp Ser Val Lys Gly
1               5                   10                  15

<210> SEQ ID NO 161
<211> LENGTH: 13
<212> TYPE: PRT
<213> ORGANISM: Artificial Sequence
<220> FEATURE:
<223> OTHER INFORMATION: Description of the artificial sequence: amino
      acid sequence of HCDR3 of CADM3458

<400> SEQUENCE: 161

Arg Arg Val Val Pro Gly Val Ile Asp Tyr Phe Asp Ser
1               5                   10

<210> SEQ ID NO 162
<211> LENGTH: 321
<212> TYPE: DNA
<213> ORGANISM: Artificial Sequence
<220> FEATURE:
<223> OTHER INFORMATION: Description of the artificial sequence: base
      sequence of VL of CADM3402, CADM3404, CADM3432, CADM3448 and
      CADM3458 excluding signal sequence

<400> SEQUENCE: 162
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
``` gaagatttg caacttacta ctgtcaacag agttacagta ccccctcgaac gttcggccaa    300 gggaccaagg tggaaatcaa a    321

<210> SEQ ID NO 163
<211> LENGTH: 107
<212> TYPE: PRT
<213> ORGANISM: Artificial Sequence
<220> FEATURE:
<223> OTHER INFORMATION: Description of the artificial sequence: amino
      acid sequence of VL of CADM3402, CADM3404, CADM3432, CADM3448 and
      CADM3458 excluding signal sequence

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105

<210> SEQ ID NO 164
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR1 of CADM3402, CADM3404, CADM3432, CADM3448
      and CADM3458

<400> SEQUENCE: 164

Arg Ala Ser Gln Ser Ile Ser Ser Tyr Leu Asn
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CADM3402, CADM3404, CADM3432, CADM3448
      and CADM3458

<400> SEQUENCE: 165

Ala Ala Ser Ser Leu Gln Ser
1               5

<210> SEQ ID NO 166
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CADM3402, CADM3404, CADM3432, CADM3448
      and CADM3458

<400> SEQUENCE: 166

Gln Gln Ser Tyr Ser Thr Pro Arg Thr
1               5

<210> SEQ ID NO 167
<211> LENGTH: 357
<212> TYPE: DNA
<213> ORGANISM: Artificial Sequence
<220> FEATURE:
<223> OTHER INFORMATION: Description of the artificial sequence: base
      sequence of VH of CADM3501 excluding signal sequence

<400> SEQUENCE: 167
gaggtgcagc tggtggagtc tgggggaggc ttagttcagc ctggggggc cctgagactc    60 tcctgttcag cctccggatt caccttcagt gggtactgga tgcactgggt ccgccaagct   120
ccagggaagg ggctggagtg ggtgtcacaa attagtagta gtggtactat catagactcc   180
gcagactttg tgaagggccg attcgccgtc tccagggaca acgccaagga cttattgtat   240
ctgcaaatga acagcctgag agccgatgac acggccgtct attactgtgc gagggggcca   300
ctggcgaaga atggttttga catttggggc caagggacaa tggtcaccgt ctcttca      357

<210> SEQ ID NO 168
<211> LENGTH: 119
<212> TYPE: PRT
<213> ORGANISM: Artificial Sequence
<220> FEATURE:
<223> OTHER INFORMATION: Description of the artificial sequence: amino
      acid sequence of VH of CADM3501 excluding signal sequence

<400> SEQUENCE: 168

Glu Val Gln Leu Val Glu Ser Gly Gly Gly Leu Val Gln Pro Gly Gly
1               5                   10                  15

Ala Leu Arg Leu Ser Cys Ser Ala Ser Gly Phe Thr Phe Ser Gly Tyr
            20                  25                  30

Trp Met His Trp Val Arg Gln Ala Pro Gly Lys Gly Leu Glu Trp Val
        35                  40                  45

Ser Gln Ile Ser Ser Ser Gly Thr Ile Ile Asp Ser Ala Asp Phe Val
    50                  55                  60

Lys Gly Arg Phe Ala Val Ser Arg Asp Asn Ala Lys Asp Leu Leu Tyr
65                  70                  75                  80

Leu Gln Met Asn Ser Leu Arg Ala Asp Asp Thr Ala Val Tyr Tyr Cys
                85                  90                  95

Ala Arg Gly Pro Leu Ala Lys Asn Gly Phe Asp Ile Trp Gly Gln Gly
            100                 105                 110

Thr Met Val Thr Val Ser Ser
        115

<210> SEQ ID NO 169
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CADM3501

<400> SEQUENCE: 169

Gly Tyr Trp Met His
1               5

<210> SEQ ID NO 170
<211> LENGTH: 17
<212> TYPE: PRT

<213> ORGANISM: Artificial Sequence
<220> FEATURE:
<223> OTHER INFORMATION: Description of the artificial sequence: amino
    acid sequence of HCDR2 of CADM3501

<400> SEQUENCE: 170

Gln Ile Ser Ser Ser Gly Thr Ile Ile Asp Ser Ala Asp Phe Val Lys
1               5                   10                  15

Gly

<210> SEQ ID NO 171
<211> LENGTH: 10
<212> TYPE: PRT
<213> ORGANISM: Artificial Sequence
<220> FEATURE:
<223> OTHER INFORMATION: Description of the artificial sequence: amino
    acid sequence of HCDR3 of CADM3501

<400> SEQUENCE: 171

Gly Pro Leu Ala Lys Asn Gly Phe Asp Ile
1               5                   10

<210> SEQ ID NO 172
<211> LENGTH: 339
<212> TYPE: DNA
<213> ORGANISM: Artificial Sequence
<220> FEATURE:
<223> OTHER INFORMATION: Description of the artificial sequence: base
    sequence of VL of CADM3501 excluding signal sequence

<400> SEQUENCE: 172
gacatcgtga tgacccagtc tccagactcc ctggctgtgt ctctgggcga gagggccacc      60
atcaactgca gtccagcca gagtgtttta tacagctcca acaataagaa ctacttagct     120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgtacactt ttggccaggg gaccaagctg gagatcaaa                          339

<210> SEQ ID NO 173
<211> LENGTH: 113
<212> TYPE: PRT
<213> ORGANISM: Artificial Sequence
<220> FEATURE:
<223> OTHER INFORMATION: Description of the artificial sequence: amino
    acid sequence of VL of CADM3501 excluding signal sequence

<400> SEQUENCE: 173

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile

Lys

<210> SEQ ID NO 174
<211> LENGTH: 17
<212> TYPE: PRT
<213> ORGANISM: Artificial Sequence
<220> FEATURE:
<223> OTHER INFORMATION: Description of the artificial sequence: amino
      acid sequence of LCDR1 of CADM3501

<400> SEQUENCE: 174

Lys Ser Ser Gln Ser Val Leu Tyr Ser Ser Asn Asn Lys Asn Tyr Leu
1               5                   10                  15

Ala

<210> SEQ ID NO 175
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CADM3501

<400> SEQUENCE: 175

Trp Ala Ser Thr Arg Glu Ser
1               5

<210> SEQ ID NO 176
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CADM3501

<400> SEQUENCE: 176

Gln Gln Tyr Tyr Ser Thr Pro Tyr Thr
1               5

<210> SEQ ID NO 177
<211> LENGTH: 124
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L8_00 excluding signal sequence

<400> SEQUENCE: 177

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Arg Gly Trp Val Arg Gln Ala Pro Gly Lys Gly Leu Glu Trp Val
        35                  40                  45

Ser Ala Ile Asp Tyr Ser Gly Gly Ser Thr Asn Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Ser Arg Arg Pro Ser Trp Asp Ala Asp Gly Tyr Asp
            100                 105                 110

```
Tyr Trp Gly Gln Gly Thr Leu Val Thr Val Ser Ser
        115                 120

<210> SEQ ID NO 178
<211> LENGTH: 120
<212> TYPE: PRT
<213> ORGANISM: Artificial Sequence
<220> FEATURE:
<223> OTHER INFORMATION: Description of the artificial sequence: amino
      acid sequence of VHH of iCADM3_3R1-L11_00 excluding signal
      sequence

<400> SEQUENCE: 178

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Phe Asn
            20                  25                  30

Ala Met Gly Trp Val Arg Gln Ala Pro Gly Lys Gly Leu Glu Trp Val
        35                  40                  45

Ser Val Ile Thr Ser Gly Gly Tyr Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Val Tyr Ser Asp Tyr Val Ile Met Asn Tyr Trp Gly Gln
            100                 105                 110

Gly Thr Leu Val Thr Val Ser Ser
        115                 120
```